United States Patent
Sagehashi et al.

(10) Patent No.: US 12,275,693 B2
(45) Date of Patent: Apr. 15, 2025

(54) ONIUM SALT, CHEMICALLY AMPLIFIED RESIST COMPOSITION AND PATTERNING PROCESS

(71) Applicant: Shin-Etsu Chemical Co., Ltd., Tokyo (JP)

(72) Inventors: Masayoshi Sagehashi, Joetsu (JP); Takayuki Fujiwara, Joetsu (JP); Masahiro Fukushima, Joetsu (JP); Masaki Ohashi, Joetsu (JP); Kazuhiro Katayama, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 332 days.

(21) Appl. No.: 16/858,160

(22) Filed: Apr. 24, 2020

(65) Prior Publication Data

US 2020/0369605 A1    Nov. 26, 2020

(30) Foreign Application Priority Data

May 24, 2019   (JP) .................................. 2019-097582

(51) Int. Cl.
 *C07C 309/12*  (2006.01)
 *C07C 317/06*  (2006.01)
 (Continued)

(52) U.S. Cl.
 CPC .......... *C07C 317/06* (2013.01); *G03F 7/0045* (2013.01); *G03F 7/029* (2013.01);
 (Continued)

(58) Field of Classification Search
 CPC ..... C07C 317/06; C07C 303/32; C07C 69/78; C07C 69/753; C07C 309/12; C07C 69/95;
 (Continued)

(56) References Cited

U.S. PATENT DOCUMENTS 6,410,204 B1   6/2002  Kodama et al.
6,541,178 B2   4/2003  Jung et al.
    (Continued)

FOREIGN PATENT DOCUMENTS

EP   1690685 A2    8/2006
JP   H05-005993 A  1/1993
    (Continued)

OTHER PUBLICATIONS

Office Action dated May 6, 2021, issued in counterpart TW Application No. 109116819. (6 pages).
(Continued)

*Primary Examiner* — Sean M DeGuire
*Assistant Examiner* — Richard David Champion
(74) *Attorney, Agent, or Firm* — WHDA, LLP

(57) ABSTRACT

An onium salt of formula (1) and a chemically amplified resist composition comprising the same as a PAG are provided. When processed by lithography, the resist composition exhibits a high sensitivity, minimal LWR and improved CDU independent of whether it is of positive or negative tone.

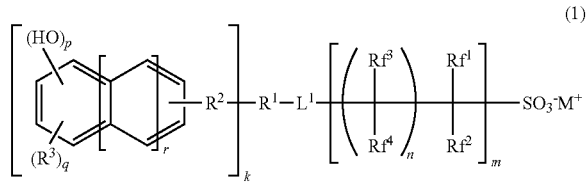

8 Claims, 12 Drawing Sheets

(51) Int. Cl.
  *G03F 7/004* (2006.01)
  *G03F 7/029* (2006.01)
  *G03F 7/038* (2006.01)
  *G03F 7/039* (2006.01)
  *G03F 7/32* (2006.01)

(52) U.S. Cl.
  CPC .......... *G03F 7/0382* (2013.01); *G03F 7/0392* (2013.01); *G03F 7/322* (2013.01)

(58) Field of Classification Search
  CPC ... C07C 309/24; C07C 309/73; C07C 69/757; C07C 309/20; C07C 309/06; C07C 205/06; C07C 205/11; C07C 309/04; C07C 69/74; C07C 2603/86; C07C 2603/18; C07C 2601/08; C07C 2602/24; C07C 2602/08; C07C 2601/02; C07C 2601/04; C07C 2603/74; C07C 2602/42; C07C 2602/10; C07C 2603/68; C07C 2603/24; C07C 2603/50; C07C 2601/20; C07C 2601/18; C07C 2603/16; C07C 2602/28; C07C 2601/14; C07C 309/65; C07C 381/12; C07C 69/08; C07C 2602/003; G03F 7/0045; G03F 7/029; G03F 7/0382; G03F 7/0392; G03F 7/322; G03F 7/2059; G03F 7/2037; G03F 7/0397; G03F 7/046; G03F 7/38; G03F 7/2004; G03F 7/162; G03F 7/168; G03F 7/325; C07J 31/006; C07J 43/003; C07D 307/00; C07D 327/08; C07D 333/46; C08F 228/02; C08F 220/1812; C08F 212/22; C08F 8/12; C08F 220/1807; C08F 220/282; C08F 212/32; C09D 133/10; C09D 125/18
  See application file for complete search history.

(56) References Cited

U.S. PATENT DOCUMENTS

| | | | |
|---|---|---|---|
| 7,527,910 | B2 | 5/2009 | Yamaguchi et al. |
| 7,923,167 | B2 | 4/2011 | Lee et al. |
| 9,477,149 | B2 | 10/2016 | Namai et al. |
| 9,488,914 | B2 | 11/2016 | Mori et al. |
| 2002/0048719 | A1 | 4/2002 | Jung et al. |
| 2007/0099055 | A1 | 5/2007 | Lee et al. |
| 2007/0184382 | A1 | 8/2007 | Yamaguchi et al. |
| 2009/0233223 | A1* | 9/2009 | Tachibana ............. G03F 7/0045 430/296 |
| 2011/0112306 | A1 | 5/2011 | Nagamori et al. |
| 2012/0171616 | A1* | 7/2012 | Thackeray ............ G03F 7/0397 430/311 |
| 2012/0322007 | A1 | 12/2012 | Kato et al. |
| 2015/0004545 | A1 | 1/2015 | Namai et al. |
| 2015/0086911 | A1* | 3/2015 | Tsuruta ................. G03F 7/0045 430/296 |
| 2015/0198879 | A1 | 7/2015 | Mori et al. |
| 2017/0115566 | A1* | 4/2017 | Hatakeyama ......... G03F 7/0397 |
| 2017/0369698 | A1 | 12/2017 | Suzuki et al. |
| 2019/0384174 | A1* | 12/2019 | Arai ..................... G03F 7/0045 |

FOREIGN PATENT DOCUMENTS

| | | |
|---|---|---|
| JP | 2001-100402 A | 4/2001 |
| JP | 2001-192573 A | 7/2001 |
| JP | 2006-220843 A | 8/2006 |
| JP | 2007-103372 A | 4/2007 |
| JP | 2007-197432 A | 8/2007 |
| JP | 2009-053518 A | 3/2009 |
| JP | 2011-191753 A | 9/2011 |
| JP | 2013-040164 A | 2/2013 |
| JP | 2013-133281 A | 7/2013 |
| JP | 2018-197226 A | 12/2018 |
| KR | 10-2011-0031236 A | 3/2011 |
| TW | 201403227 A | 1/2014 |
| TW | 201815750 A | 5/2018 |
| WO | 2013/111667 A1 | 8/2013 |
| WO | 2013/140969 A1 | 9/2013 |

OTHER PUBLICATIONS

Office Action dated Nov. 2, 2021, issued in counterpart KR Application No. 10-2020-0061910, with machine translation. (21 pages).
Office Action dated Mar. 8, 2022, issued in counterpart JP application No. 2019-097582, with English translation. (9 pages).

* cited by examiner

ONIUM SALT, CHEMICALLY AMPLIFIED RESIST COMPOSITION AND PATTERNING PROCESS

CROSS-REFERENCE TO RELATED APPLICATION

This non-provisional application claims priority under 35 U.S.C. § 119(a) on Patent Application No. 2019-097582 filed in Japan on May 24, 2019, the entire contents of which are hereby incorporated by reference.

TECHNICAL FIELD

This invention relates to a novel onium salt, a chemically amplified resist composition, and a pattern forming process.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of wavelength 13.5 nm, and double patterning version of the ArF lithography, on which active research efforts have been made.

As the pattern feature size is reduced, approaching to the diffraction limit of light, light contrast lowers. In the case of positive resist film, a lowering of light contrast leads to reductions of resolution and focus margin of hole and trench patterns.

As the pattern feature size is reduced, the edge roughness (LWR) of line patterns or the critical dimension uniformity (CDU) of hole patterns is regarded significant. It is pointed out that LWR is affected by the segregation or agglomeration of a base polymer and acid generator and the diffusion of generated acid. There is a tendency that as the resist film becomes thinner, LWR becomes greater. A film thickness reduction to comply with the progress of size reduction causes a degradation of LWR, which becomes a serious problem.

The EUV lithography resist material must meet high sensitivity, high resolution, and low LWR at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR.

DISCLOSURE OF INVENTION

For the acid-catalyzed chemically amplified resist, it is desired to develop an acid generator capable of providing a high sensitivity and reducing the LWR of line patterns or improving the CDU of hole patterns.

An object of the invention is to provide a resist composition which exhibits a high sensitivity and a reduced LWR or improved CDU, independent of whether it is of positive tone or negative tone; and a pattern forming process using the same.

The inventors have found that using a sulfonium or iodonium salt of sulfonic acid having a phenolic hydroxyl group as the acid generator, a resist material having a high sensitivity, reduced LWR, improved CDU, high contrast, improved resolution, and wide process margin is obtainable.

In one aspect, the invention provides an onium salt having the formula (1).

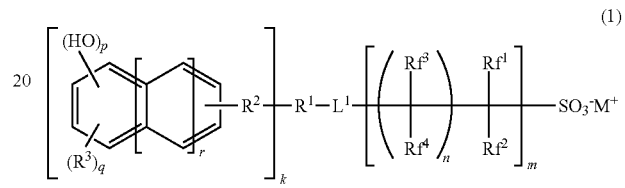

Herein $R^1$ is a single bond or a $C_1$-$C_{20}$ di- to tetravalent hydrocarbon group. $R^2$ is a single bond or a $C_1$-$C_{20}$ divalent hydrocarbon group which may contain a heteroatom. $R^3$ is fluorine, a $C_1$-$C_{20}$ to alkoxy group, nitro group, or $C_1$-$C_{10}$ monovalent hydrocarbon group which may contain a heteroatom. $R^{f1}$, $R^{f2}$, $R^{f3}$, and $R^{f4}$ are each independently hydrogen, fluorine or trifluoromethyl. $L^1$ is a single bond, —CO—O—, —O—CO—, —O—CO—O— or —O—. The subscript m is 0 or 1, n is 0 or 1, k is 1, 2 or 3, p is an integer of 1 to 3, q is an integer of 0 to 3, r is 0 or 1.

$M^+$ is a sulfonium cation having the formula (1A) or iodonium cation having the formula (1B):

wherein $R^{11}$ to $R^{15}$ are each independently a $C_1$-$C_{20}$ monovalent hydrocarbon group which may contain a heteroatom, any two of $R^{11}$, $R^{12}$ and $R^{13}$ may bond together to form a ring with the sulfur atom to which they are attached.

In a preferred embodiment, $L^1$ is —CO—O—, m and n each are 1, $R^{f1}$ and $R^{f2}$ each are fluorine, $R^{f3}$ and $R^{f4}$ each are hydrogen.

In another preferred embodiment, $L^1$ is —CO—O—, m and n each are 1, $R^{f1}$ and $R^{f2}$ each are fluorine, $R^{f3}$ is trifluoromethyl, and $R^{f4}$ is hydrogen.

In a second aspect, the invention provides a photoacid generator comprising the onium salt defined above.

In a third aspect, the invention provides a chemically amplified resist composition comprising the photoacid generator defined above.

The resist composition may further comprise a base polymer comprising recurring units adapted for polarity switch under the action of acid, of at least one type selected from recurring units having the formulae (A1) and (A2), and recurring units of at least one type selected from recurring units having the formulae (B) to (E).

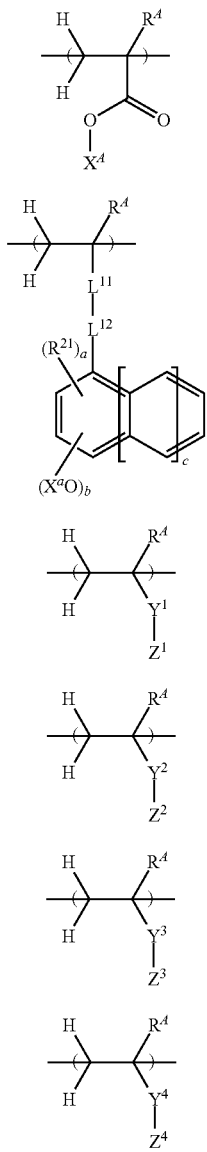

Herein $R^A$ is hydrogen, fluorine, methyl or trifluoromethyl. $R^{21}$ is each independently hydrogen or a $C_1$-$C_6$ alkyl group which may contain an ether bond or carbonyl moiety. $L^{11}$ is a single bond, carbonyloxy or amide group. $L^{12}$ is a single bond or a $C_1$-$C_7$ alkanediyl group which may contain an ether bond or carbonyl moiety. The subscript "a" is an integer to satisfying a≤5+2c−b, b is an integer of 1 to 5, c is an integer of 0 to 2. $X^A$ is an acid labile group. $Y^1$ to $Y^4$ are each independently a single bond, methylene, ethylene, phenylene, fluorinated phenylene, naphthylene, —O—$Y^5$—, —C(=O)—O—$Y^5$— or —C(=O)—NH—$Y^5$—, $Y^5$ is a $C_1$-$C_6$ alkanediyl, $C_2$-$C_6$ alkenediyl, phenylene, or naphthylene group, which may contain a carbonyl moiety, ester bond, ether bond or hydroxyl moiety. $Z^1$ is a $C_1$-$C_{20}$ fluoroalcohol-containing substituent group. $Z^2$ is a $C_1$-$C_{20}$ phenolic hydroxyl-containing substituent group. $Z^3$ is a $C_1$-$C_{20}$ carboxy-containing substituent group. $Z^4$ is a substituent group containing a lactone skeleton, sultone skeleton, carbonate skeleton, cyclic ether skeleton, acid anhydride skeleton, alcoholic hydroxyl moiety, alkoxycarbonyl moiety, sulfonamide moiety or carbamoyl moiety.

In a preferred embodiment, the base polymer further comprises recurring units of at least one type selected from recurring units having the formulae (F1) to (F4).

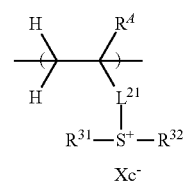

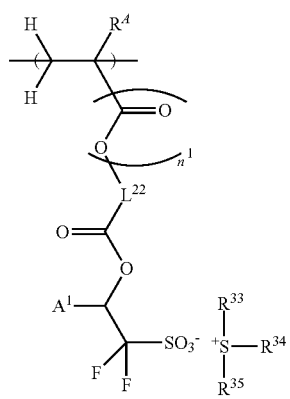

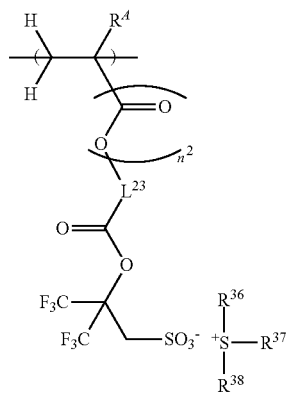

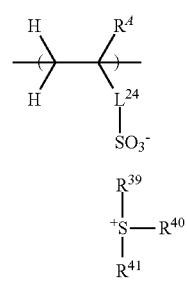

Herein $R^A$ is hydrogen, fluorine, methyl or trifluoromethyl. $L^{21}$ is a single bond, phenylene, —O-$L^{21A}$—, —C(=O)—O-$L^{21A}$-, or —C(=O)—NH-$L^{21A}$-, wherein $L^{21A}$ is a $C_1$-$C_{20}$ alkanediyl, $C_2$-$C_{20}$ alkenediyl or phenylene group, which may contain a heteroatom. $L^{22}$ and $L^{23}$ are each independently a single bond or a $C_1$-$C_{20}$ divalent hydrocarbon group which may contain a heteroatom. $L^{24}$ is a single bond, methylene, ethylene, phenylene, fluorinated phenylene, —O-L$^{24A}$—, —C(=O)—O-L$^{24A}$- or —C(=O)—NH-L$^{24A}$-, wherein L$^{24A}$ is an optionally substituted phenylene group. R$^{31}$ to R$^{41}$ are each independently a C$_1$-C$_{20}$ monovalent hydrocarbon group which may contain a heteroatom, any two of L$^{21}$, R$^{31}$ and R$^{32}$ may bond together to form a ring with the sulfur atom to which they are attached, any two of R$^{33}$, R$^{34}$ and R$^{35}$, any two of R$^{36}$, R$^{37}$ and R$^{38}$, or any two of R$^{39}$, R$^{49}$ and R$^{41}$ may bond together to form a ring with the sulfur atom to which they are attached. Xc$^-$ is a non-nucleophilic counter ion. A$^1$ is hydrogen or trifluoromethyl. The subscript n$^1$ is 0 or 1, n$^1$ is 0 when L$^{22}$ is a single bond, n$^2$ is 0 or 1, n$^2$ is 0 when L$^{23}$ is a single bond.

In a fourth aspect, the invention provides a process for forming a pattern comprising the steps of applying the resist composition defined above onto a substrate to form a resist film thereon, exposing a selected region of the resist film to high-energy radiation, and developing the exposed resist film in a developer.

In one preferred embodiment, the developing step uses an alkaline aqueous solution as the developer, thereby forming a positive pattern in which an exposed region of the resist film is dissolved away and an unexposed region of the resist film is not dissolved.

In another preferred embodiment, the developing step uses an organic solvent as the developer, thereby forming a negative pattern in which an unexposed region of the resist film is dissolved away and an exposed region of the resist film is not dissolved.

ADVANTAGEOUS EFFECTS OF INVENTION

The onium salt of the invention is a sulfonium or iodonium salt of sulfonic acid of to specific structure having a phenolic hydroxyl group. When used in EB and EUV resist compositions as a photoacid generator, the onium salt contributes to increases in sensitivity and resolution. As the same time, acid diffusion length is adequately controlled and improvements in LWR and CDU are achieved.

DESCRIPTION OF EMBODIMENTS

Figure 1:
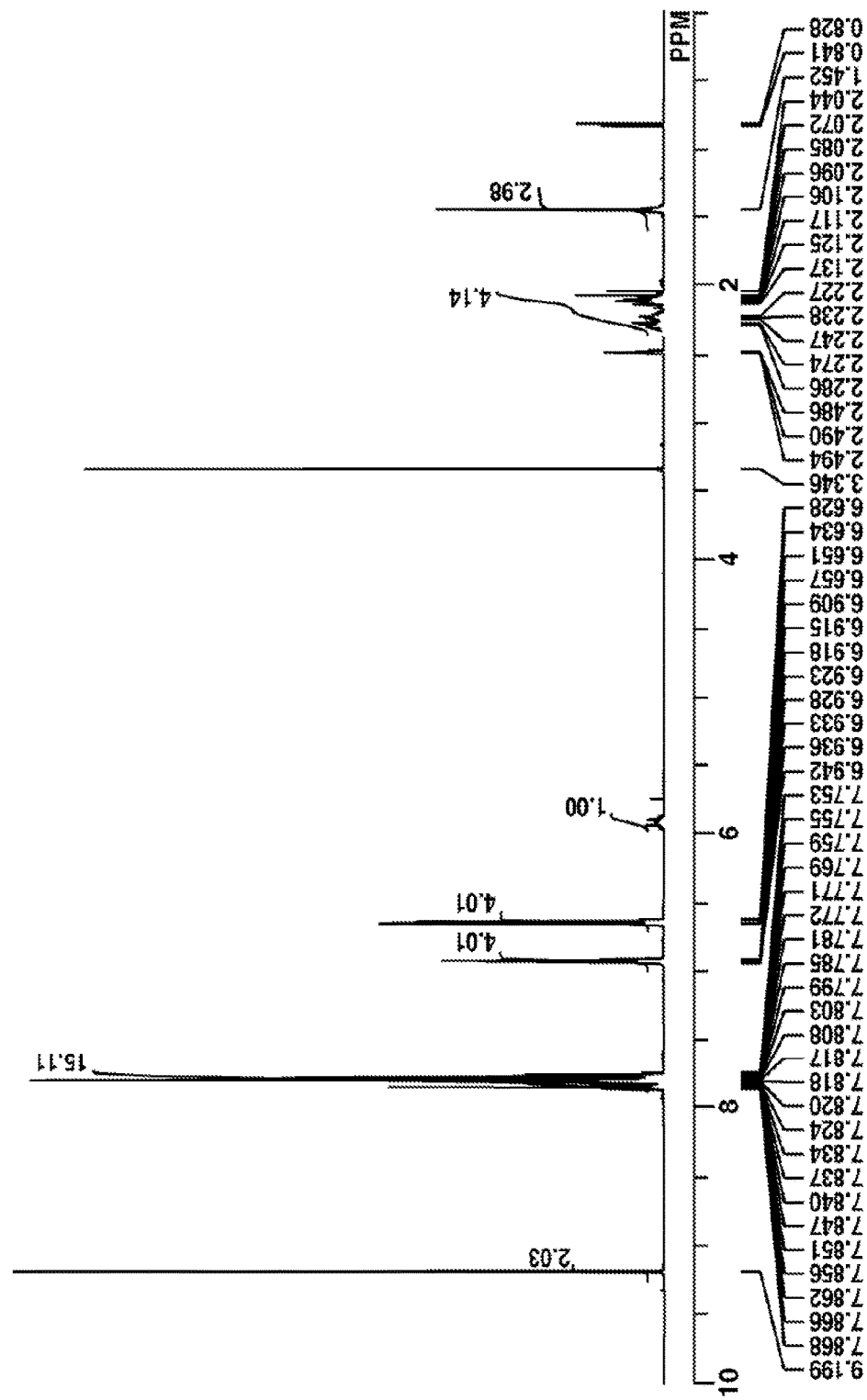
FIG. 1 is a diagram showing the $^1$H-NMR spectrum of sulfonium salt (PAG-1) in Example 1-1.

As used herein, the singular forms "a," "an" and "the" include plural referents unless the context clearly dictates otherwise. The notation (C$_n$-C$_m$) means a group containing from n to m carbon atoms per group. As used herein, the terms "group" and "moiety" are interchangeable. In chemical formulae, the broken line designates a valence bond, Me stands for methyl, Ac for acetyl, nBu for n-butyl, tBu for tert-butyl, and Ph for phenyl.

The abbreviations and acronyms have the following meaning.
 EB: electron beam
 EUV: extreme ultraviolet
 Mw: weight average molecular weight
 Mu: number average molecular weight
 Mw/Mn: molecular weight distribution or dispersity
 GPC: gel permeation chromatography
 PEB: post-exposure bake
 PAG: photoacid generator
 LWR: line width roughness
 CDU: critical dimension uniformity Onium Salt One embodiment of the invention is an onium salt having the formula (1).

$$\left[ \begin{array}{c} (HO)_p \\ \phantom{x} \\ (R^3)_q \end{array} \right]_r \!\!\!\!\!\!\!\!\!\!\!\! -R^2-\!\!\left[R^1-L^1-\!\!\left(\!\!\begin{array}{cc} Rf^3 & Rf^1 \\ & \\ Rf^4 & Rf^2 \end{array}\!\!\right)_n\!\!\right]_m\!\!\!\!-SO_3^-M^+ \quad (1)$$

In formula (1), R$^1$ is a single bond or a C$_1$-C$_{20}$ di- to tetravalent hydrocarbon group. R$^2$ is a single bond or a C$_1$-C$_{20}$ divalent hydrocarbon group which may contain a heteroatom. R$^3$ is fluorine, a C$_1$-C$_{10}$ alkoxy group, a nitro group, or a C$_1$-C$_{10}$ monovalent hydrocarbon group which may contain a heteroatom. R$^{f1}$, R$^{f2}$, R$^{f3}$, and R$^{f4}$ are each independently hydrogen, fluorine or trifluoromethyl. L$^1$ is a single bond, —CO—O—, —O—CO—, —O—CO—O— or —O—. The subscript m is 0 or 1, n is 0 or 1, k is 1, 2 or 3, p is an integer of 1 to 3, q is an integer of 0 to 3, and r is 0 or 1.

The C$_1$-C$_{20}$ di- to tetravalent hydrocarbon groups represented by R$^1$ are derived from aliphatic or aromatic hydrocarbons by removing 2 to 4 hydrogen atoms. The aliphatic hydrocarbons may be straight, branched or cyclic and examples thereof include alkanes such as methane, ethane, propane, butane, 2-methylpropane, and cyclohexane, and alkenes such as ethylene, propene, 1-butene, 2-butene, 2-methylpropene, and cyclohexene.

Suitable aromatic hydrocarbons include benzene, naphthalene, toluene, xylene, and anthracene. R$^1$ is preferably a single bond or a C$_1$-C$_6$ divalent aliphatic hydrocarbon group.

The C$_1$-C$_{20}$ divalent hydrocarbon groups represented by R$^2$ may be straight, branched or cyclic while they may contain a heteroatom. Examples thereof include straight or branched alkanediyl groups such as methylene, ethane-1,1-diyl, ethane-1,2-diyl, propane-1,1-diyl, propane-1,2-diyl, propane-1,3-diyl, propane-2,2-diyl, 2-methylpropane-1,1-diyl, butane-1,4-diyl, pentane-1,5-diyl, hexane-1,6-diyl, heptane-1,7-diyl, octane-1,8-diyl, nonane-1,9-diyl, decane-1,10-diyl, undecane-1,11-diyl, dodecane-1,12-diyl, tridecane-1,13-diyl, tetradecane-1,14-diyl, pentadecane-1,15-diyl, hexadecane-1,16-diyl, and heptadecane-1,17-diyl; divalent aliphatic hydrocarbon groups, typically saturated cyclic divalent hydrocarbon groups such as cyclopentanediyl, cyclohexanediyl, norbornanediyl and adamantanediyl; and divalent aromatic hydrocarbon groups such as phenylene and naphthylene. In these groups, some hydrogen may be substituted by an alkyl moiety such as methyl, ethyl, propyl, n-butyl or t-butyl; some hydrogen may be substituted by a moiety containing a heteroatom such as oxygen, sulfur, nitrogen or halogen; or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride (—C(=O)—O—C(=O)—) or haloalkyl moiety. Of the heteroatoms, oxygen is preferred. $R^2$ is preferably a single bond or a $C_1$-$C_6$ divalent aliphatic hydrocarbon group.

The $C_1$-$C_{10}$ alkoxy group represented by $R^3$ may be straight, branched or cyclic. Examples thereof include methoxy, ethoxy, n-propyloxy, isopropyloxy, n-butyloxy, isobutyloxy, sec-butyloxy, tert-butyloxy, n-pentyloxy, sec-pentyloxy, tert-pentyloxy, neopentyloxy, n-hexyloxy, n-heptyloxy, n-octyloxy, 2-ethylhexyloxy, n-nonyloxy, n-decyloxy, vinyloxycarbonyl, 1-propenyloxy, and 2-propenyloxy.

The $C_1$-$C_{10}$ monovalent hydrocarbon groups represented by $R^3$ may be straight, branched or cyclic while they may contain a heteroatom. Examples thereof include alkyl groups such as methyl, ethyl, propyl, isopropyl, butyl, isobutyl, sec-butyl, tert-butyl, pentyl, neopentyl, cyclopentyl, hexyl, heptyl, 2-ethylhexyl, nonyl, decyl, cyclohexyl, 1-adamantyl, 2-adamantyl, 1-adamantylmethyl, norbornyl, norbornylmethyl, tricyclodecanyl, and dicyclohexylmethyl; alkenyl groups such as allyl and 3-cyclohexenyl; aryl groups such as phenyl, 1-naphthyl and 2-naphthyl; and aralkyl groups such as benzyl and diphenylmethyl. In these groups, some hydrogen may be substituted by a moiety containing a heteroatom such as oxygen, sulfur, nitrogen or halogen; or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, to lactone ring, sultone ring, carboxylic anhydride or haloalkyl moiety.

Inter alia, $R^3$ is preferably selected from fluorine, $C_1$-$C_4$ alkoxy groups, nitro, and $C_1$-$C_4$ alkyl groups.

The compound having formula (1) is an onium salt of sulfonic acid. When the onium salt is used in chemically amplified resist compositions as a photoacid generator, the onium salt generates a sulfonic acid upon exposure. The acidity of generated sulfonic acid may be selected as appropriate. As used herein, the term "photoacid generator" (PAG) refers to a compound which generates an acid in response to actinic ray or radiation.

Where the base polymer used in the chemically amplified resist composition comprises acid labile group-containing units composed of tertiary ester, the sulfonic acid generated by the onium salt should preferably be of α-fluorinated structure, that is, of formula (1) wherein m=1, $R^{f1}$ and/or $R^{f2}$ is fluorine, and n=0 or 1, in order to acquire an appropriate acidity for sensitivity enhancement.

Among others, the sulfonate anion capable of generating α-fluorinated sulfonic acid is preferably an anion having the following formula (1a).

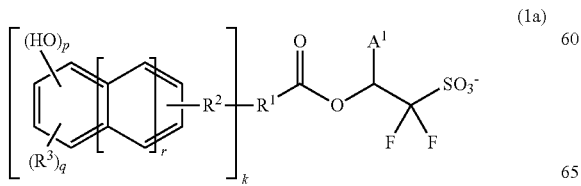

(1a)

Herein $R^1$, $R^2$, $R^3$, p, q, r and k are as defined above, and $A^1$ is hydrogen or trifluoromethyl.

Examples of the sulfonate anion in the onium salt are shown below, but not limited thereto. Herein $A^1$ is as defined above.

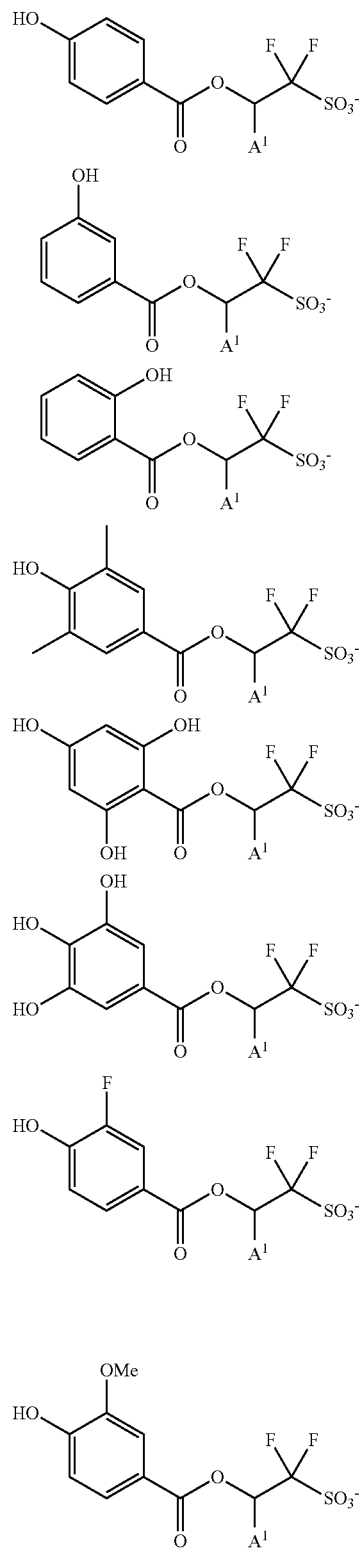

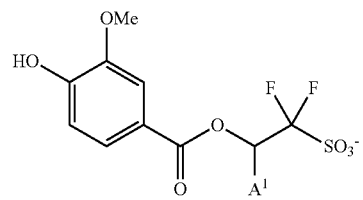

-continued
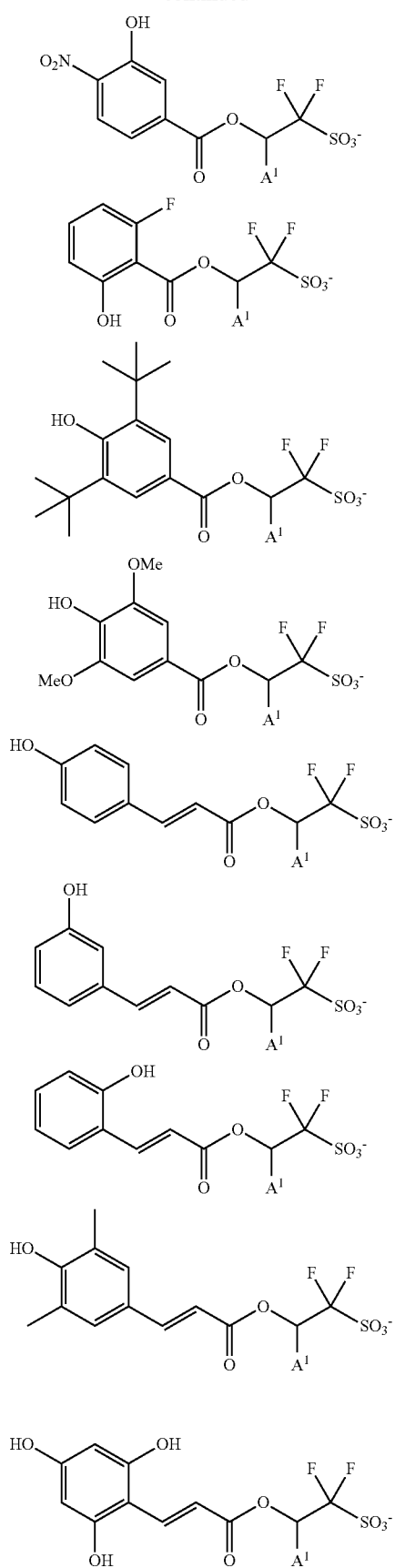
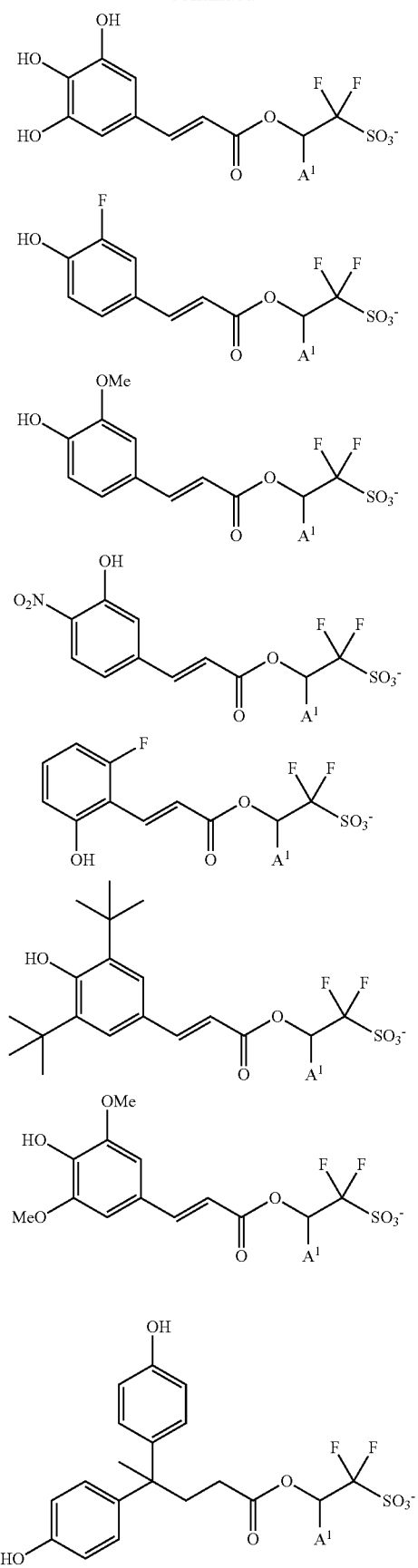

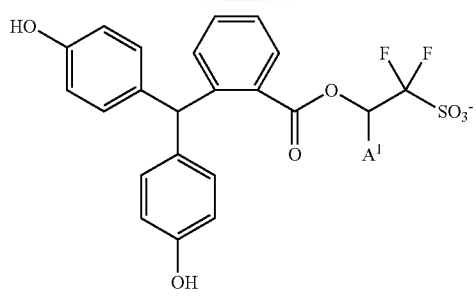
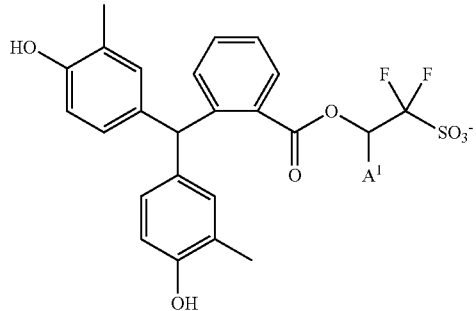
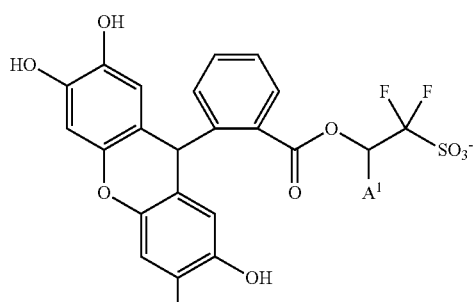
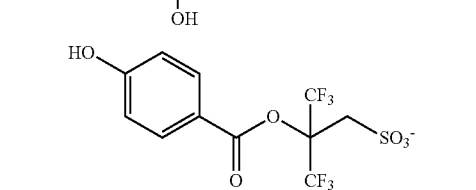
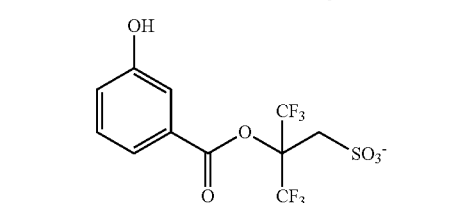
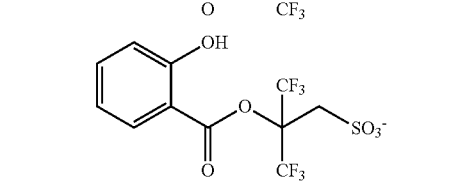
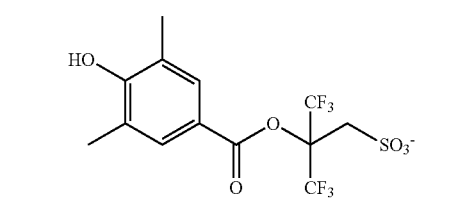
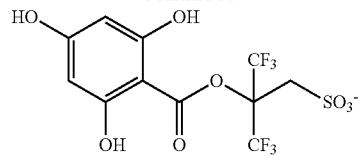
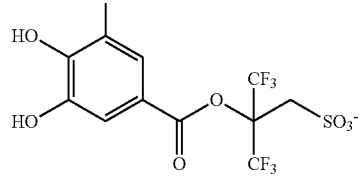
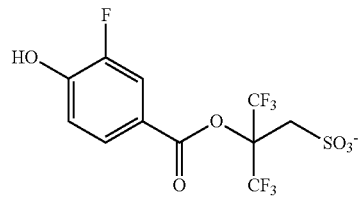
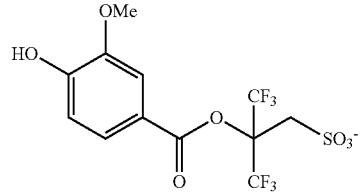
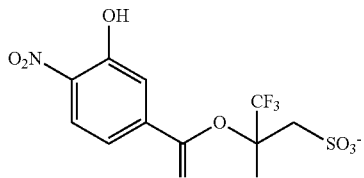
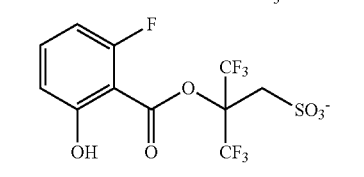
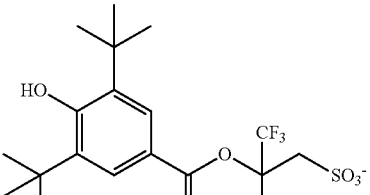
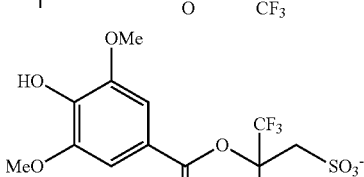
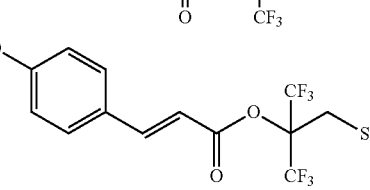

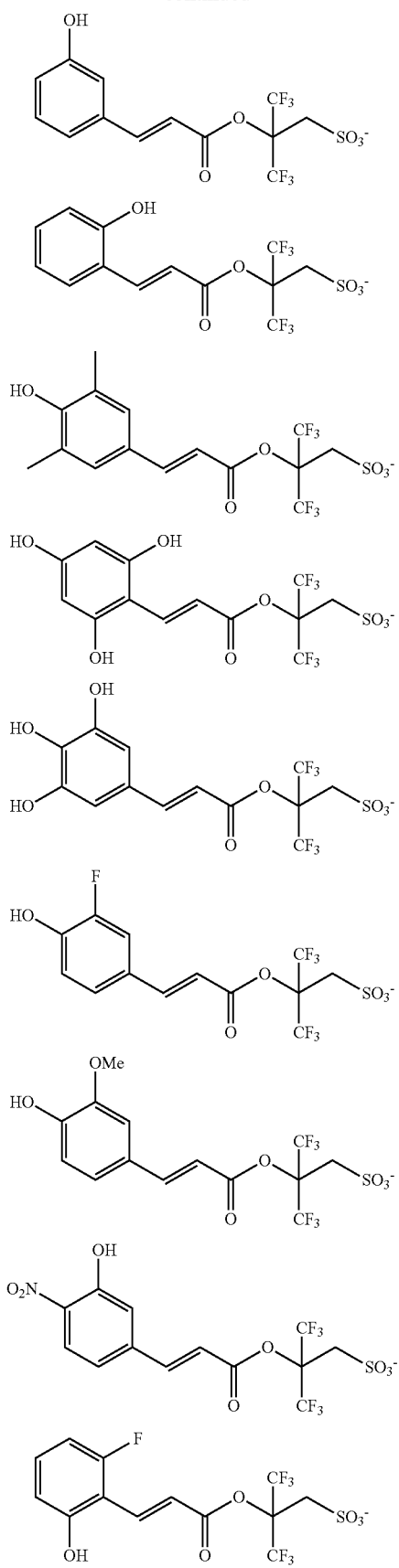
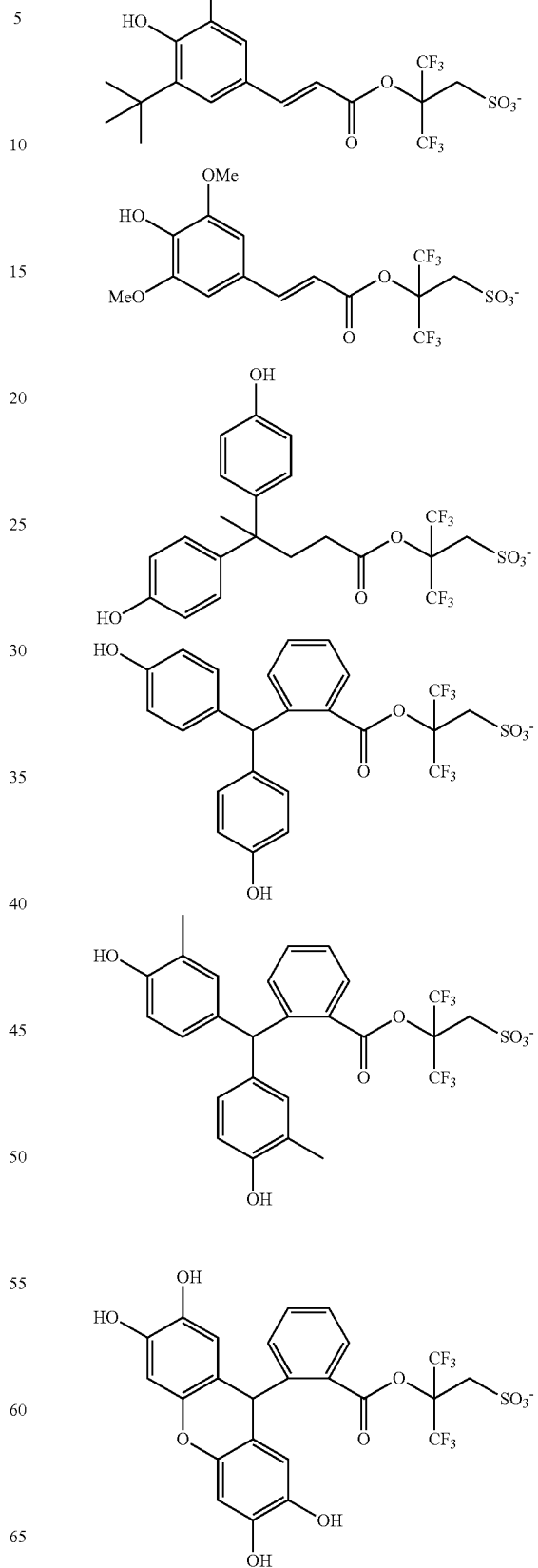

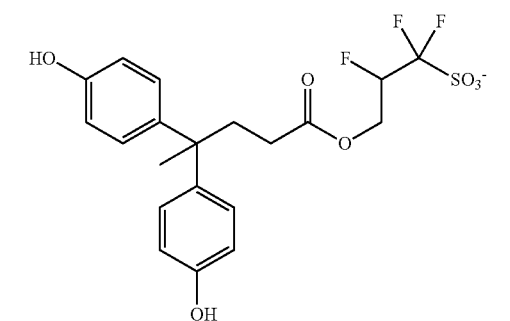
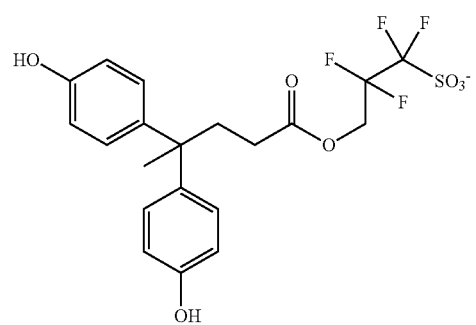
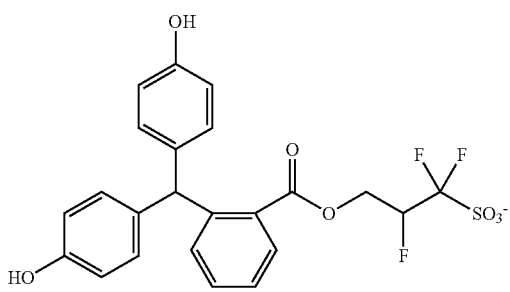
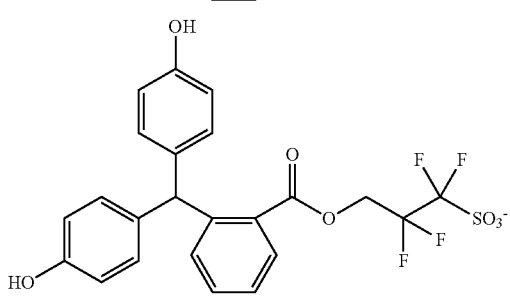
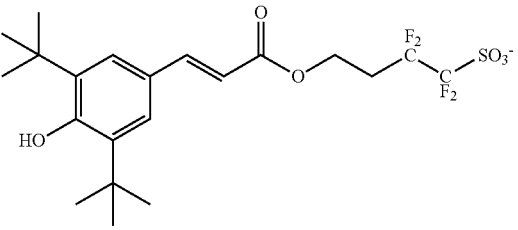
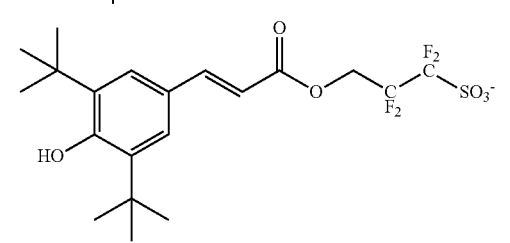
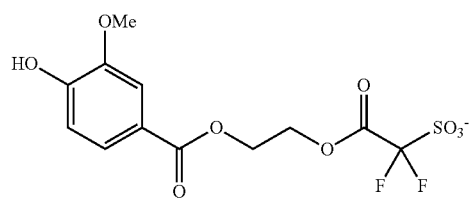
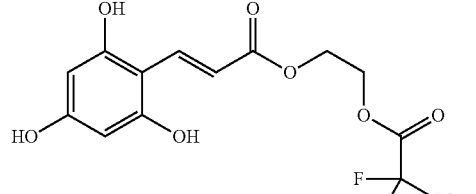
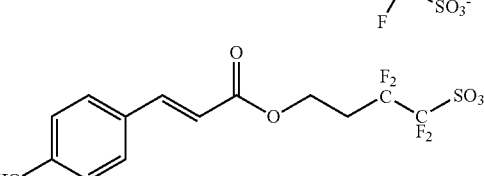
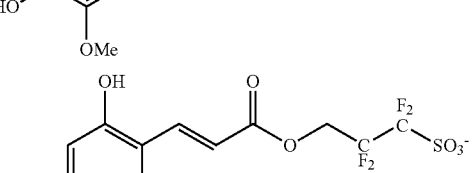
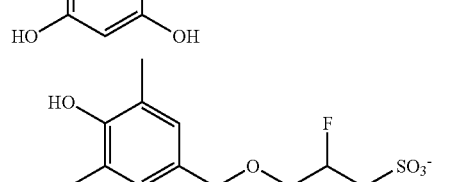
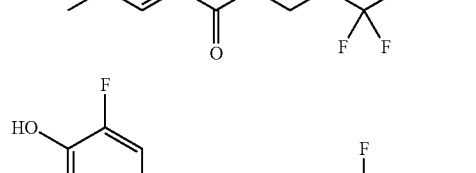
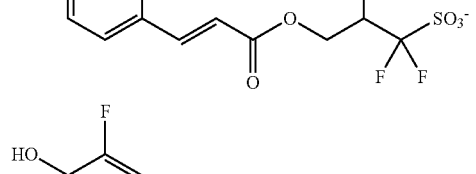
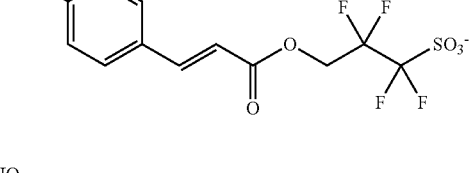
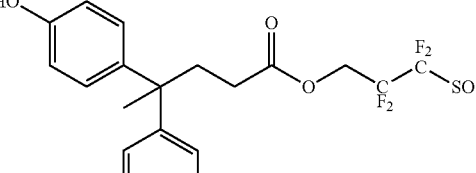
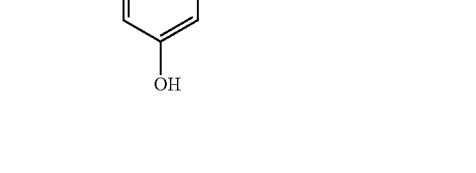

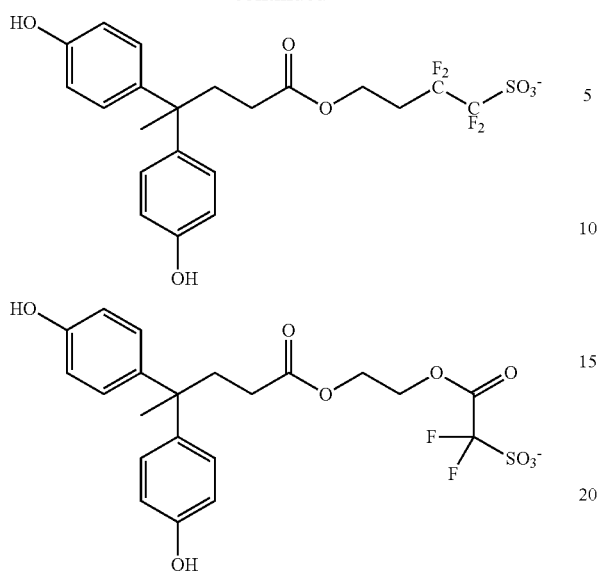

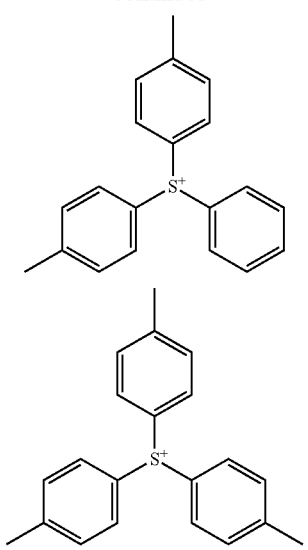

In formula (1), M⁺ is a sulfonium cation having the formula (1A) or an iodonium cation having the formula (1B).

In formulae (1A) and (1B), $R^{11}$ to $R^{15}$ are each independently a $C_1$-$C_{20}$ monovalent hydrocarbon group which may contain a heteroatom, any two of $R^{11}$, $R^{12}$ and $R^{13}$ may bond together to form a ring with the sulfur atom to which they are attached.

Examples of the sulfonium cation having formula (1A) are shown below, but not limited thereto.

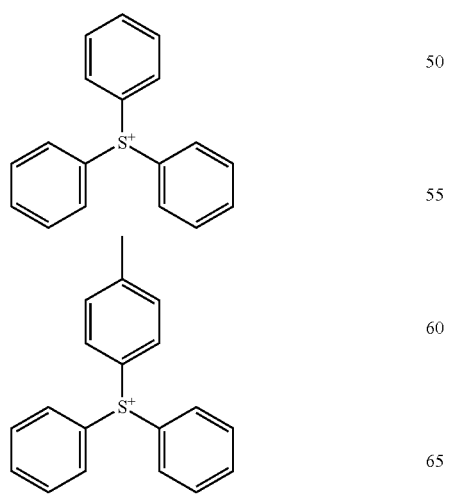

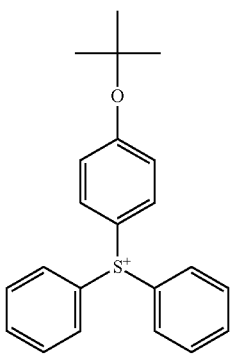

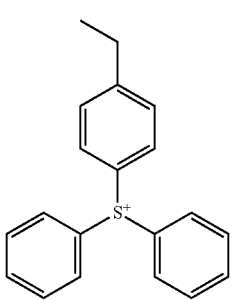

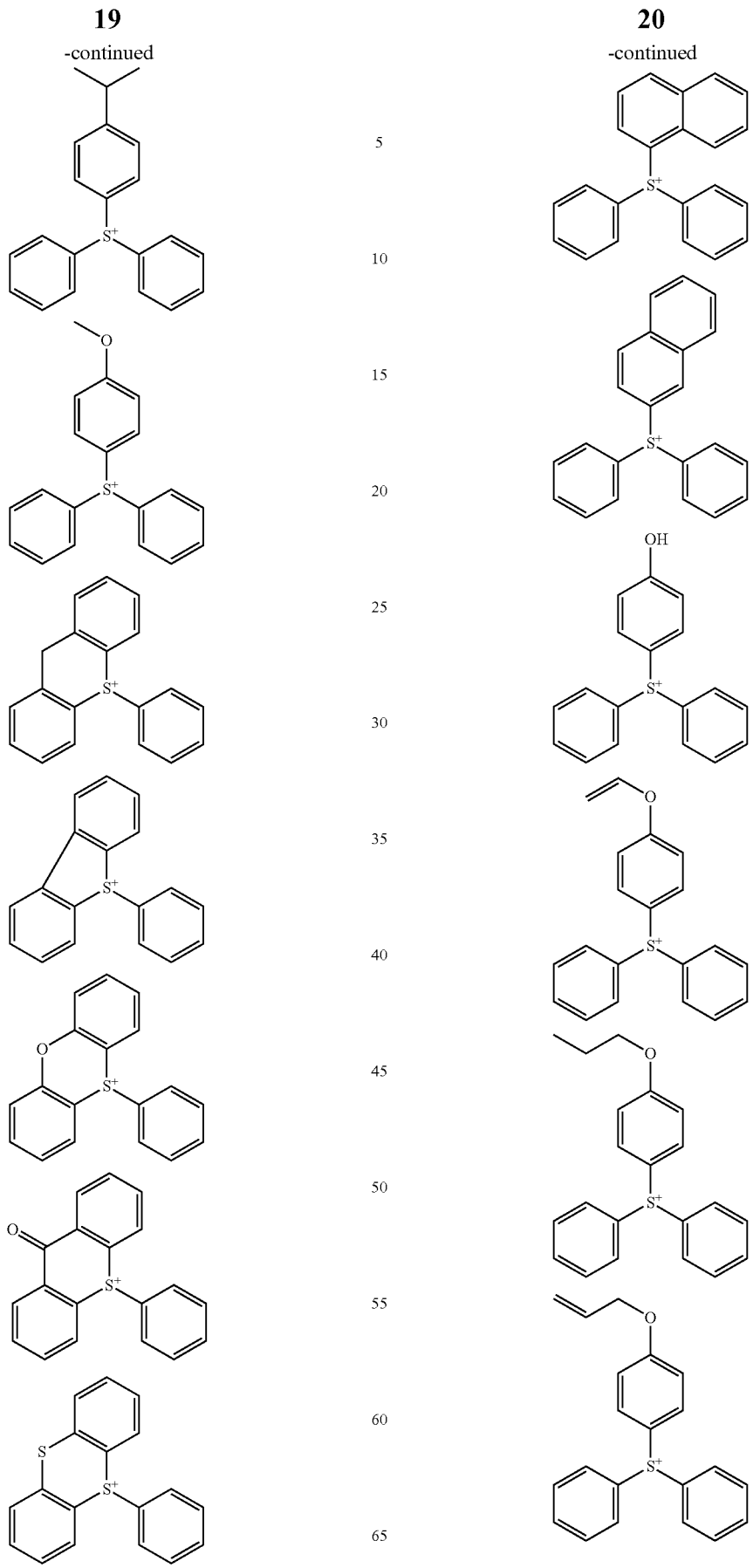

-continued
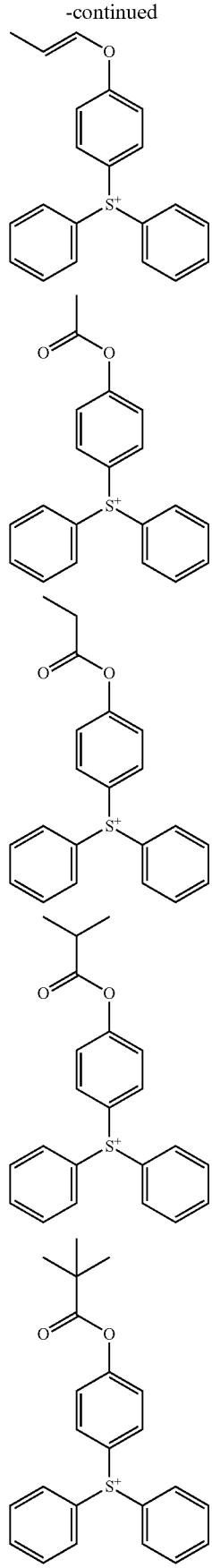
-continued
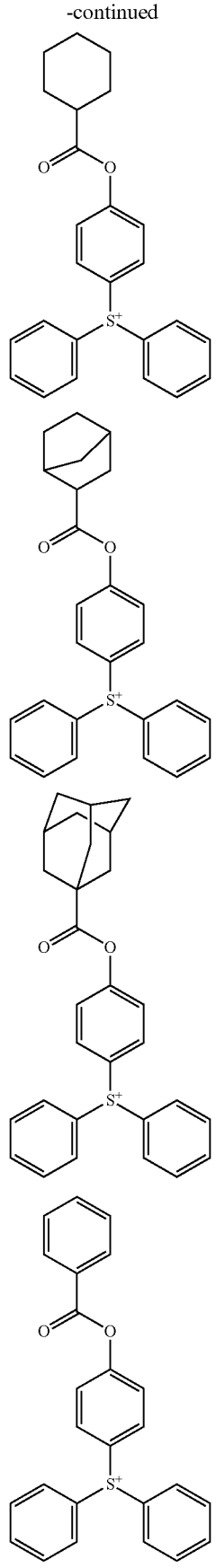

23
-continued
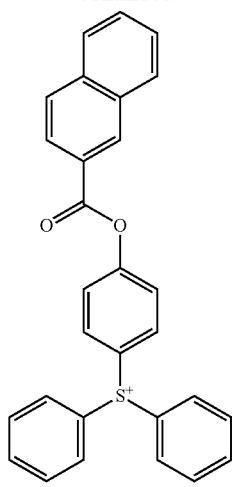
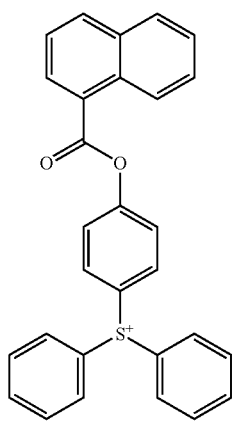
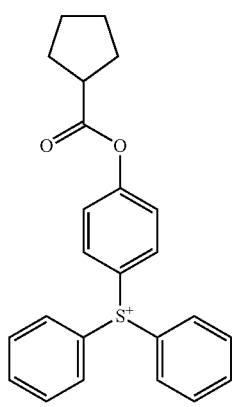
24
-continued
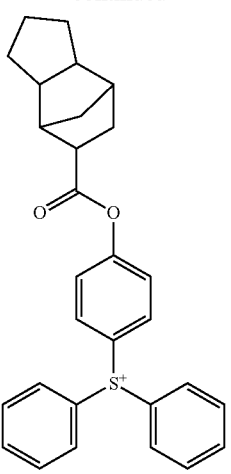
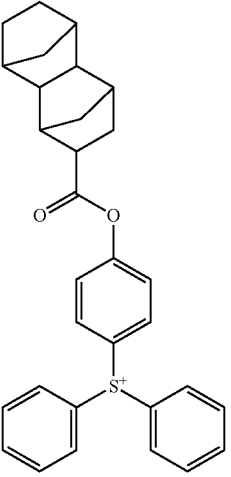

25
-continued
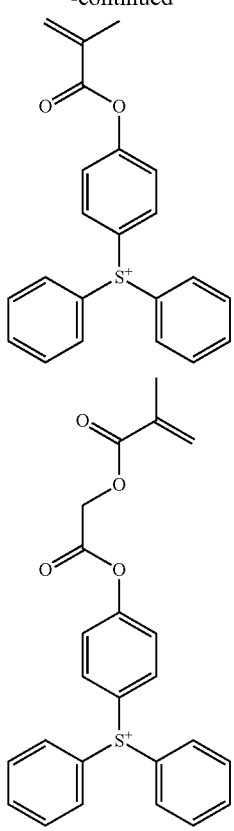
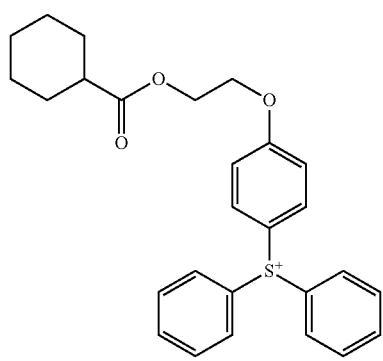
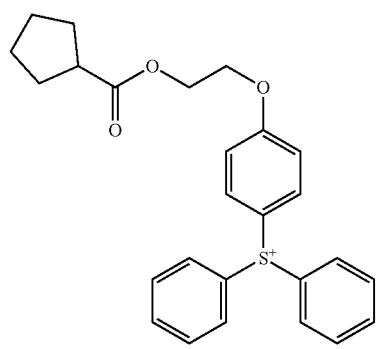
26
-continued
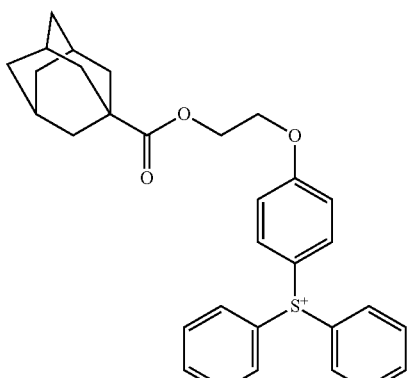
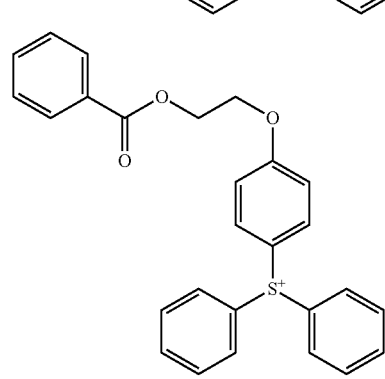
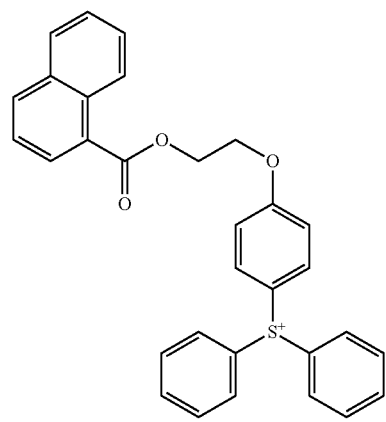
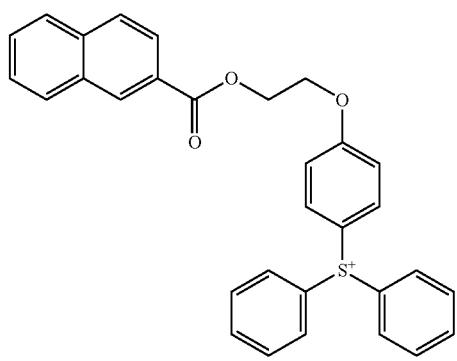

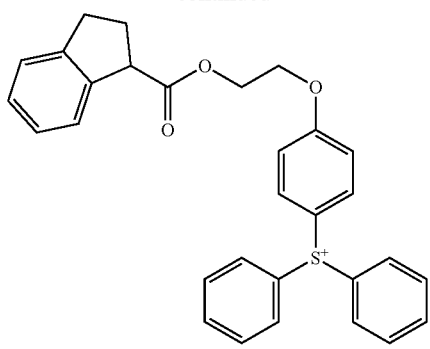
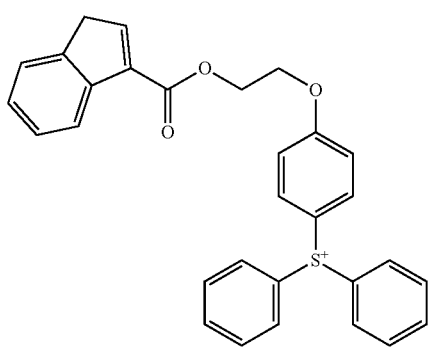
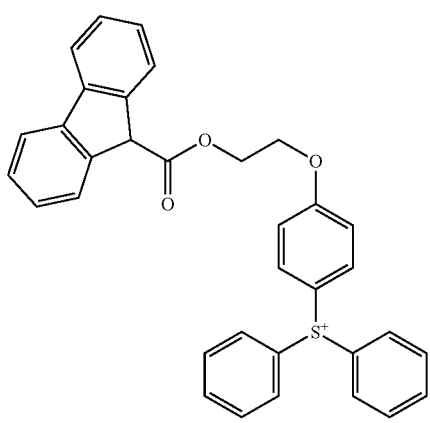
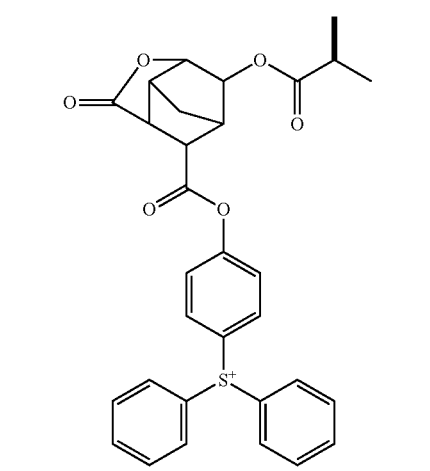
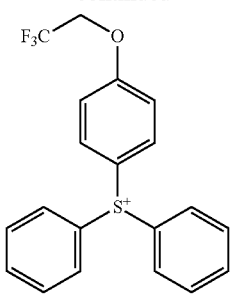
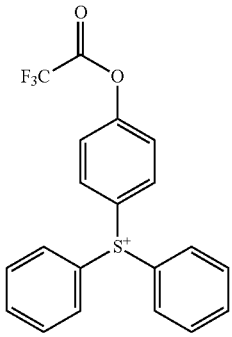
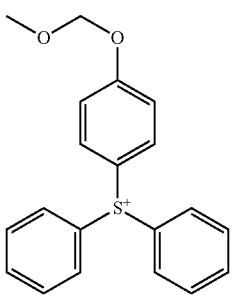
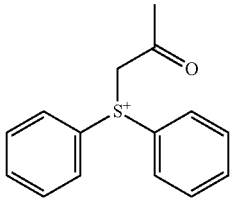
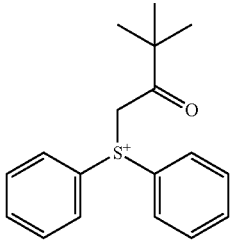
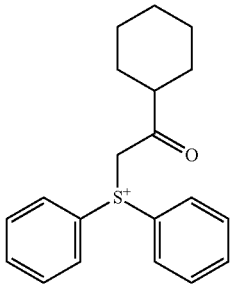

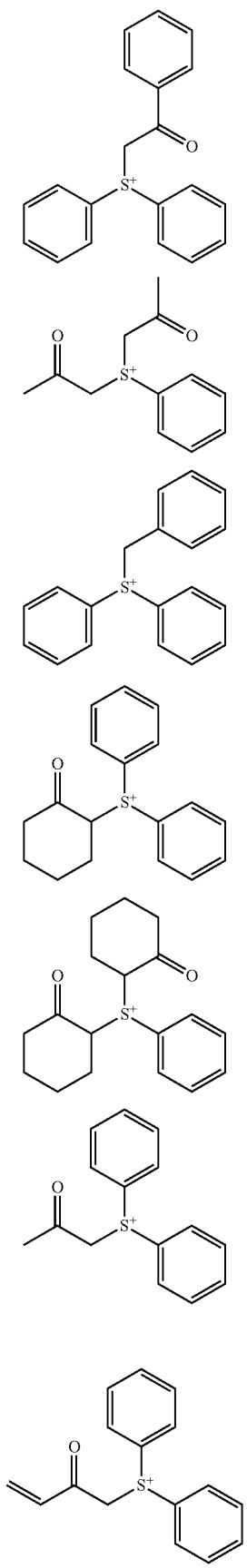
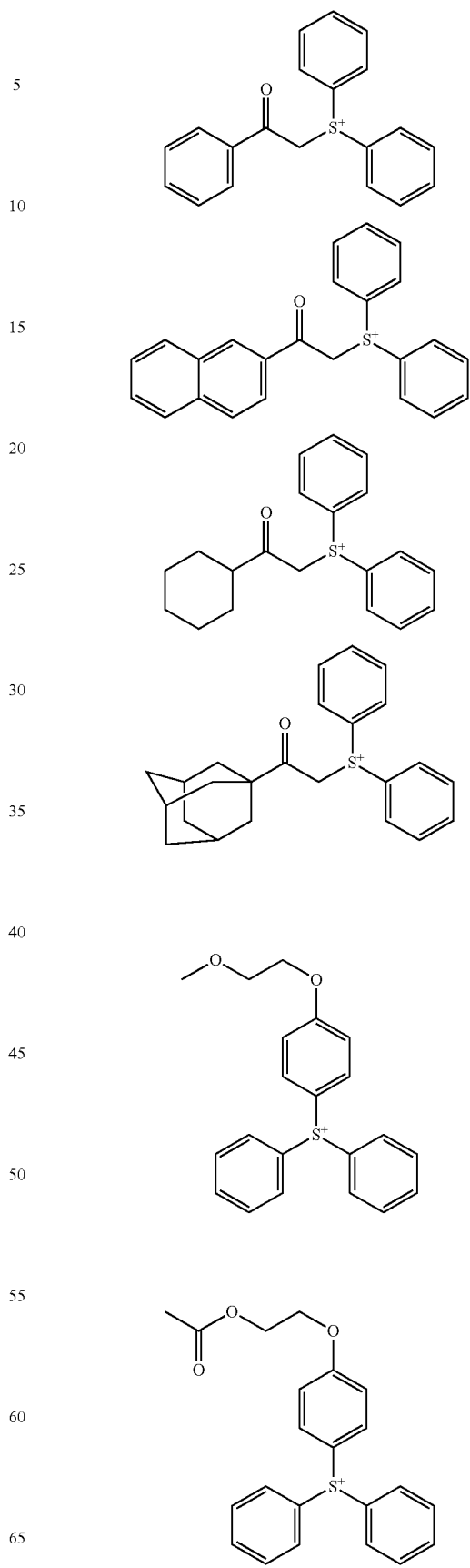

-continued
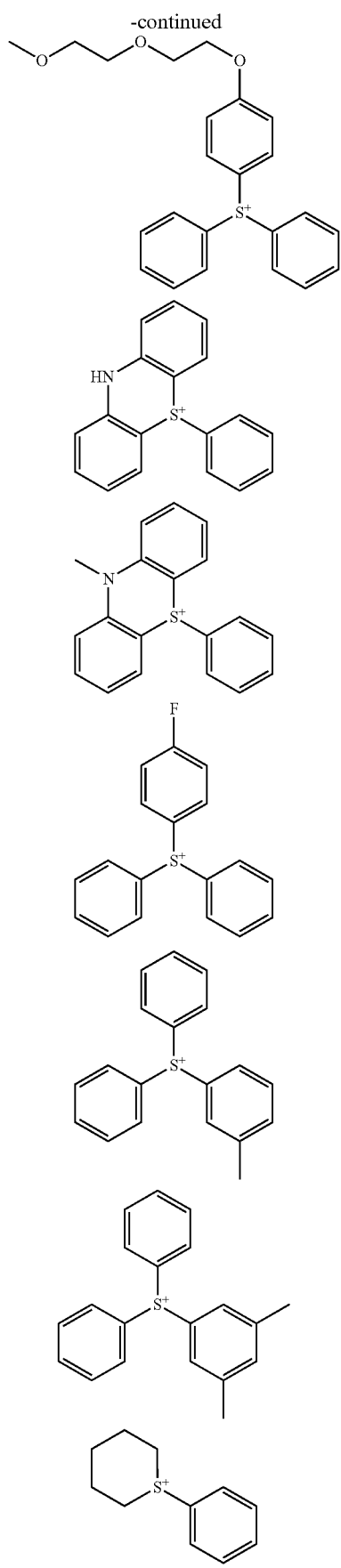
-continued
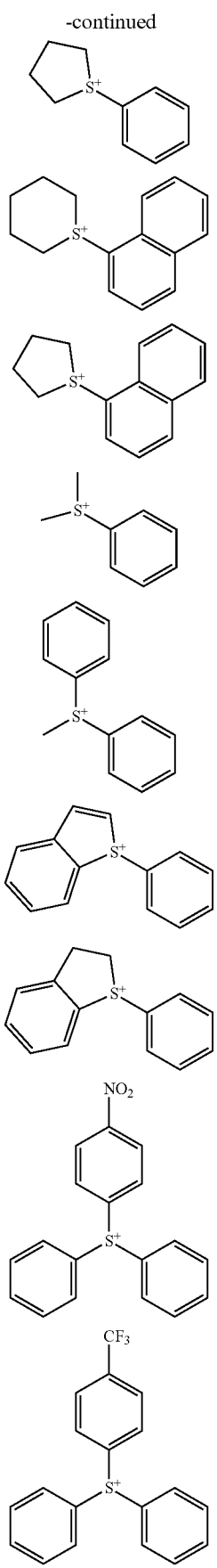

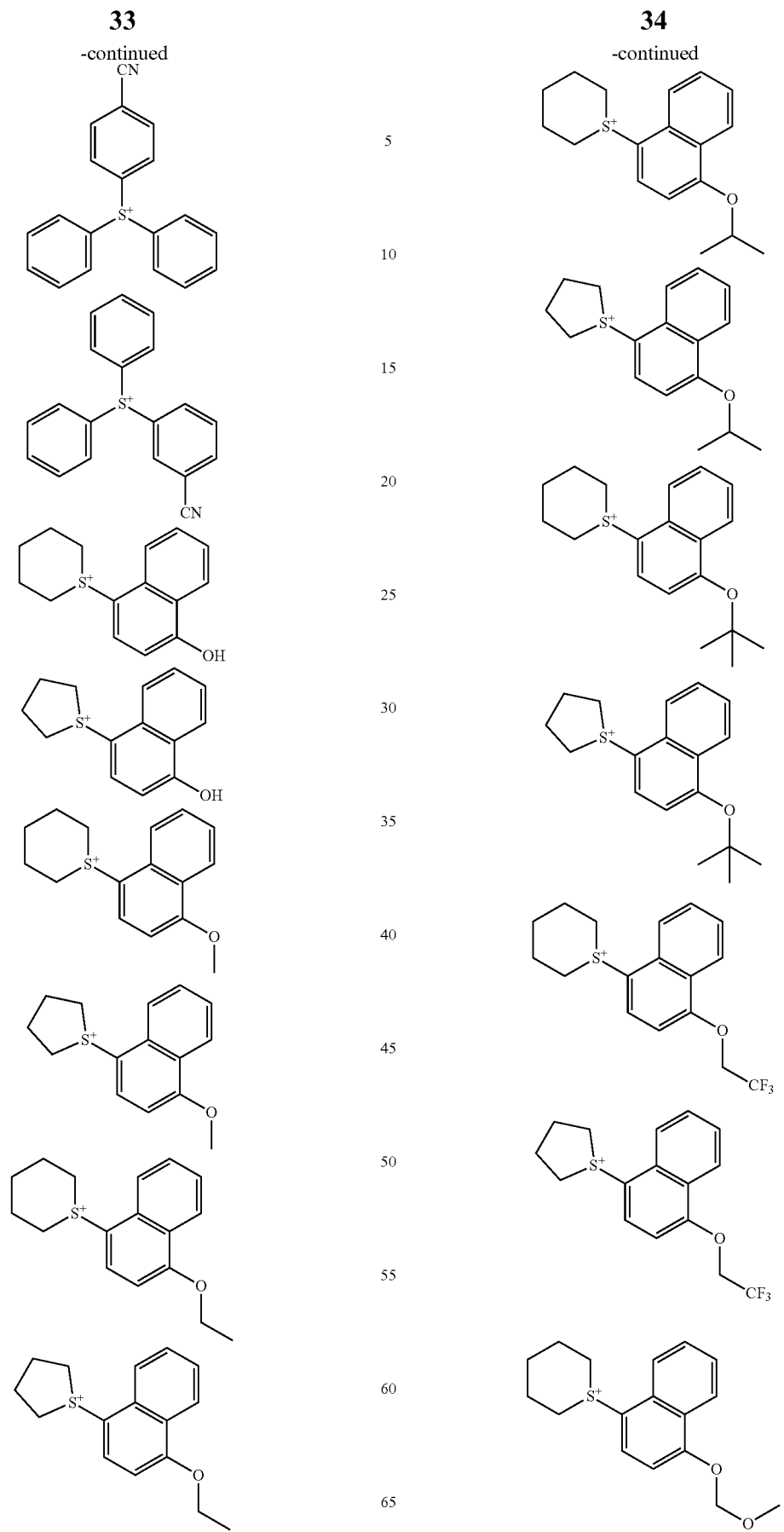

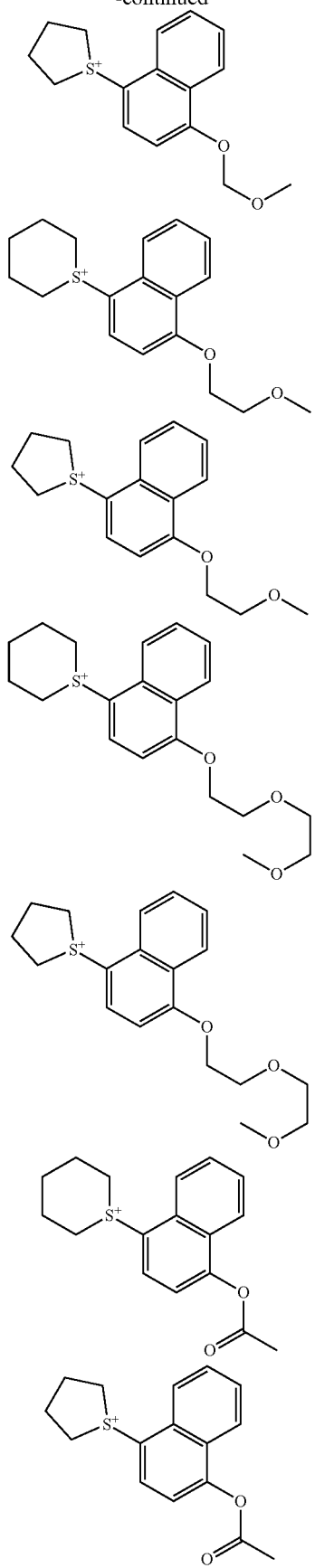

37
-continued
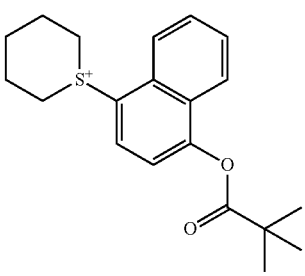
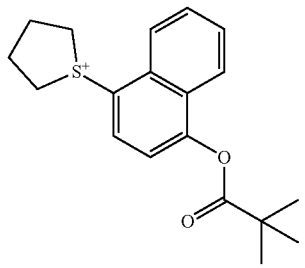
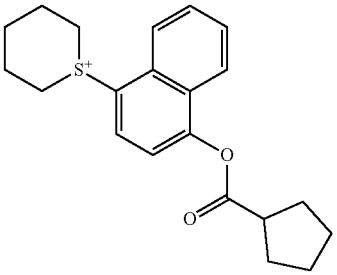
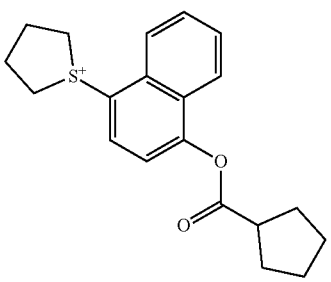
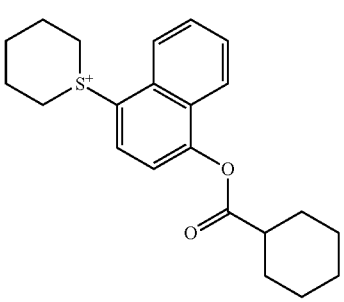
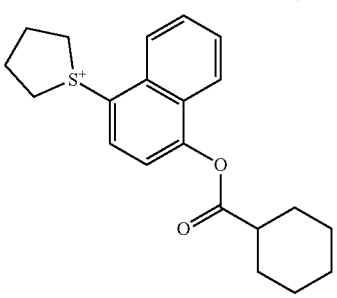
38
-continued
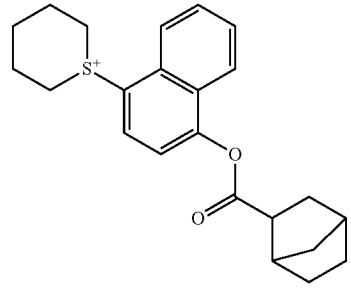
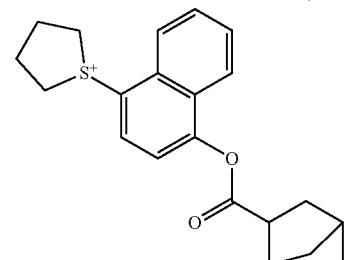
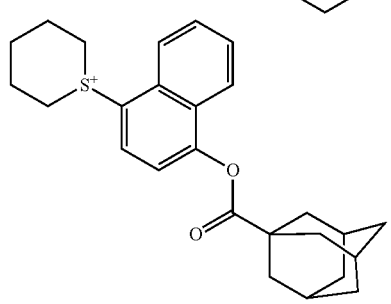
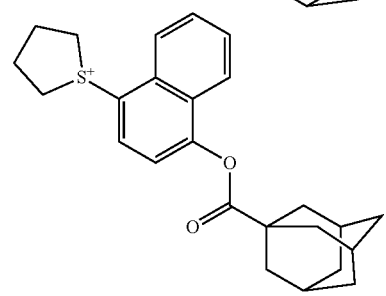
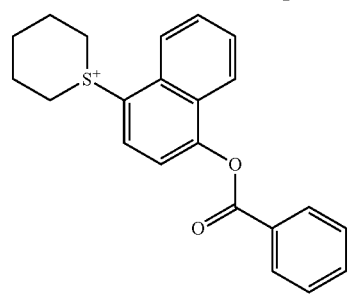
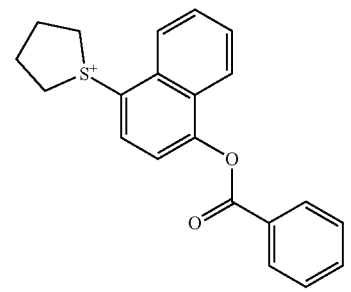

39
-continued
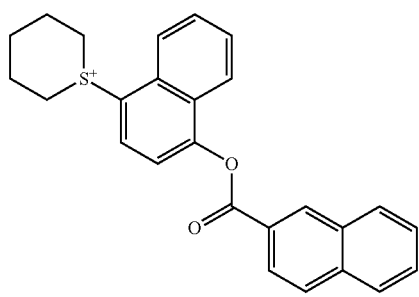
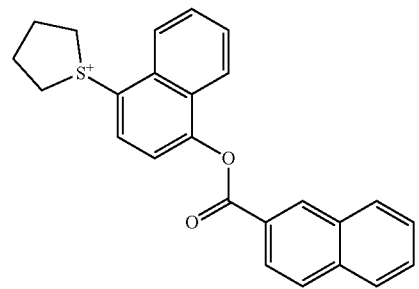
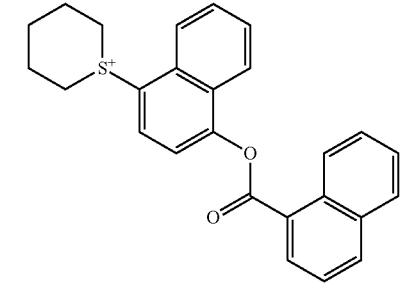
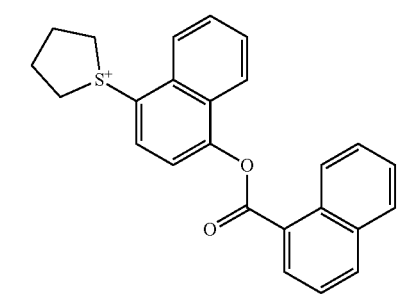
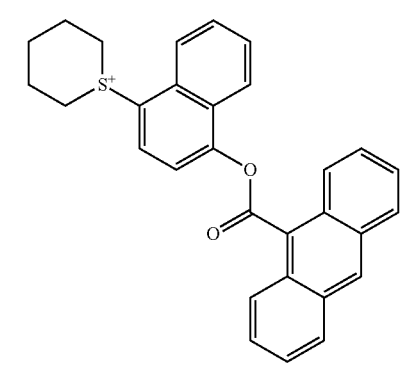
40
-continued
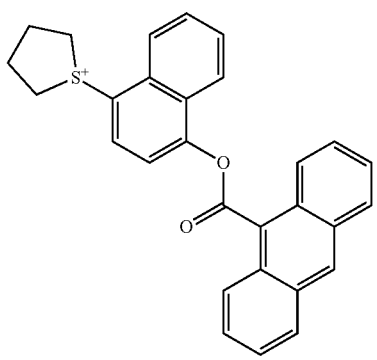
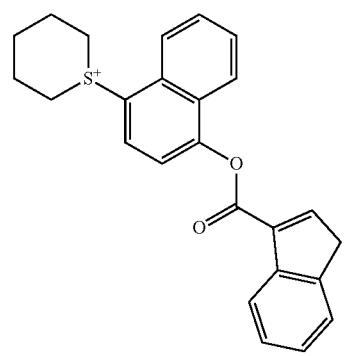
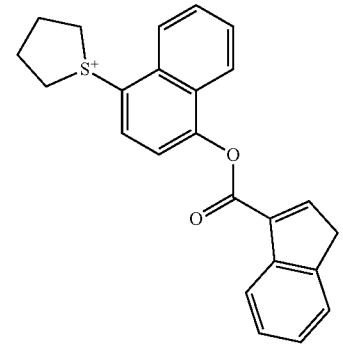
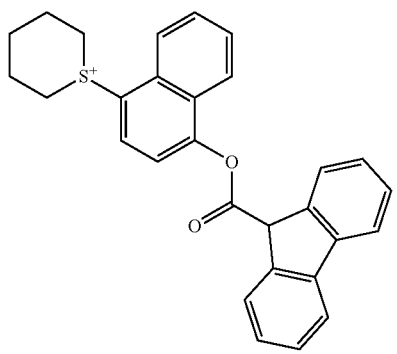

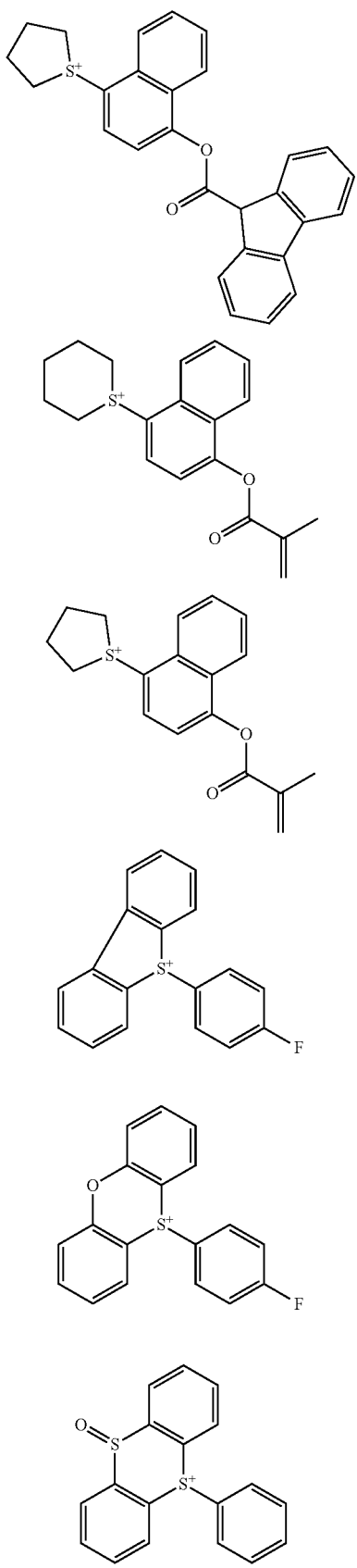
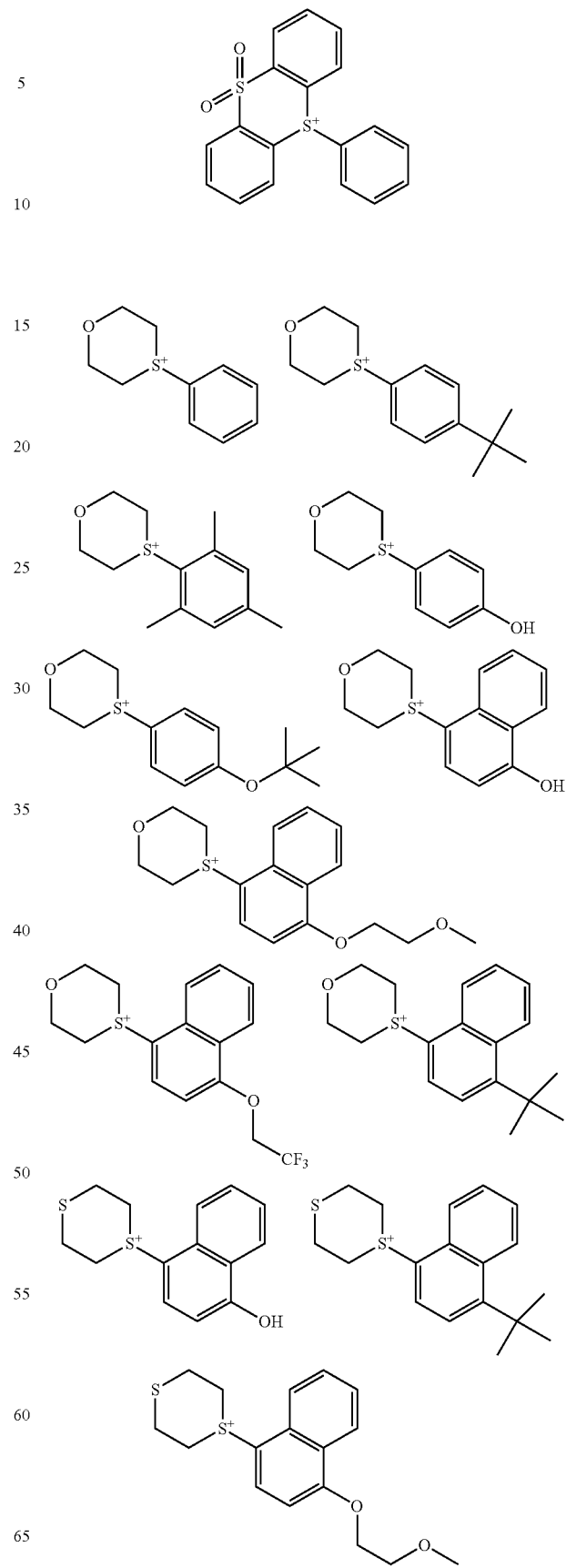

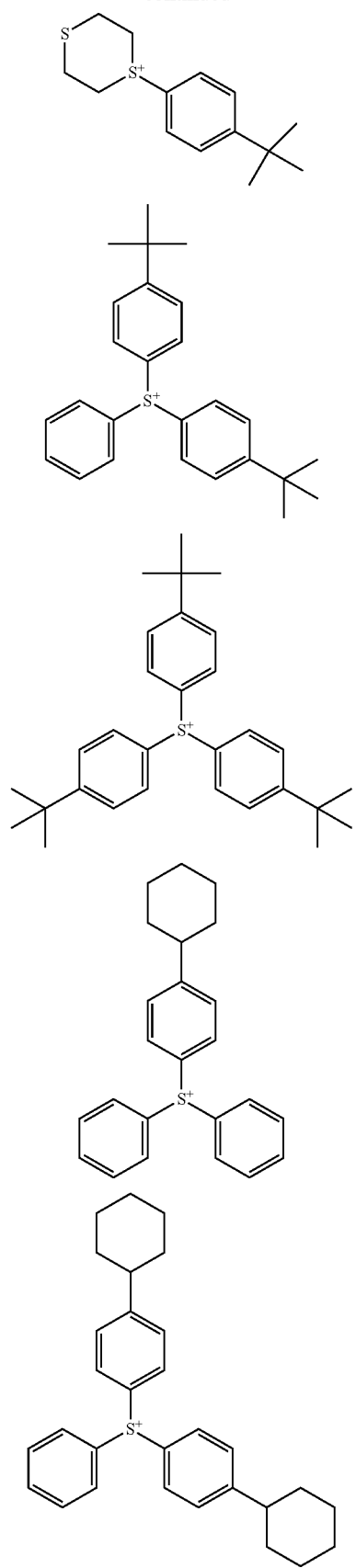
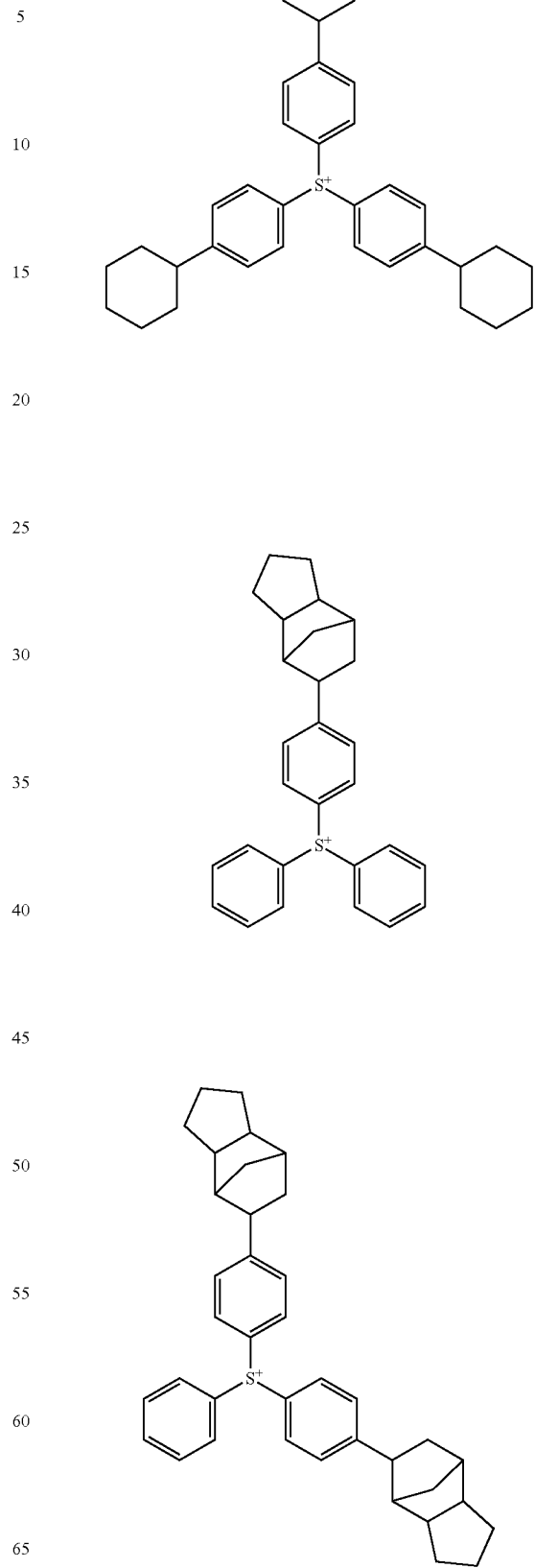

45
-continued
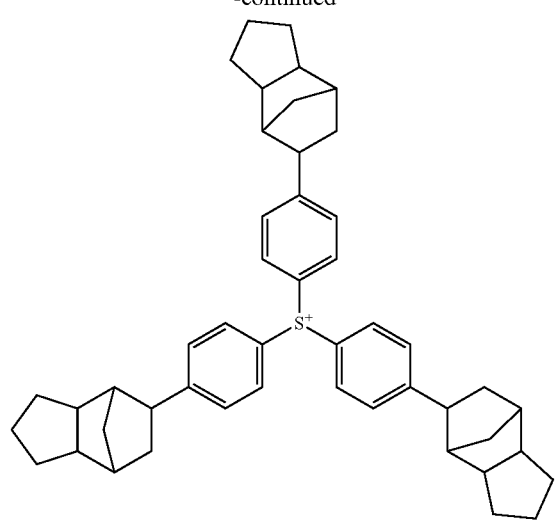
46
-continued
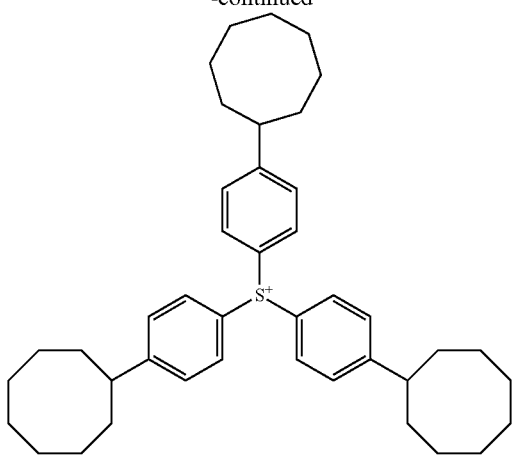
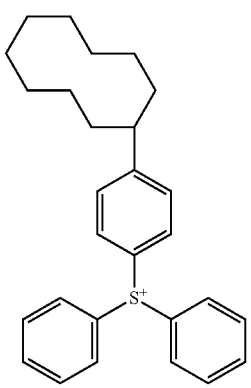
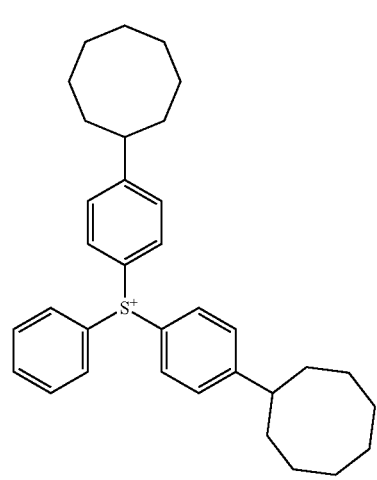
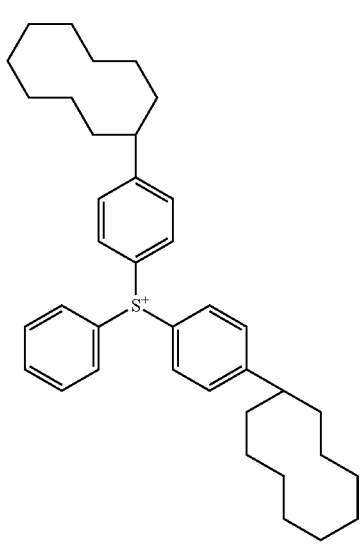

47
-continued
48
-continued
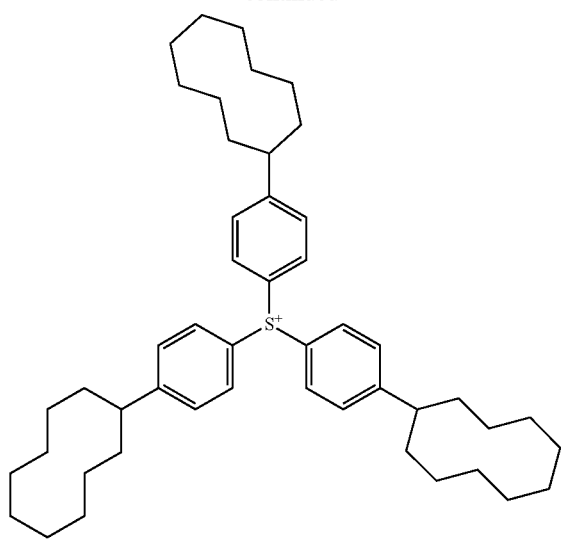
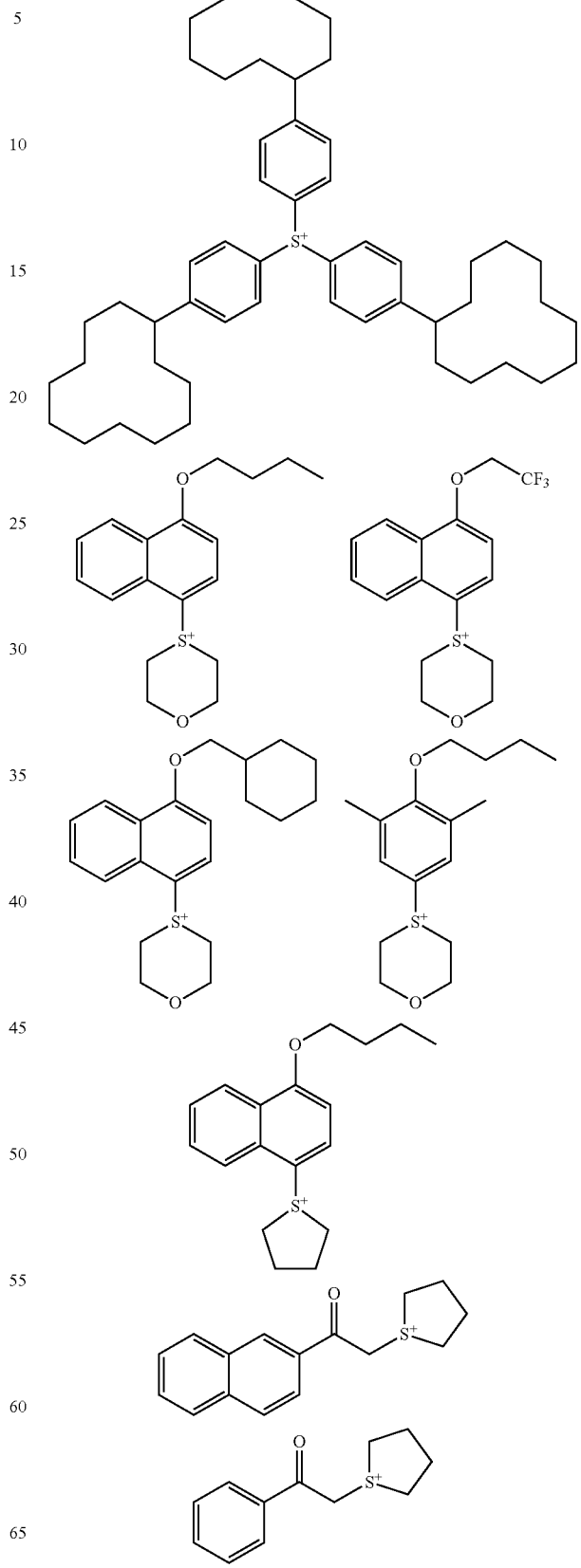

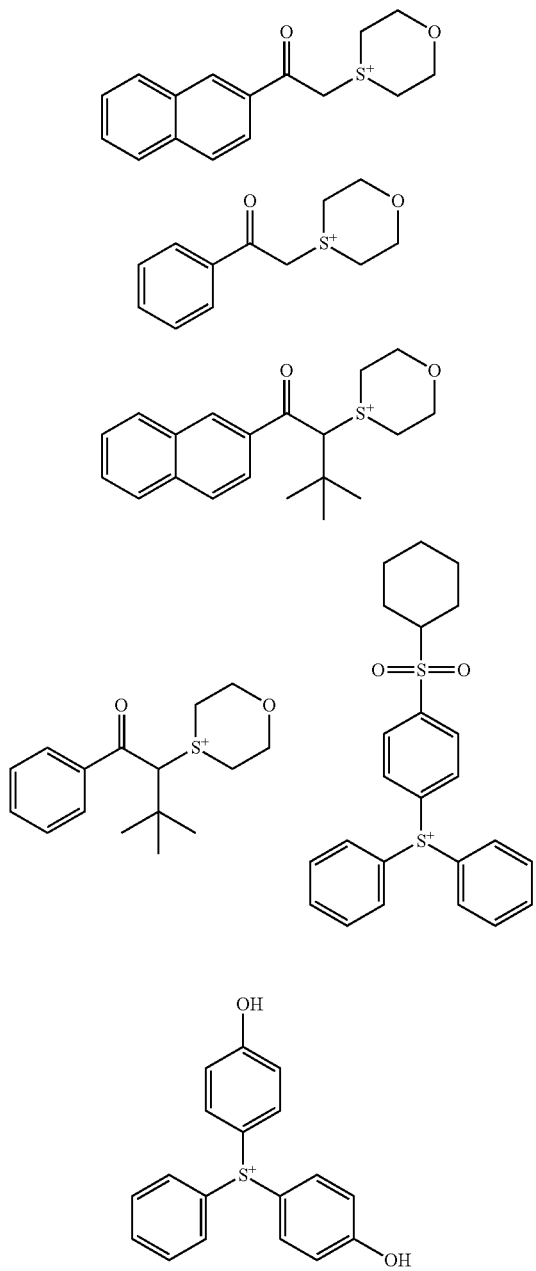
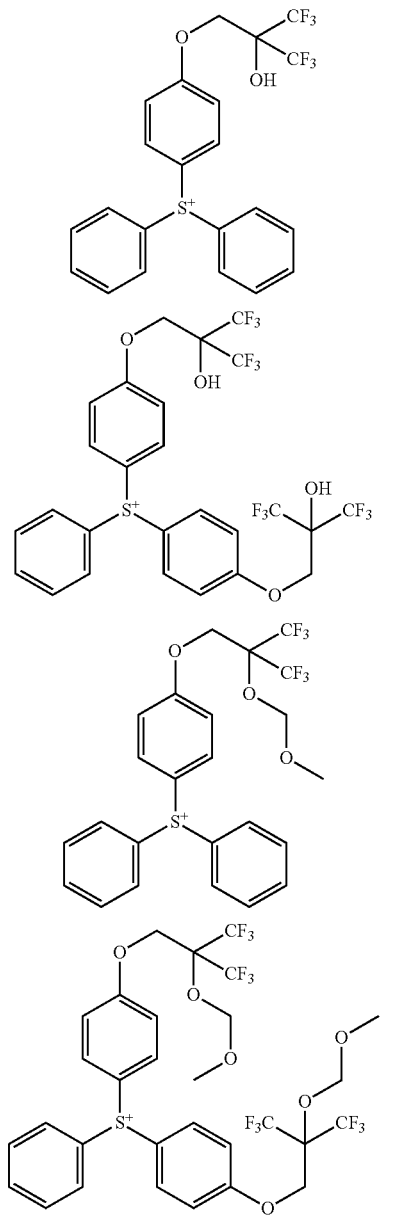
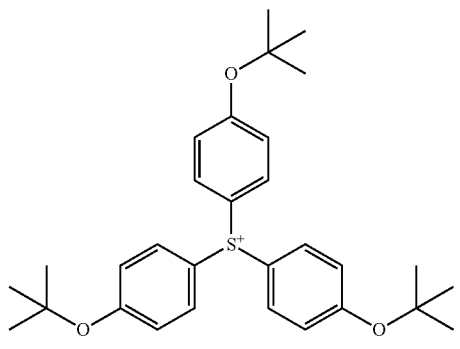
Examples of the iodonium cation having formula (1B) are shown below, but not limited thereto.
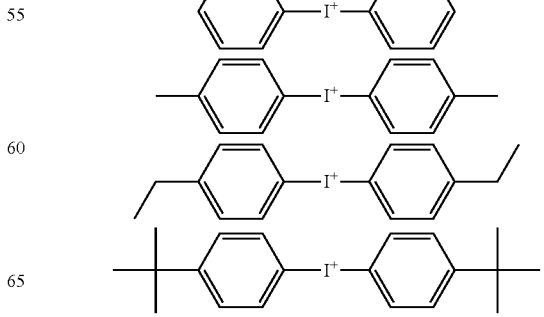

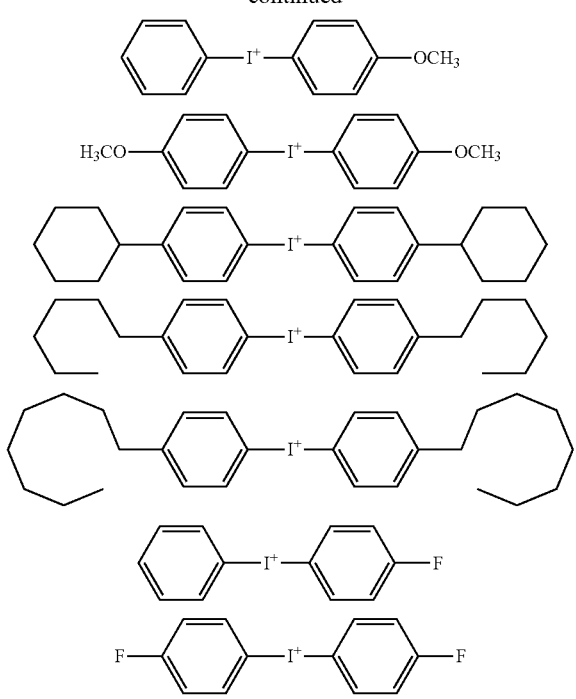

The method of preparing the inventive onium salt is described below with reference to a sulfonate anion having formula (1a) although the method is not limited thereto.

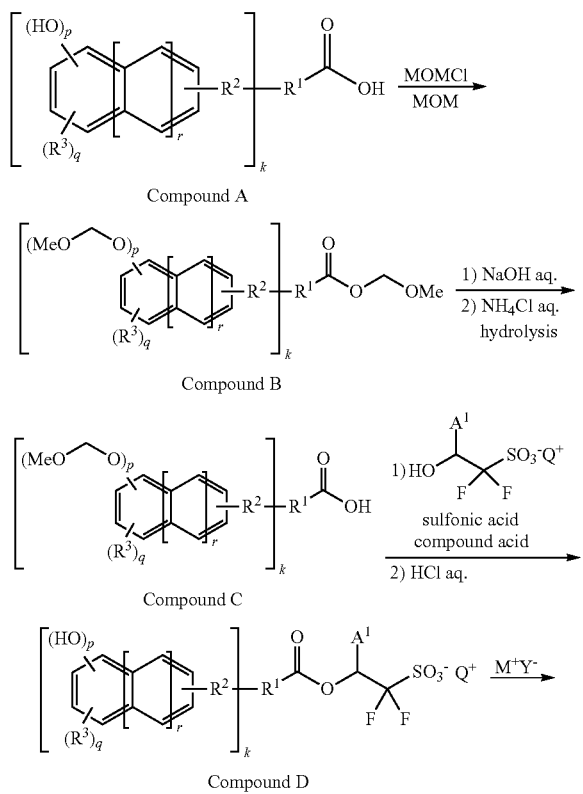

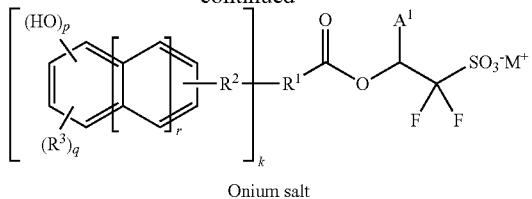

Onium salt

Herein, $R^1$, $R^2$, $R^3$, $A^1$, $M^+$, p, q, r, and k are as defined above, $Q^+$ is a counter cation, and $Y^-$ is a counter anion.

A first step starts with a carboxylic acid having a phenolic hydroxyl group (referred to as Compound A, hereinafter), and performs methoxymethylation (abbreviated as MOM, hereinafter) of all phenolic hydroxyl groups and carboxyl group for protection. The reaction may be performed under standard conditions. Preferably, methoxymethylation (MOM) is performed using reagents, for example, methoxymethyl chloride (MOMCl) and an organic base (typically an amine). As the organic base, N,N-diisopropylethylamine (DIPEA) is preferably used as well known in the standard method. The reaction may be performed in a solventless system or in a solvent (e.g., methylene chloride, acetonitrile, diethyl ether, tetrahydrofuran, N,N-dimethylformamide, toluene, or hexane) by sequentially or to simultaneously adding Compound A, MOMCl, and DIPEA and optionally cooling or heating the reaction system. The amount of MOMCl used, which varies with other reaction conditions, is preferably 1 to 5 moles, more preferably 1 to 2 moles per mole of phenolic hydroxyl group or carboxyl group on the reactant, Compound A. The amount of the base used, which varies with other reaction conditions, is preferably 1 to 5 moles, more preferably 1 to 2 moles per mole of MOMCl. It is desirable from the standpoint of yield that the reaction time is determined so as to drive the reaction to completion by monitoring the reaction process by gas chromatography (GC) or silica gel thin layer chromatography (TLC). Usually, the reaction time is about 0.5 to 24 hours. From the reaction mixture, the compound having all phenolic hydroxyl groups and carboxyl group protected with MOM (referred to as Compound B, hereinafter) is recovered through an ordinary aqueous workup. If necessary, the compound may be purified by a standard technique such as distillation, chromatography or recrystallization. It is sometimes acceptable that the aqueous workup is omitted and the reaction solution is purified directly or simply after the salt resulting from reaction is filtered off.

A second step is hydrolysis of the MOM-protected carboxyl group on Compound B with a strong base, for deprotection to resume the carboxyl group. The reaction may be performed in a solventless system or in a solvent (e.g., methanol, ethanol, tetrahydrofuran, acetonitrile, or N,N-dimethylformamide) by sequentially or simultaneously adding Compound B and an aqueous alkaline solution (e.g., 1 mol/L sodium hydroxide or potassium hydroxide) and optionally cooling or heating the reaction system. The amount of alkali used is preferably 1 to 10 moles, more preferably 1 to 5 moles per mole of MOM-protected carboxyl group. It is desirable from the standpoint of yield that the reaction time is determined so as to drive the reaction to completion by monitoring the reaction process by GC or TLC. Usually, the reaction time is about 0.5 to 24 hours. The hydrolysis reaction is stopped preferably by neutralizing with weakly acidic aqueous solution of ammonium chloride although the stopping means is not limited thereto. From the reaction mixture, the MOM ether carboxylic acid compound (referred to as Compound C, hereinafter) is recovered through an ordinary aqueous workup. If necessary, the compound may be purified by a standard technique such as distillation, chromatography or recrystallization. It is sometimes acceptable that the aqueous workup is omitted and the reaction solution is purified directly or simply after the salt resulting from reaction is filtered off.

In a third step, 1) esterifying reaction or condensation of Compound C resulting from the 2nd step with alcohol form of sulfonic acid compound A and 2) deprotection reaction of MOM group by acid treatment are continuously carried out to produce a sulfonic acid salt (referred to as Compound D, hereinafter). The reactions may be performed under standard conditions. For example, condensation reaction is performed using a variety of condensing agents. Suitable condensing agents include N,N'-dicyclohexylcarbodiimide, N,N'-diisopropylcarbodiimide, 1-[3-(dimethylamino)propyl]-3-ethylcarbodiimide, and 1-ethyl-3-(3-dimethylaminopropyl)carbodiimide hydrochloride. Inter alia, 1-ethyl-3-(3-dimethylaminopropyl)carbodiimide hydrochloride is preferably used in view of ease of removal of a urea compound formed as reaction by-product. The reaction may be performed in a halogen base solvent (e.g., methylene chloride) by sequentially or simultaneously adding the carboxylic acid, alcohol form of alkanesulfonic acid, and condensing agent, and optionally cooling or heating the reaction system. The reaction rate may be accelerated by adding 4-dimethylaminopyridine as a catalyst for the reaction. It is desirable from the standpoint of yield that the reaction time is determined so as to drive the reaction to completion by monitoring the reaction process by TLC or the like. Usually, the reaction time is about 12 to 24 hours. After the reaction is stopped, Compound D is recovered from the reaction mixture through an ordinary aqueous workup. If necessary, Compound D may be purified by a standard technique such as chromatography or recrystallization. It is noted that in the synthesis scheme, the counter cation represented by $Q^+$ is preferably an ammonium cation, for example, benzyltrimethylammonium, benzyltriethylammonium, tetrabutylammonium, triethylammonium, tributylammonium, trioctylammonium, pyridinium, lutidinium, 4-dimethylaminopyridinium, and anilinium.

A fourth step is a salt exchange of Compound D resulting from the 3rd step with a sulfonium or iodonium salt to yield the desired onium salt. It is noted that in the synthesis scheme, the counter anion represented by $Y^-$ is preferably a chloride, bromide or methylsulfate ion because the exchange reaction takes place in a quantitative manner. The salt exchange reaction may be performed by any well-known methods, for example, according to the teaching of JP-A 2007-145797. It is desirable from the standpoint of yield to monitor the reaction process by TLC or high performance liquid chromatography (HPLC). From the reaction mixture, the onium salt is recovered through an ordinary aqueous workup. If necessary, the compound may be purified by a standard technique such as chromatography or recrystallization.

Resist Composition

Another embodiment of the invention is a chemically amplified resist composition comprising
(A) a photoacid generator in the form of the onium salt having formula (1), optionally
(B) a base polymer,
(C) an organic solvent, and further optionally,
(D) a quencher, and
(E) a photoacid generator other than the onium salt having formula (1).

In the resist composition, the PAG (A) is preferably used in an amount of 0.1 to 40 parts, more preferably 1 to 30 parts by weight per 80 parts by weight of the base polymer (B). Within the range, the PAG exerts its function to the full extent without causing any performance degradations like formation of foreign particles due to shortage of sensitivity or solubility. The onium salt having formula (1) may be used alone or in admixture of two or more as the PAG (A).

(B) Base Polymer

Component (B) is a base polymer comprising recurring units adapted for polarity switch under the action of acid, of at least one type selected from recurring units having the formulae (A1) and (A2), and recurring units of at least one type selected from recurring units having the formulae (B) to (E). Notably, the recurring units having formulae (A1) and (A2) are simply referred to as recurring units (A1) and (A2), and the recurring units having formulae (B) to (E) are simply referred to as recurring units (B) to (E), respectively.

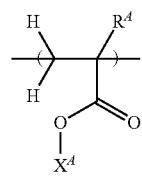

(A1)

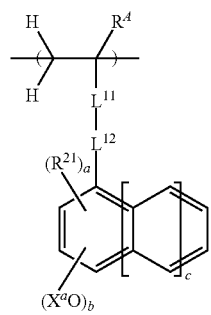

(A2)

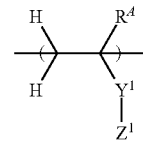

(B)

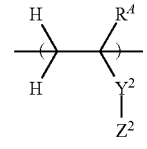

(C)

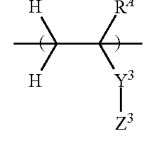

(D)

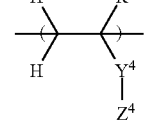

(E)

In formulae (A1), (A2), (B) to (E), $R^4$ is hydrogen, fluorine, methyl or trifluoromethyl. $R^{21}$ is each independently hydrogen or a $C_1$-$C_6$ alkyl group which may contain an ether bond or carbonyl moiety. $L^{11}$ is a single bond, carbonyloxy or amide group. $L^{12}$ is a single bond or a $C_1$-$C_7$ alkanediyl group which may contain an ether bond or carbonyl moiety. The subscript "a" is an integer satisfying a≤5+2c-b, b is an integer of 1 to 5, and c is an integer of 0 to 2. $X^4$ is an acid labile group. $Y^1$ to $Y^4$ are each to independently a single bond, methylene, ethylene, phenylene, fluorinated phenylene, naphthylene, —O—$Y^5$—, —C(=O)—O—$Y^5$— or —C(=O)—NH—$Y^5$—, wherein $Y^5$ is a $C_1$-$C_6$ alkanediyl, $C_2$-$C_6$ alkenediyl, phenylene, or naphthylene group, which may contain a carbonyl moiety, ester bond, ether bond or hydroxyl moiety. $Z^1$ is a $C_1$-$C_{20}$ fluoroalcohol-containing substituent group. $Z^2$ is a $C_1$-$C_{20}$ phenolic hydroxyl-containing substituent group. $Z^3$ is a $C_1$-$C_{20}$ carboxy-containing substituent group. $Z^4$ is a substituent group containing a lactone skeleton, sultone skeleton, carbonate skeleton, cyclic ether skeleton, acid anhydride skeleton, alcoholic hydroxyl moiety, alkoxycarbonyl moiety, sulfonamide moiety or carbamoyl moiety.

Non-limiting examples of the $C_1$-$C_6$ alkyl group optionally containing an ether bond or carbonyl moiety, represented by $R^{21}$, include methyl, ethyl, propyl, isopropyl, n-butyl, sec-butyl, tert-butyl, pentyl, hexyl, heptyl, octyl, cyclopentyl, and cyclohexyl as well as the following.

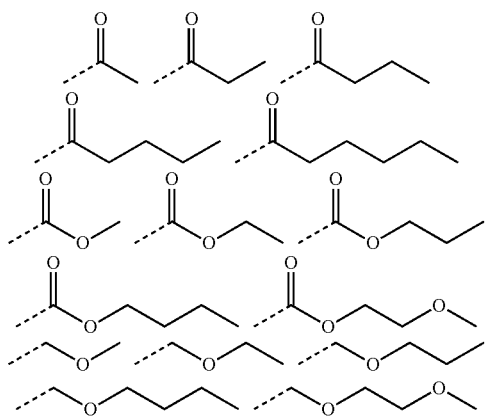

Non-limiting examples of the $C_1$-$C_7$ alkanediyl group optionally containing an ether bond or carbonyl moiety, represented by $L^{12}$, include methylene, ethylene, propane-1,3-diyl, butane-1,4-diyl, pentane-1,5-diyl, hexane-1,6-diyl, and heptane-1,7-diyl as well as the following.

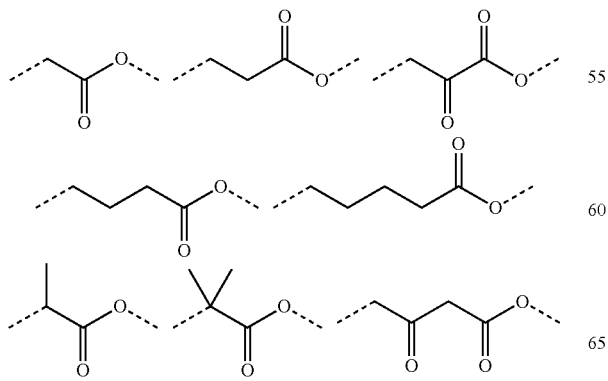

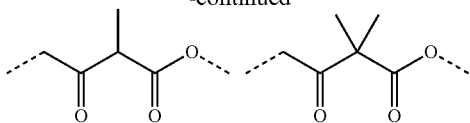

A polymer comprising recurring units (A1) and/or (A2) is decomposed under the action of acid to generate a carboxyl or phenolic hydroxyl group so that it may turn alkali soluble. The acid labile group $X^4$ may be selected from a variety of such groups. Examples of the acid labile group are groups of the following formulae (L1) to (L9), $C_4$-$C_{20}$, preferably $C_4$-$C_{15}$ tertiary alkyl groups, trialkylsilyl groups in which each alkyl moiety has 1 to 6 carbon atoms, and $C_4$-$C_{20}$ oxoalkyl groups.

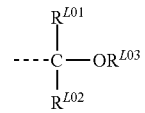
(L1)

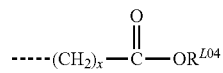
(L2)

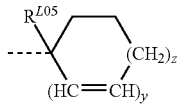
(L3)

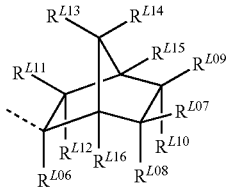
(L4)

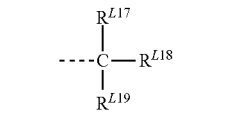
(L5)

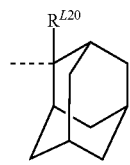
(L6)

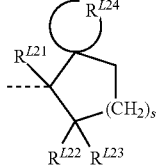
(L7)

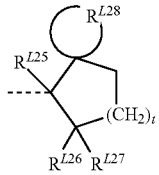
(L8)

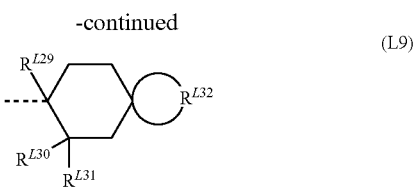
(L9)

In formula (L1), $R^{L01}$ and $R^{L02}$ are each independently hydrogen or a $C_1$-$C_{18}$, preferably $C_1$-$C_{10}$ alkyl group. The alkyl group may be straight, branched or cyclic, and to examples thereof include methyl, ethyl, propyl, isopropyl, n-butyl, sec-butyl, tert-butyl, cyclopentyl, cyclohexyl, 2-ethylhexyl, n-octyl, norbornyl, tricyclodecanyl, tetracyclododecanyl, and adamantyl.

In formula (L1), $R^{L03}$ is a $C_1$-$C_{18}$, preferably $C_1$-$C_{10}$ monovalent hydrocarbon group which may contain a heteroatom. Suitable heteroatoms include oxygen, nitrogen, and sulfur. Examples of the monovalent hydrocarbon group include straight, branched or cyclic alkyl groups, substituted forms of the alkyl groups in which some hydrogen is substituted by hydroxyl, alkoxy, oxo, amino, alkylamino or the like, and substituted forms of the alkyl groups in which some carbon is replaced by a moiety containing a heteroatom such as oxygen. Suitable alkyl groups are as exemplified for $R^{L01}$ and $R^{L02}$. Exemplary substituted alkyl groups are illustrated below.

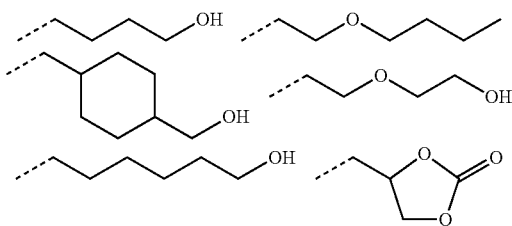

A pair of $R^{L01}$ and $R^{L02}$, $R^{L01}$ and $R^{L03}$, or $R^{L02}$ and $R^{L03}$ may bond together to form a ring with the carbon and oxygen atoms to which they are attached. A ring-forming combination of $R^{L01}$, $R^{L02}$, and $R^{L03}$ is a $C_1$-$C_{18}$, preferably $C_1$-$C_{10}$ straight or branched alkanediyl group.

In formula (L2), $R^{L04}$ is a $C_4$-$C_{20}$, preferably $C_4$-$C_{15}$ tertiary alkyl group, a trialkylsilyl group in which each alkyl moiety has 1 to 6 carbon atoms, a $C_4$-$C_{20}$ oxoalkyl group, or a to group of formula (L1), and x is an integer of 0 to 6.

Suitable tertiary alkyl groups include tert-butyl, tert-pentyl, 1,1-diethylpropyl, 2-cyclopentylpropan-2-yl, 2-cyclohexylpropan-2-yl, 2-(bicyclo[2.2.1]heptan-2-yl)propan-2-yl, 2-(adamantan-1-yl)propan-2-yl, 1-ethylcyclopentyl, 1-butylcyclopentyl, 1-ethylcyclohexyl, 1-butylcyclohexyl, 1-ethyl-2-cyclopentenyl, 1-ethyl-2-cyclohexenyl, 2-methyl-2-adamantyl, and 2-ethyl-2-adamantyl. Suitable trialkylsilyl groups include trimethylsilyl, triethylsilyl, and dimethyl-tert-butylsilyl. Suitable oxoalkyl groups include 3-oxocyclohexyl, 4-methyl-2-oxooxan-4-yl, and 5-methyl-2-oxooxolan-5-yl.

In formula (L3), $R^{L05}$ is a $C_1$-$C_8$ alkyl group which may contain a heteroatom or a $C_6$-$C_{20}$ aryl group which may contain a heteroatom. The alkyl group may be straight, branched or cyclic and examples thereof include methyl, ethyl, propyl, isopropyl, n-butyl, sec-butyl, tert-butyl, n-pentyl, tert-pentyl, n-hexyl, cyclopentyl, and cyclohexyl, and substituted forms of the foregoing in which some hydrogen is substituted by hydroxyl, alkoxy, carboxyl, alkoxycarbonyl, oxo, amino, alkylamino, cyano, mercapto, alkylthio, sulfo or the like. Exemplary aryl groups include phenyl, methylphenyl, naphthyl, anthryl, phenanthryl, and pyrenyl. In formula (L3), y is 0 or 1, z is an integer of 0 to 3, and 2y+z is equal to 2 or 3.

In formula (L4), $R^{L06}$ is a $C_1$-$C_{10}$ alkyl group which may contain a heteroatom or a $C_6$-$C_{20}$ aryl group which may contain a heteroatom. Examples of alkyl and aryl groups are as exemplified for $R^{L05}$.

In formula (L4), $R^{L07}$ to $R^{L06}$ are each independently hydrogen or a $C_1$-$C_{15}$ monovalent hydrocarbon group. The monovalent hydrocarbon group may be straight, branched or cyclic and examples thereof include straight, branched or cyclic alkyl groups such as methyl, ethyl, propyl, isopropyl, n-butyl, sec-butyl, tert-butyl, n-pentyl, tert-pentyl, n-hexyl, n-octyl, n-nonyl, n-decyl, cyclopentyl, cyclohexyl, cyclopentylmethyl, cyclopentylethyl, cyclopentylbutyl, cyclohexylmethyl, cyclohexylethyl and cyclohexylbutyl, and substituted forms of the foregoing in which some hydrogen is substituted by hydroxyl, alkoxy, carboxyl, alkoxycarbonyl, oxo, amino, alkylamino, cyano, mercapto, alkylthio, sulfo or the like. Alternatively, a pair of $R^{L07}$ to $R^{L06}$ (e.g., $R^{L07}$ and $R^{L08}$, $R^{L07}$ and $R^{L09}$, $R^{L08}$ and $R^{L10}$, $R^{L09}$ and $R^{L10}$, $R^{L11}$ and $R^{L12}$, or $R^{L13}$ and $R^{L14}$) may bond together to form a ring with the carbon atom to which they are attached. The ring-forming group is a $C_1$-$C_{15}$ divalent hydrocarbon group, examples of which are those exemplified above for the monovalent hydrocarbon groups, with one hydrogen atom being eliminated. Also a pair of $R^{L07}$ to $R^{L16}$ (e.g., $R^{L07}$ and $R^{L09}$, $R^{L09}$ and $R^{L15}$, or $R^{L13}$ and $R^{L15}$) which are attached to vicinal carbon atoms may bond together directly to form a double bond.

In formula (L5), $R^{L17}$ to $R^{L19}$ are each independently a $C_1$-$C_{15}$ alkyl group. The alkyl group may be straight, branched or cyclic and examples thereof include methyl, ethyl, propyl, isopropyl, n-butyl, sec-butyl, tert-butyl, cyclopentyl, cyclohexyl, 2-ethylhexyl, n-octyl, 1-adamantyl and 2-adamantyl.

In formula (L6), $R^{L20}$ is a $C_1$-$C_{10}$ alkyl group which may contain a heteroatom or $C_6$-$C_{20}$ aryl group which may contain a heteroatom. Examples of the alkyl and aryl groups are as exemplified for $R^{L05}$.

In formula (L7), $R^{L21}$ is a $C_1$-$C_{10}$ alkyl group which may contain a heteroatom or a $C_6$-$C_{20}$ aryl group which may contain a heteroatom. Examples the alkyl and aryl groups are as exemplified for $R^{L05}$. $R^{L22}$ and $R^{L23}$ are each independently hydrogen or a $C_1$-$C_{10}$ monovalent hydrocarbon group. The monovalent hydrocarbon group may be straight, branched or cyclic, and examples thereof are as exemplified for $R^{L07}$ to $R^{L16}$. $R^{L22}$ and $R^{L23}$ may bond together to form a substituted or unsubstituted cyclopentane or cyclohexane ring with the carbon atom to which they are attached. $R^{L24}$ is a divalent group which forms a substituted or unsubstituted cyclopentane, cyclohexane or norbomane ring with the carbon atom to which it is attached. In formula (L7), s is 1 or 2.

In formula (L8), $R^{L05}$ is a $C_1$-$C_{10}$ alkyl group which may contain a heteroatom or a $C_6$-$C_{20}$ aryl group which may contain a heteroatom. Examples of the alkyl and aryl groups are as exemplified for $R^{L05}$. $R^{L26}$ and $R^{L27}$ are each independently hydrogen or a $C_1$-$C_{10}$ monovalent hydrocarbon group. The monovalent hydrocarbon group may be straight, branched or cyclic and examples thereof are as exemplified for $R^{L07}$ to $R^{L16}$. $R^{L26}$ and $R^{L27}$ may bond together to form a substituted or unsubstituted cyclopentane or cyclohexane ring with the carbon atom to which they are attached. $R^{L28}$ is a divalent group which forms a substituted or unsubstituted cyclopentane, cyclohexane or norbornane ring with the carbon atom to which it is attached. In formula (L8), t is 1 or 2.

In formula (L9), $R^{L29}$ is a $C_1$-$C_{10}$ alkyl group which may contain a heteroatom or a $C_6$-$C_{20}$ aryl group which may contain a heteroatom. Examples of the alkyl and aryl groups are as exemplified for $R^{L05}$. $R^{L30}$ and $R^{L31}$ are each independently hydrogen or a $C_1$-$C_{10}$ monovalent hydrocarbon group. The monovalent hydrocarbon group may be straight, branched or cyclic and examples thereof are as exemplified for $R^{L07}$ to $R^{L16}$. $R^{L30}$ and $R^{L31}$ may bond together to form a substituted or unsubstituted cyclopentane or cyclohexane ring with the carbon atom to which they are attached. $R^{L32}$ is a divalent group which forms a substituted or unsubstituted cyclopentane, cyclohexane or norbornane ring with the carbon atom to which it is attached.

Of the acid labile groups of formula (L1), the straight or branched groups are exemplified below, but not limited thereto.

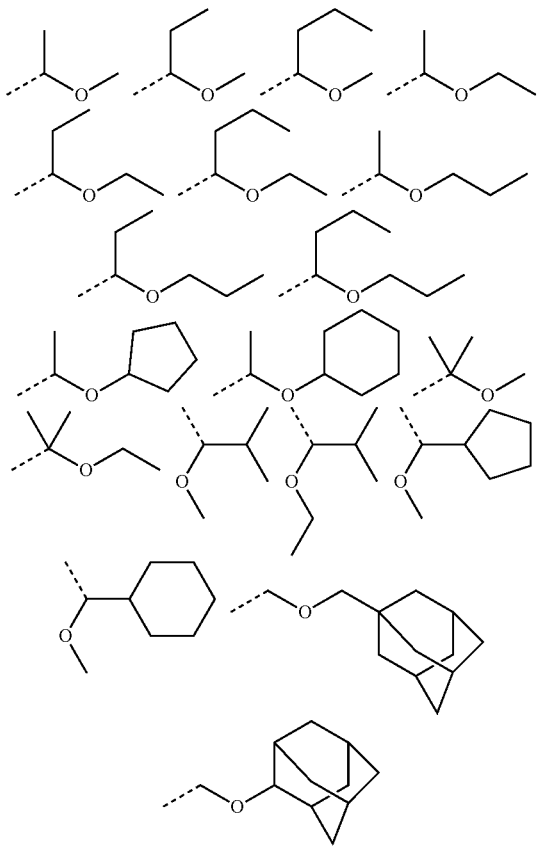

Of the acid labile groups of formula (L1), the cyclic groups are, for example, tetrahydrofuran-2-yl, 2-methyltetrahydrofuran-2-yl, tetrahydropyran-2-yl, and 2-methyltetrahydropyran-2-yl.

Examples of the acid labile group of formula (L2) include tert-butoxycarbonyl, tert-butoxycarbonylmethyl, tert-pentyloxycarbonyl, tert-pentyloxycarbonylmethyl, 1,1-diethylpropyloxycarbonyl, 1,1-diethylpropyloxycarbonylmethyl, 1-ethylcyclopentyloxycarbonyl, 1-ethylcyclopentyloxycarbonylmethyl, 1-ethyl-2-cyclopentenyloxycarbonyl, 1-ethyl-2-cyclopentenyloxycarbonylmethyl, 1-ethoxyethoxycarbonylmethyl, 2-tetrahydropyranyloxycarbonylmethyl, and 2-tetrahydrofuranyloxycarbonylmethyl.

Examples of the acid labile group of formula (L3) include 1-methylcyclopentyl, 1-ethylcyclopentyl, 1-n-propylcyclopentyl, 1-isopropylcyclopentyl, 1-n-butylcyclopentyl, 1-sec-butylcyclopentyl, 1-tert-butylcyclopentyl, 1-cyclohexylcyclopentyl, 1-(4-methoxy-n-butyl)cyclopentyl, 1-methylcyclohexyl, 1-ethylcyclohexyl, 3-methyl-1-cyclopenten-3-yl, 3-ethyl-1-cyclopenten-3-yl, 3-methyl-1-cyclohexen-3-yl, and 3-ethyl-1-cyclohexen-3-yl.

Of the acid labile groups of formula (L4), those groups of the following formulae (L4-1) to (L4-4) are preferred.

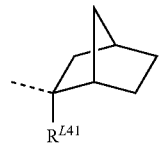
(L4-1)

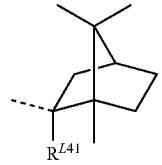
(L4-2)

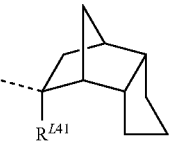
(L4-3)

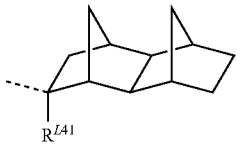
(L4-4)

In formulas (L4-1) to (L4-4) and the formulae shown below, the broken line denotes a point and direction of attachment. $R^{L41}$ is each independently a $C_1$-$C_{10}$ monovalent hydrocarbon group which may be straight, branched or cyclic. Exemplary groups include alkyl groups such as methyl, ethyl, propyl, isopropyl, n-butyl, sec-butyl, tert-butyl, n-pentyl, tert-pentyl, n-hexyl, cyclopentyl and cyclohexyl.

For formulas (L4-1) to (L4-4), there can exist enantiomers and diastereomers. Each of formulae (L4-1) to (L4-4) collectively represents all such stereoisomers. When the acid labile group $X^A$ is of formula (L4), a plurality of stereoisomers may be included.

For example, the formula (L4-3) represents one or a mixture of two selected from groups having the following formulas (L4-3-1) and (L4-3-2).

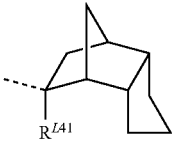
(L4-3-1)

(L4-3-2)

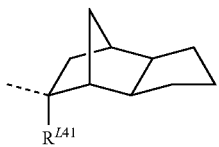

Note that $R^{L41}$ is as defined above.

Similarly, the formula (L4-4) represents one or a mixture of two or more selected from groups having the following formulas (L4-4-1) to (L4-4-4).

(L4-4-1)

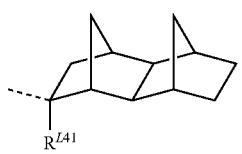

(L4-4-2)

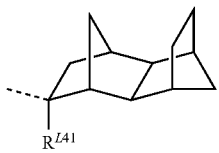

(L4-4-3)

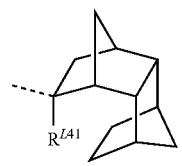

(L4-4-4)

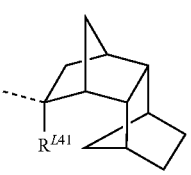

Note that $R^{L41}$ is as defined above.

Each of formulas (L4-1) to (L4-4), (L4-3-1) and (L4-3-2), and (L4-4-1) to (L4-4-4) collectively represents an enantiomer thereof and a mixture of enantiomers.

It is noted that in the above formulas (L4-1) to (L4-4), (L4-3-1) and (L4-3-2), and (L4-4-1) to (L4-4-4), the direction of attachment is on the exo side relative to the bicyclo[2.2.1]heptane ring, which ensures high reactivity for acid catalyzed elimination reaction (see JP-A 2000-336121). In preparing these monomers having a tertiary exo-alkyl group of bicyclo[2.2.1]heptane structure as a substituent group, there may be contained monomers substituted with an endo-alkyl group as represented by the following formulas (L4-1-endo) to (L4-4-endo). For good reactivity, an exo proportion of at least 50 mol % is preferred, with an exo proportion of at least 80 mol % being more preferred.

(L4-1-endo)

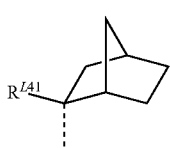

(L4-2-endo)

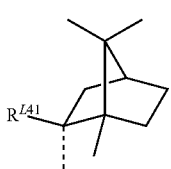

(L4-3-endo)

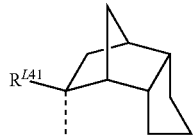

(L4-4-endo)

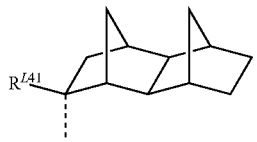

Note that $R^{L41}$ is as defined above.

Illustrative examples of the acid labile group of formula (L4) are given below.

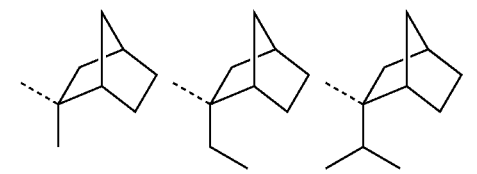

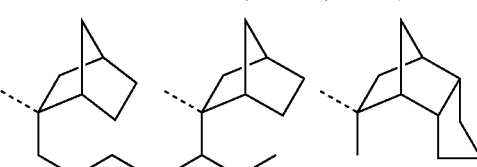

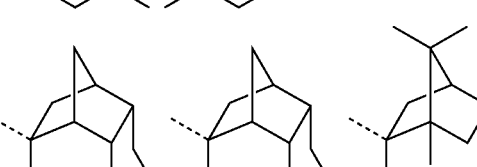

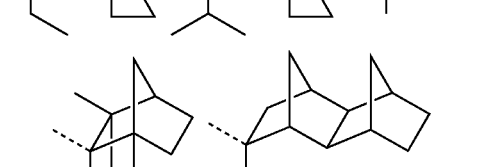

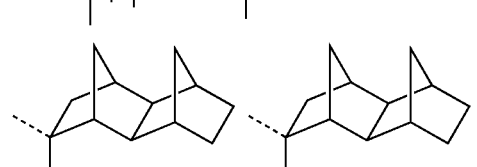

Illustrative examples of the acid labile group of formula (L5) include tert-butyl, tert-pentyl and the groups shown below, but are not limited thereto.

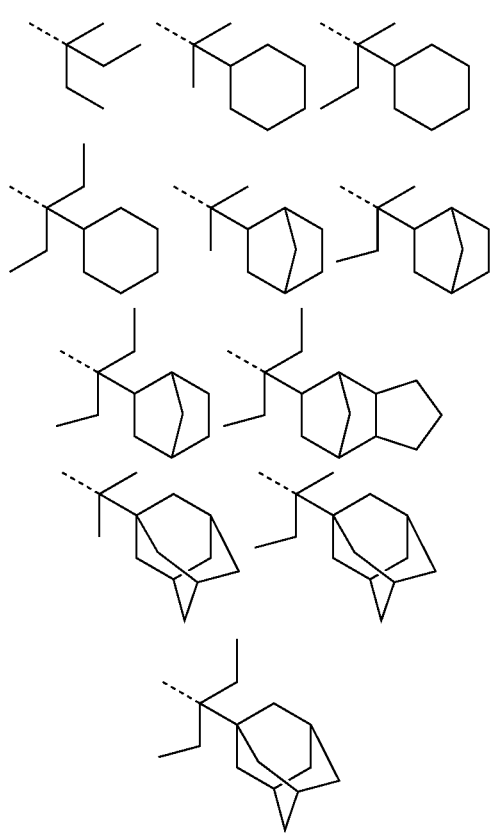
Illustrative examples of the acid labile group of formula (L6) are given below, but not limited thereto.
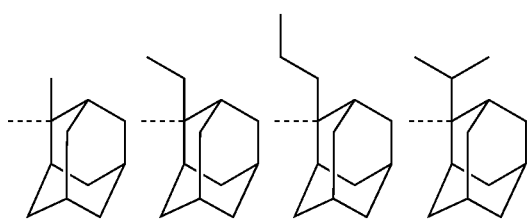
Illustrative examples of the acid labile group of formula (L7) are given below, but not limited thereto.
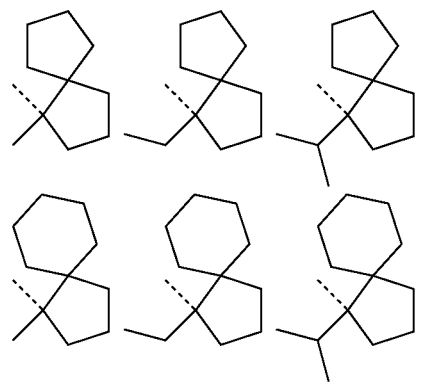
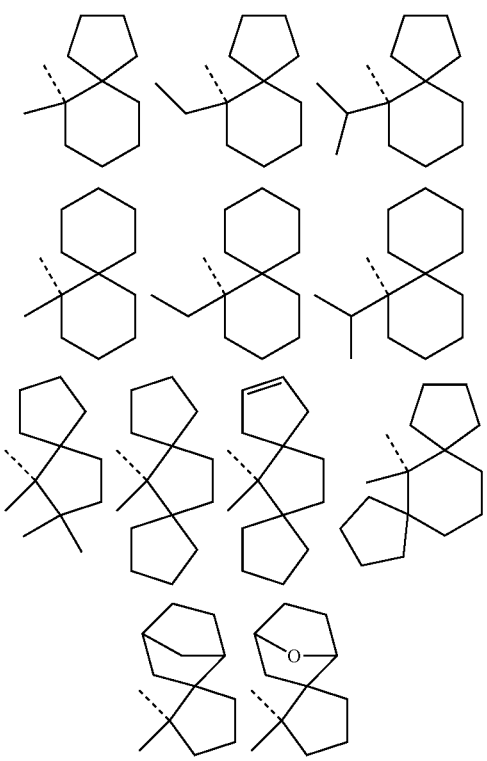
Illustrative examples of the acid labile group of formula (L8) are given below, but not limited thereto.
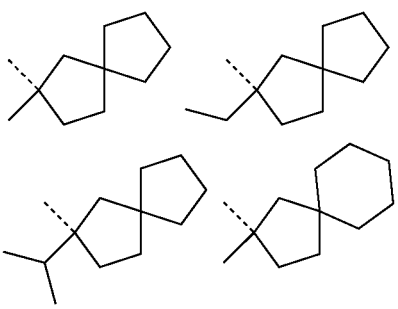
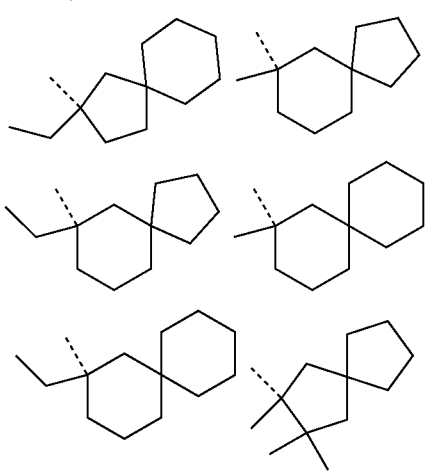

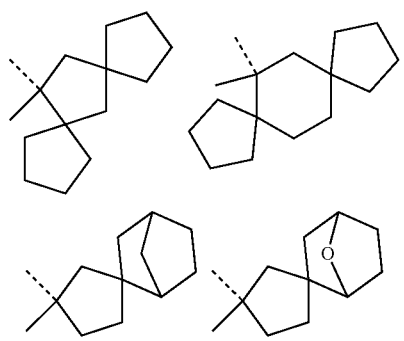

Illustrative examples of the acid labile group of formula (L9) are given below, but not limited thereto.

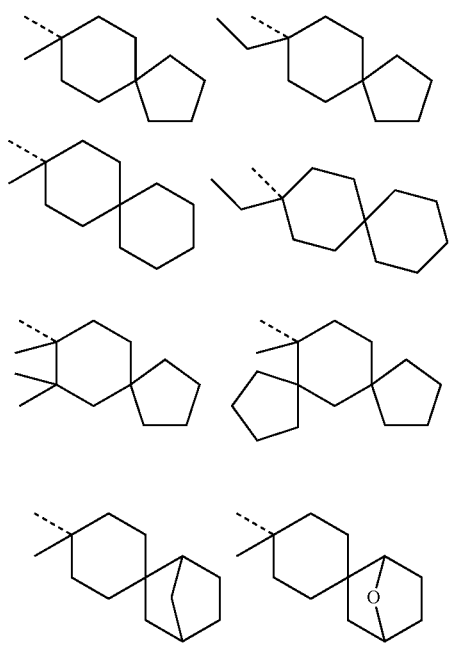

Of the acid labile groups $X^A$, suitable $C_4$-$C_{20}$ tertiary alkyl groups, trialkylsilyl groups in which each alkyl moiety has 1 to 6 carbon atoms, and $C_1$-$C_{20}$ oxoalkyl groups are as exemplified for $R^{LO4}$.

Examples of the monomer from which recurring units (A1) are derived are given below, but not limited thereto. $R^A$ is as defined above.

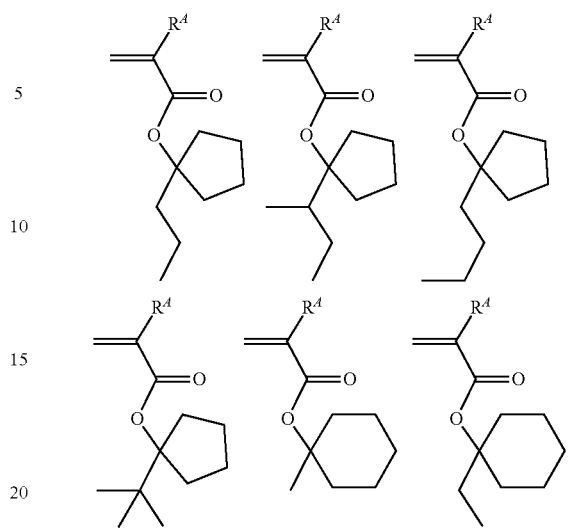

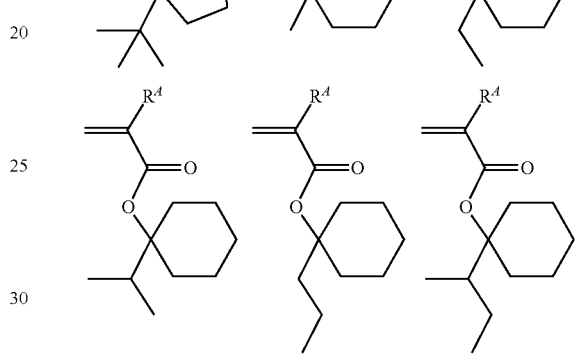

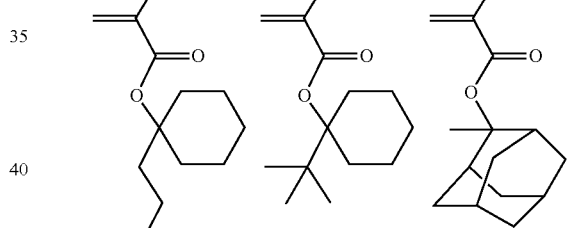

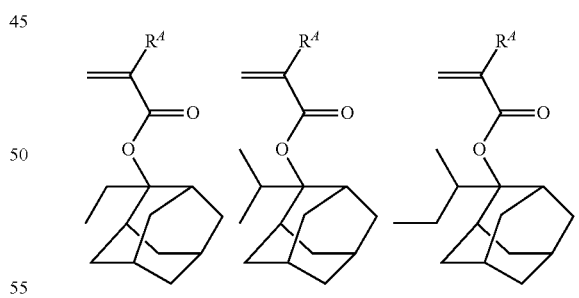

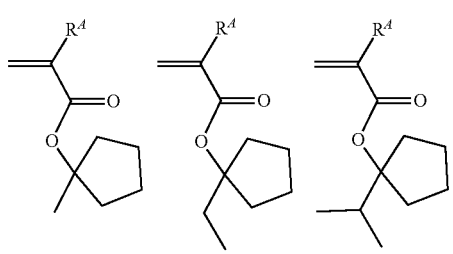

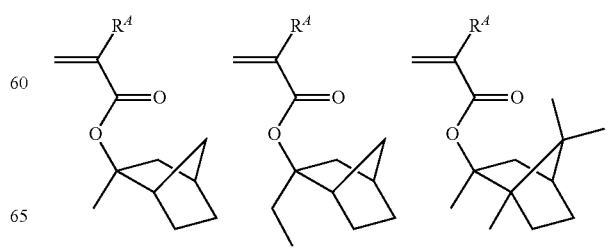

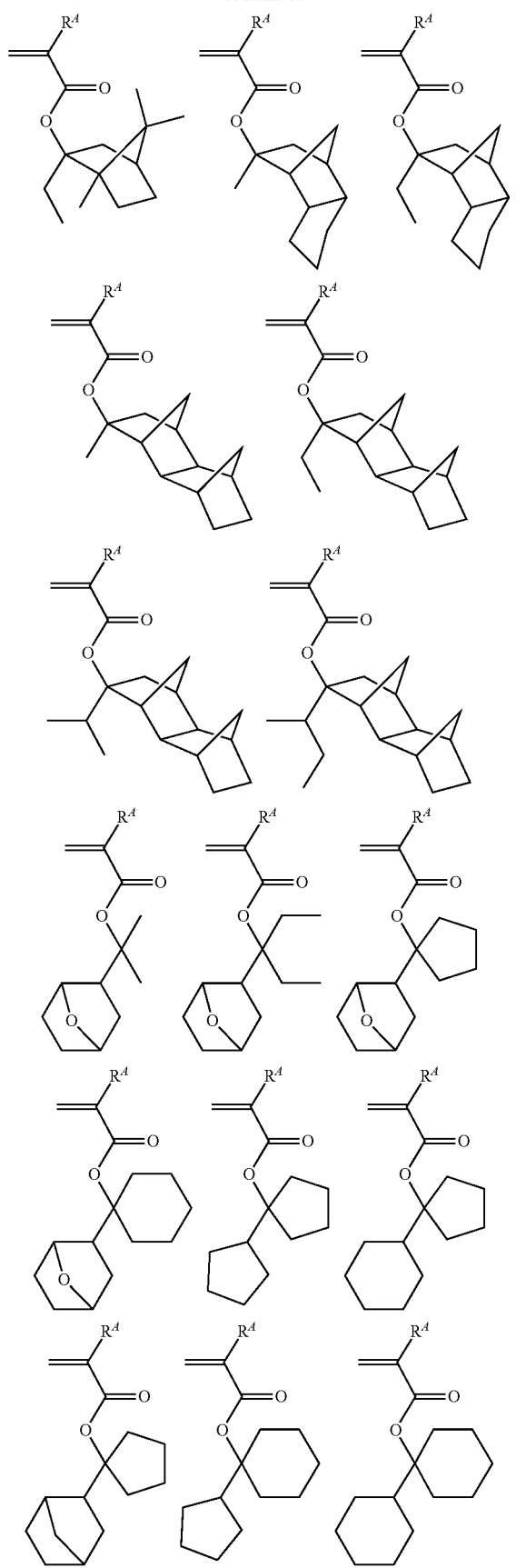
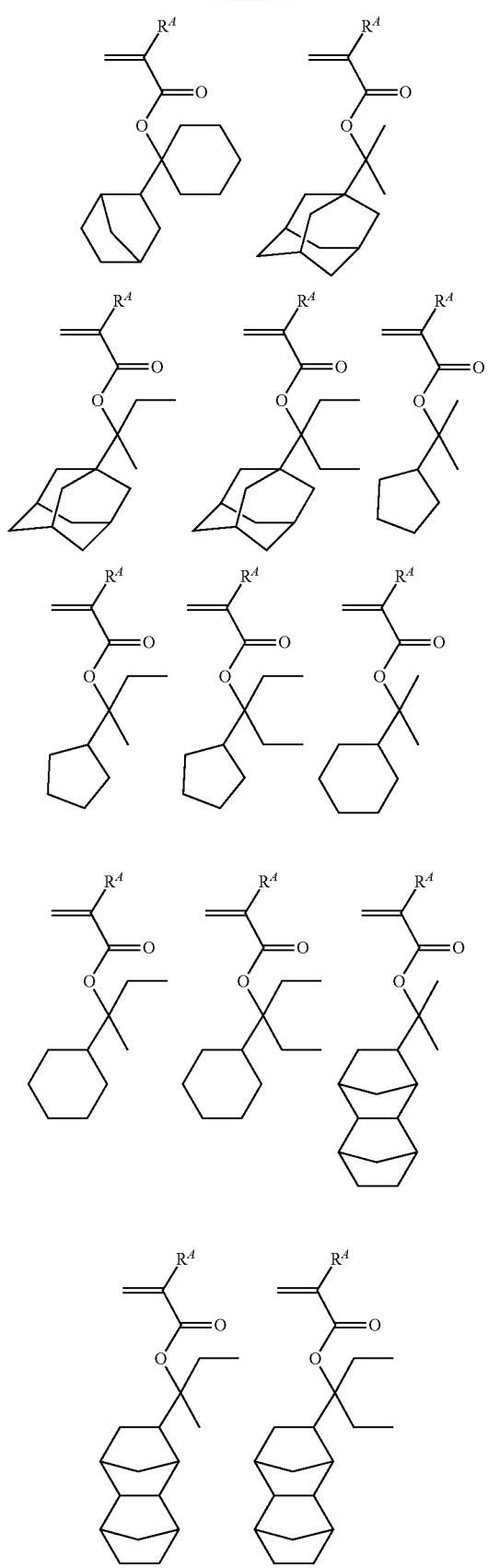

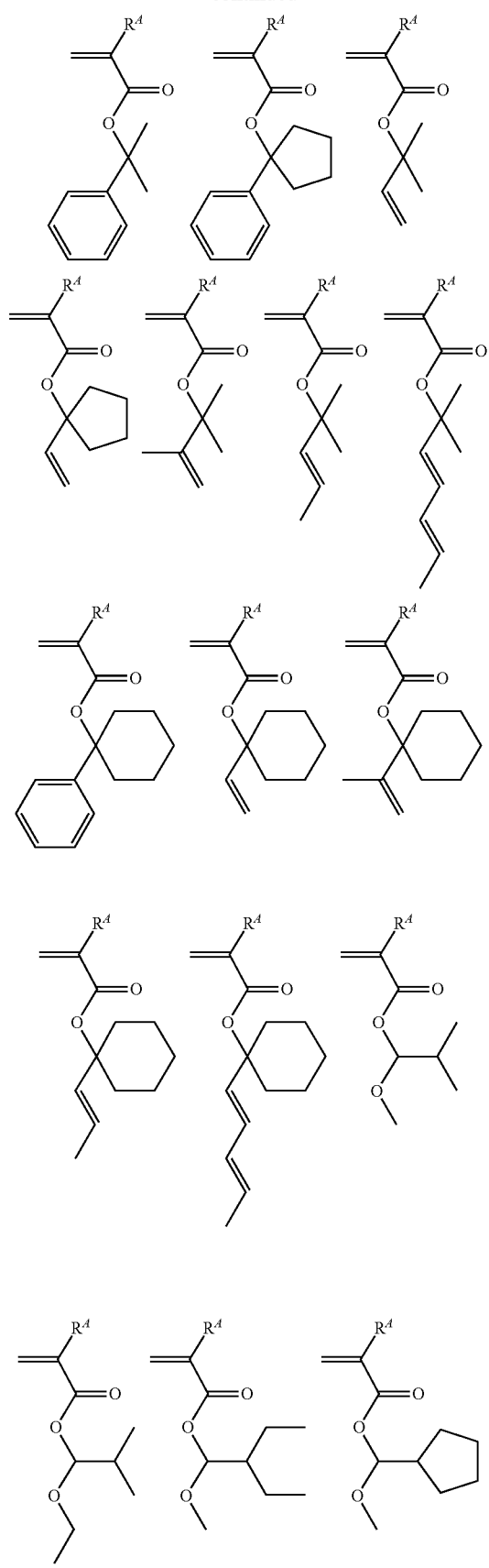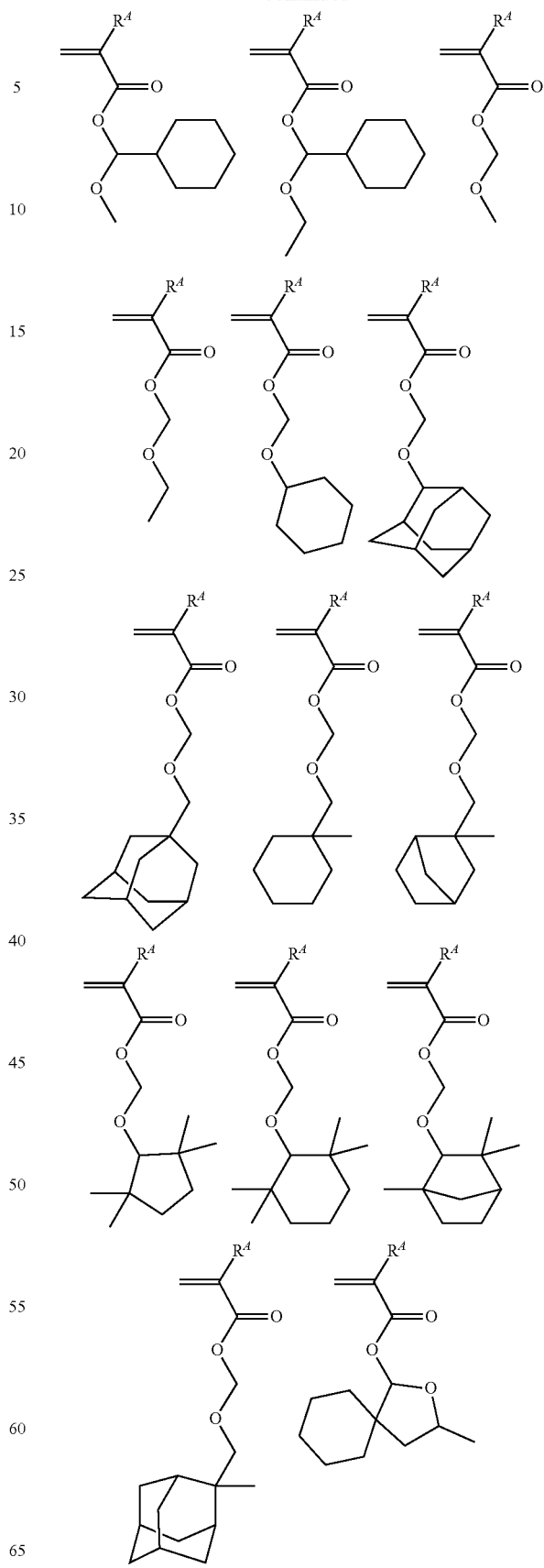

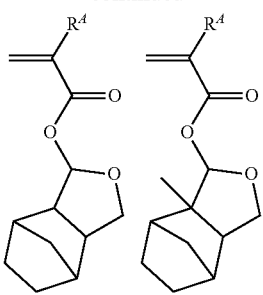
Examples of the monomer from which recurring units (A2) are derived are given below, but not limited thereto. $R^A$ is as defined above.
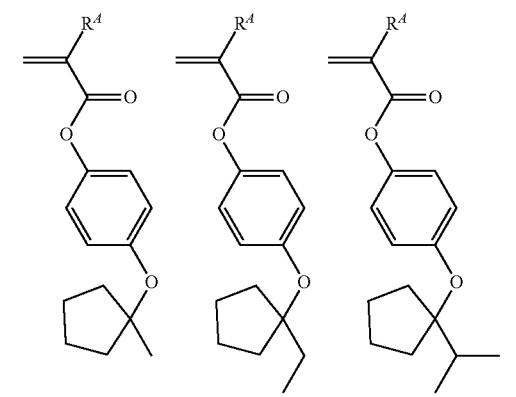
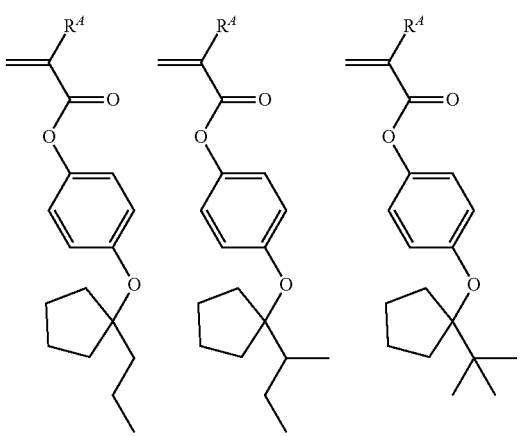
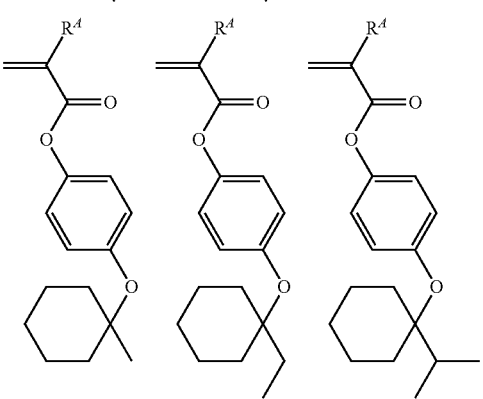
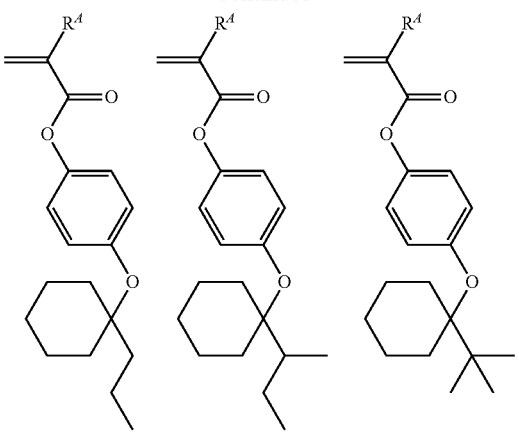
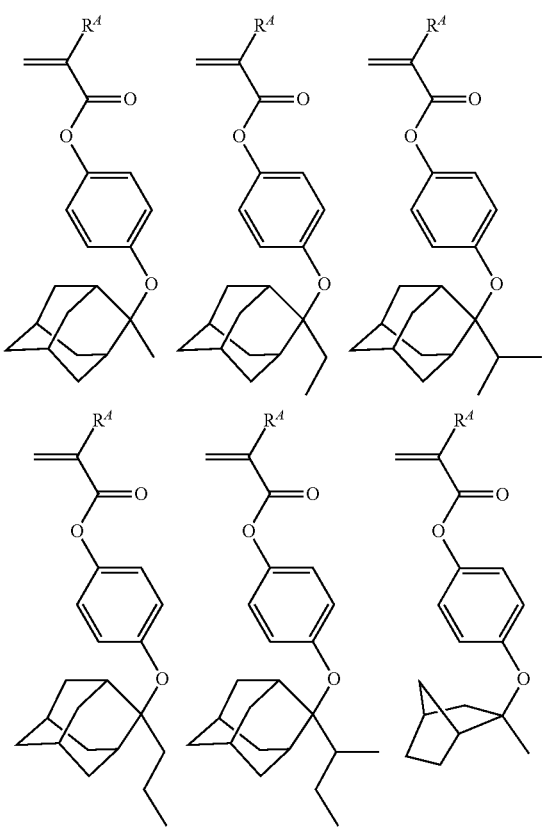

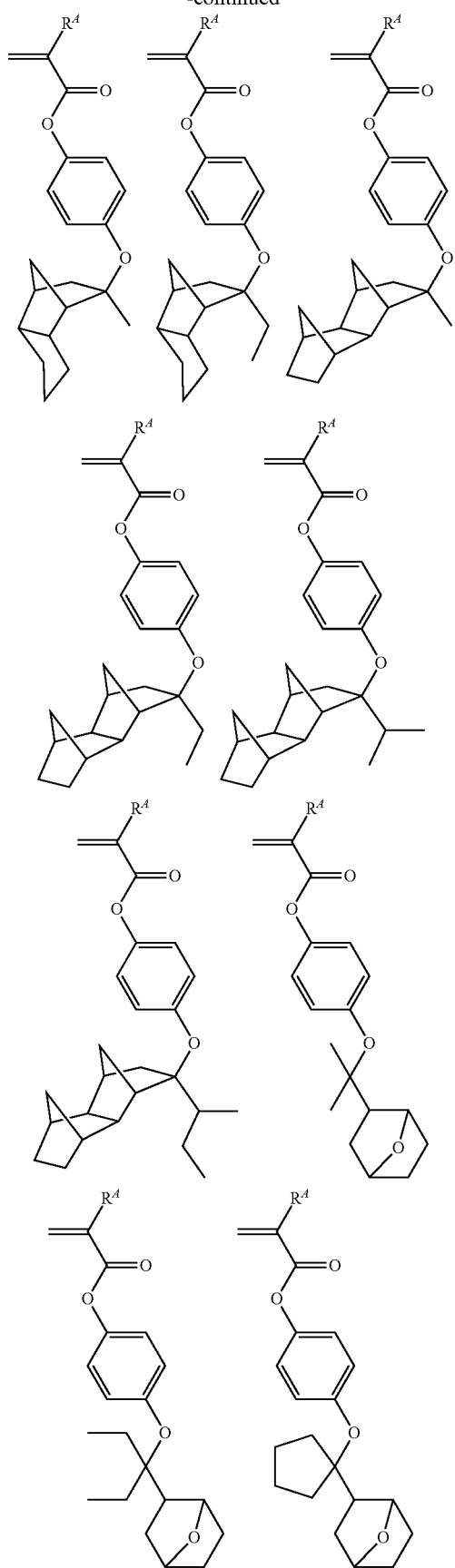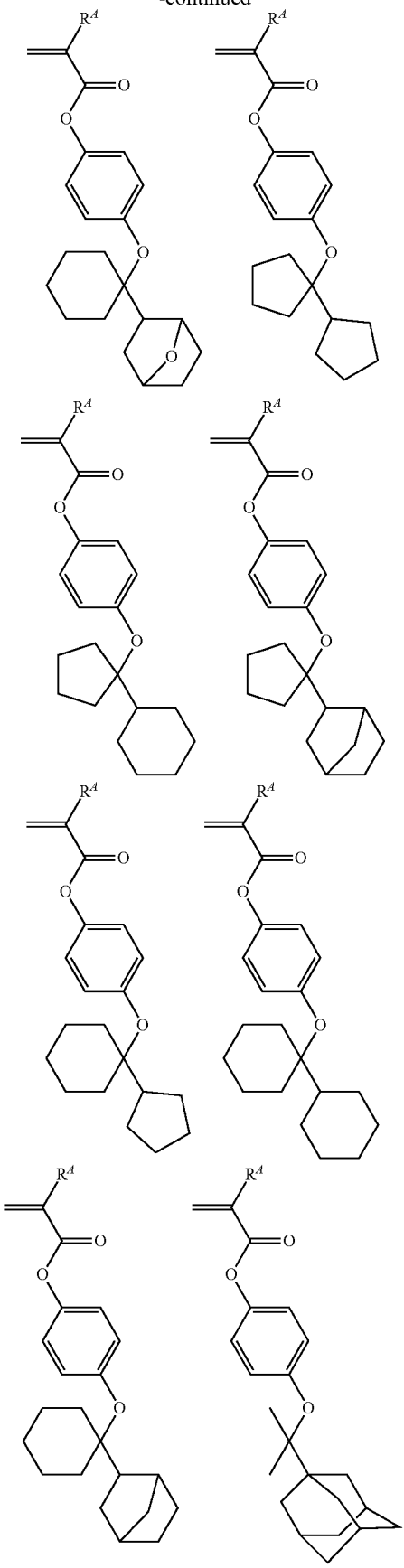

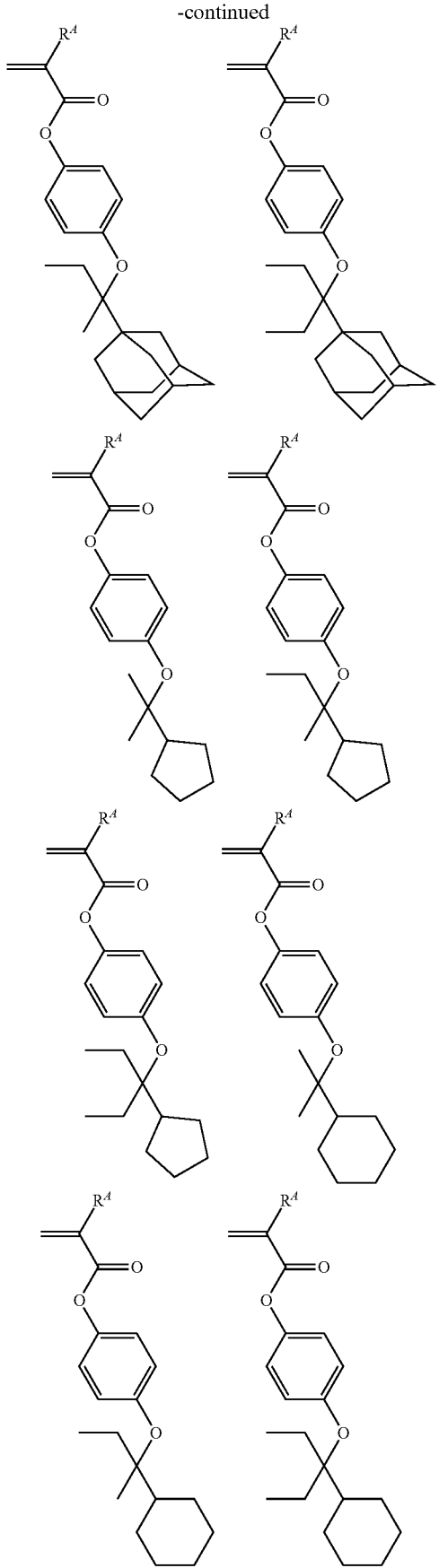
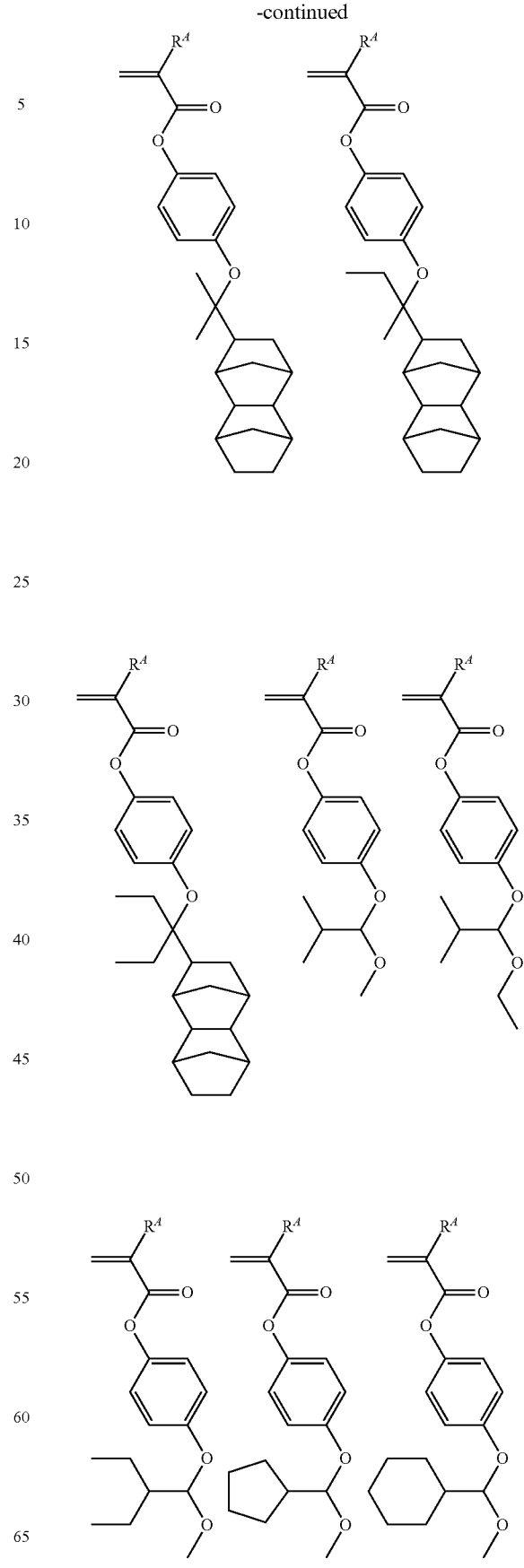

-continued
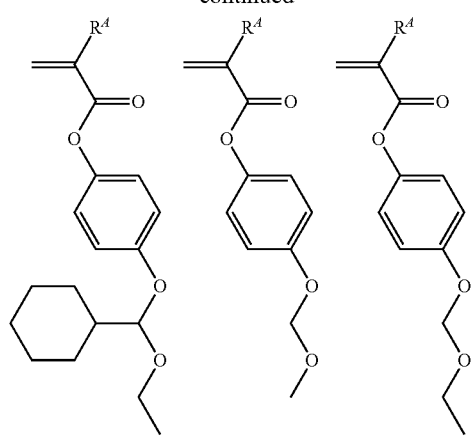
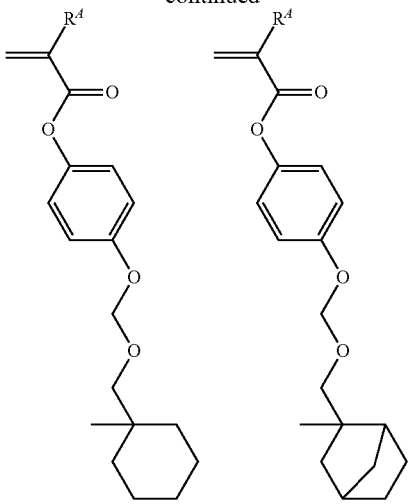
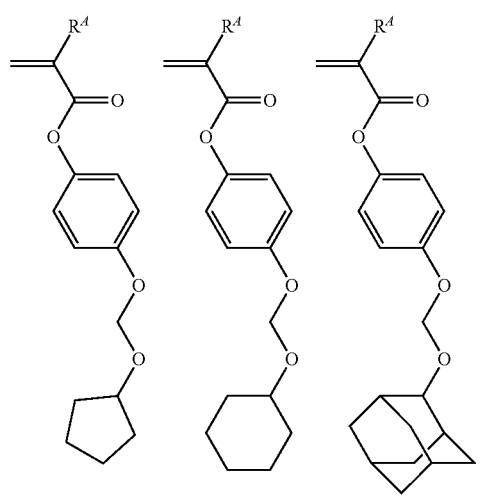
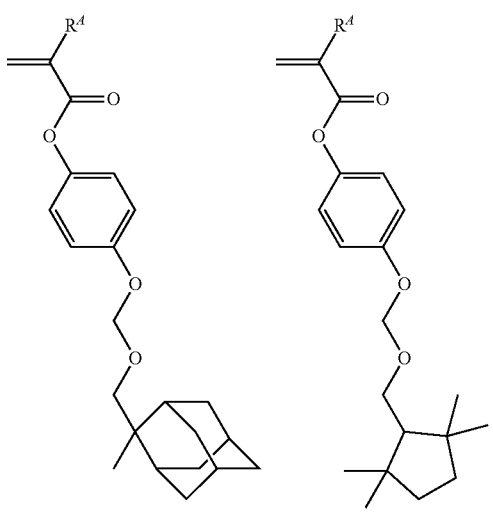
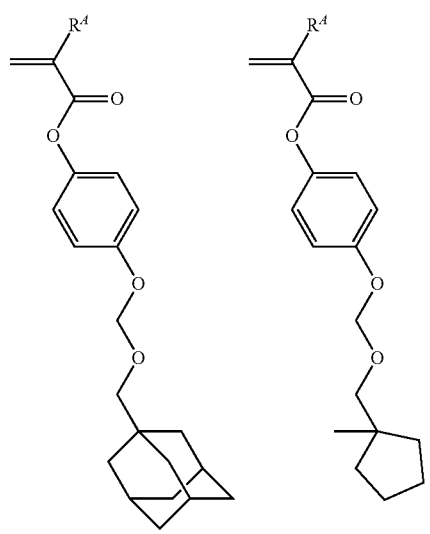
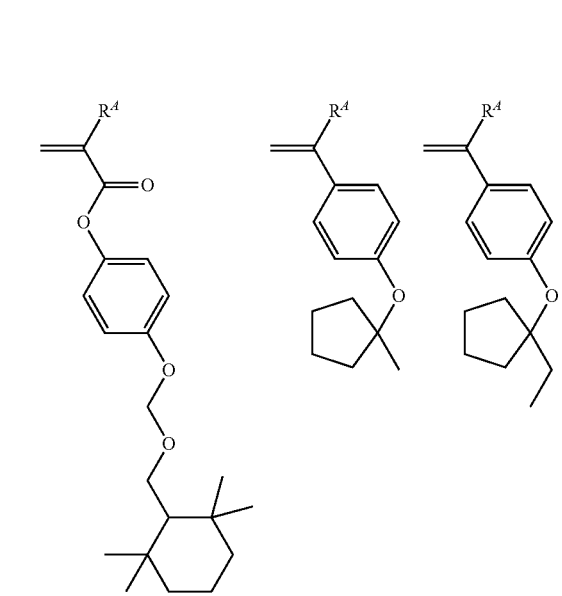

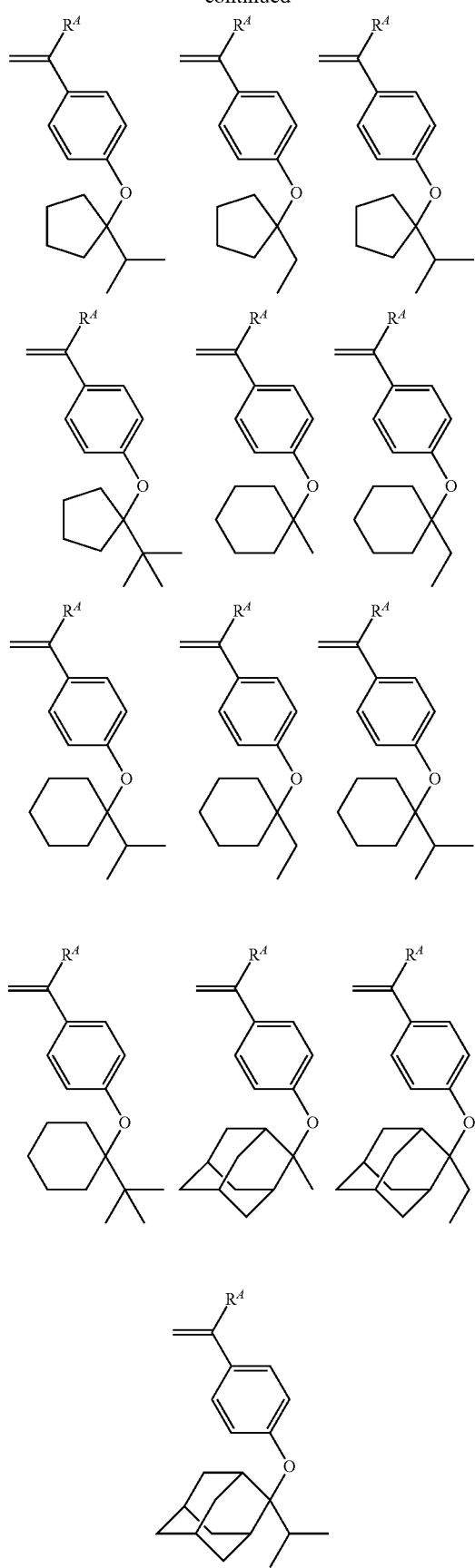
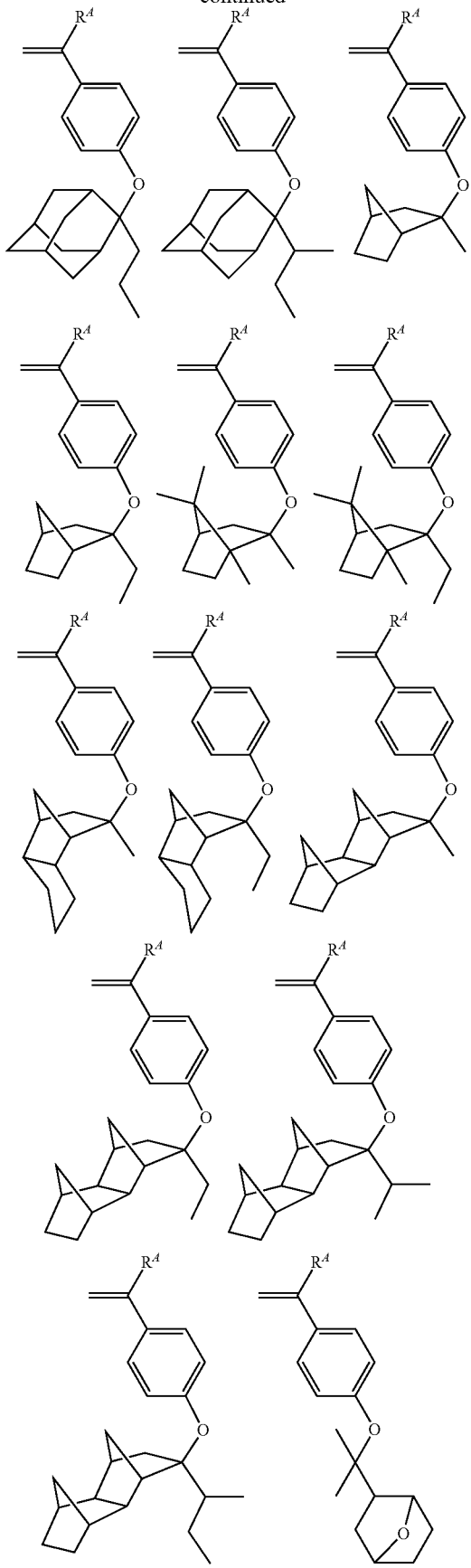

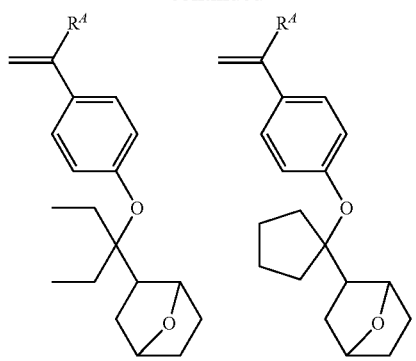
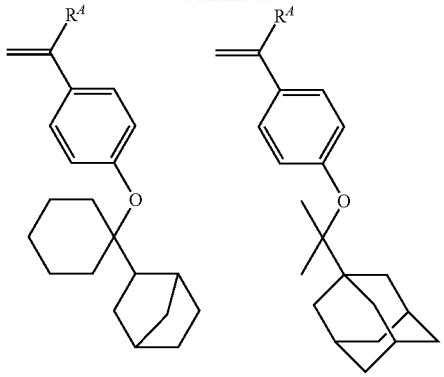
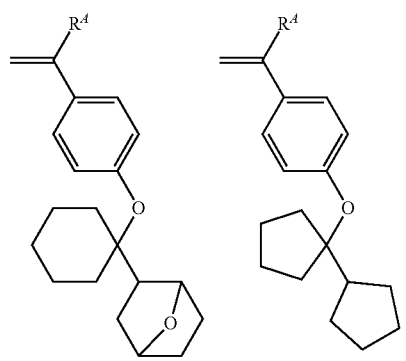
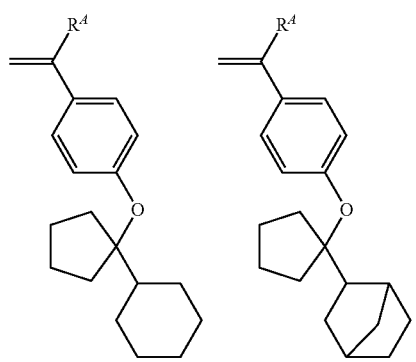
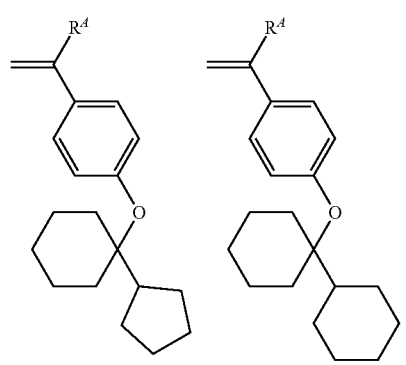
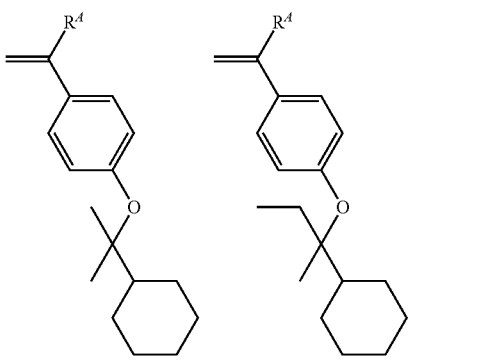

-continued
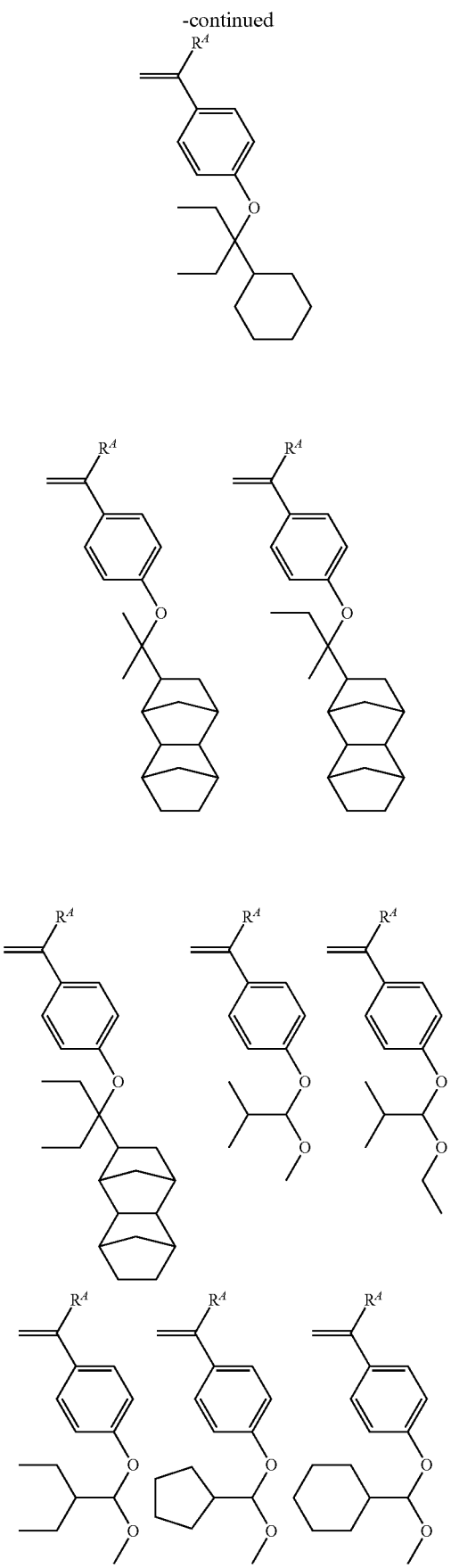
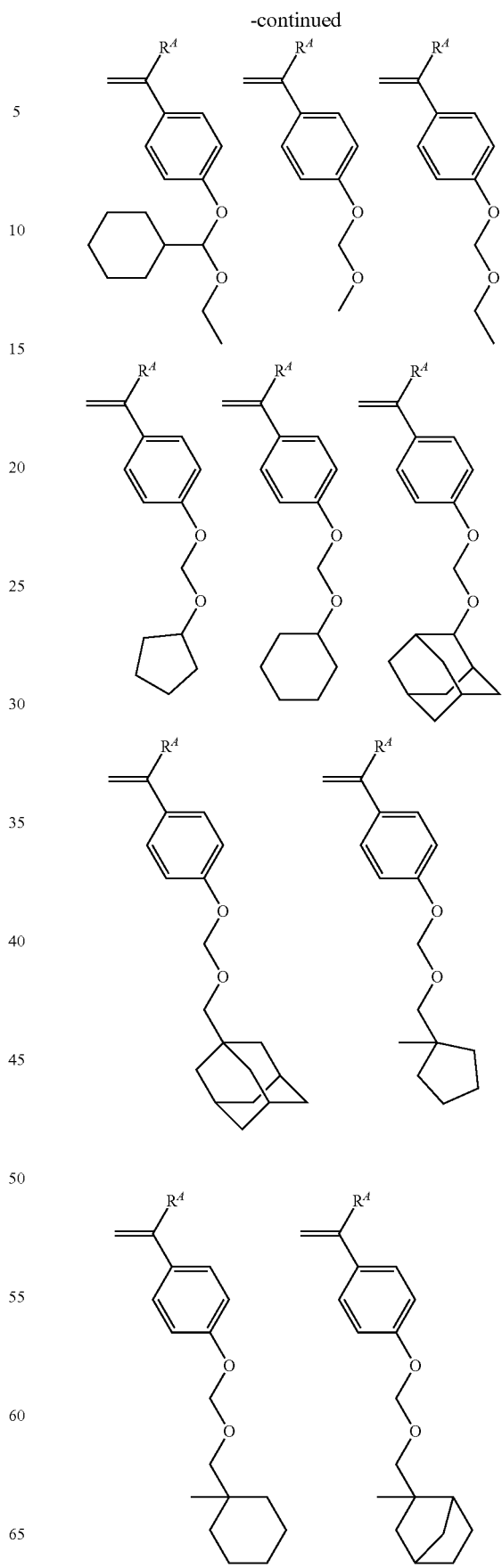

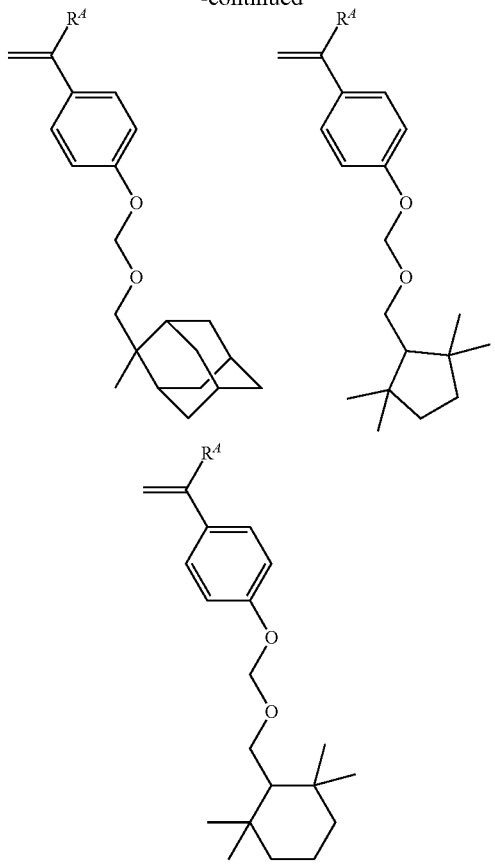

The recurring unit (B) has a $C_1$-$C_{20}$ fluoroalcohol-containing substituent group having high affinity to alkaline aqueous solution. Preferred examples of the fluoroalcohol-containing unit include recurring units having a 1,1,1,3,3,3-hexafluoro-2-propanol residue or 2-hydroxy-2-trifluoromethyloxolane structure as described in JP-A 2007-297590, JP-A 2008-111103, JP-A 2008-122932, and JP-A 2012-128067.

It is possible that once fluoroalcohol is protected with an acyl group or acid labile group, a fluoroalcohol-containing unit corresponding to formula (B) is generated by hydrolysis in alkaline aqueous solution developer or deprotection with acid after exposure. Preferred examples of the recurring unit in this embodiment include those described in JP-A 2012-128067, paragraphs [0036]-[0040] and specifically those of formulae (2a), (2b) and (2f) in paragraph [0041].

Examples of the monomer from which recurring units (B) are derived are shown below, but not limited thereto. $R^A$ is as defined above.

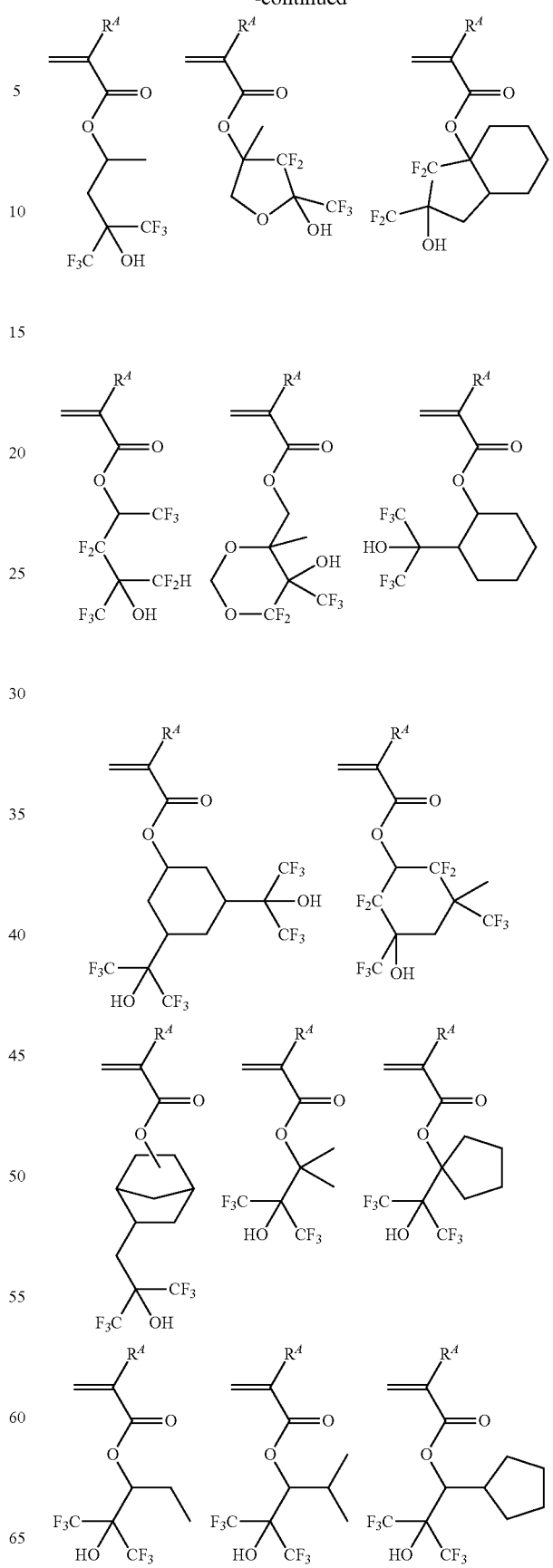

-continued

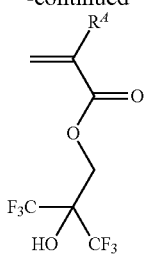

The recurring units (C) are units having a phenolic hydroxyl group, for example, units derived from a monomer having the formula (C1).

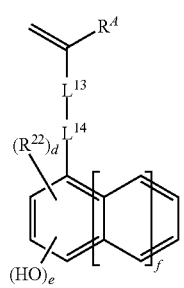

(C1)

Herein $R^4$ is as defined above. $R^{22}$ is each independently hydrogen or a $C_1$-$C_6$ alkyl group which may contain an ether bond or carbonyl moiety. $L^{13}$ is a single bond, carbonyloxy group or amide group. $L^{14}$ is a single bond or a $C_1$-$C_7$ alkanediyl group which may contain an ether bond or carbonyl moiety. The subscript d is an integer meeting: d≤5+2f-e, e is an integer of 1 to 5, and f is an integer of 0 to 2.

Examples of the $C_1$-$C_6$ alkyl group which may contain an ether bond or carbonyl moiety, represented by $R^{22}$, include, but are not limited to, methyl, ethyl, propyl, isopropyl, n-butyl, sec-butyl, tert-butyl, pentyl, hexyl, heptyl, octyl, cyclopentyl, and cyclohexyl as well as the groups shown below.

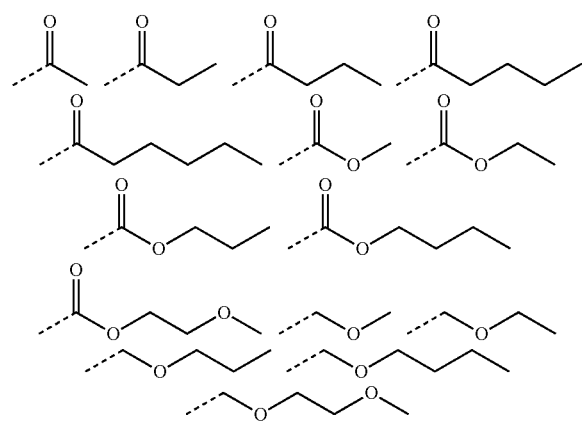

Examples of the $C_1$-$C_7$ alkanediyl group which may contain an ether bond or carbonyl moiety, represented by $L^{14}$, include, but are not limited to, methylene, ethylene, propane-1,3-diyl, butane-1,4-diyl, pentane-1,5-diyl, hexane-1,6-diyl, and heptane-1,7-diyl as well as the groups shown below.

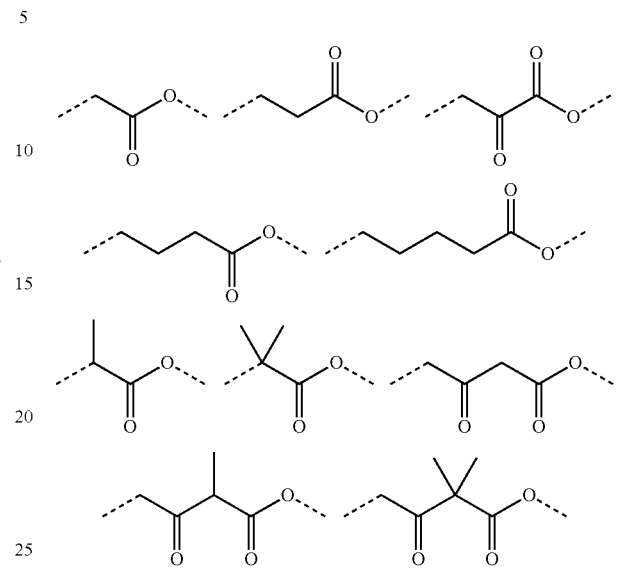

Examples of the monomer from which recurring units (C) are derived are shown below, but not limited thereto. $R^4$ is as defined above.

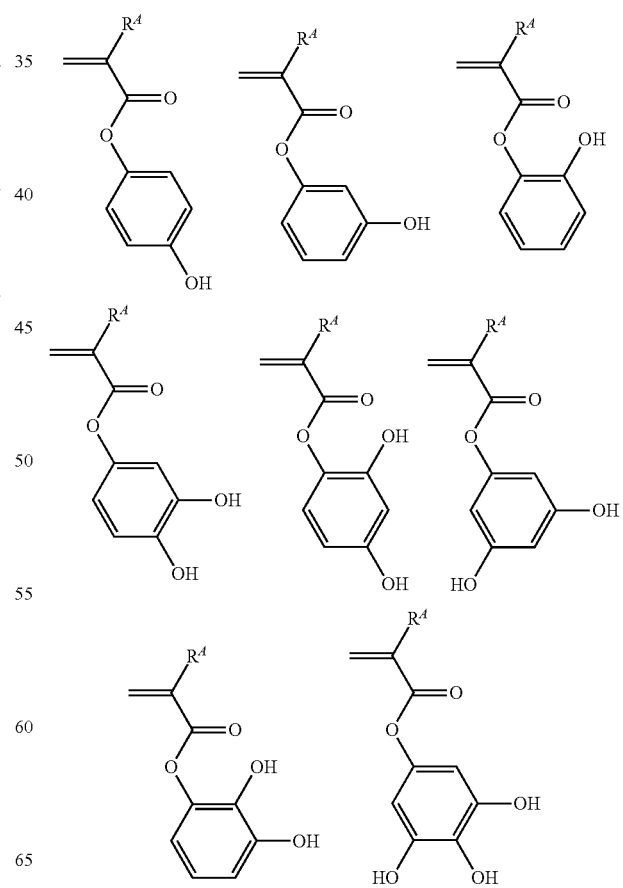

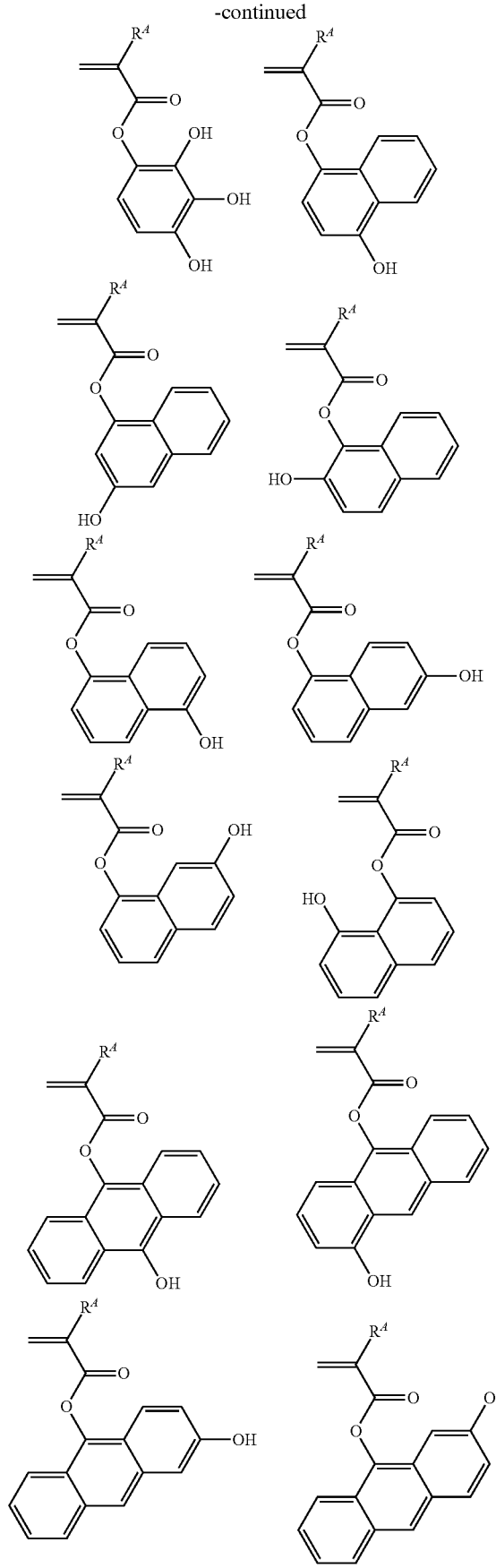
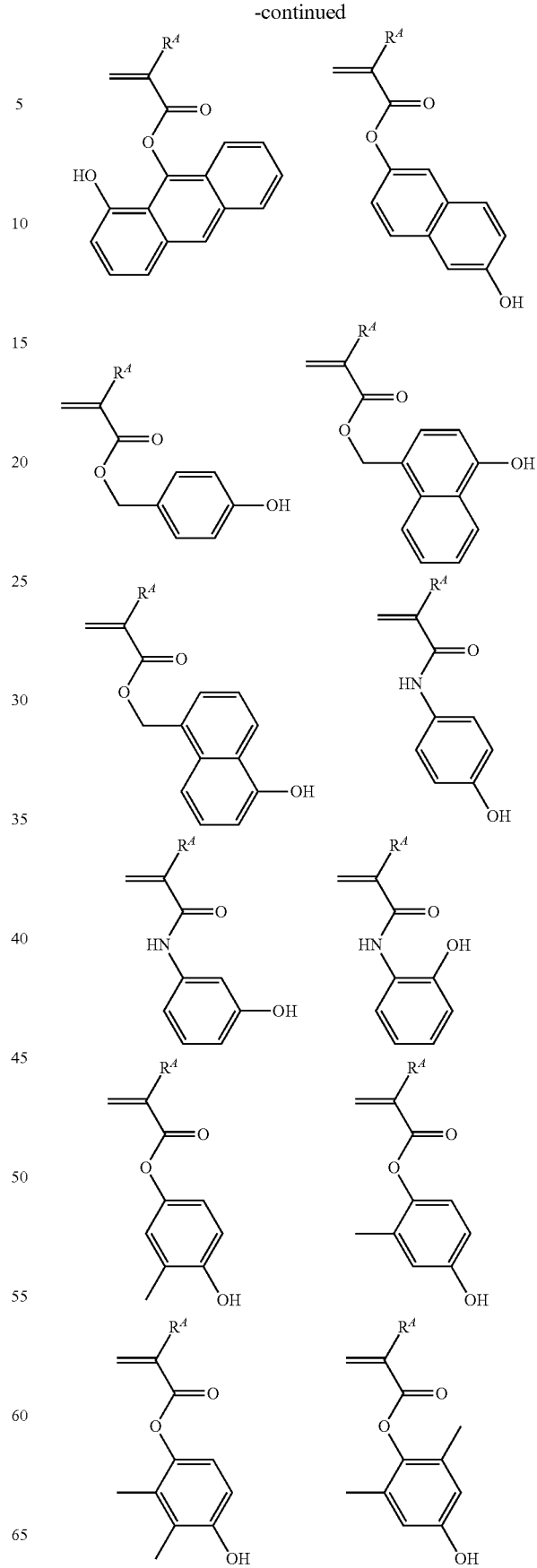

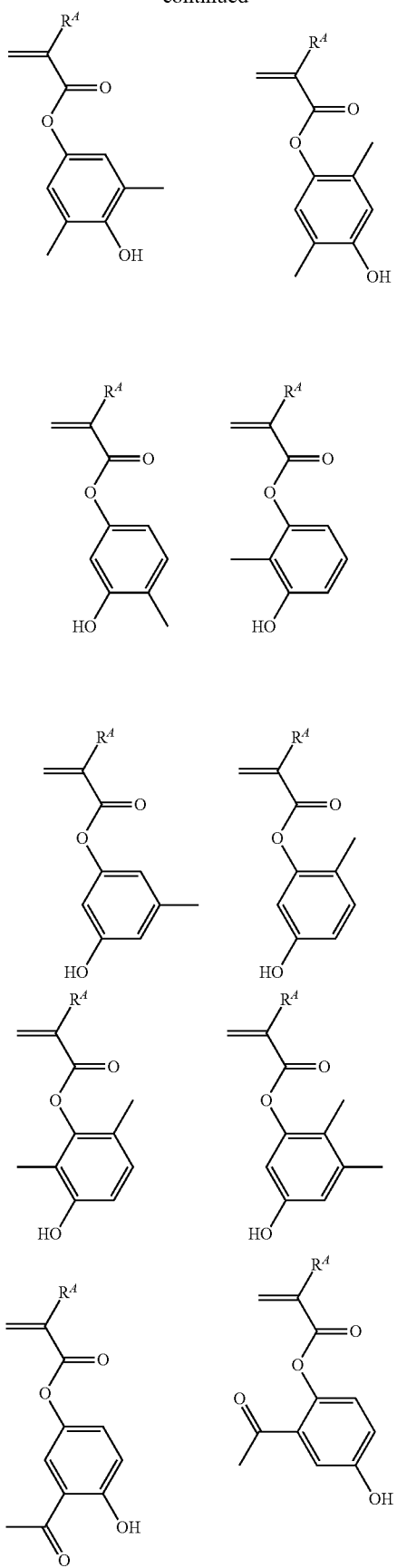
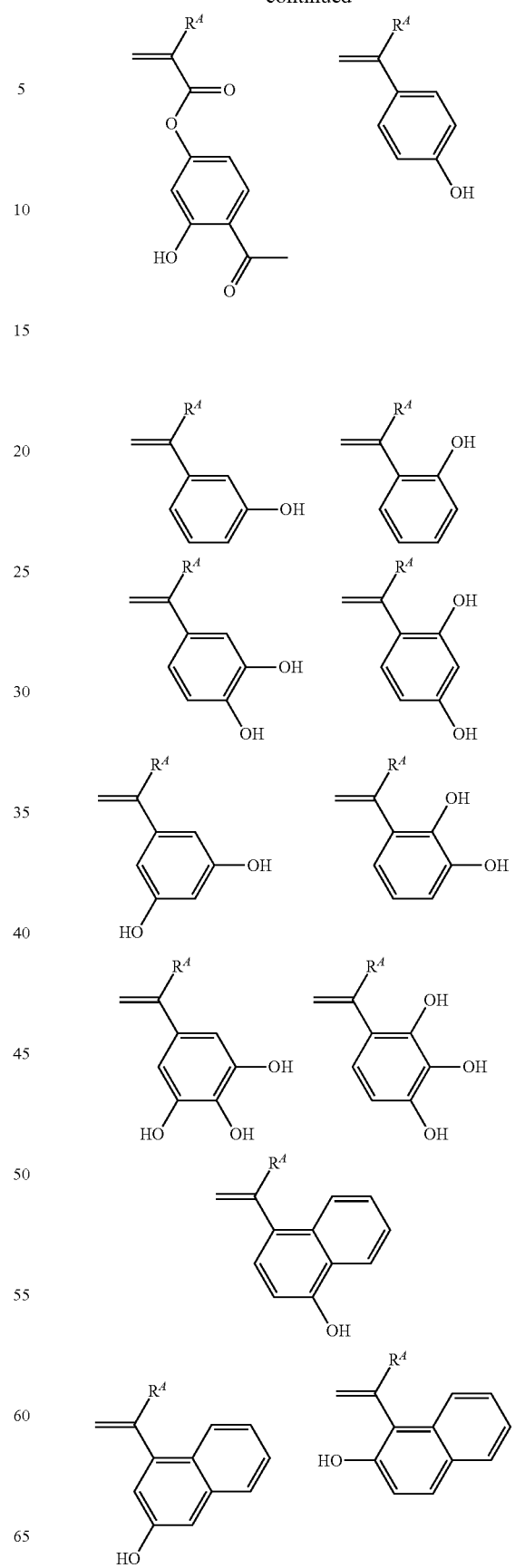

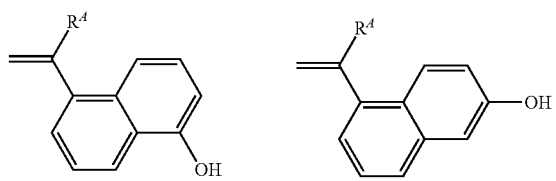
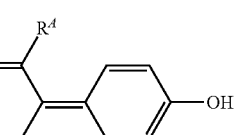
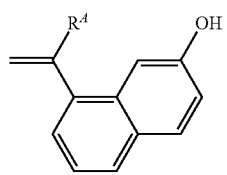
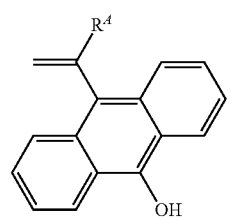
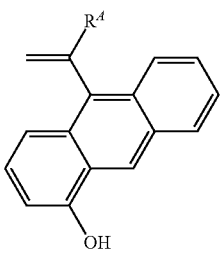
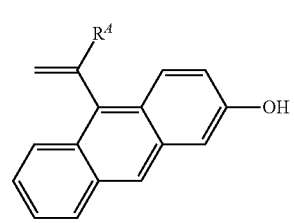
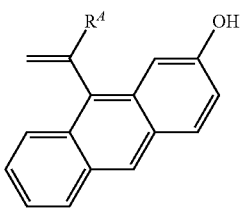
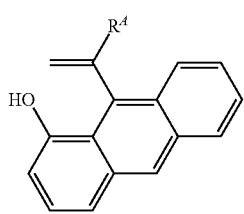
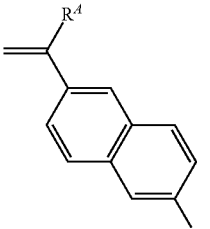

The recurring units (D) are units having a carboxyl group, for example, units derived from monomers having the following formulae. $R^A$ is as defined above.

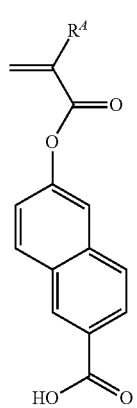
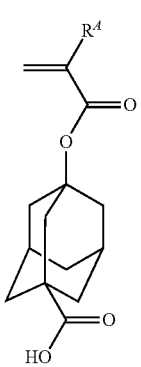

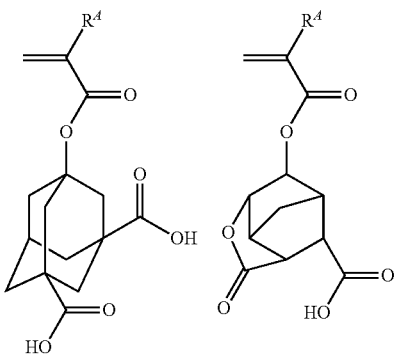

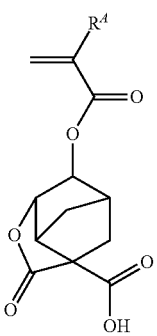

The recurring units (E) are units containing a lactone skeleton, sultone skeleton, carbonate skeleton, cyclic ether skeleton, acid anhydride skeleton, alcoholic hydroxyl group, alkoxycarbonyl group, sulfonamide group or carbamoyl group. Examples of the monomer from which recurring units (E) are derived are shown below, but not limited thereto. $R^A$ is as defined above.

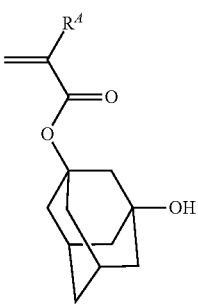
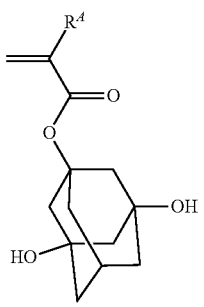

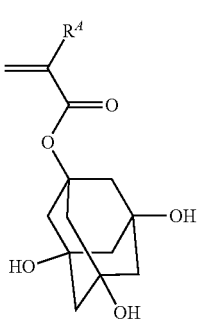
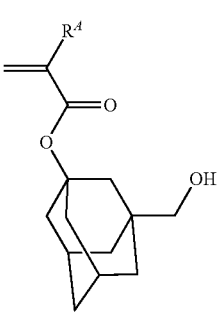

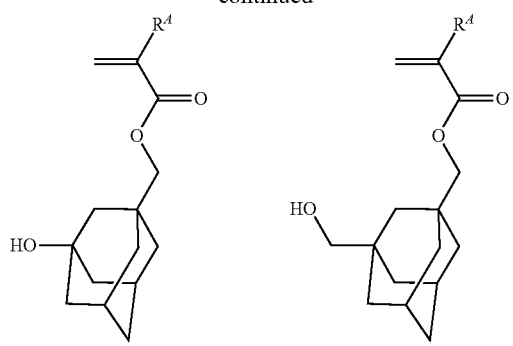
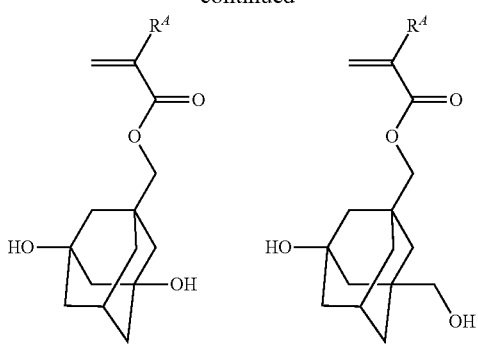
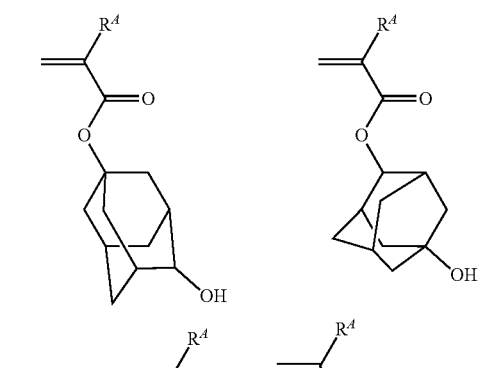
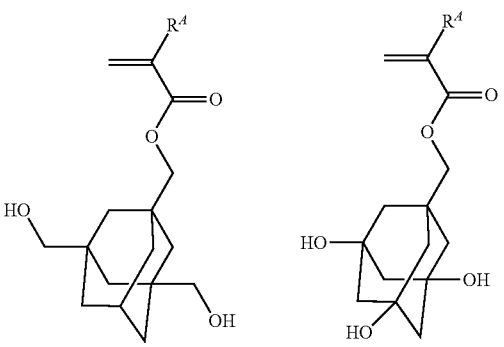
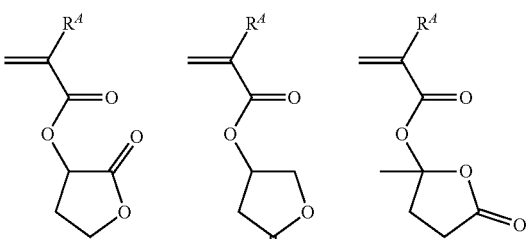
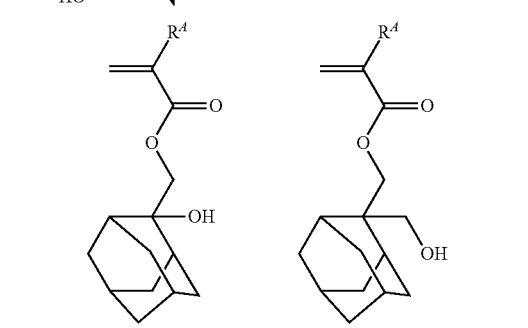
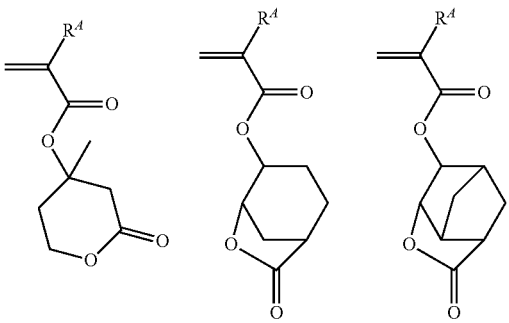
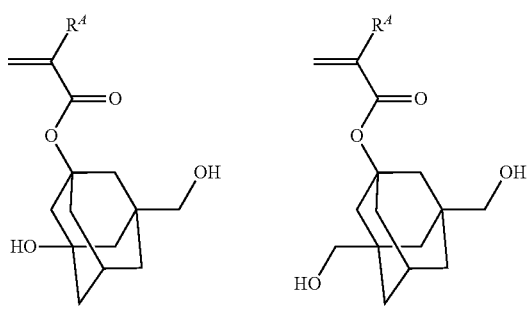

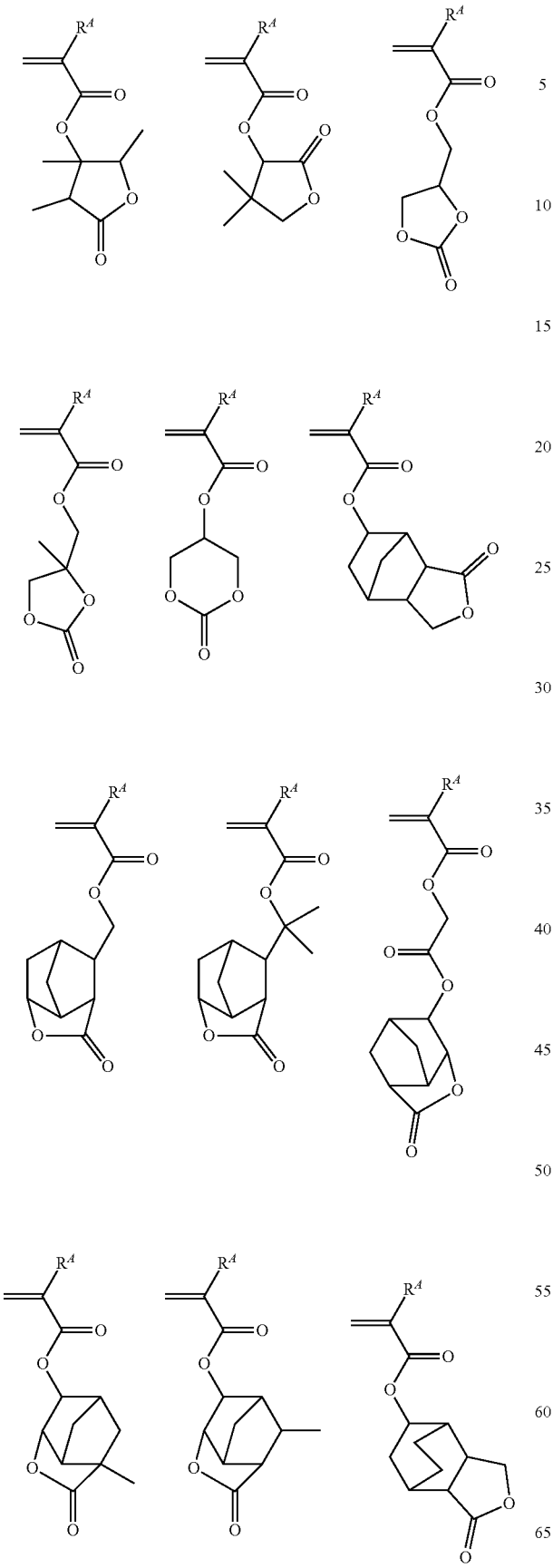
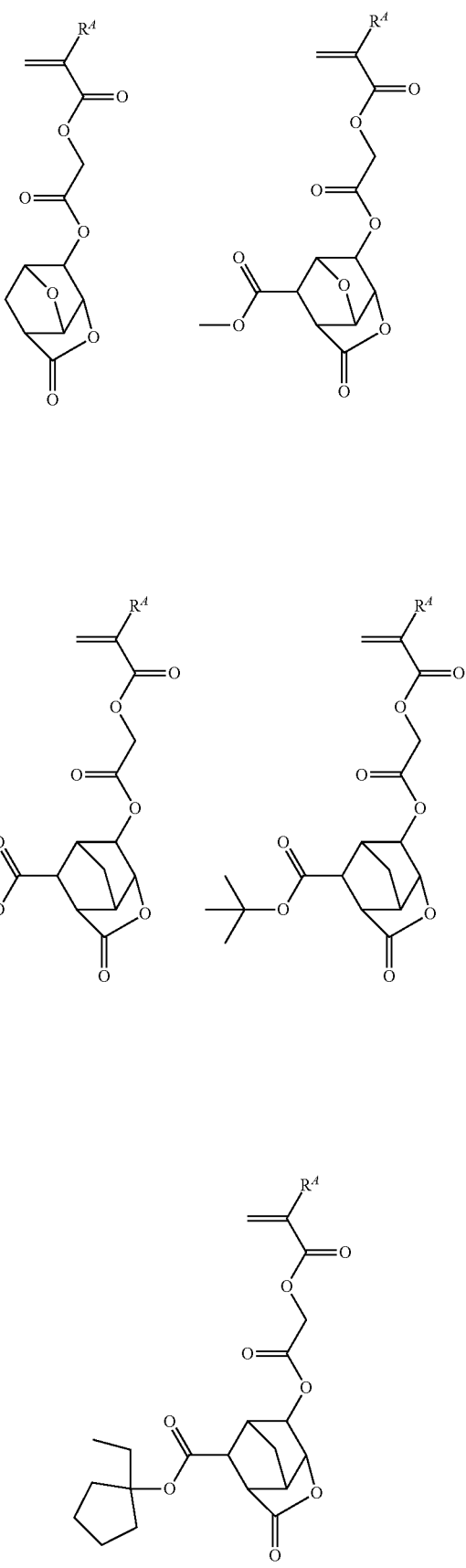

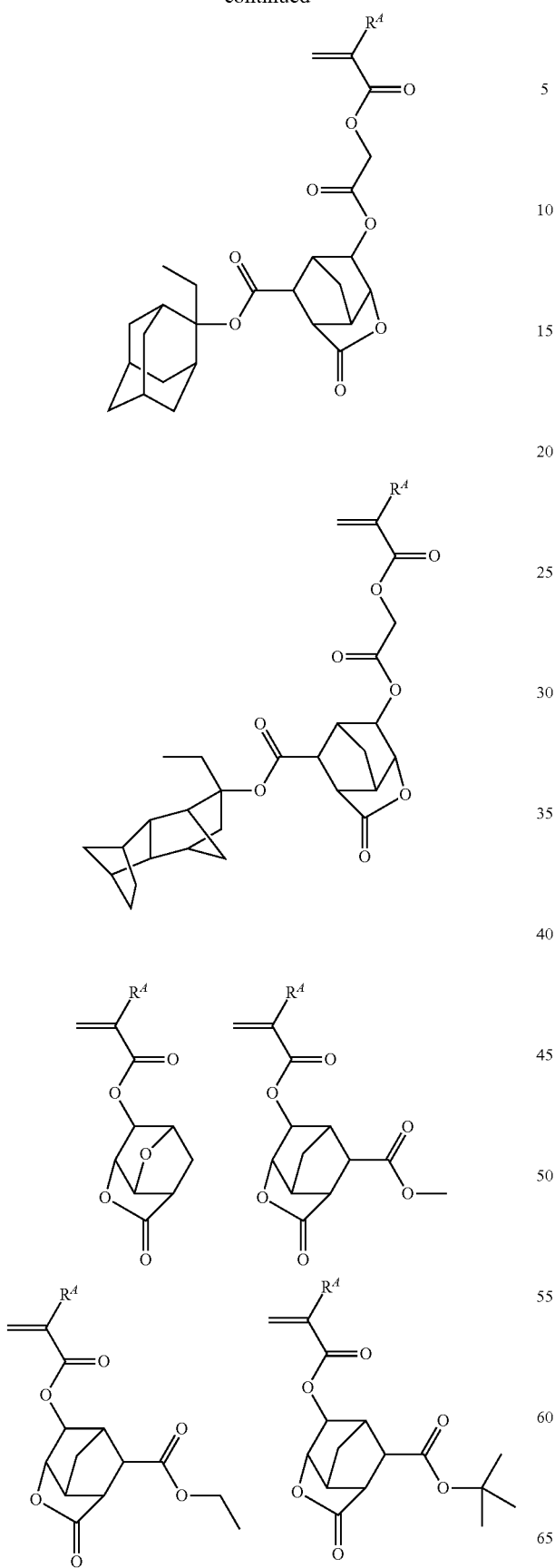

101
-continued
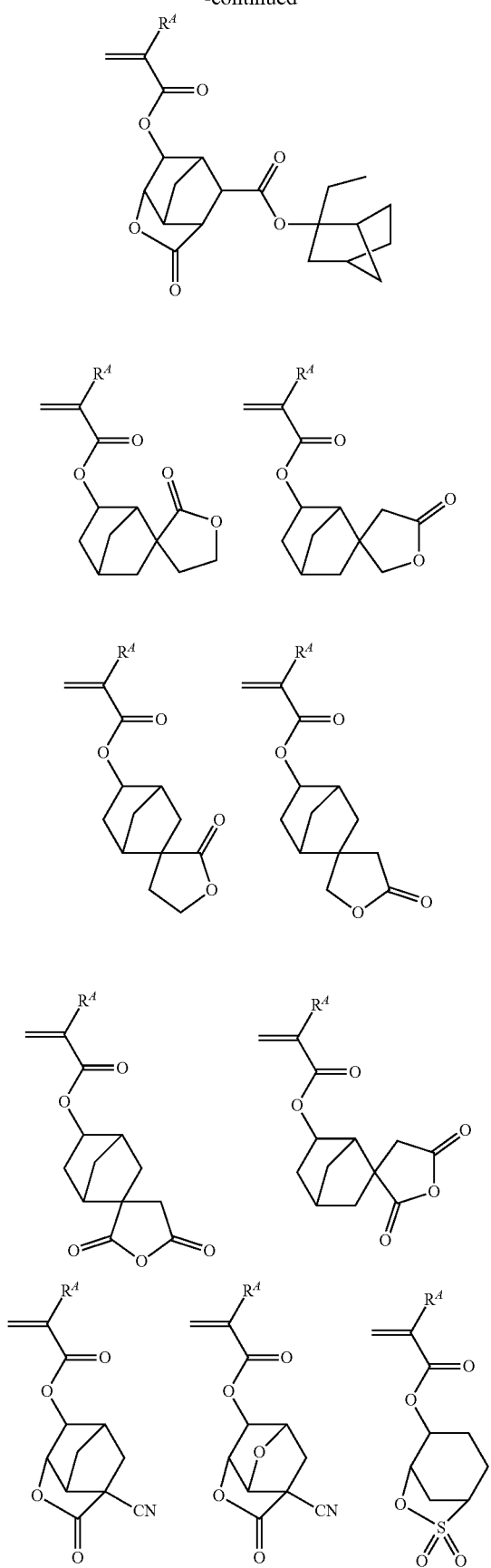
102
-continued
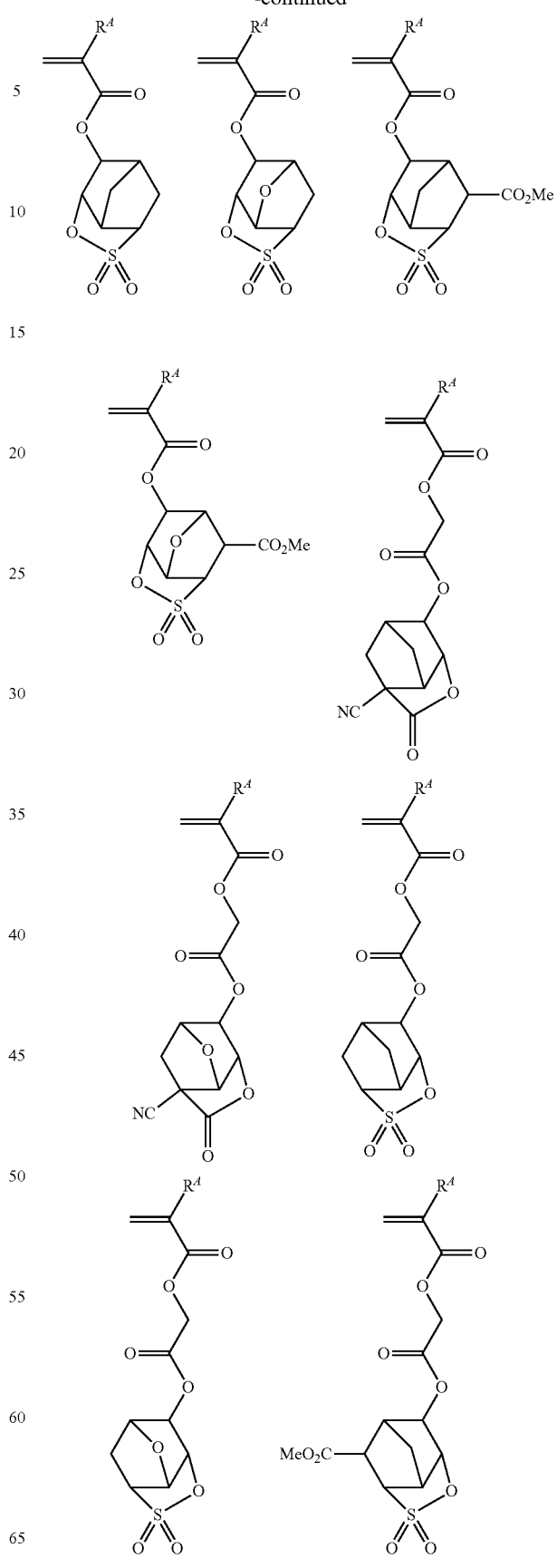

having the formula (F4), all defined below. These recurring units are also referred to as recurring units (F1) to (F4), respectively.

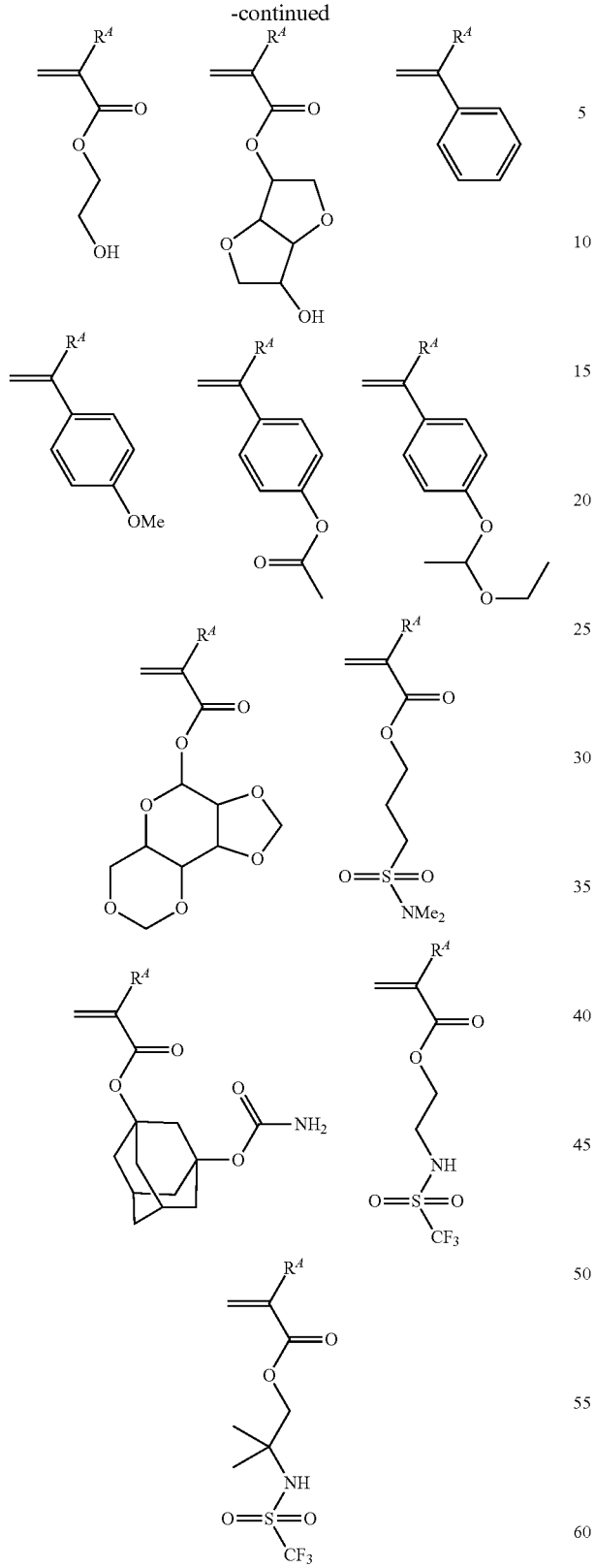

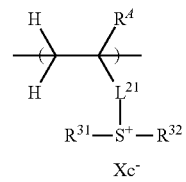

(F1)

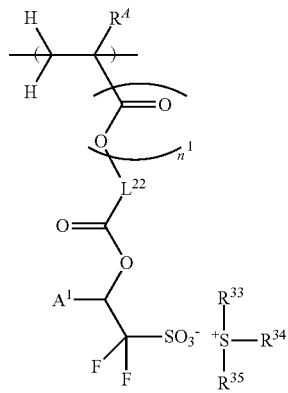

(F2)

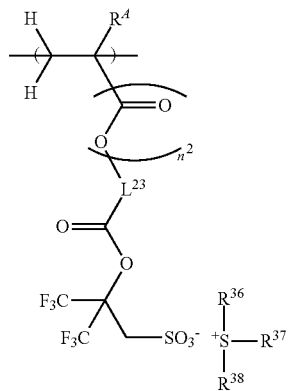

(F3)

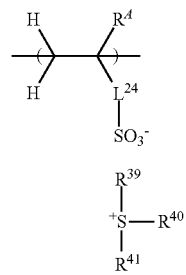

(F4)

The base polymer may further comprise recurring units of at least one type selected from recurring units having the formula (F1), recurring units having the formula (F2), recurring units having the formula (F3), and recurring units In formulae (F1) to (F4), $R^A$ is hydrogen, fluorine, methyl or trifluoromethyl. $L^{21}$ is a single bond, phenylene, —O-$L^{21A}$-, —C(=O)—O-$L^{21A}$-, or —C(=O)—NH-$L^{21A}$-, wherein $L^{21A}$ is a $C_1$-$C_{20}$ alkanediyl, $C_2$-$C_{20}$ alkenediyl, or phenylene group which may contain a heteroatom. $L^{22}$ and $L^{23}$ are each independently a single bond or a $C_1$-$C_{20}$ divalent hydrocarbon group which may contain a heteroatom. $L^{24}$ is a single bond, methylene, ethylene, phenylene, fluorinated phenylene, —O-$L^{24A}$-, —C(=O)—O-$L^{24A}$-, or —C(=O)—NH-$L^{24A}$-, wherein $L^{24A}$ is an optionally substituted phenylene group.

The alkanediyl group $L^{21A}$ may be straight, branched or cyclic and examples thereof include methylene, ethane-1,1-diyl, ethane-1,2-diyl, propane-1,2-diyl, propane-2,2-diyl, propane-1,3-diyl, 2-methylpropane-1,3-diyl, butane-1,3-diyl, butane-2,3-diyl, butane-1,4-diyl, pentane-1,3-diyl, pentane-1,4-diyl, 2,2-dimethylpropane-1,3-diyl, pentane-1,5-diyl, hexane-1,6-diyl, cyclopentane-1,2-diyl, cyclopentane-1,3-diyl, and cyclohexane-1,4-diyl. The alkenediyl group $L^{21A}$ may be straight, branched or cyclic and examples thereof include ethene-1,2-diyl, 1-propene-1,3-diyl, 2-butene-1,4-diyl, 1-methyl-1-butene-1,4-diyl, and 2-cyclohexene-1,4-diyl.

The divalent hydrocarbon groups $L^{22}$ and $L^{23}$ may be straight, branched or cyclic and examples thereof include alkanediyl and alkenediyl groups as exemplified above.

In formulae (F1) to (F4), $R^{31}$ to $R^{41}$ are each independently a $C_1$-$C_{20}$ monovalent hydrocarbon group which may contain a heteroatom. The monovalent hydrocarbon group may be straight, branched or cyclic. Examples thereof include, but are not limited to, alkyl groups such as methyl, ethyl, n-propyl, isopropyl, n-butyl, and tert-butyl; monovalent saturated alicyclic hydrocarbon groups such as cyclopropyl, cyclopentyl, cyclohexyl, cyclopropylmethyl, 4-methylcyclohexyl, cyclohexylmethyl, norbornyl, and adamantyl: alkenyl groups such as vinyl, allyl, propenyl, butenyl and hexenyl; monovalent unsaturated alicyclic hydrocarbon groups such as cyclohexenyl; aryl groups such as phenyl and naphthyl;

heteroaryl groups such as thienyl; and aralkyl groups such as benzyl, 1-phenylethyl and 2-phenylethyl. Of these, aryl groups are preferred. In these groups, some hydrogen may be substituted by a moiety containing a heteroatom such as oxygen, sulfur, nitrogen or halogen, or some carbon may be replaced by a moiety containing a heteroatom such as oxygen, sulfur or nitrogen, so that the group may contain a hydroxyl, cyano, carbonyl, ether bond, ester bond, sulfonic acid ester bond, carbonate bond, lactone ring, sultone ring, carboxylic anhydride or haloalkyl moiety.

Any two of $L^{21}$, $R^{31}$ and $R^{32}$ may bond together to form a ring with the sulfur atom to which they are attached. Any two of $R^{33}$, $R^{34}$ and $R^{35}$, any two of $R^{36}$, $R^{37}$ and $R^{38}$, or any two of $R^{39}$, $R^{40}$ and $R^{41}$ may bond together to form a ring with the sulfur atom to which they are attached.

In formula (F1), $Xc^-$ is a non-nucleophilic counter ion. Examples of the non-nucleophilic counter ion include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imide ions such as bis(trifluoromethylsulfonyl)imide, bis(perfluoroethylsulfonyl) imide and bis(perfluorobutylsulfonyl)imide; methide ions such as tris(trifluoromethylsulfonyl)methide and tris(perfluoroethylsulfonyl)methide.

Also included are anions having the formulae (F1a) and (F1b).

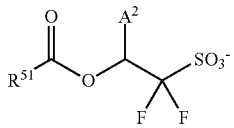

(F1a)

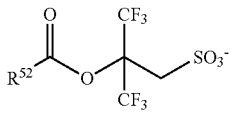

(F1b)

In formulae (F1a) and (F1b), $R^{51}$ and $R^{52}$ are each independently a $C_1$-$C_{40}$ monovalent hydrocarbon group which may contain a heteroatom. $A^2$ is hydrogen or trifluoromethyl. The $C_1$-$C_{40}$ monovalent hydrocarbon group may be straight, branched or cyclic.

In formula (F2), $A^1$ is hydrogen or trifluoromethyl. Exemplary structures of the anion in formula (F2) include those described in JP-A 2014-177407, paragraphs [0021]-[0026]. Exemplary structures of the anion in formula (F2) wherein $A^1$ is hydrogen include those described in JP-A 2010-116550, paragraphs [0021]400281 Exemplary to structures of the anion in formula (F2) wherein $A^1$ is trifluoromethyl include those described in JP-A 2010-077404, paragraphs [0021]-[0027].

Exemplary structures of the anion in formula (F3) include those examples of formula (F2) wherein —$CH(A^1)CF_2SO_3^-$ is replaced by —$C(CF_3)_2CH_2SO_3^-$.

Preferred examples of the anion in the monomer from which recurring units (F2) are derived are shown below, but not limited thereto. Herein $A^1$ is as defined above.

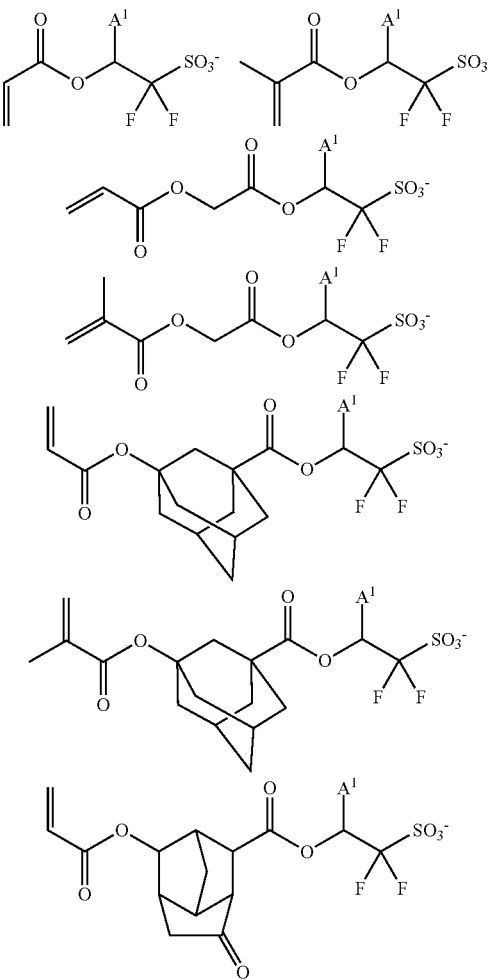

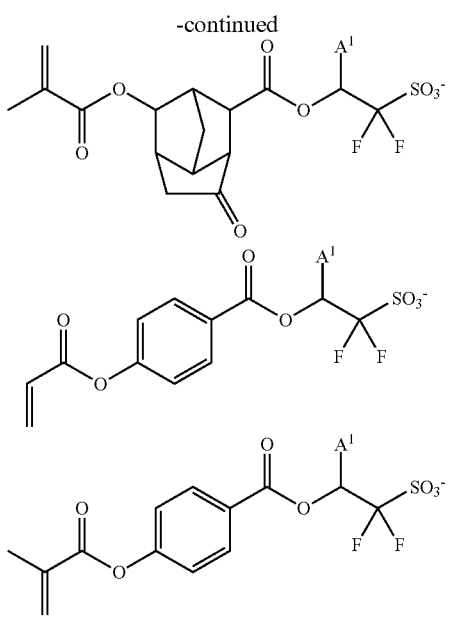
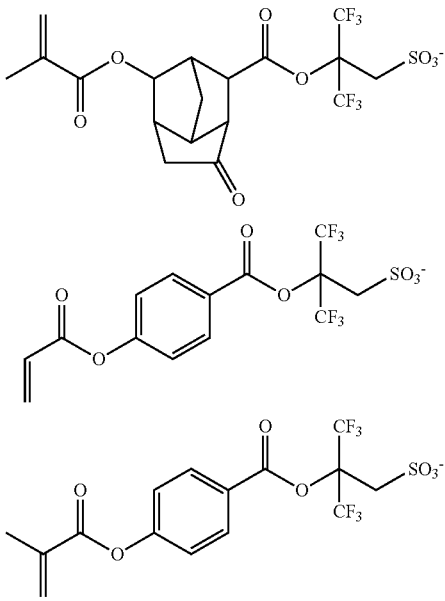
Preferred examples of the anion in the monomer from which recurring units (F3) are derived are shown below, but not limited thereto.
Examples of the sulfonium cation in formulae (F2) to (F4) are shown below, but not limited thereto.
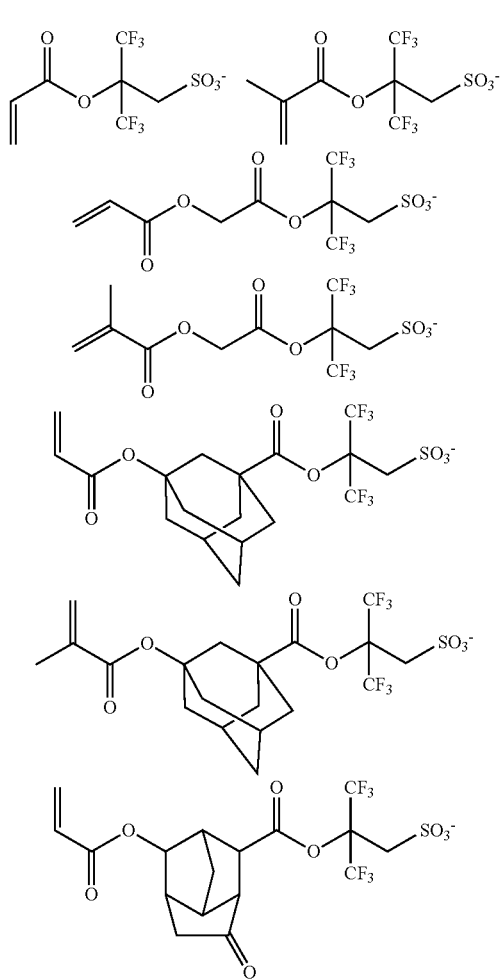
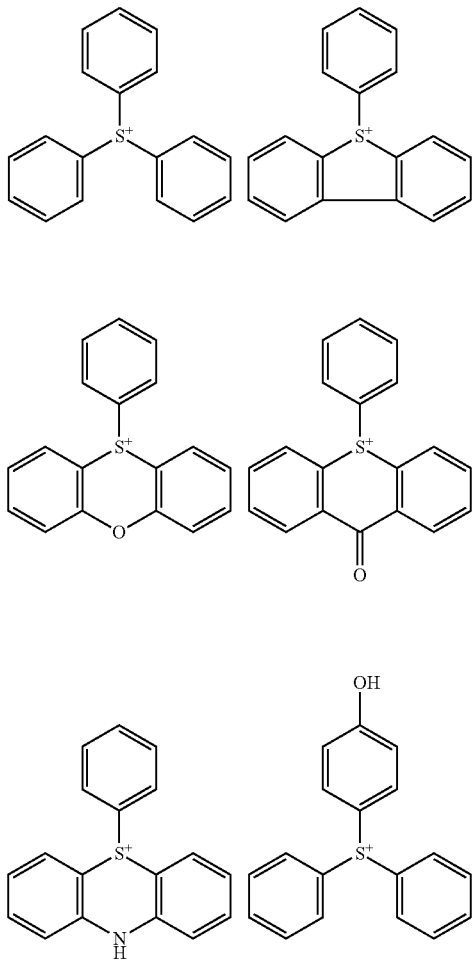

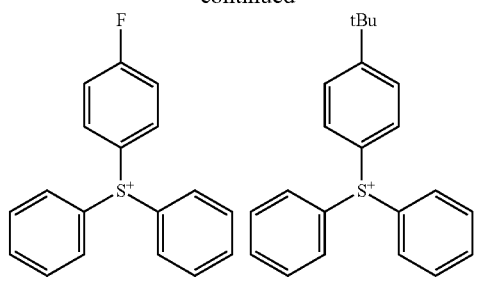
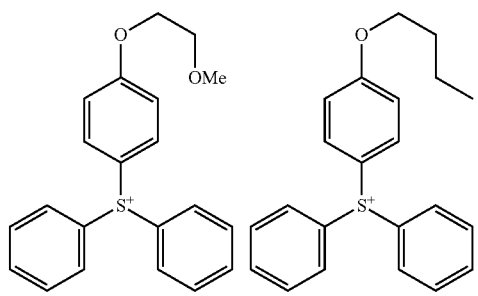
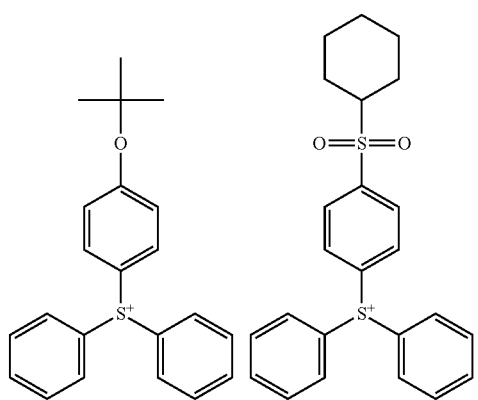
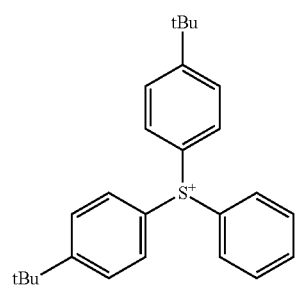
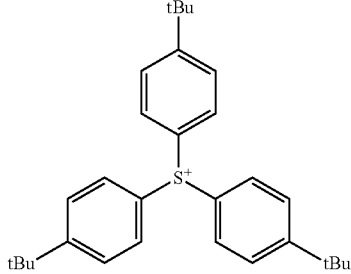
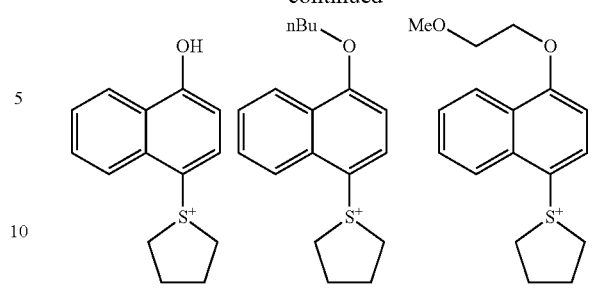
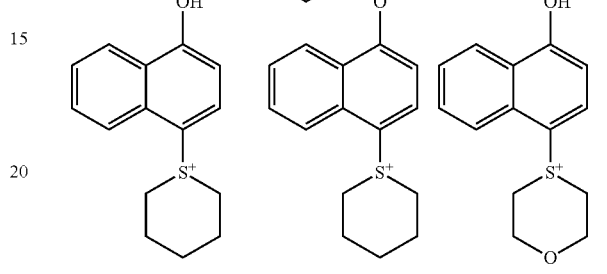
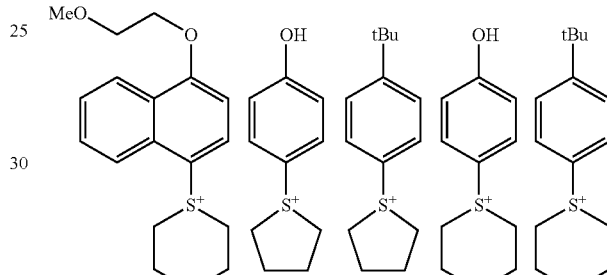
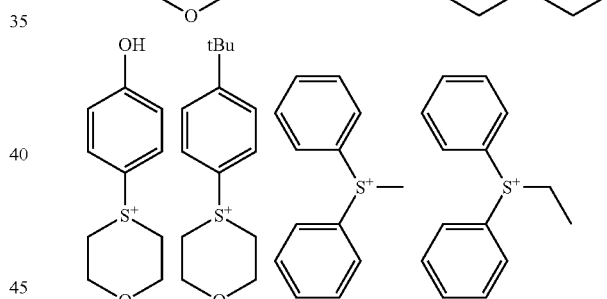
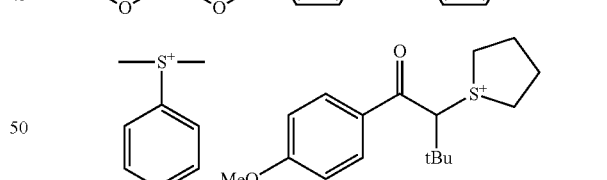
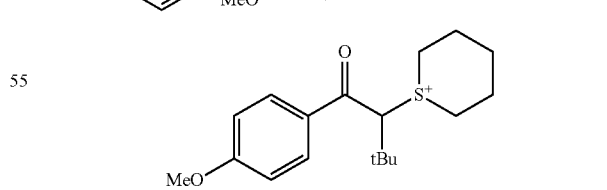
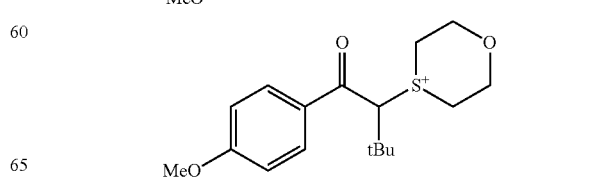

-continued

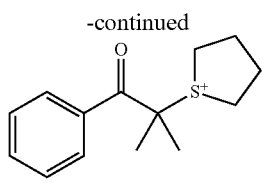

The recurring units (F1) to (F4) have an acid generator function. The base polymer comprising the same also functions as an acid generator.

In addition to the foregoing units, the base polymer may further comprise recurring units derived from other monomers having a carbon-carbon double bond, for example, substituted acrylates such as methyl methacrylate, methyl crotonate, dimethyl maleate, and dimethyl itaconate, unsaturated carboxylic acids such as maleic acid, fumaric acid, and itaconic acid, cyclic olefins such as norbornene, norbornene derivatives, tetracyclo[4.4.0.1$^{2,5}$.1$7^{7,10}$]dodecene derivatives, unsaturated acid anhydrides such as itaconic anhydride, α-methylene-γ-butyrolactone, indene, acenaphthylene and the like.

While the base polymer comprises recurring units derived from monomers, the molar fractions of respective units preferably fall in the following range (mol %), but are not limited thereto:
(I) 1 to 98 mol %, more preferably 1 to 80 mol %, even more preferably 10 to 70 mol % of recurring units (A1) and/or (A2),
(II) 2 to 99 mol %, more preferably 2 to 80 mol %, even more preferably 2 to 70 mol % of recurring units of at least one type selected from units (B) to (E),
(III) 0 to 50 mol %, more preferably 0 to 30 mol %, and even more preferably 0 to 20 mol % of recurring units of at least one type selected from units (F1) to (F4), and
(IV) 0 to 97 mol %, more preferably 0 to 70 mol %, and even more preferably 0 to 50 mol % of other reaming units of at least one type.

The base polymer should preferably have a Mw of 1,000 to 500,000, more preferably 3,000 to 100,000. A Mw within the range ensures satisfactory etching resistance, a contrast before and after exposure, and satisfactory resolution. As used herein, Mw is measured versus polystyrene standards by GPC using tetrahydrofuran (THF) or N,N-dimethylformamide (DMF) solvent.

If a polymer has a wide molecular weight distribution or dispersity (Mw/Mn), which indicates the presence of lower and higher molecular weight polymer fractions, there is a possibility that foreign matter is left on the pattern or the pattern profile is degraded. The influences of Mw and Mw/Mn become stronger as the pattern rule becomes finer. Therefore, the polymer should preferably have a narrow dispersity (Mw/Mn) of 1 to 3, more preferably 1 to 2.5 in order to provide a resist composition suitable for micropatterning to a small feature size.

The base polymer may be used alone or in admixture.

The method of synthesizing the polymer involves the steps of feeding a solution of monomers providing any desired recurring units to a reactor and effecting polymerization reaction in the reactor.

For example, the polymer is synthesized by dissolving monomers in a solvent, adding a polymerization initiator to the monomer solution, and heating for polymerization. Examples of the solvent which can be used for polymerization include toluene, benzene, THF, diethyl ether, dioxane, cyclohexane, cyclopentane, methyl ethyl ketone (MEK), propylene glycol monomethyl ether acetate (PGMEA), and γ-butyrolactone (GBL). to Examples of the polymerization initiator used herein include 2,2'-azobisisobutyronitrile (AIBN), 2,2'-azobis(2,4-dimethylvaleronitrile), dimethyl 2,2-azobis(2-methylpropionate), 1,1'-azobis(1-acetoxy-1-phenylethane), benzoyl peroxide, and lauroyl peroxide. The initiator is preferably added in an amount of 0.01 to 25 mol % based on the total of monomers to be polymerized. Preferably the reaction temperature is 50 to 150° C., more preferably 60 to 100° C. The reaction time is preferably 2 to 24 hours, more preferably 2 to 12 hours in view of production efficiency.

The polymerization initiator may be fed to the reactor either by adding the initiator to the monomer solution and feeding the solution to the reactor, or by preparing an initiator solution separate from the monomer solution and feeding the initiator solution and the monomer solution independently to the reactor. Since there is a possibility that in the standby duration, the initiator generates a radical which triggers polymerization reaction to form a ultra-high-molecular-weight polymer, it is preferred from the standpoint of quality control to prepare and add dropwise the monomer solution and the initiator solution separately. The acid labile group that has been incorporated in the monomer may be kept as such, or polymerization may be followed by protection or partial protection. During the polymer synthesis, any known chain transfer agent such as dodecyl mercaptan or 2-mercaptoethanol may be added for molecular weight control purpose. The amount of chain transfer agent added is preferably 0.01 to 20 mol % based on the total of monomers to be polymerized.

When hydroxystyrene or hydroxyvinylnaphthalene is copolymerized, one method is by dissolving hydroxystyrene or hydroxyvinylnaphthalene and another monomer in an organic solvent, adding a radical polymerization initiator thereto, and heating the solution for polymerization. In an alternative method, acetoxystyrene or acetoxyvinylnaphthalene is used instead, and after polymerization, the acetoxy group is deprotected by alkaline hydrolysis, for thereby converting the polymer product to polyhydroxystyrene or polyhydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The amounts of monomers in the monomer solution may be determined appropriate so as to provide the preferred fractions of recurring units.

It is now described how to use the polymer obtained by the above preparation method. The reaction solution resulting from polymerization reaction may be used as the final product. Alternatively, the polymer may be recovered in powder form through a purifying step such as re-precipitation step of adding the reaction solution to a poor solvent and letting the polymer precipitate as powder, after which the polymer powder is used as the final product. It is preferred from the standpoints of operation efficiency and consistent quality to handle a polymer solution which is obtained by dissolving the powder polymer resulting from the purifying step in a solvent, as the final product. The solvents which can be used herein are described in JP-A 2008-111103, paragraphs [0144]-[0145] (U.S. Pat. No. 7,537,880). Exemplary solvents include ketones such as cyclohexanone and methyl-2-n-pentyl ketone; alcohols such as 3-methoxybutanol, 3-methyl-3-methoxybutanol, 1-methoxy-2-propanol, 1-ethoxy-2-propanol, and diacetone alcohol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, tert-butyl acetate, tert-butyl propionate, and propylene glycol mono-tert-butyl ether acetate; lactones such as γ-butyrolactone (GBL); and high-boiling alcohols such as diethylene glycol, propylene glycol, glycerol, 1,4-butanediol, and 1,3-butanediol, which may be used alone or in admixture.

The polymer solution preferably has a polymer concentration of 0.01 to 30% by weight, more preferably 0.1 to 20% by weight.

Prior to use, the reaction solution or polymer solution is preferably filtered through a filter. Filtration is effective for consistent quality because foreign particles and gel which can cause defects are removed.

Suitable materials of which the filter is made include fluorocarbon, cellulose, nylon, polyester, and hydrocarbon base materials. Preferred for the filtration of a resist composition are filters made of fluorocarbons commonly known as Teflon®, hydrocarbons such as polyethylene and polypropylene, and nylon. While the pore size of the filter may be selected appropriate to comply with the desired cleanness, the filter preferably has a pore size of up to 100 nm, more preferably up to 20 nm. A single filter may be used or a plurality of filters may be used in combination. Although the filtering method may be single pass of the solution, preferably the filtering step is repeated by flowing the solution in a circulating manner. In the polymer preparation process, the filtering step may be carried out any times, in any order and in any stage. The reaction solution as polymerized or the polymer solution may be filtered, preferably both are filtered.

Organic Solvent

Examples of the organic solvent used in the resist composition include ketones such as cyclohexanone, cyclopentanone, methyl-2-n-pentyl ketone, and diacetone alcohol (DAA); alcohols such as 3-methoxybutanol, 3-methyl-3-methoxybutanol, 1-methoxy-2-propanol, and 1-ethoxy-2-propanol; ethers such as propylene glycol monomethyl ether (PGME), ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, methyl lactate, ethyl lactate, n-butyl lactate, ethyl pyruvate, butyl acetate, methyl 3-methoxypropionate, ethyl 3-ethoxypropionate, tert-butyl acetate, tert-butyl propionate, propylene glycol mono-tert-butyl ether acetate, methyl 2-hydroxyisobutyrate, isopropyl 2-hydroxyisobutyrate, isobutyl 2-hydroxyisobutyrate, and n-butyl 2-hydroxyisobutyrate; and lactones such as γ-butyrolactone (GBL), which may be used alone or in admixture.

In the resist composition, the organic solvent is preferably used in an amount of 50 to 10,000 parts, and more preferably 100 to 5,000 parts by weight per 80 parts by weight of the base polymer.

Quencher

The resist composition may further comprises a quencher or acid diffusion regulator. As used herein, the quencher refers to a compound capable of trapping the acid generated by the PAG in the resist composition to prevent the acid from diffusing to the unexposed region for thereby forming the desired pattern.

Examples of the quencher include primary, secondary, and tertiary amine compounds, specifically amine compounds having a hydroxyl group, ether bond, ester bond, lactone ring, cyano group or sulfonate bond as described in JP-A 2008-111103, paragraphs [0146]-[0164], and compounds having a carbamate group as described in JP 3790649.

Onium salts having the formulae (xa) and (xb) are also useful as the quencher.

In formula (xa), $R^{q1}$ is hydrogen or a $C_1$-$C_{40}$ monovalent hydrocarbon group which may contain a heteroatom, exclusive of the hydrocarbon group in which the hydrogen atoms bonded to the carbon atoms at α- and β-positions of the sulfone group are substituted by fluorine or fluoroalkyl. In formula (xb), $R^{q2}$ is hydrogen or a $C_1$-$C_{40}$ monovalent hydrocarbon group which may contain a heteroatom.

Examples of the monovalent hydrocarbon group $R^{q1}$ include methyl, ethyl, propyl, isopropyl, n-butyl, sec-butyl, tert-butyl, tert-pentyl, n-pentyl, n-hexyl, n-octyl, n-nonyl, n-decyl, cyclopentyl, cyclohexyl, 2-ethylhexyl, cyclopentylmethyl, cyclopentylethyl, cyclopentylbutyl, cyclohexylmethyl, cyclohexylethyl, cyclohexylbutyl, norbornyl, oxanorbornyl, tricyclo[5.2.1.0$^{2.6}$]decanyl, adamantyl, phenyl, naphthyl, and anthracenyl. In these groups, some hydrogen may be substituted by a moiety containing a heteroatom such as oxygen, sulfur, nitrogen or halogen, and a moiety containing a heteroatom such as oxygen, sulfur or nitrogen may intervene between carbon atoms, so that the group may contain a hydroxyl moiety, cyano moiety, carbonyl moiety, ether bond, ester bond, sulfonate bond, carbonate bond, lactone ring, sultone ring, carboxylic anhydride, or haloallcyl moiety.

Examples of the monovalent hydrocarbon group $R^{q2}$ are as exemplified above for $R^{q1}$. Also included are fluorinated alkyl groups such as trifluoromethyl and trifluoroethyl, and fluorinated aryl groups such as pentafluorophenyl and 4-trifluoromethylphenyl.

Illustrative structures of the anion in formula (xa) are shown below, but not limited thereto.

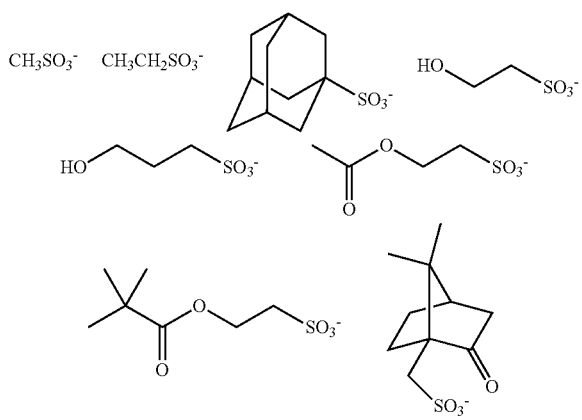

115
-continued
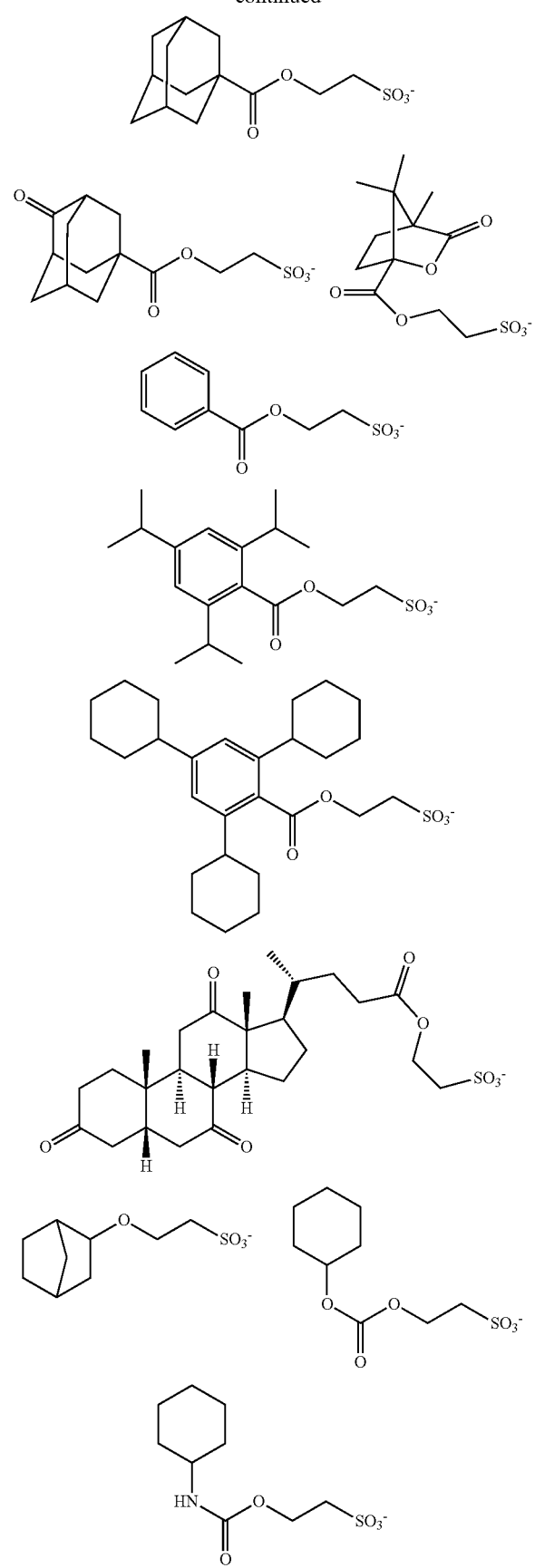
116
-continued
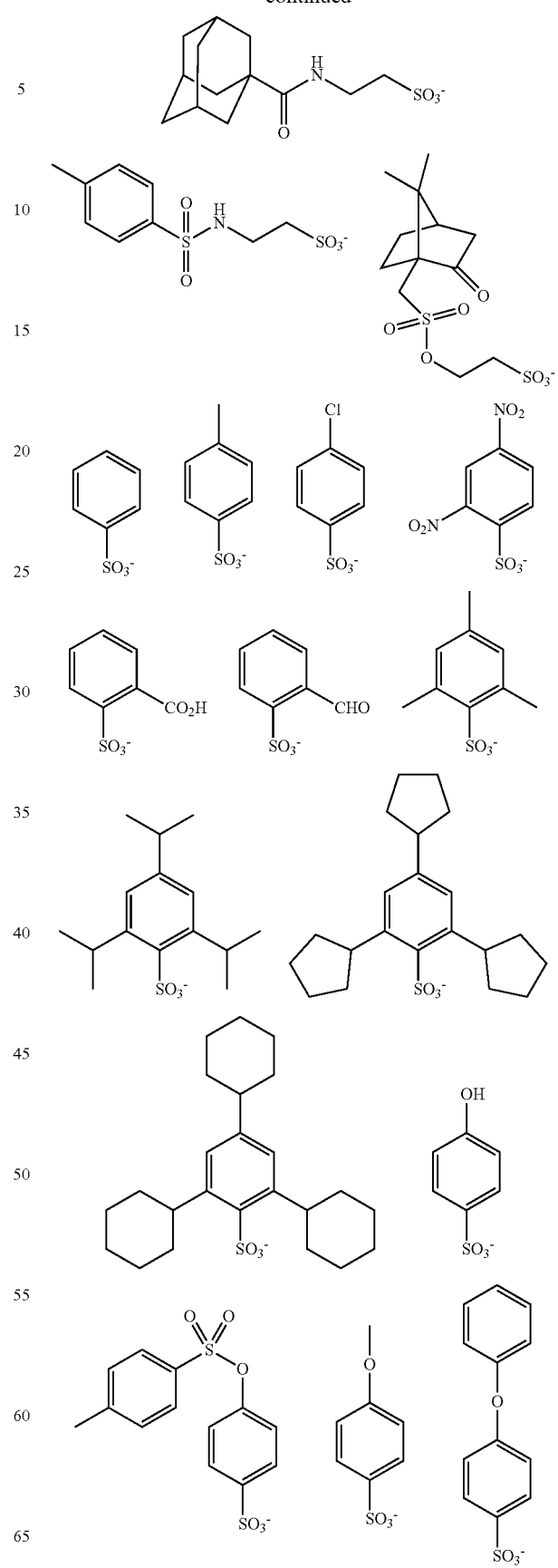

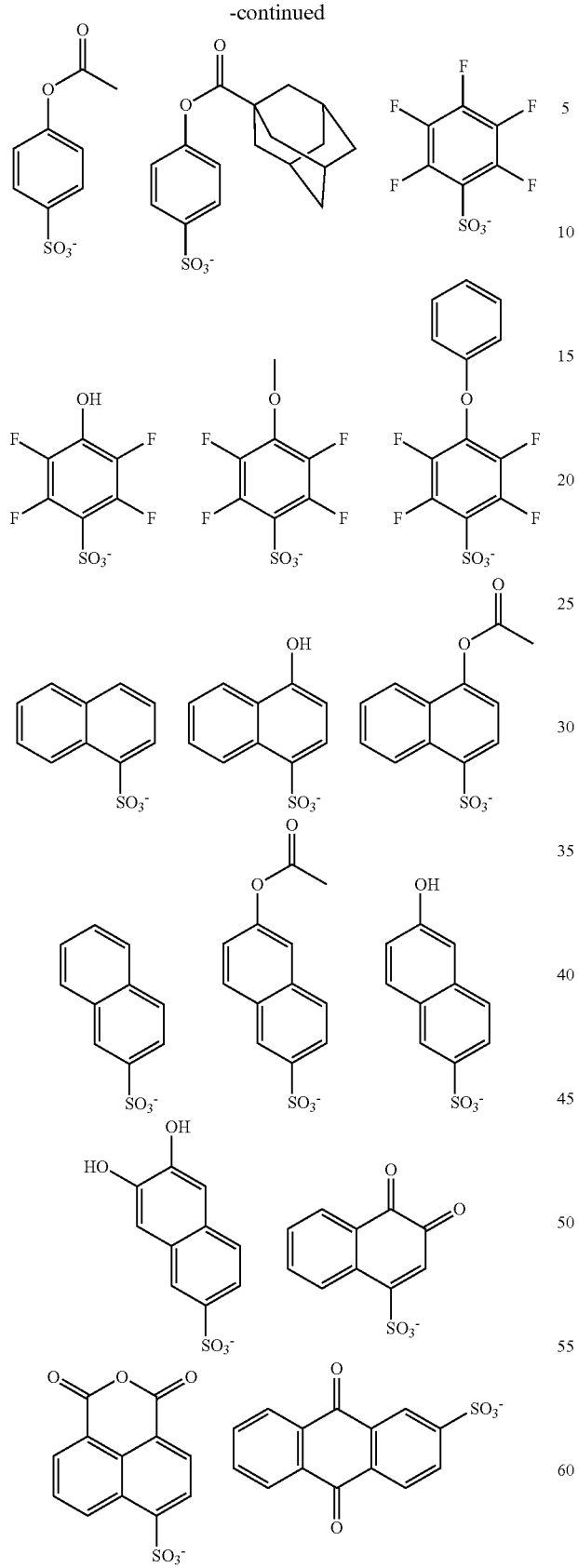
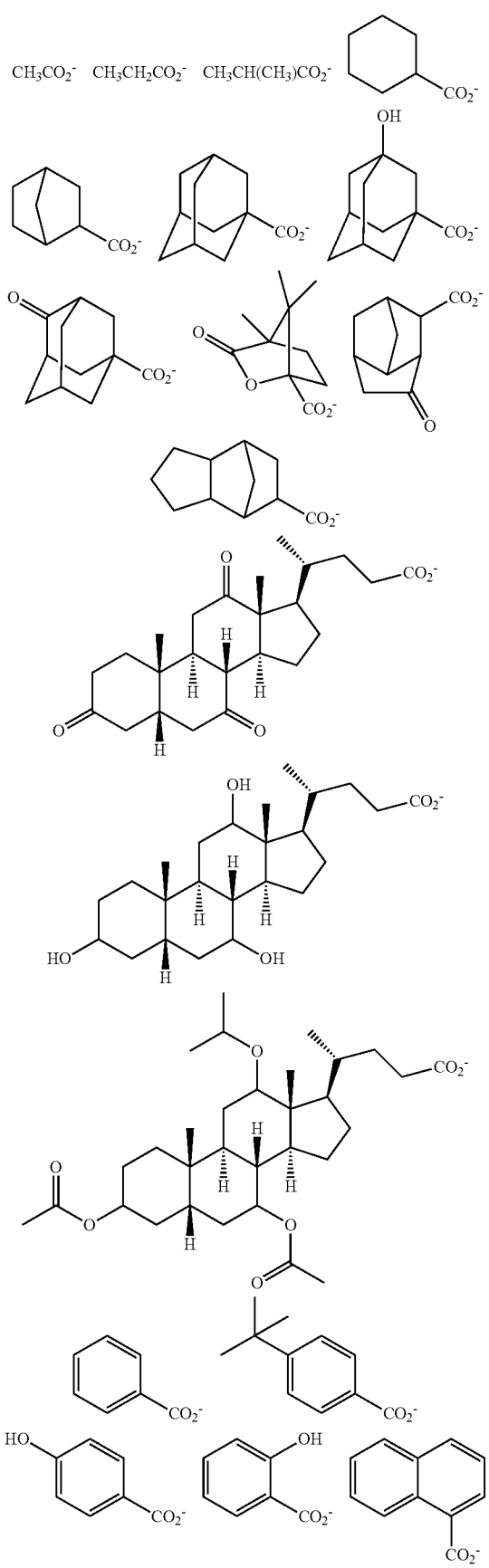
Illustrative structures of the anion in formula (xb) are shown below, but not limited thereto.

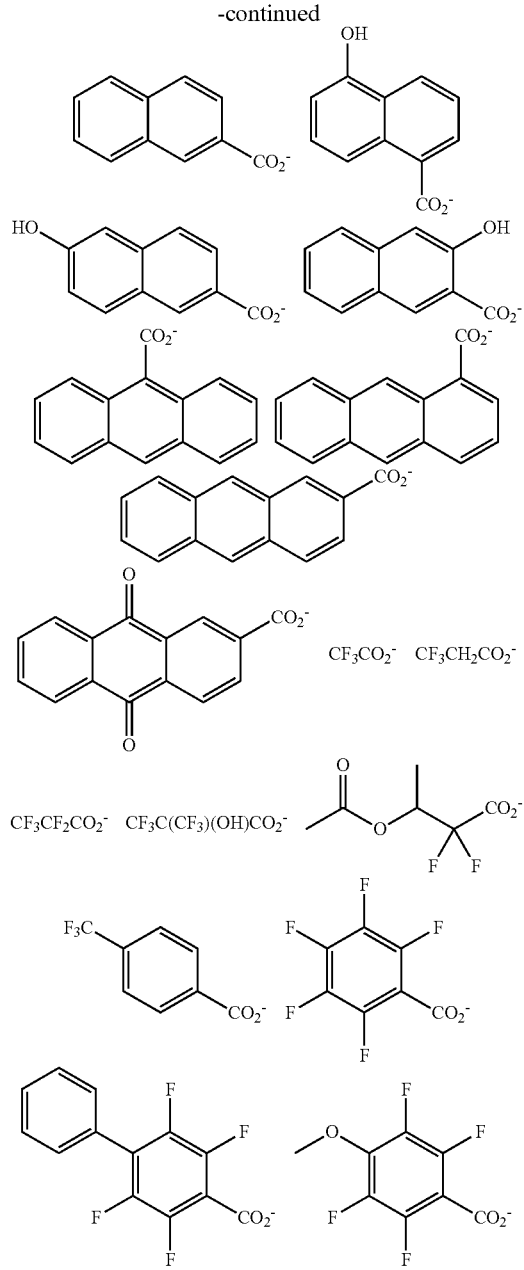

In formulae (xa) and (xb), Me is an onium cation having the formula (xc), (xd) or (xe).

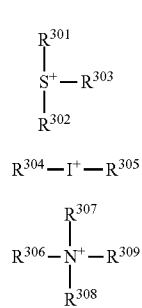

In formulae (xc) to (xe), $R^{301}$ to $R^{309}$ are each independently a $C_1$-$C_{40}$ monovalent hydrocarbon group which may contain a heteroatom. A pair of $R^{301}$ and $R^{302}$ may bond together to form a ring with the sulfur atom to which they are attached. A pair of $R^{306}$ and $R^{307}$ may bond together to form a ring with the nitrogen atom to which they are attached. Examples of the monovalent hydrocarbon group represented by $R^{301}$ to $R^{309}$ are as exemplified above for $R^{q1}$ in formula (xa).

Examples of the cation ($Mq^+$) in formulae (xa) and (xb) are shown below, but not limited thereto.

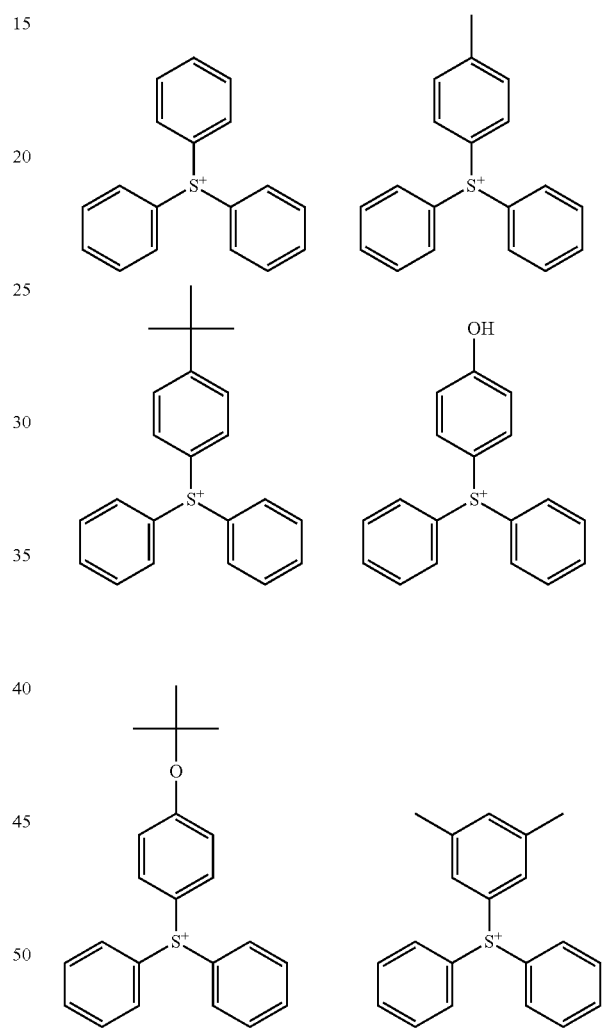

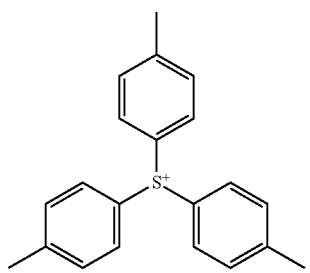

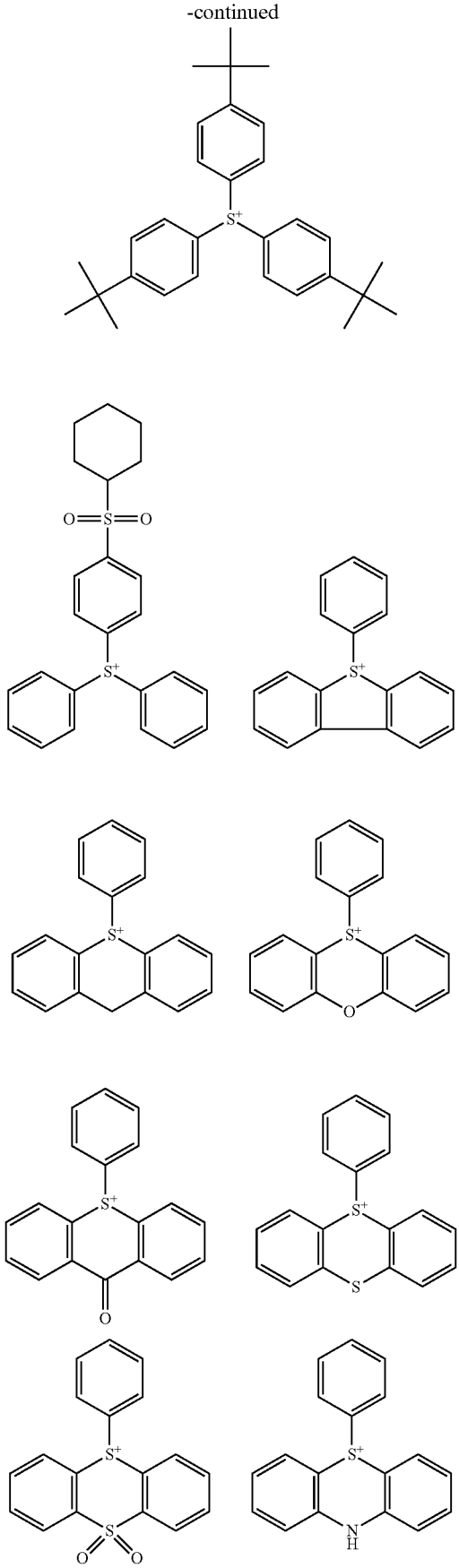
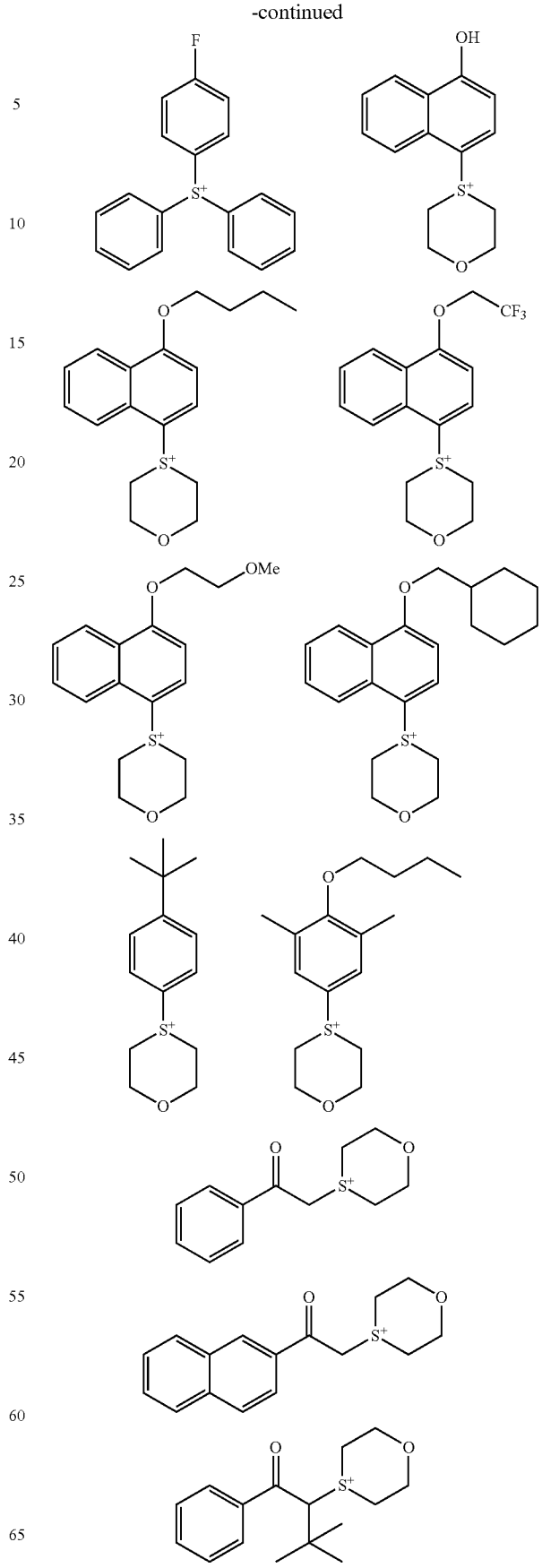

-continued

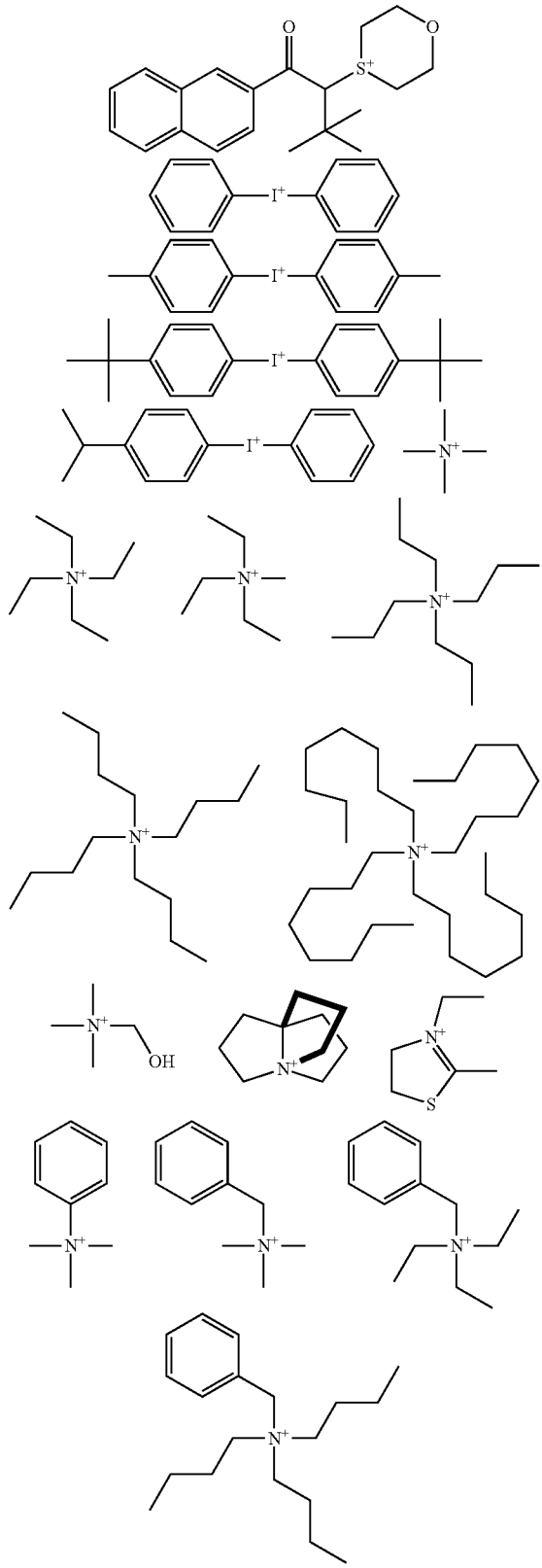

Examples of the onium salt having formula (xa) or (xb) include combinations of anions with cations, both as mentioned above. These onium salts are readily synthesized via ion exchange reaction by any well-known organic chemistry methods. For the ion exchange reaction, reference is made to JP-A 2007-145797, for example.

The onium salt having formula (xa) or (xb) functions as a quencher in the resist composition. This is because the counter anion of the onium salt is a conjugated base of weak acid. As used herein, the weak acid indicates an acidity insufficient to deprotect an acid labile group from an acid labile group-containing unit in the base polymer. The to onium salt having formula (xa) or (xb) functions as a quencher when used in combination with an onium salt type photoacid generator having a conjugated base of a strong acid, typically a sulfonic acid which is fluorinated at α-position as the counter anion.

In a system using a mixture of an onium salt capable of generating a strong acid (e.g., α-position fluorinated sulfonic acid) and an onium salt capable of generating a weak acid (e.g., non-fluorinated sulfonic acid or carboxylic acid), if the strong acid generated from the photoacid generator upon exposure to high-energy radiation collides with the unreacted onium salt having a weak acid anion, then a salt exchange occurs whereby the weak acid is released and an onium salt having a strong acid anion is formed. In this course, the strong acid is exchanged into the weak acid having a low catalysis, incurring apparent deactivation of the acid for enabling to control acid diffusion.

If a photoacid generator capable of generating a strong acid is an onium salt, an to exchange from the strong acid generated upon exposure to high-energy radiation to a weak acid as above can take place, but it rarely happens that the weak acid generated upon exposure to high-energy radiation collides with the unreacted onium salt capable of generating a strong acid to induce a salt exchange. This is because of a likelihood of an onium cation forming an ion pair with a stronger acid anion.

Also a compound having the formula (xf) is useful as the quencher in the form of an onium salt of weak acid.

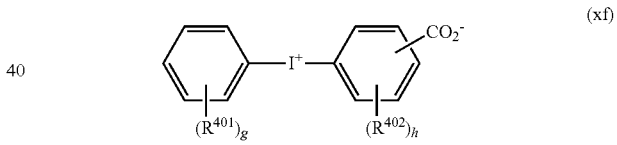

In formula (xf), $R^{401}$ and $R^{402}$ are each independently a $C_1$-$C_{12}$ monovalent hydrocarbon group, nitro group, $C_1$-$C_{12}$ alkoxy group, $C_2$-$C_{12}$ acyl group, or $C_2$-$C_{12}$ acyloxy group, g and h are each independently an integer of 0 to 4.

Examples of the compound having formula (xf) are shown below, but not limited thereto.

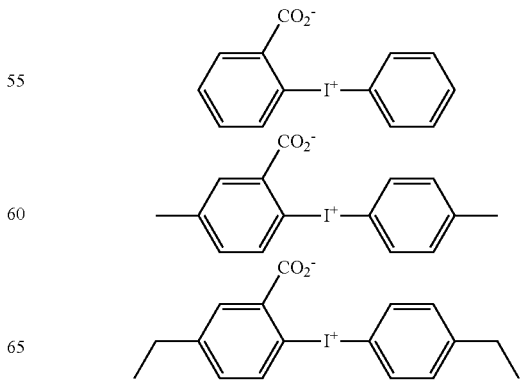

125

-continued

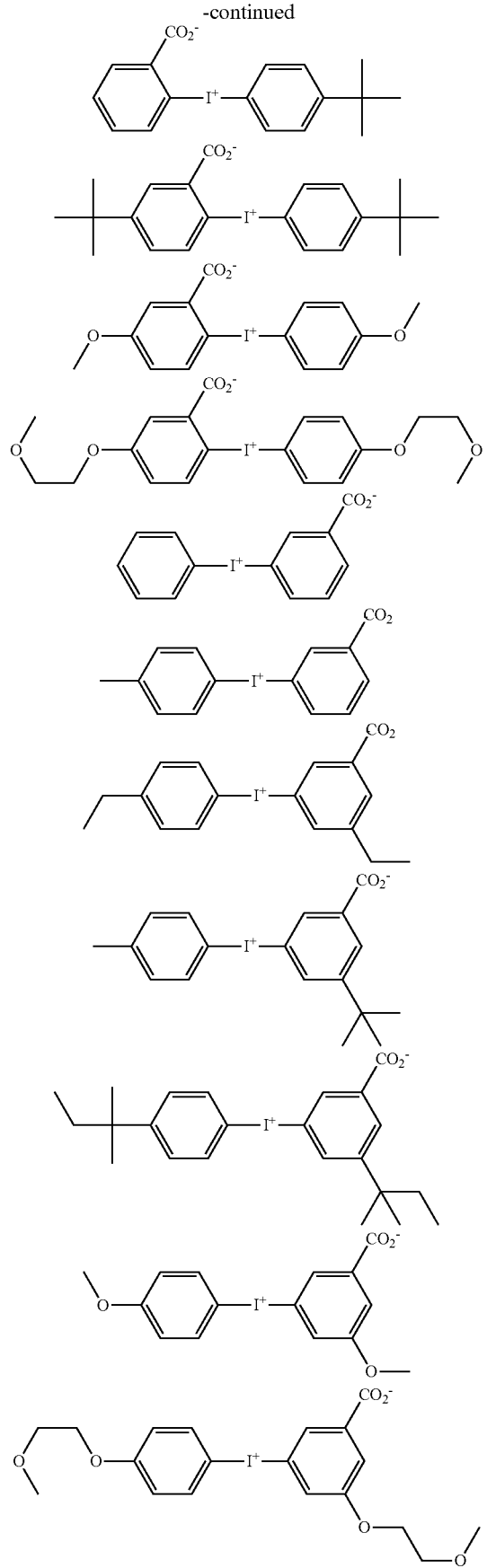

126

-continued

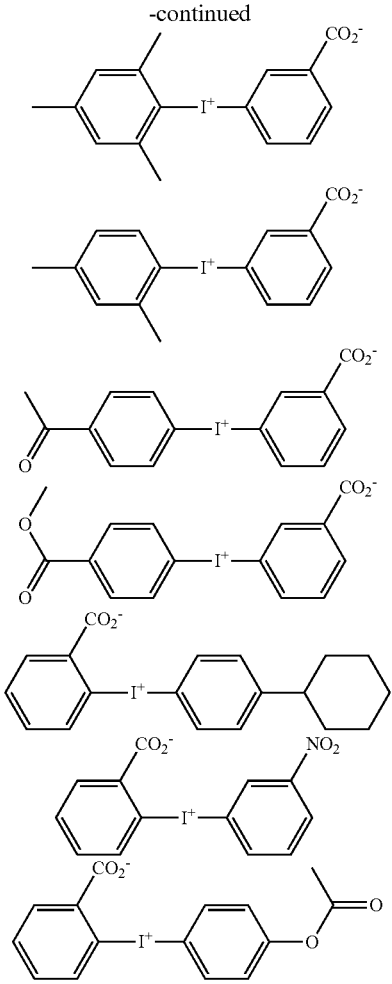

In the resist composition, the quencher (D) is used in an amount of 0 to 100 parts by weight, and when added, preferably 0.001 to 50 parts by weight, per 80 parts by weight of the base polymer (B). The quencher may be used alone or in admixture.

(E) Other Acid Generator

The resist composition may further comprise (E) a photoacid generator other than component (A). Examples of the other PAG are described in JP-A 2008-111103, paragraphs [0122]-[0142] (U.S. Pat. No. 7,537,880). More preferred structures are described in JP-A 2014-001259, paragraphs [0088]-[0092], JP-A 2012-041320, paragraphs [0015]-[0017] (U.S. Pat. No. 8,535,869), and JP-A 2012-106986, paragraphs [0015]-[0029]. The PAGs capable of generating partially fluorinated sulfonic acids described in these patent documents are advantageous for use in the ArF lithography because the strength and diffusion length of generated acid are adequate.

The other PAG preferably generates a strong acid such as sulfonic acid, imide acid (imidic acid) or methide acid. As used herein, the strong acid refers to a compound having a sufficient acidity to induce deprotection reaction of an acid labile group on the base polymer. Of these, sulfonic acids which are fluorinated at α-position are most commonly used. The fluorination at α-position is not essential when the acid labile group is an acetal group susceptible to deprotection.

The other PAG is preferably selected from compounds having the formulae (AG1) and (AG2).

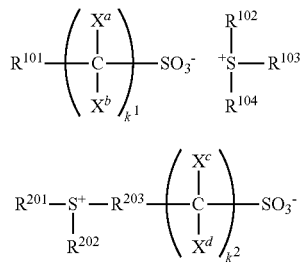

(AG1)

(AG2)

In formula (AG1), $R^{101}$ is hydrogen, fluorine or a $C_1$-$C_{35}$ monovalent hydrocarbon group which may contain a heteroatom. $R^{102}$, $R^{103}$ and $R^{104}$ are each independently a $C_1$-$C_{20}$ monovalent hydrocarbon group which may contain a heteroatom. Any two of $R^{102}$, $R^{103}$ and $R^{104}$ may bond together to form a ring with the sulfur atom to which they are attached.

The monovalent hydrocarbon group $R^{101}$ may be straight, branched or cyclic. Examples thereof include, but are not limited to, methyl, ethyl, propyl, isopropyl, butyl, isobutyl, sec-butyl, tert-butyl, pentyl, neopentyl, cyclopentyl, hexyl, cyclohexyl, 3-cyclohexenyl, heptyl, 2-ethylhexyl, nonyl, undecyl, tridecyl, pentadecyl, heptadecyl, 1-adamantyl, 2-adamantyl, 1-adamantylmethyl, norbornyl, norbornylmethyl, tricyclodecanyl, tetracyclododecanyl, tetracyclododecanylmethyl, dicyclohexylmethyl, eicosanyl, allyl, benzyl, diphenylmethyl, tetrahydrofuryl, methoxymethyl, ethoxymethyl, methylthiomethyl, acetamidomethyl, trifluoroethyl, (2-methoxyethoxy)methyl, acetoxymethyl, 2-carboxy-1-cyclohexyl, 2-oxopropyl, 4-oxo-1-adamantyl, and 3-oxocyclohexyl. In these groups, some hydrogen may be substituted by a moiety containing a heteroatom such as oxygen, sulfur, nitrogen or halogen, or a moiety containing a heteroatom such as oxygen, sulfur or nitrogen may intervene between carbon atoms, so that the group may contain a hydroxyl, cyano, carbonyl, ether bond, ester bond, sulfonic acid ester bond, carbonate bond, to lactone ring, sultone ring, carboxylic anhydride or haloalkyl moiety.

In formula (AG2), $R^{201}$ and $R^{202}$ are each independently a $C_1$-$C_{20}$ monovalent hydrocarbon group which may contain a heteroatom. $R^{203}$ is a $C_1$-$C_{20}$ divalent hydrocarbon group which may contain a heteroatom. Any two of $R^{201}$, $R^{202}$ and $R^{203}$ may bond together to form a ring with the sulfur atom to which they are attached. $L^A$ is a single bond, ether bond or a $C_1$-$C_{20}$ divalent hydrocarbon group which may contain a heteroatom.

In formulae (AG1) and (AG2), $X^a$, $X^b$, $X^c$ and $X^d$ are each independently hydrogen, fluorine or trifluoromethyl, $k^1$ and $k^2$ are each independently an integer of 1 to 4.

The PAG having formula (AG1) is preferably one having the formula (AG1'). The PAG having formula (AG2) is preferably one having the formula (AG2').

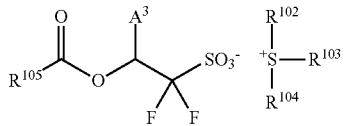

(AG1')

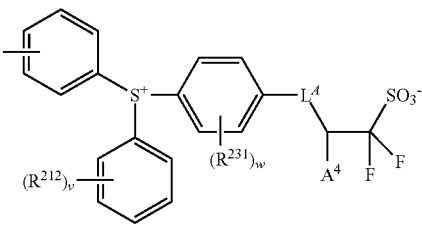

(AG2')

In formulae (AG1') and (AG2'), $R^{102}$, $R^{103}$, $R^{104}$, and $L^A$ are as defined above. $A^3$ and $A^4$ are each independently hydrogen or trifluoromethyl. $R^{105}$ is a $C_1$-$C_{35}$ monovalent hydrocarbon group which may contain a heteroatom. $R^{211}$, $R^{212}$ and $R^{213}$ are each independently hydrogen or a $C_1$-$C_{20}$ monovalent hydrocarbon group which may contain a heteroatom. The subscripts u and v are each independently an integer of 0 to 5, and w is an integer of 0 to 4.

In one preferred embodiment wherein the other PAG has formula (AG1') or (AG2'), more preferably wherein $A^3$ or $A^4$ is trifluoromethyl, for example, a line-and-space pattern with low LWR and improved acid diffusion length control or a hole pattern with good roundness and improved dimensional control is formed.

Examples of the PAG having formula (AG1) are given below, but not limited thereto. Herein $A^3$ is as defined above.

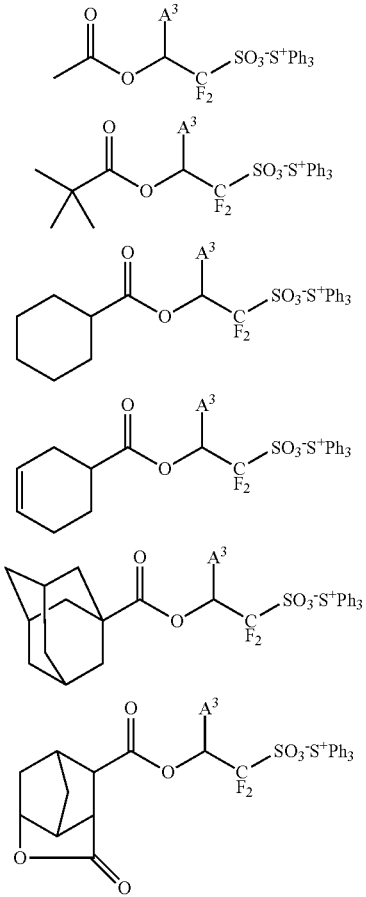

-continued
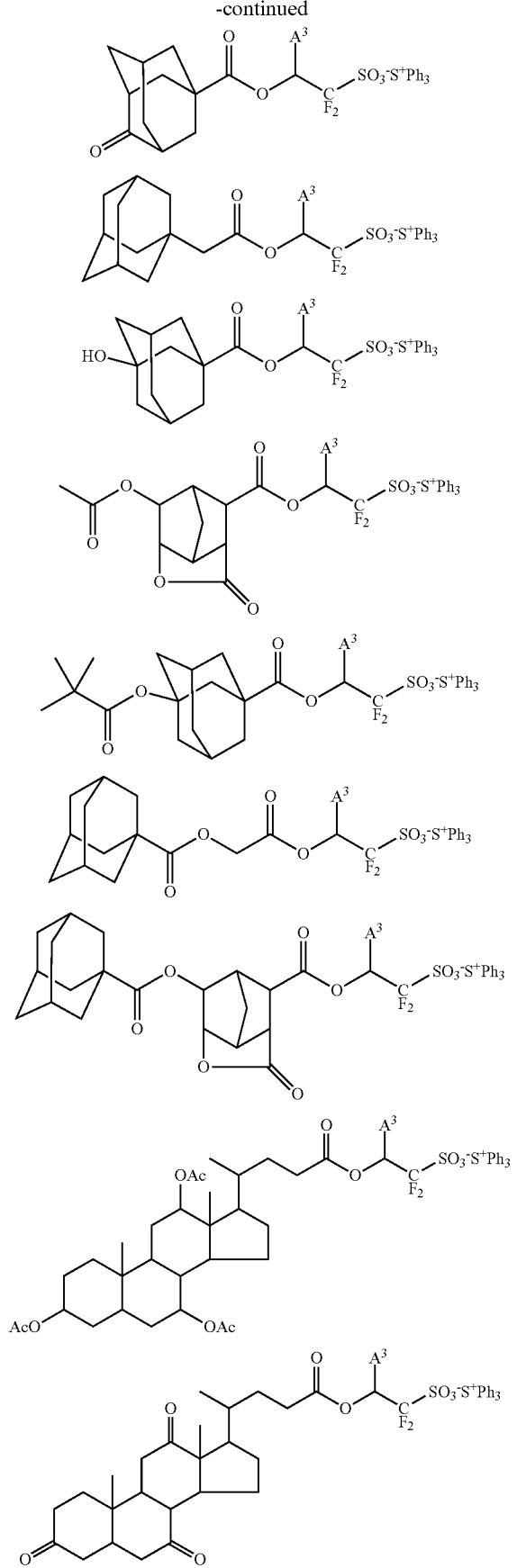
-continued
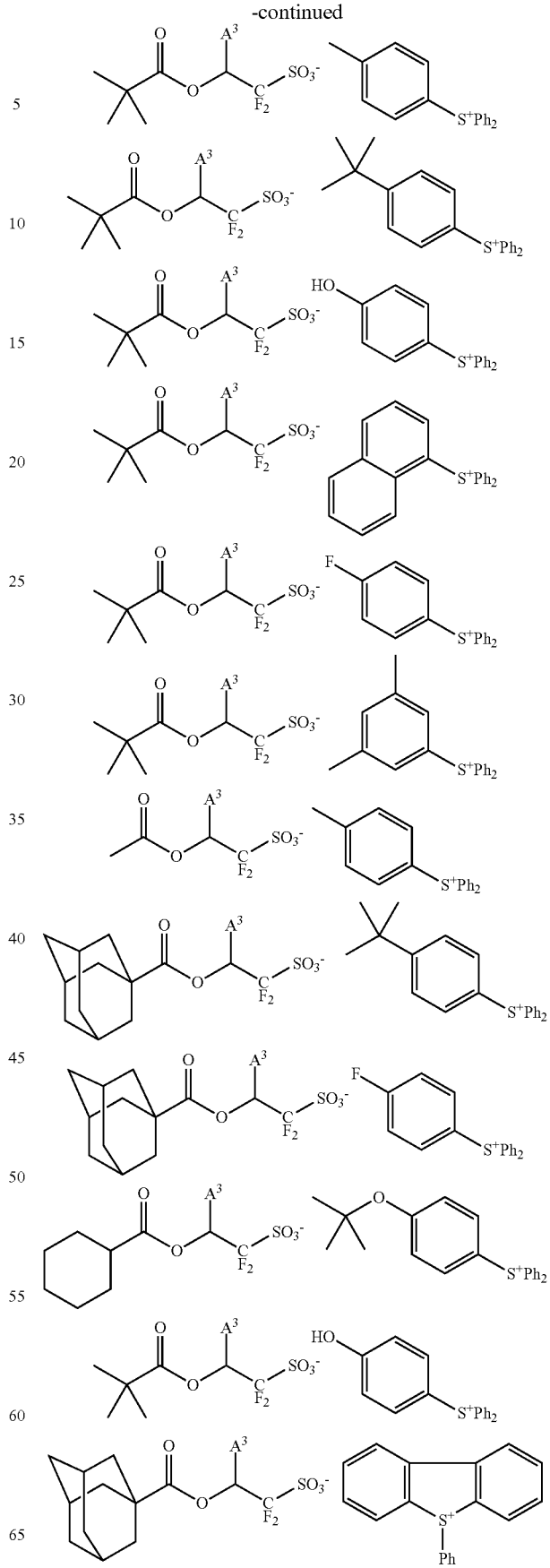

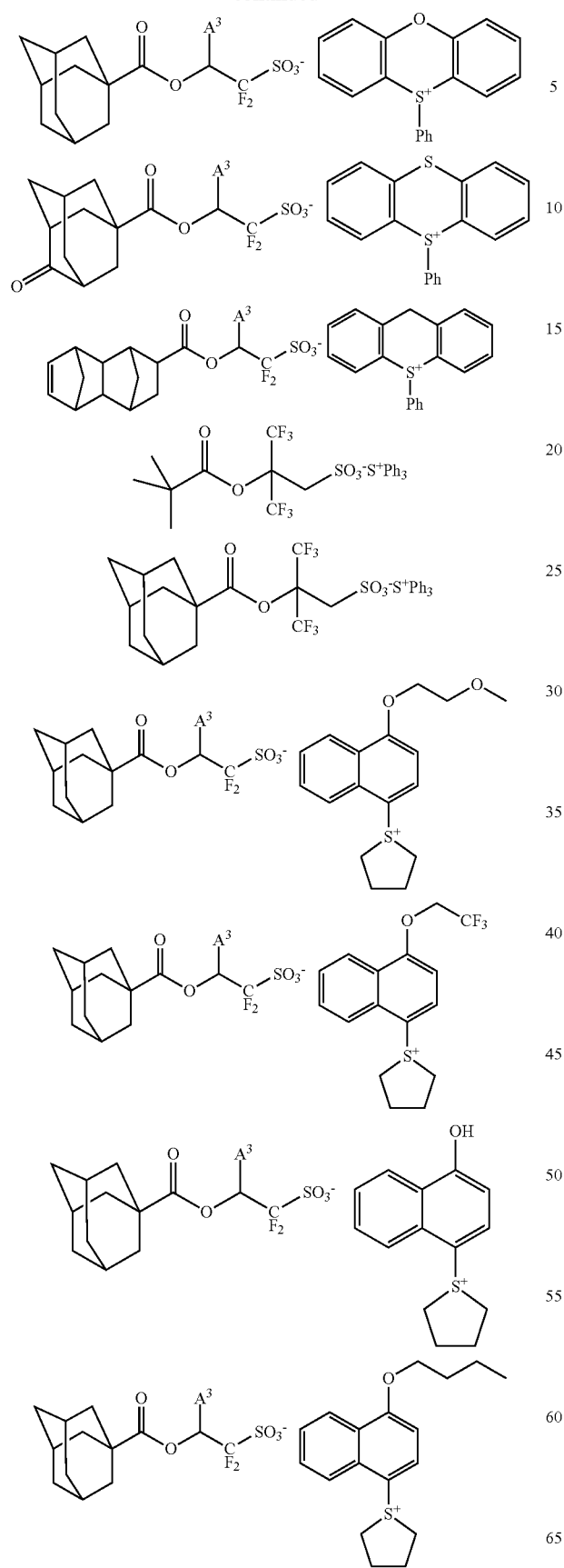
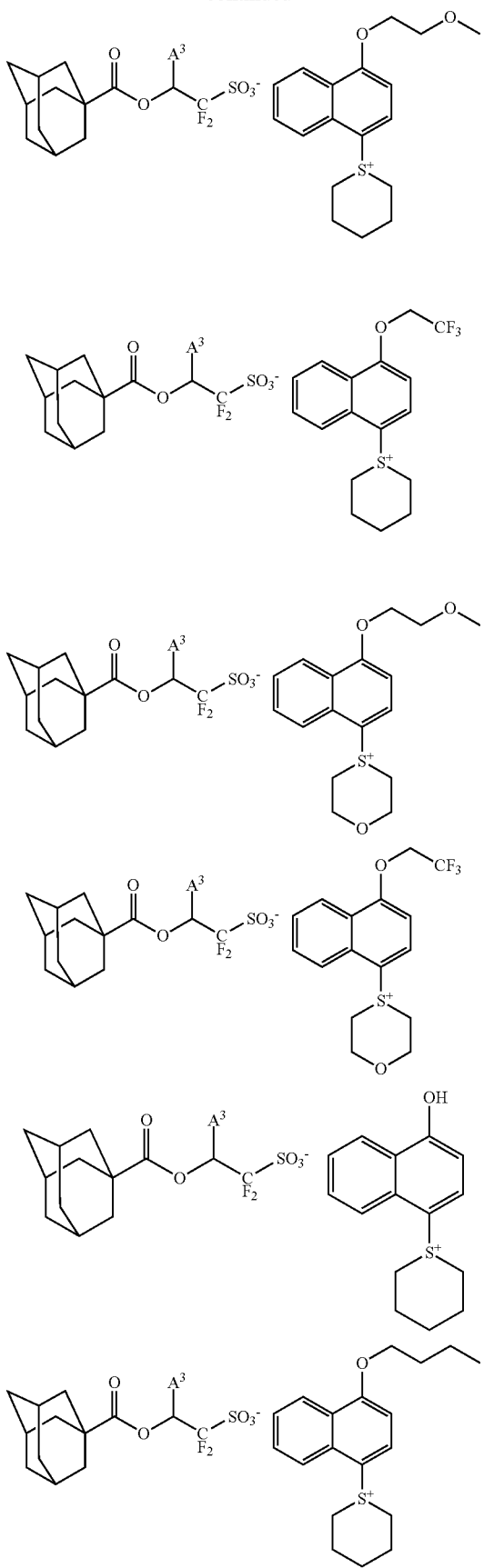

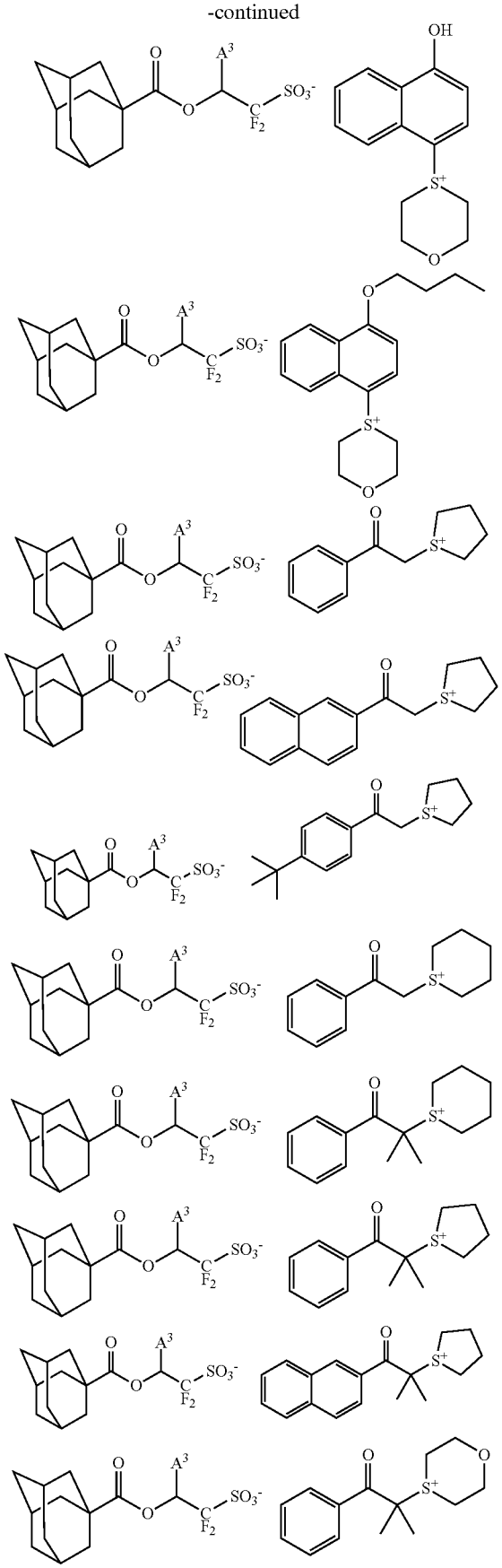

-continued
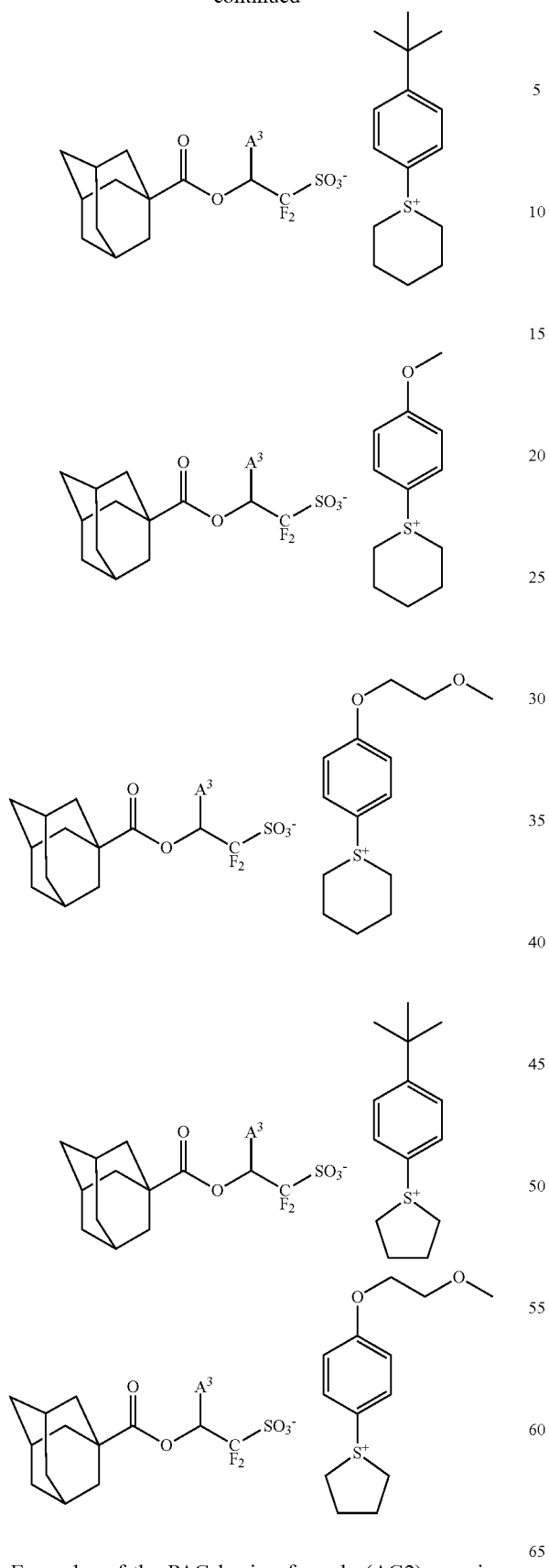
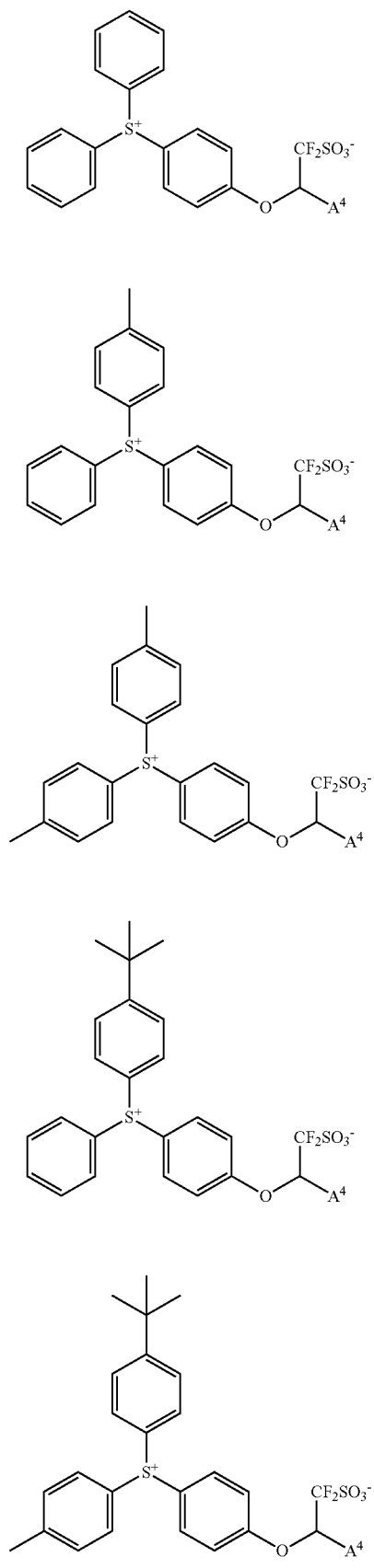
Examples of the PAG having formula (AG2) are given below, but not limited thereto. Herein $A^4$ is as defined above.

137
-continued
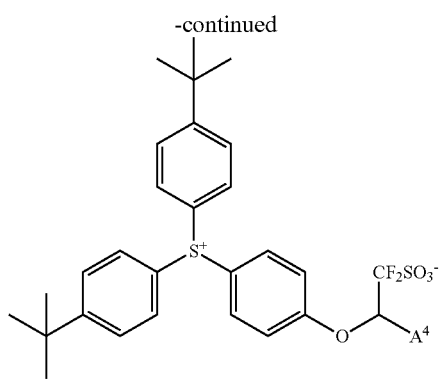
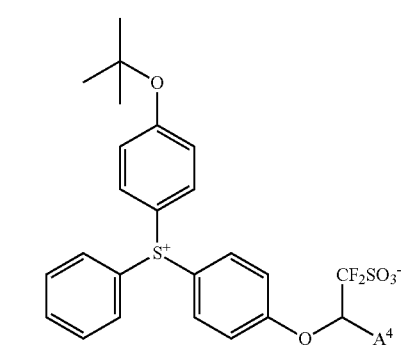
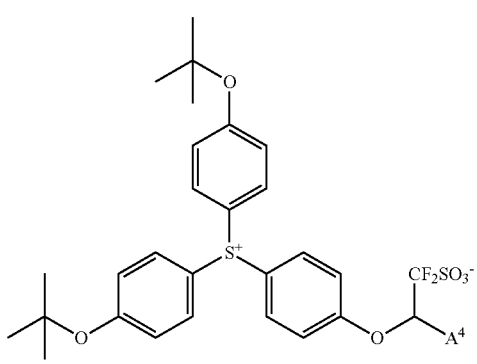
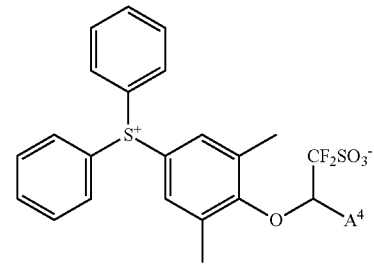
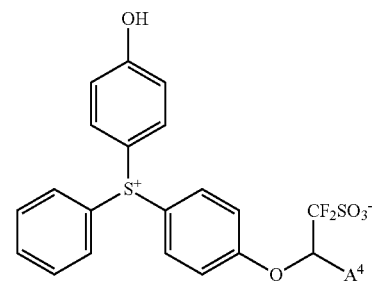
138
-continued
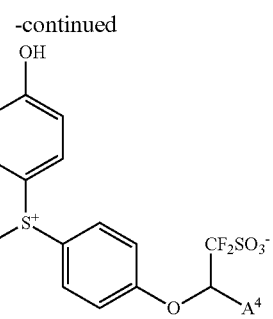
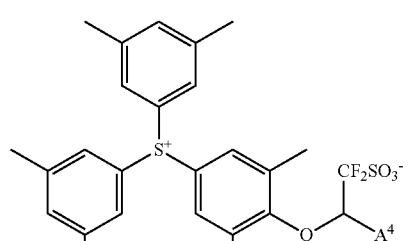
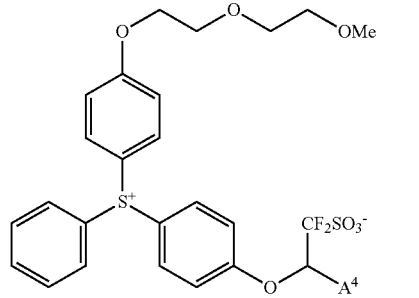
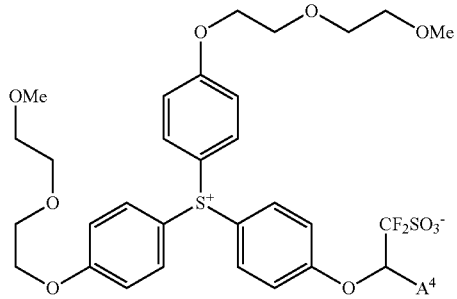
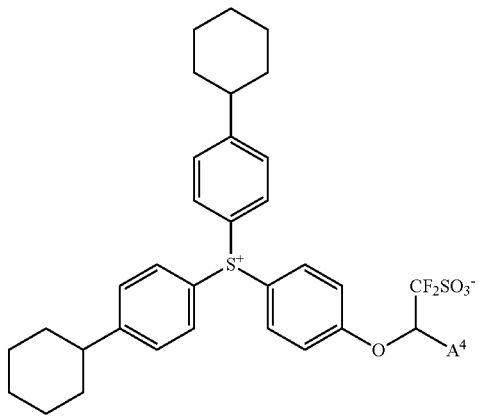

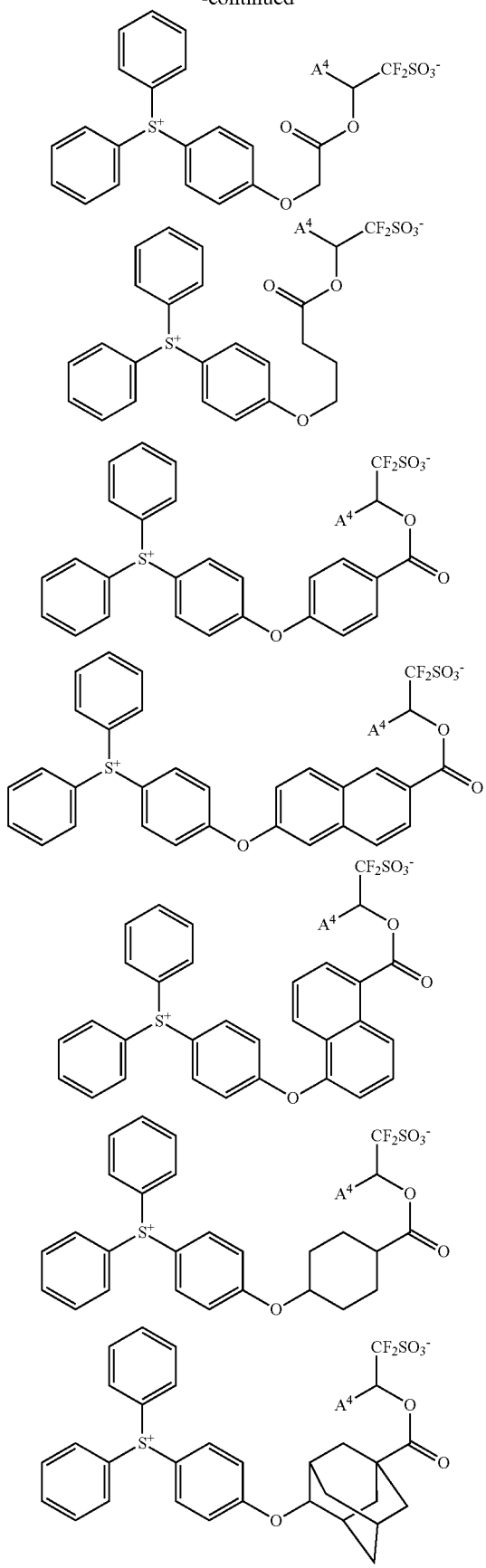
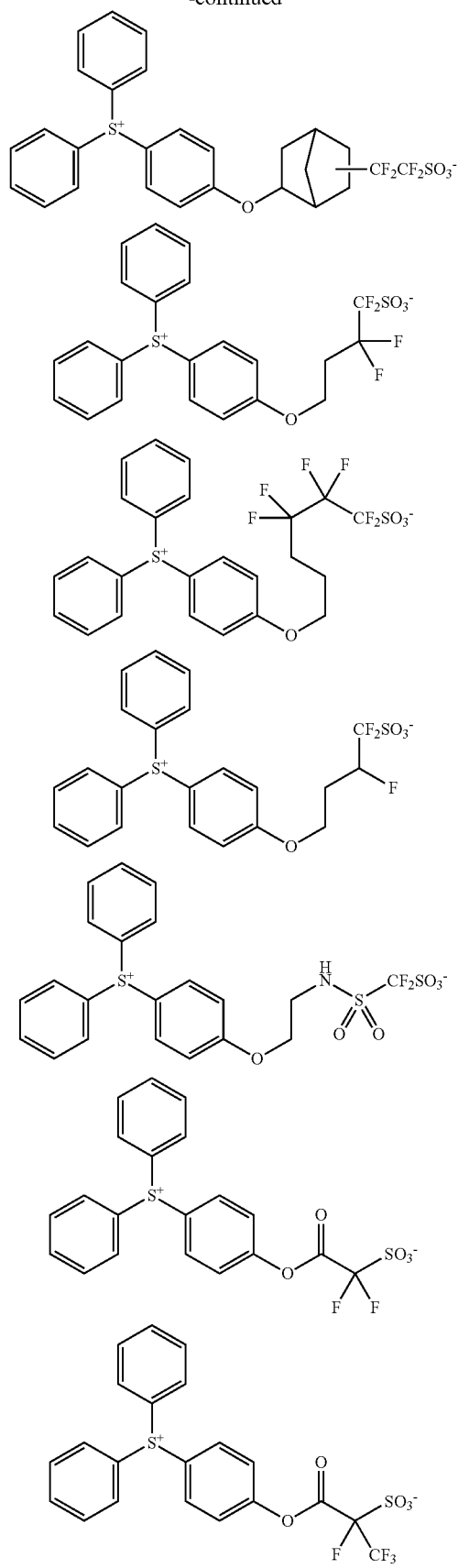

When the resist composition contains the other PAG (E), the amount thereof is preferably 0.5 to 30 parts by weight, more preferably 1 to 20 parts by weight per 80 parts by weight of the base polymer (B). The other PAG may be used alone or in admixture.

Other Components

In addition to the foregoing components, the resist composition may comprise other components such as a surfactant, dissolution inhibitor, acetylene alcohol, and water repellency improver, which may be blended in any desired combination for a particular purpose. Suitable surfactants are described in JP-A 2008-111103, paragraphs [0165]-[0166] (U.S. Pat. No. 7,537,880). Suitable dissolution inhibitors are described in JP-A 2008-122932, paragraphs [0155]-[0178] (U.S. Pat. No. 7,771,914). Suitable acetylene alcohols are described in JP-A 2008-122932, paragraphs [0179]-[0182] (U.S. Pat. No. 7,771,914). The dissolution inhibitor is preferably added in an amount of 0 to 50 parts, more preferably 0 to 40 parts by weight per 80 parts by weight of the base polymer. The amounts of the surfactant and acetylene alcohol may be selected appropriate for their purpose.

To the resist composition, a water repellency improver may also be added for improving the water repellency on surface of a resist film as spin coated. The water repellency improver may be used in the topcoatless immersion lithography. Suitable water repellency improvers include compounds of specific structure having a 1,1,1,3,3,3-hexafluoro-2-propanol residue and are described in JP-A 2007-297590, JP-A 2008-111103, JP-A 2008-122932, JP-A 2012-128067, and JP-A 2013-057836.

Suitable water repellency improvers include polymers capable of improving water repellency, preferably polymers consisting of fluorinated units of one type, copolymers consisting of fluorinated units of more than one type, and copolymers consisting of fluorinated units and fluorine-free units.

Examples of the fluorinated units and other units are shown below, but not limited thereto. Herein $R^B$ is hydrogen or methyl.

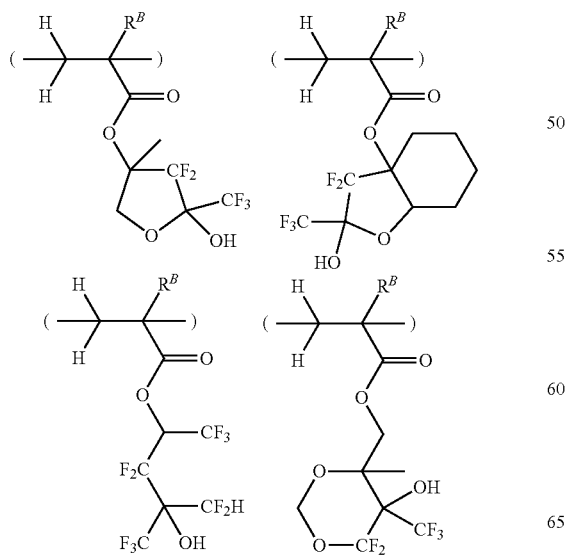

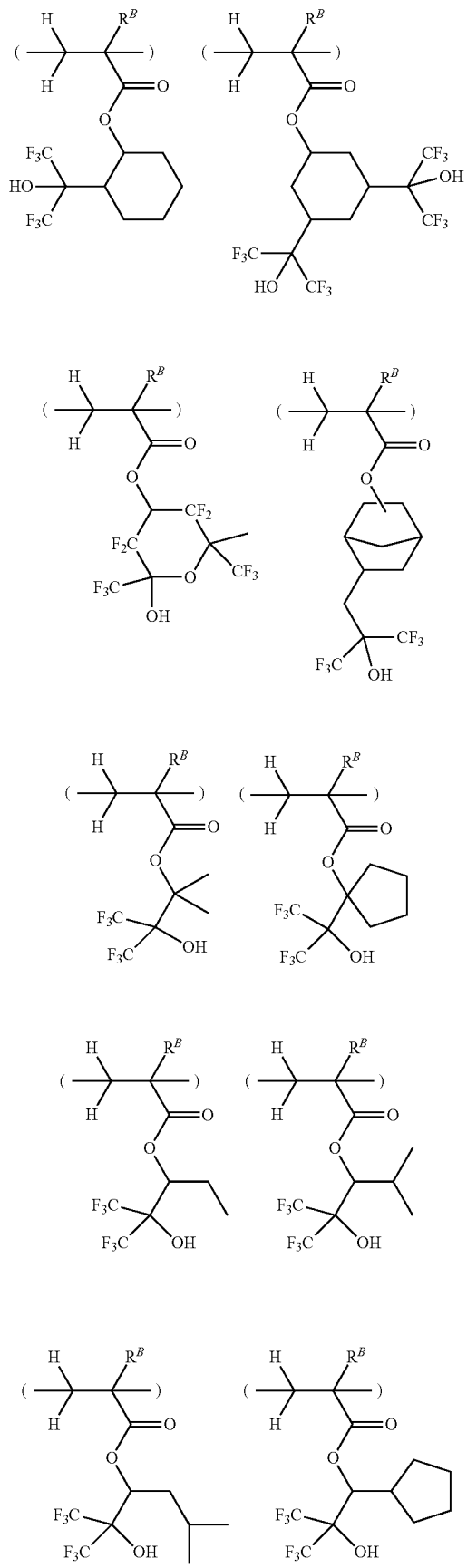

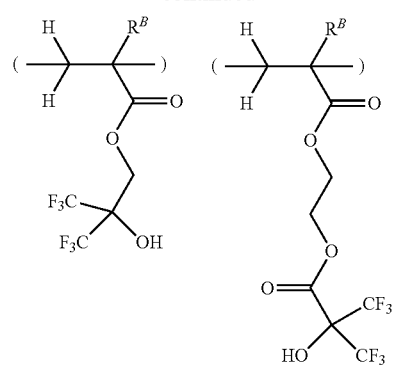
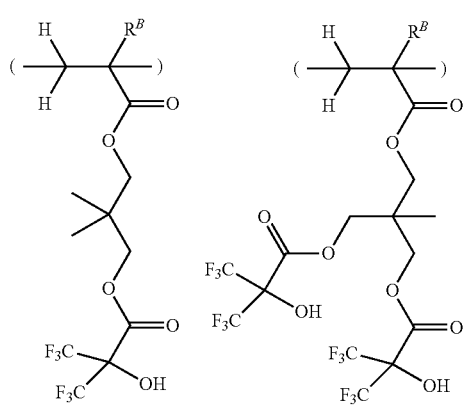
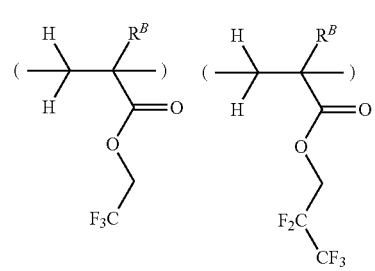
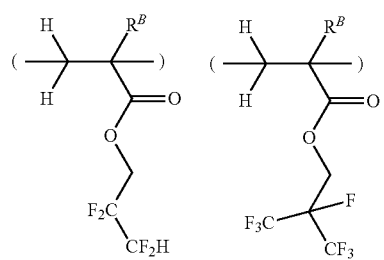
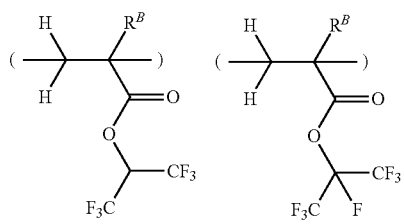
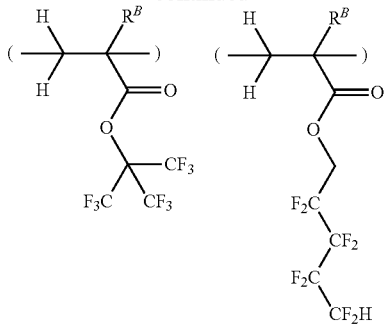
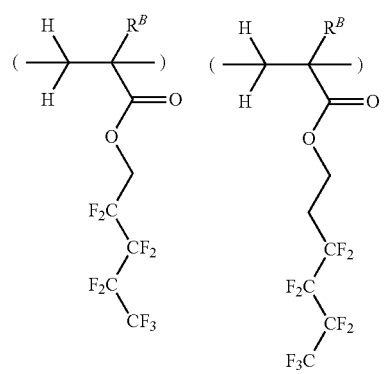
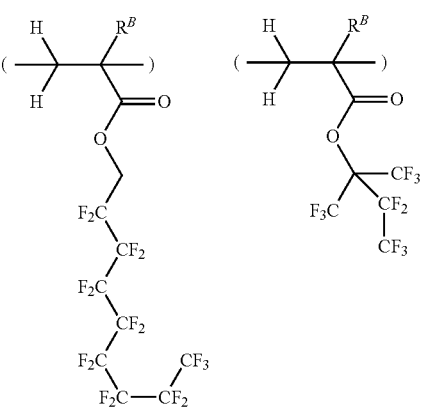
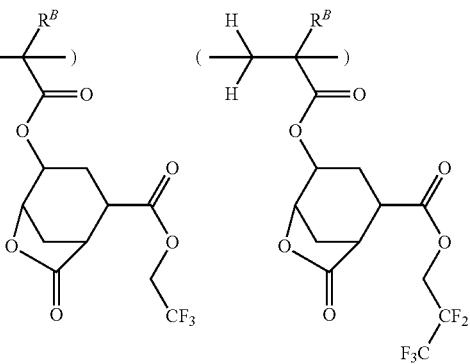

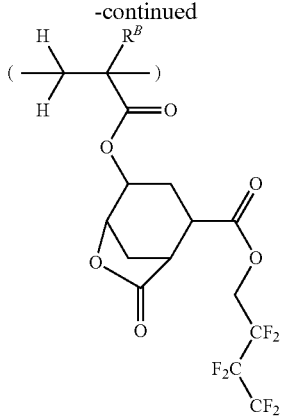
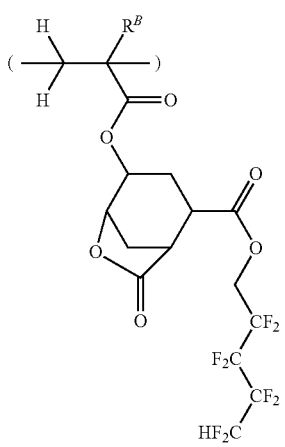
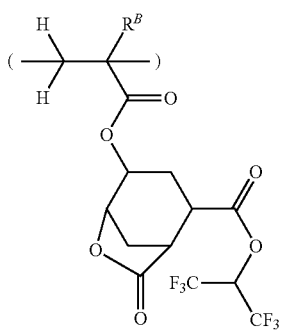
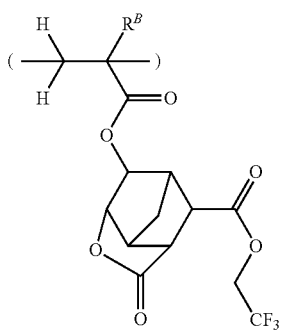
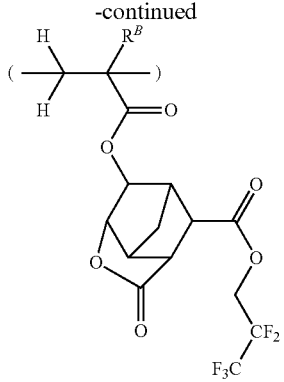
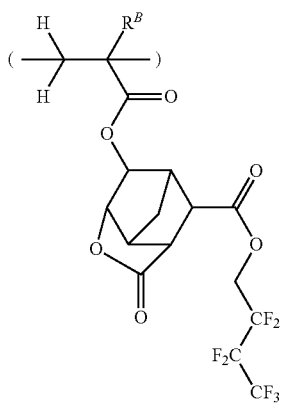
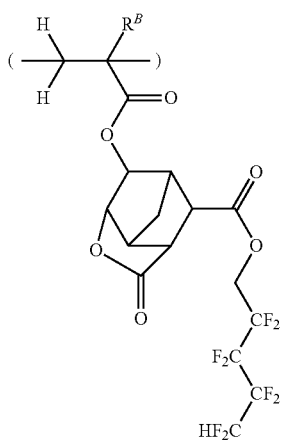
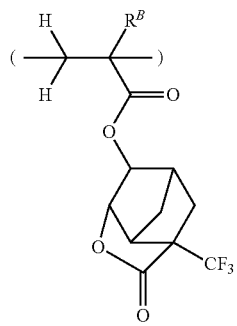

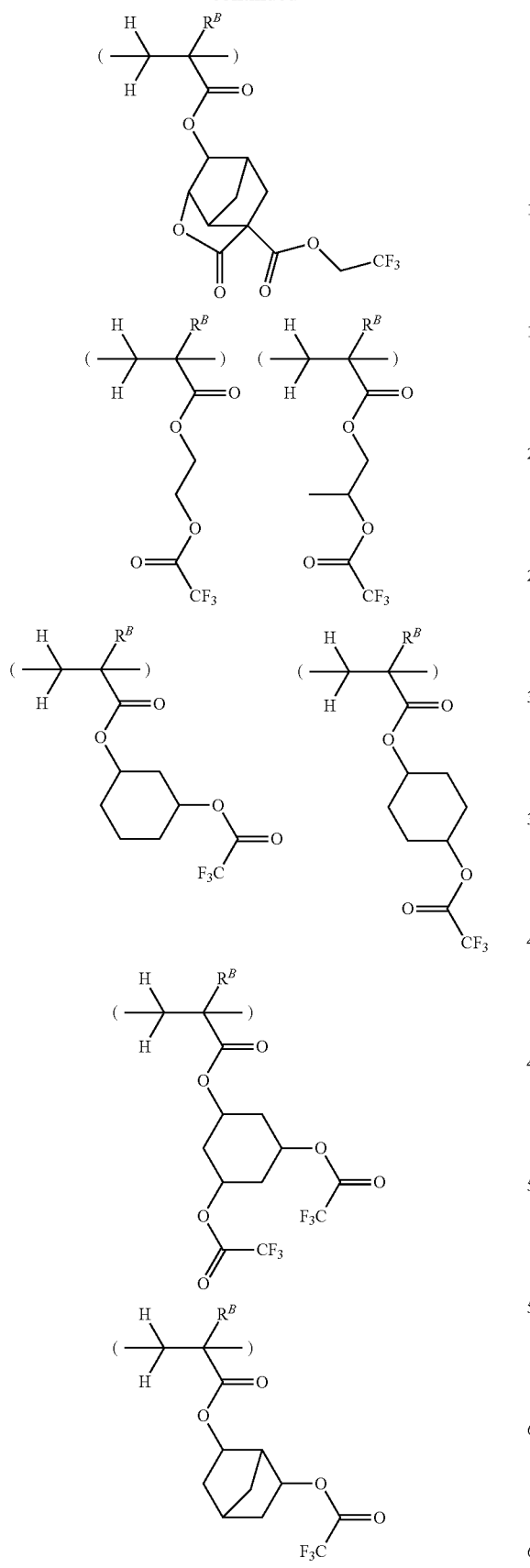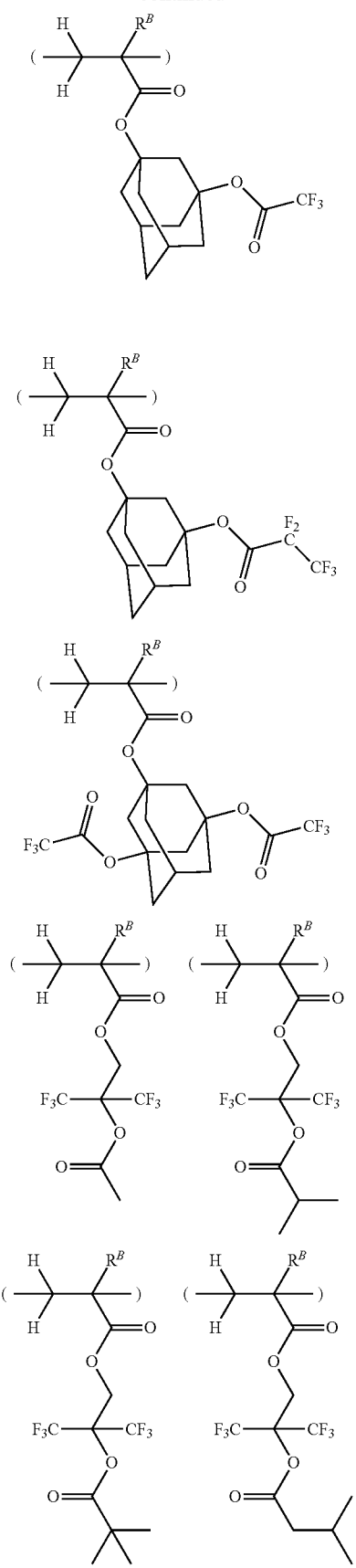

-continued
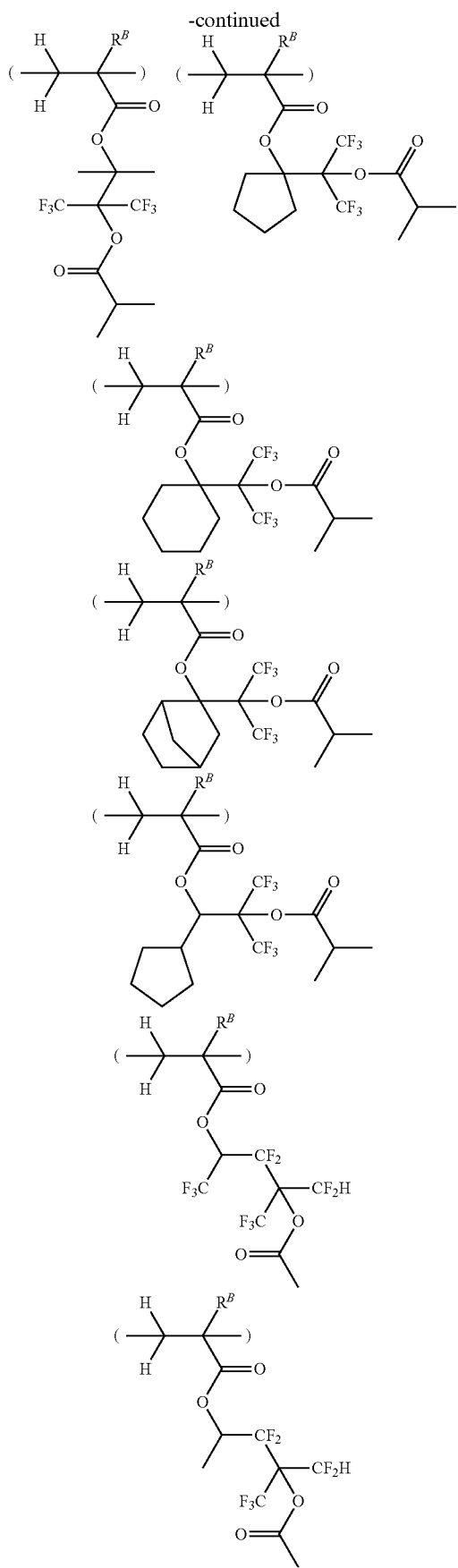
-continued
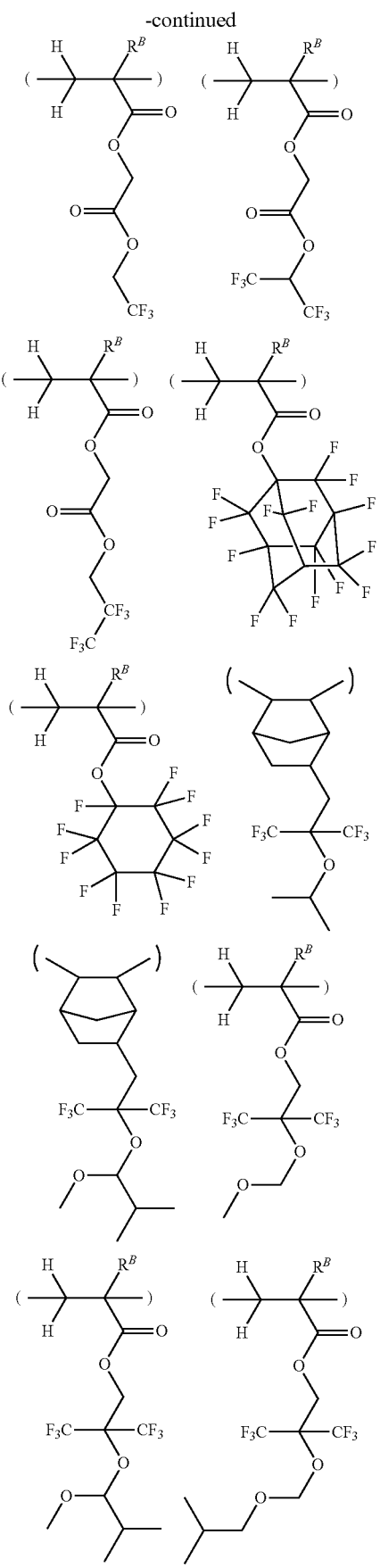

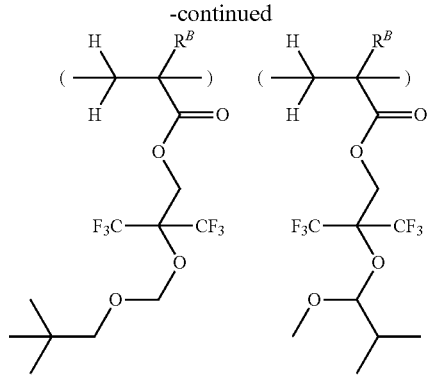
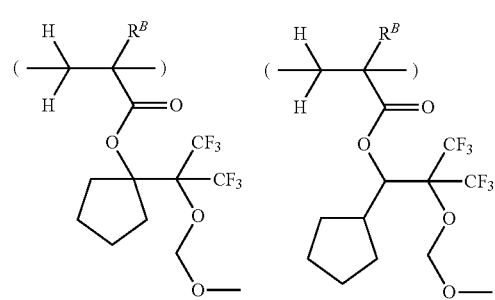
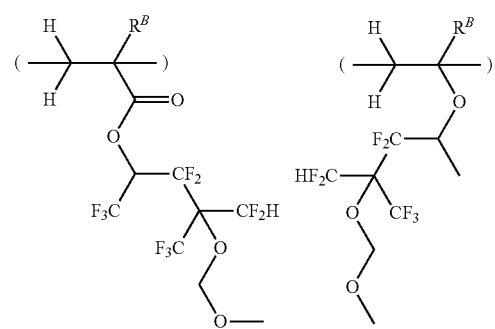
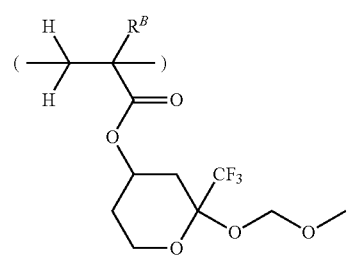
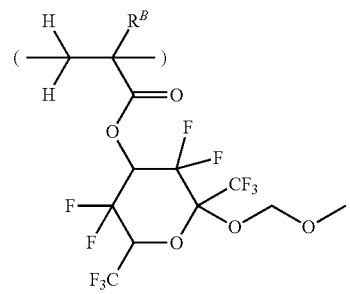
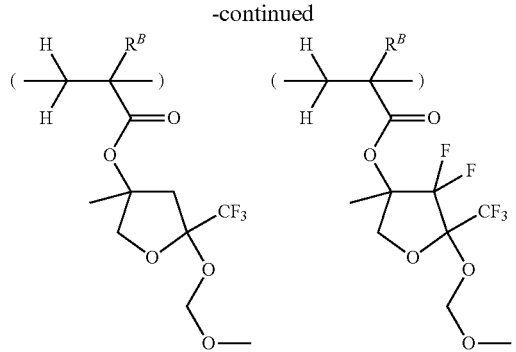
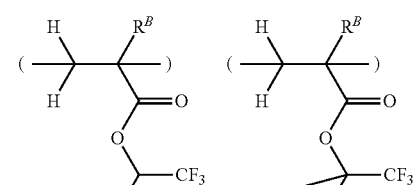
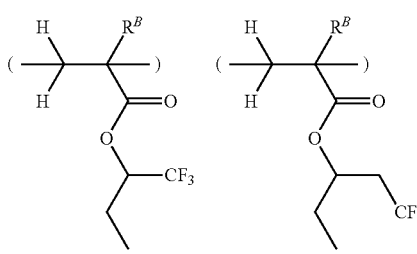
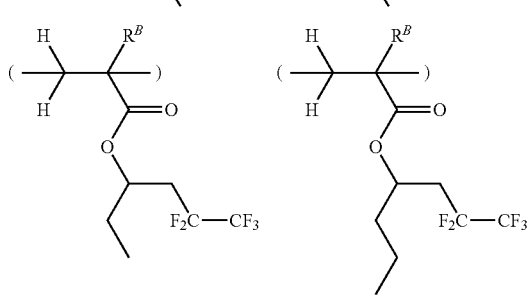
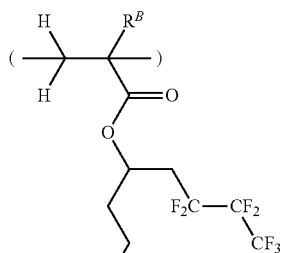
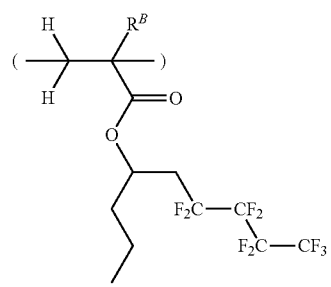

-continued
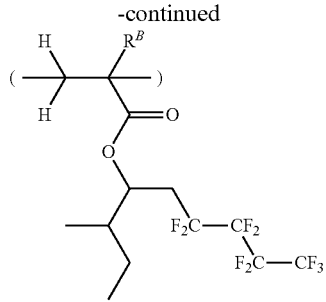
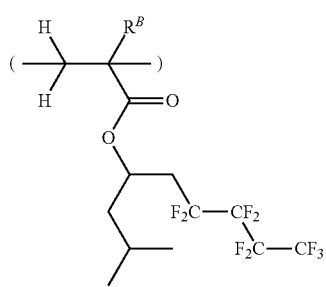
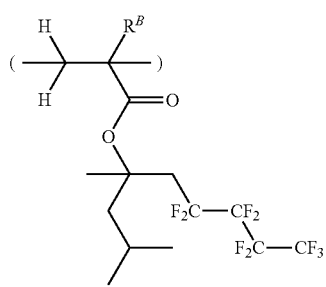
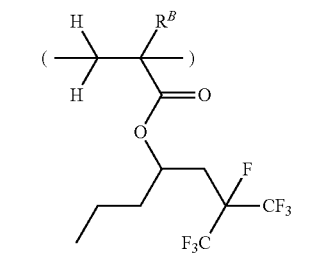
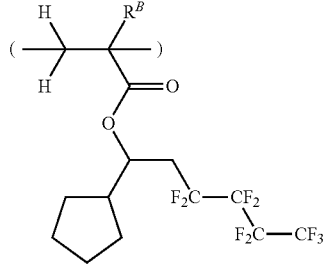
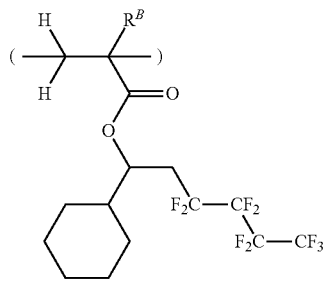
-continued
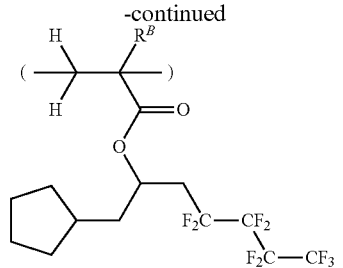
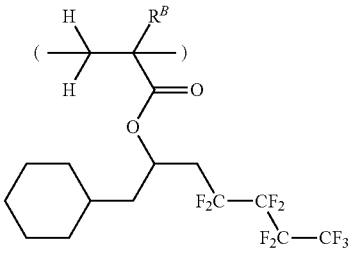
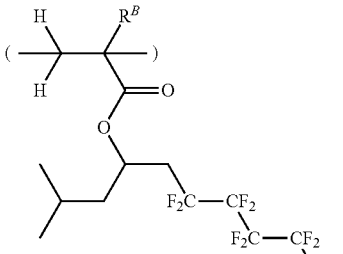
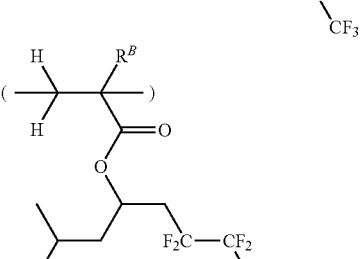
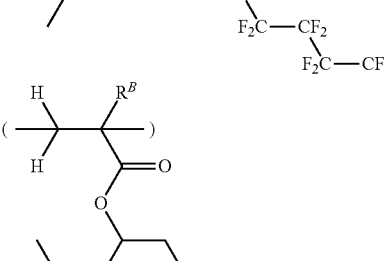
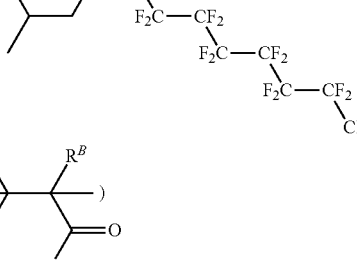
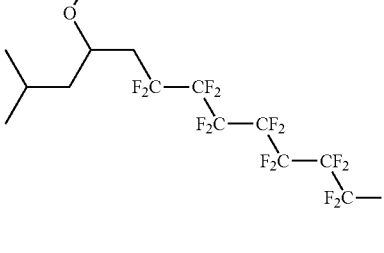

-continued
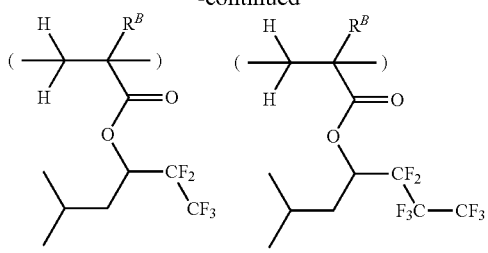
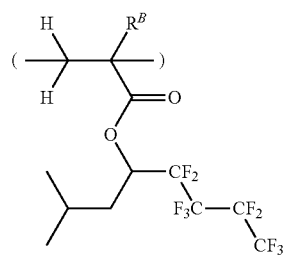
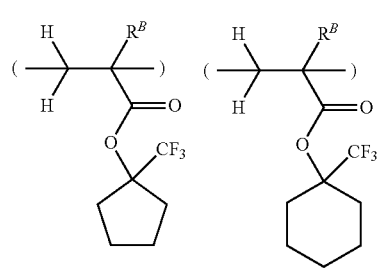
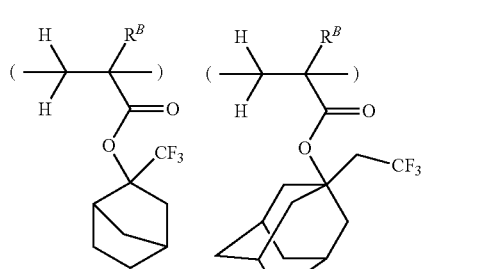
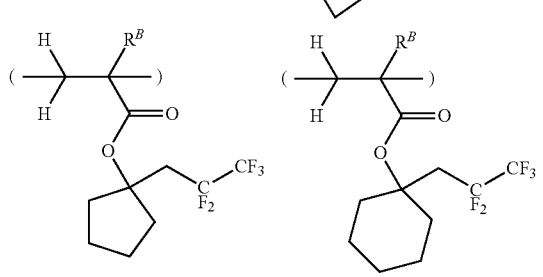
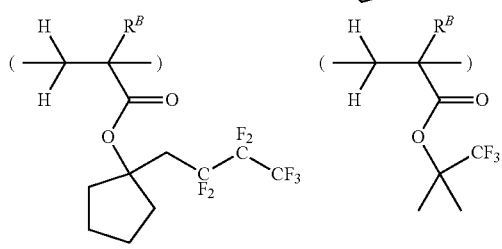
-continued
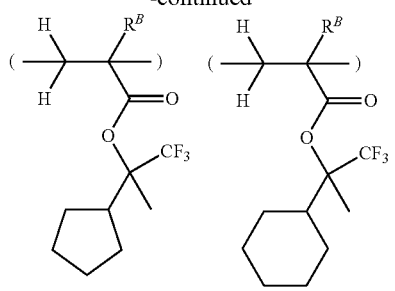
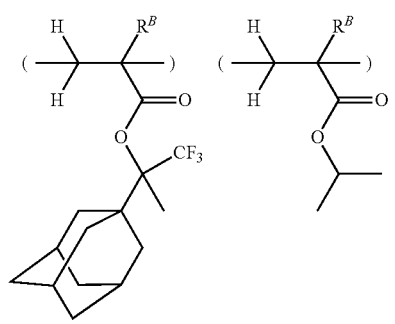
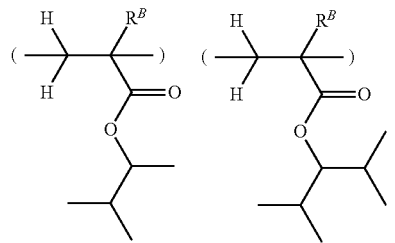
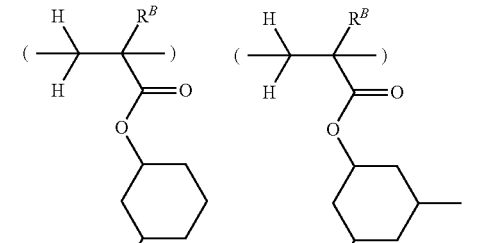
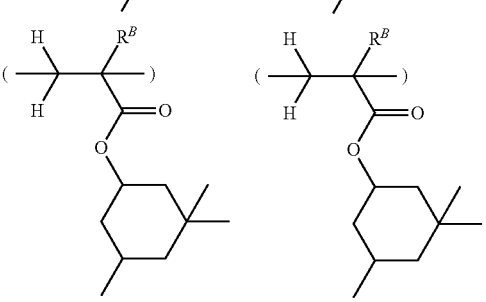
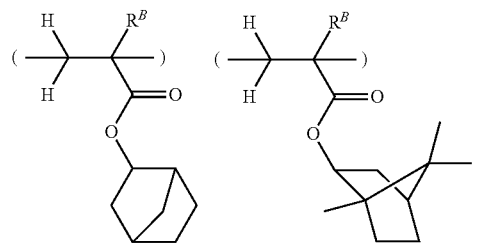

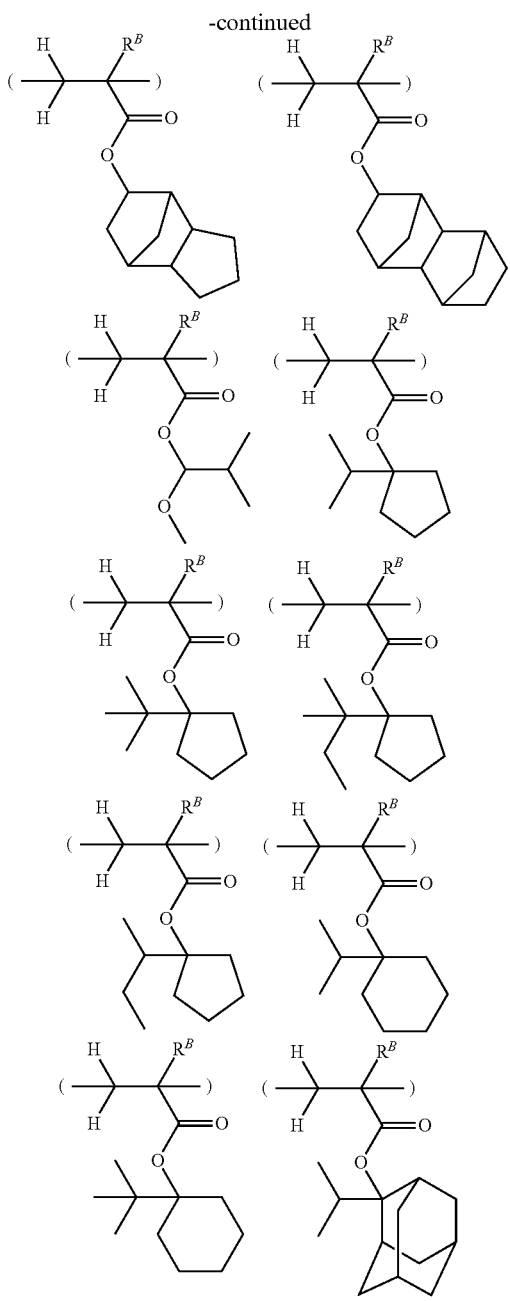

The water repellency improver should be soluble in alkaline aqueous solution as the developer. The water repellency improver having a 1,1,1,3,3,3-hexafluoro-2-propanol residue is well soluble in the developer. A polymer comprising recurring units having an amino group or amine salt serves as the water repellency improver and is effective for preventing evaporation of acid during PEB, thus preventing any opening failure of hole patterns or bridging of line-and-space patterns after development. An appropriate amount of the water repellency improver is 0 to 20 parts, preferably 0.1 to 20 parts, more preferably 0.5 to 10 parts by weight per 80 parts by weight of the base polymer.

Process

A further embodiment of the invention is a pattern forming process comprising the steps of applying the resist composition onto a substrate to form a resist film thereon, exposing the resist film to high-energy radiation, and developing the exposed resist film in a developer to form a pattern. If necessary, any additional steps may be added.

For example, the resist composition is first applied onto a substrate on which an integrated circuit is to be formed (e.g., Si, $SiO_2$, SiN, SiON, TiN, WSi, BPSG, SOG, silicon-containing antireflective coating, or multilayer film including organic hydrocarbon film) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably at 80 to 120° C. for 30 seconds to 20 minutes. The resulting resist film is generally 0.01 to 2 μm thick.

The resist film is then exposed to a desired pattern of high-energy radiation such as UV, deep-UV, EB, x-ray, excimer laser light, γ-ray, synchrotron radiation, EUV, or soft x-ray. When UV, deep-UV, x-ray, excimer laser light, γ-ray, synchrotron radiation, EUV or soft x-ray is used as the high-energy radiation, the resist film is exposed thereto through a mask having a desired pattern in a dose of preferably about 1 to 200 $mJ/cm^2$, more preferably about 10 to 100 $mJ/cm^2$. When EB is used as the high-energy radiation, the resist film is exposed thereto through a mask having a desired pattern or directly in a dose of preferably about 0.1 to 100 $\mu C/cm^2$, more preferably about 0.5 to 50 $\mu C/cm^2$. It is appreciated that the inventive resist composition is suited in micropatterning using KrF excimer laser, ArF excimer laser, EB, EUV, x-ray, soft x-ray, γ-ray or synchrotron radiation.

The exposure is generally performed by conventional lithography whereas the immersion lithography of holding a liquid having a refractive index of at least 1.0 between the resist film and a projection lens may also be employed. The liquid is typically water, and in this case, a protective film which is insoluble in water may be formed on the resist film.

While the water-insoluble protective film which is used in the immersion lithography serves to prevent any components from being leached out of the resist film and to improve water sliding on the film surface, it is generally divided into two types. The first type is an organic solvent-strippable protective film which must be stripped, prior to alkaline to development, with an organic solvent in which the resist film is not dissolvable. The second type is an alkali-soluble protective film which is soluble in an alkaline developer so that it can be removed simultaneously with the removal of solubilized regions of the resist film. The protective film of the second type is preferably of a material comprising a polymer having a 1,1,1,3,3,3-hexafluoro-2-propanol residue (which is insoluble in water and soluble in an alkaline developer) as a base in an alcohol solvent of at least 4 carbon atoms, an ether solvent of 8 to 12 carbon atoms or a mixture thereof. Alternatively, the aforementioned surfactant which is insoluble in water and soluble in an alkaline developer may be dissolved in an alcohol solvent of at least 4 carbon atoms, an ether solvent of 8 to 12 carbon atoms or a mixture thereof to form a material from which the protective film of the second type is formed.

After the exposure, the resist film may be baked (PEB) on a hot plate preferably at 60 to 150° C. for 10 seconds to 30 minutes, more preferably at 80 to 120° C. for 30 seconds to 20 minutes.

After the exposure or PEB, the resist film is developed in a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed region is dissolved in the developer whereas the resist film in the unexposed region is not dissolved. In this way, the desired positive pattern is formed on the substrate.

In an alternative embodiment using the resist composition, a negative pattern may be formed via organic solvent development. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film may be rinsed with water by standard techniques such as dip, puddle and spray techniques, preferably for 3 seconds to 3 minutes, more preferably 5 seconds to 2 minutes.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLES

Synthesis Examples, Examples and Comparative Examples are given below by way of illustration and not by way of limitation. The abbreviation "pbw" is parts by weight. For all polymers, Mw and Mn are determined by GPC versus polystyrene standards using tetrahydrofuran (THF) or N,N-dimethylformamide (DMF) solvent.

The monomers used for the preparation of polymers in Examples are shown below.

MA-1
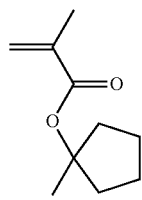

MA-2
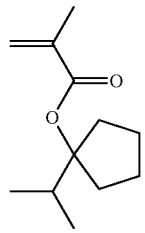

MA-3
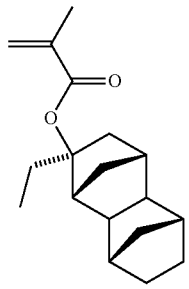

MA-4
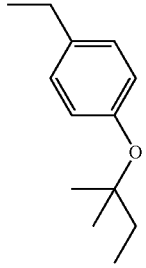

MC-1
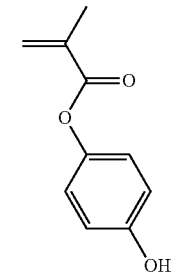

MC-2
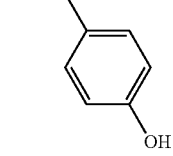

ME-1
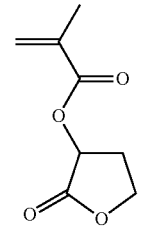

ME-2

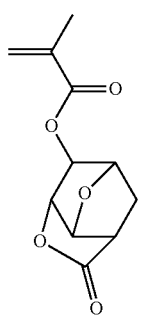

MF-1

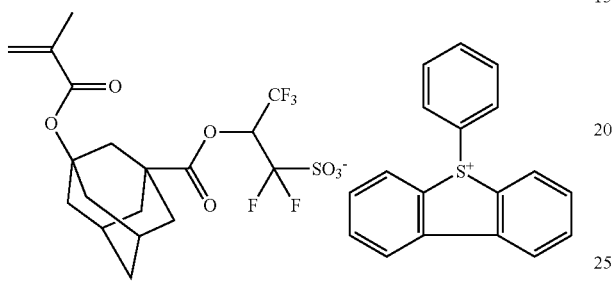

[1] Preparation of Polymers

Synthesis Example 1-1

Synthesis of Polymer P-1

Under nitrogen atmosphere, 62.8 g of MA-2, 18.2 g of ME-1, 19 g of MC-1, and 6.1 g of dimethyl 2,2'-azobisisobutyrate were dissolved in 140 g of methyl ethyl ketone (MEK). With stirring under nitrogen atmosphere, the resulting solution was added dropwise to 47 g of MEK at 80° C. over 4 hours. After the completion of dropwise addition, the polymerization solution was continuously stirred for 2 hours while keeping the to temperature of 80° C. The polymerization solution was cooled to room temperature and added dropwise to 1,500 g of hexane. The resulting precipitate was collected by filtration, and vacuum dried at 60° C. for 20 hours, obtaining Polymer P-1 in white solid form (amount 92 g, yield 92%). On $^{13}$C-NMR analysis, Polymer P-1 had a compositional ratio of MA-2/ME-1/MC-1=60/20/20 (molar ratio). On GPC analysis using THF, Polymer P-1 had a Mw of 8,400 and a Mw/Mn of 1.64.

Synthesis Examples 1-2 to 1-4

Synthesis of Polymers P-2 to P-4

Polymers P-2 to P-4 were synthesized by the same procedure as in Synthesis Example 1-1 aside from changing the type and amount of monomers. Polymer P-2 was determined for Mw and Mw/Mn by GPC analysis using THE Polymers P-3 and P-4 were determined for Mw and Mw/Mn by GPC analysis using DMF.

The compositional ratio, Mw and Mw/Mn of Polymers P-1 to P-4 are tabulated in Table 1.

TABLE 1

| Polymer | Unit 1 | Ratio (mol %) | Unit 2 | Ratio (mol %) | Unit 3 | Ratio (mol %) | Unit 4 | Ratio (mol %) | Mw | Mw/Mn |
|---|---|---|---|---|---|---|---|---|---|---|
| P-1 | MA-2 | 60.0 | ME-1 | 20.0 | MC-1 | 20.0 | — | — | 8,400 | 1.64 |
| P-2 | MA-1 | 30.0 | MA-4 | 30.0 | MC-2 | 40.0 | — | — | 9,000 | 1.62 |
| P-3 | MF-1 | 15.0 | MA-1 | 55.0 | MC-2 | 30.0 | — | — | 10,000 | 1.60 |
| P-4 | MF-1 | 20.0 | MA-3 | 30.0 | ME-2 | 30.0 | MC-1 | 20.0 | 11,000 | 1.60 |

[2] Synthesis of Onium Salts

Example 1-1

Synthesis of Sulfonium Salt (PAG-1)

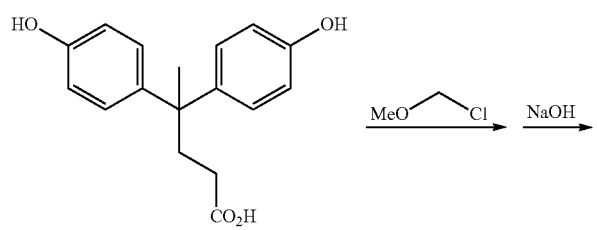

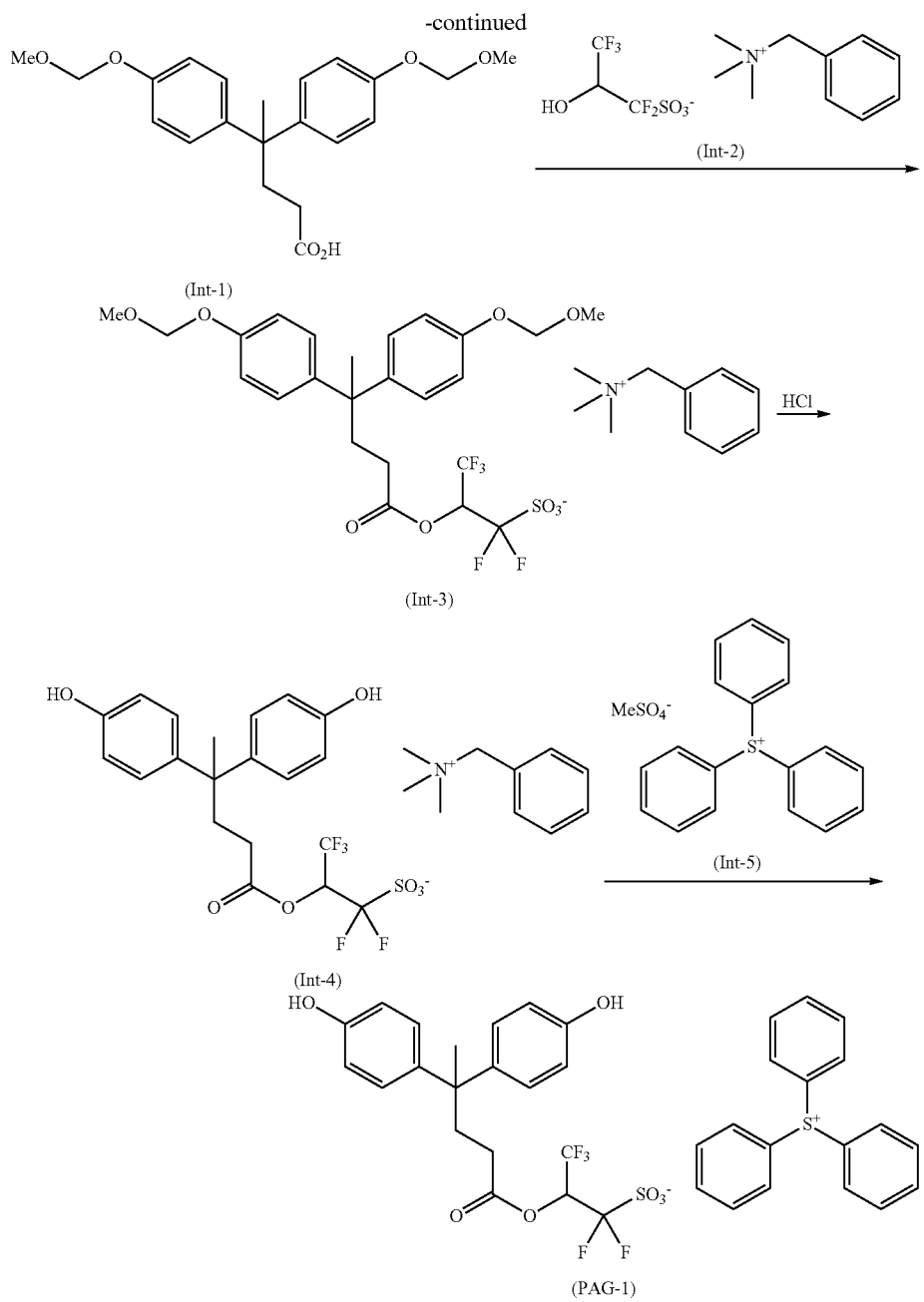

Under ice cooling, 154.6 g of chloromethyl methyl ether was added dropwise to a mixture of 100 g 4,4-bis(4-hydroxyphenyl)pentanoic acid, 270.8 g diisopropylethylamine, and 300 g methylene chloride. The reaction mixture was stirred at 40° C. for 2 days, after which it was ice cooled and combined with 400 g of deionized water. Methylene chloride, 150 g, was added to the reaction mixture. After stirring, the organic layer was taken out. Using a separatory funnel, the organic layer was washed with 150 g of deionized water, 150 g of dilute hydrochloric acid, 150 g of deionized water, 150 g of 5.0 wt % sodium hydrogencarbonate aqueous solution, and 150 g of deionized water in the described order. The resulting organic layer was concentrated under reduced pressure, obtaining 139.7 g of to a brown oily matter. 150 g of THF and 50 g of deionized water were added to the oily matter, followed by stirring. 106.3 g of 25 wt % sodium hydroxide aqueous solution was added dropwise to the solution, which was stirred at 40° C. overnight. The reaction solution was ice cooled, after which 250 g of 10 wt % hydrochloric acid was added dropwise to quench the reaction. Ethyl acetate, 200 g, was added to the solution, which was stirred. The organic layer was taken out, washed with 100 g of 5 wt % brine and 100 g of deionized water, and concentrated under reduced pressure. To the concentrate was added 700 g of hexane. After stirring, the supernatant was removed. The remaining oil was concentrated under reduced pressure, obtaining 116.6 g of carboxylic acid (Int-1) as brown oily matter (two-step yield 82%).

Next, 12 g of the carboxylic acid (Int-1) was mixed with 13.7 g of benzyltrimethylammonium 2-hydroxy-1,1,3,3,3- pentafluoropropanesulfonate (Int-2), 0.4 g of N,N-dimethylaminopyridine, 7.5 g of 1-ethyl-3-(3-dimethylaminopropyl)carbodiimide hydrochloride, and 55 g of methylene chloride, which was stirred at room temperature overnight. To the reaction mixture was added 40 g of 10 wt % benzyltrimethylammonium chloride aqueous solution. After stirring, the organic layer was taken out. The organic layer was washed with 30 g of deionized water, 30 g of dilute hydrochloric acid, and 30 g of deionized water in the described order, after which it was concentrated under reduced pressure. Diisopropyl ether was added to the concentrate. After stirring, the supernatant was removed. The remaining oil was concentrated under reduced pressure, obtaining 22.1 g of ammonium salt (Int-3) as brown oily matter.

Next, 22.1 g of the ammonium salt (Int-3) was mixed with 21.9 g of THF and 21.9 g of 5 wt % hydrochloric acid, which was stirred at 40° C. overnight. To the solution, 27.8 g of 10 wt % sodium hydrogencarbonate aqueous solution was added to quench the reaction. To the solution were added 100 g of methylene chloride and 20 g of 1-pentanol. After stirring, the organic layer was taken out. It was washed with 30 g of deionized water, 30 g of 10 wt % benzyltrimethylammonium chloride aqueous solution, and 30 g of deionized water in the described order, and concentrated under reduced pressure. Diisopropyl ether was added to the concentrate. After stirring, the supernatant was removed. The remaining oil was concentrated under reduced pressure. As the solvent was removed, a solid to precipitated out. The precipitate was taken out and dried under vacuum, obtaining 17 g of ammonium salt (Int-4) as pale brown solid (two-step yield 86%).

A mixture of 7 g of the ammonium salt (Int-4), 4.6 g of triphenylsulfonium methylsulfate (Int-5), 10 g of 1-pentanol, 60 g of methylene chloride, and 20 g of deionized water was stirred at room temperature for 30 minutes, after which the organic layer was taken out. It was washed with 30 g of deionized water, 30 g of 5.0 wt % sodium hydrogencarbonate aqueous solution, 30 g of deionized water, 30 g of dilute hydrochloric acid, and 30 g of deionized water in the described order, and concentrated under reduced pressure. The concentrate was dissolved in methyl isobutyl ketone. The solution was concentrated under reduced pressure again. Diisopropyl ether was added to the concentrate. After stirring, the supernatant was removed. The remainder oil was diluted with 5 g of methanol, which was stirred. Diisopropyl ether was added to the dilution, which was stirred for 2 days. Thereafter, a solid precipitated out. The solid precipitate was collected by filtration, washed with diisopropyl ether, and dried in vacuum. There was obtained 8 g (yield 90%) of the target sulfonium salt (PAG-1).

Figure 2:
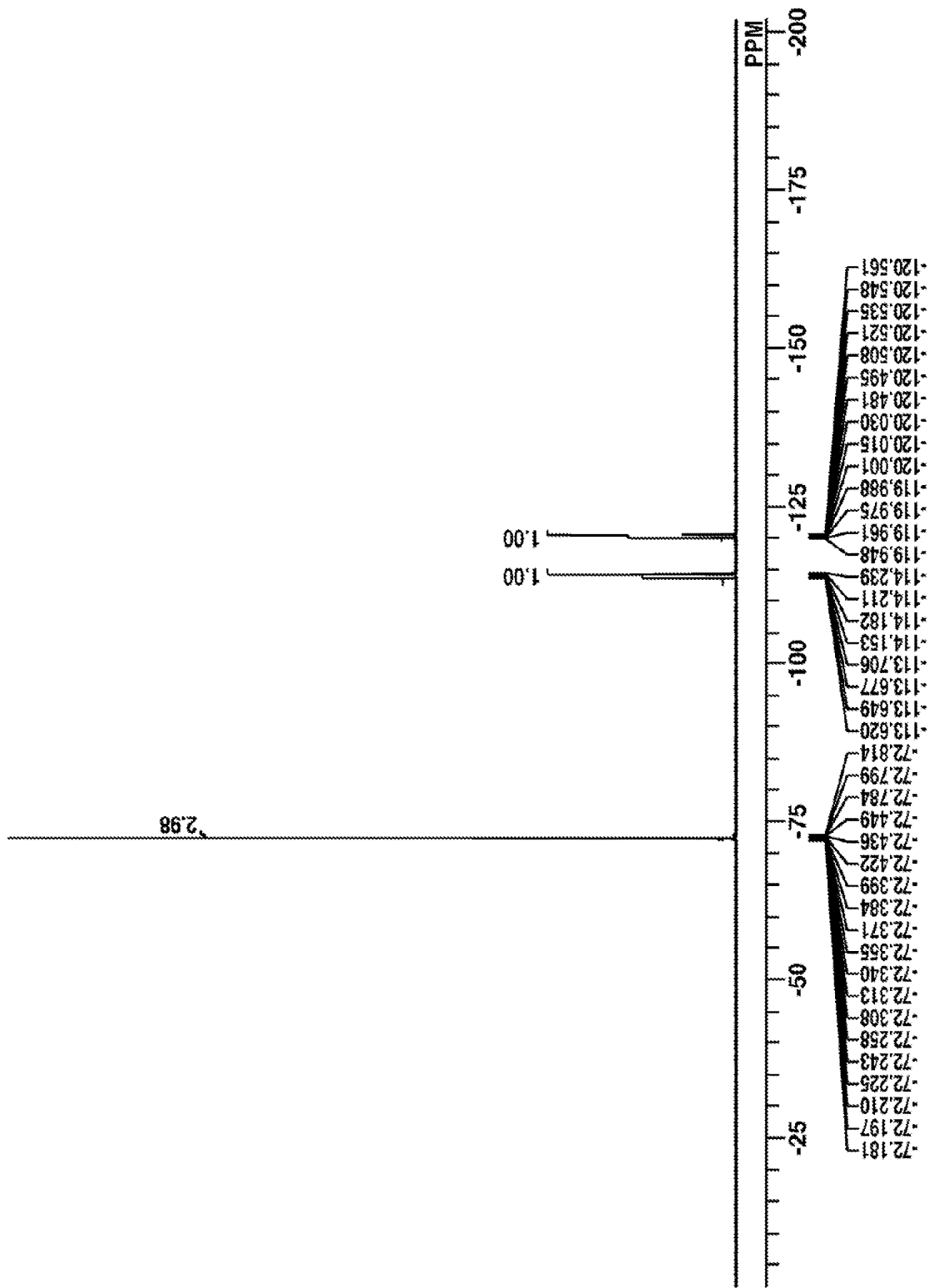
FIG. 2 is a diagram showing the $^{19}$F-NMR spectrum of sulfonium salt (PAG-1) in Example 1-1.

The sulfonium salt (PAG-1) was analyzed by IR absorption and NMR spectroscopy. The IR spectral data are shown below. The $^1$H- and $^{19}$F-NMR/DMSO-$d_6$ spectra are shown in FIGS. 1 and 2, respectively. It is noted that in the $^1$H-NMR spectroscopy, traces of residual solvents (methylene chloride, methyl isobutyl ketone, water) were observed.

IR Spectra (D-ATR):
 3333, 3066, 2969, 1770, 1614, 1593, 1477, 1448, 1372, 1272, 1227, 1179, 1127, 1092, 1075, 996, 917, 836, 748, 683, 641, 579, 561 cm$^{-1}$ Example 1-2

Synthesis of Sulfonium Salt (PAG-2)

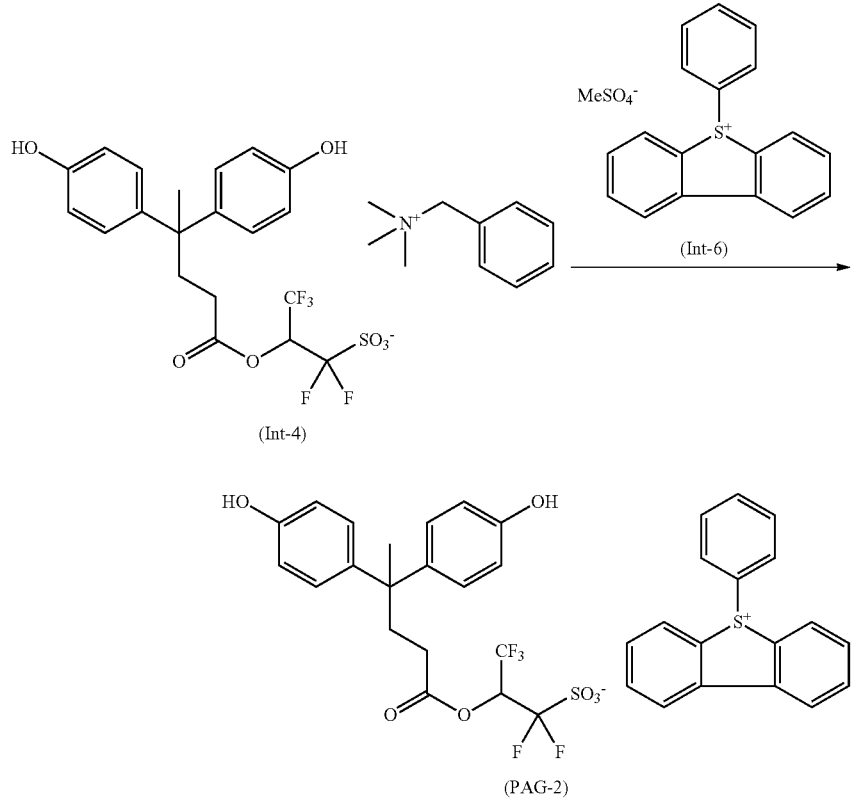

A mixture of 7 g of the ammonium salt (Int-4), 4.7 g of 5-phenyldibenzothiophenium methylsulfate (Int-6), 10 g of 1-pentanol, 60 g of methylene chloride, and 20 g of deionized water was stirred at room temperature for 1 hour, after which the organic layer was taken out. It was washed with 30 g of deionized water, 30 g of 5.0 wt % sodium hydrogencarbonate aqueous solution, 30 g of deionized water, 30 g of dilute hydrochloric acid, and 30 g of deionized water in the described order. The organic layer was combined with 0.7 g of active carbon and stirred overnight. The active carbon was filtered off and the filtrate was concentrated under reduced pressure. The concentrate was dissolved in methyl isobutyl ketone. The solution was concentrated under reduced pressure again. To the concentrate was added tert-butyl methyl ether. After stirring, the supernatant was removed. The remainder oil was diluted with methylene chloride, which was stirred. To the dilution was added tert-butyl methyl ether. After stirring, a solid precipitated out. The solid precipitate was collected by filtration, washed with tert-butyl methyl ether, and dried in vacuum. There was obtained 5.9 g (yield 71%) of the target sulfonium salt (PAG-2).

Figure 3:
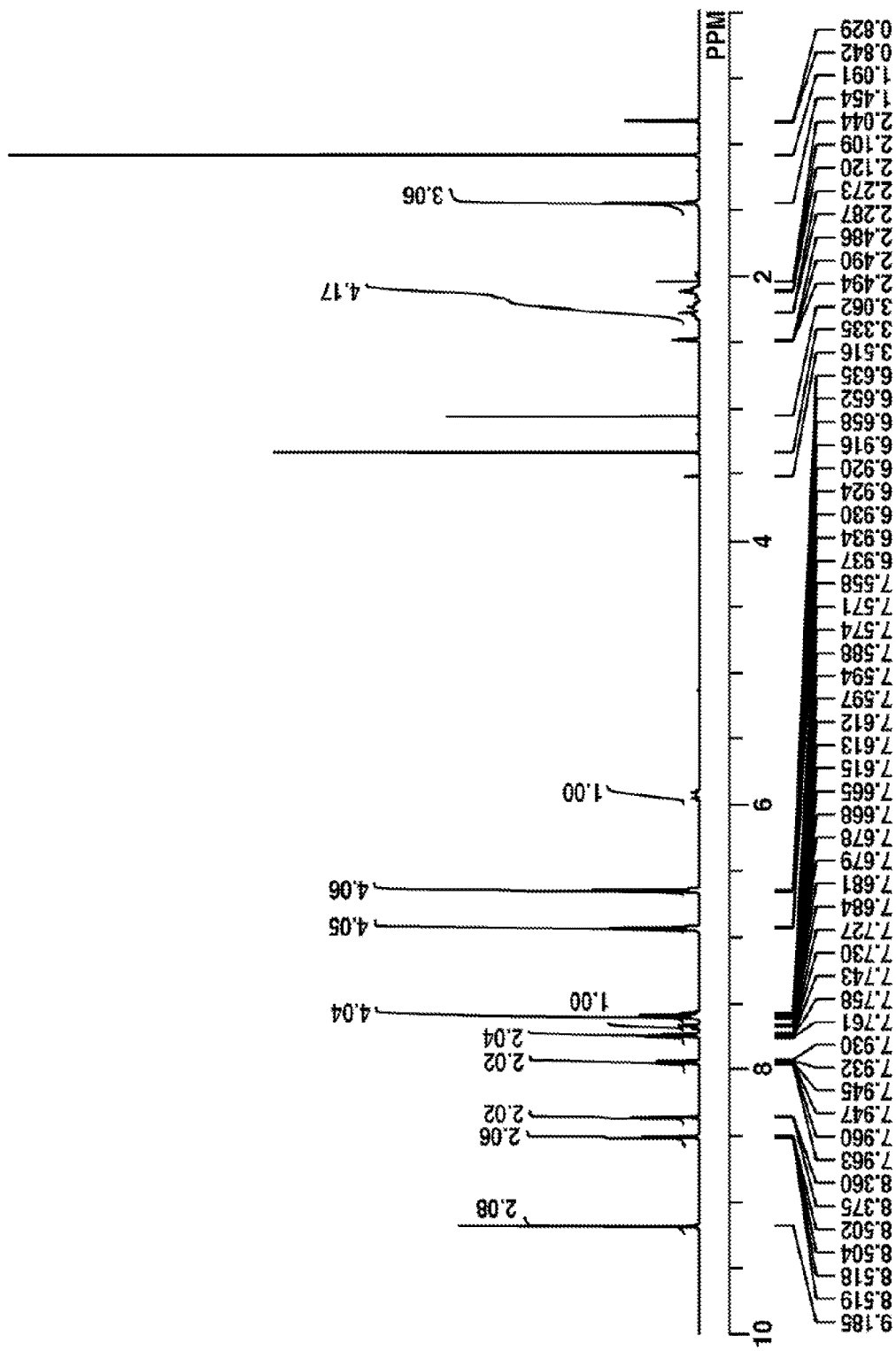
FIGS. 3 and 4 are diagrams showing the $^{19}$H-NMR and $^{19}$F-NMR spectra of sulfonium salt (PAG-2) in Example 1-2, respectively.
Figure 4:
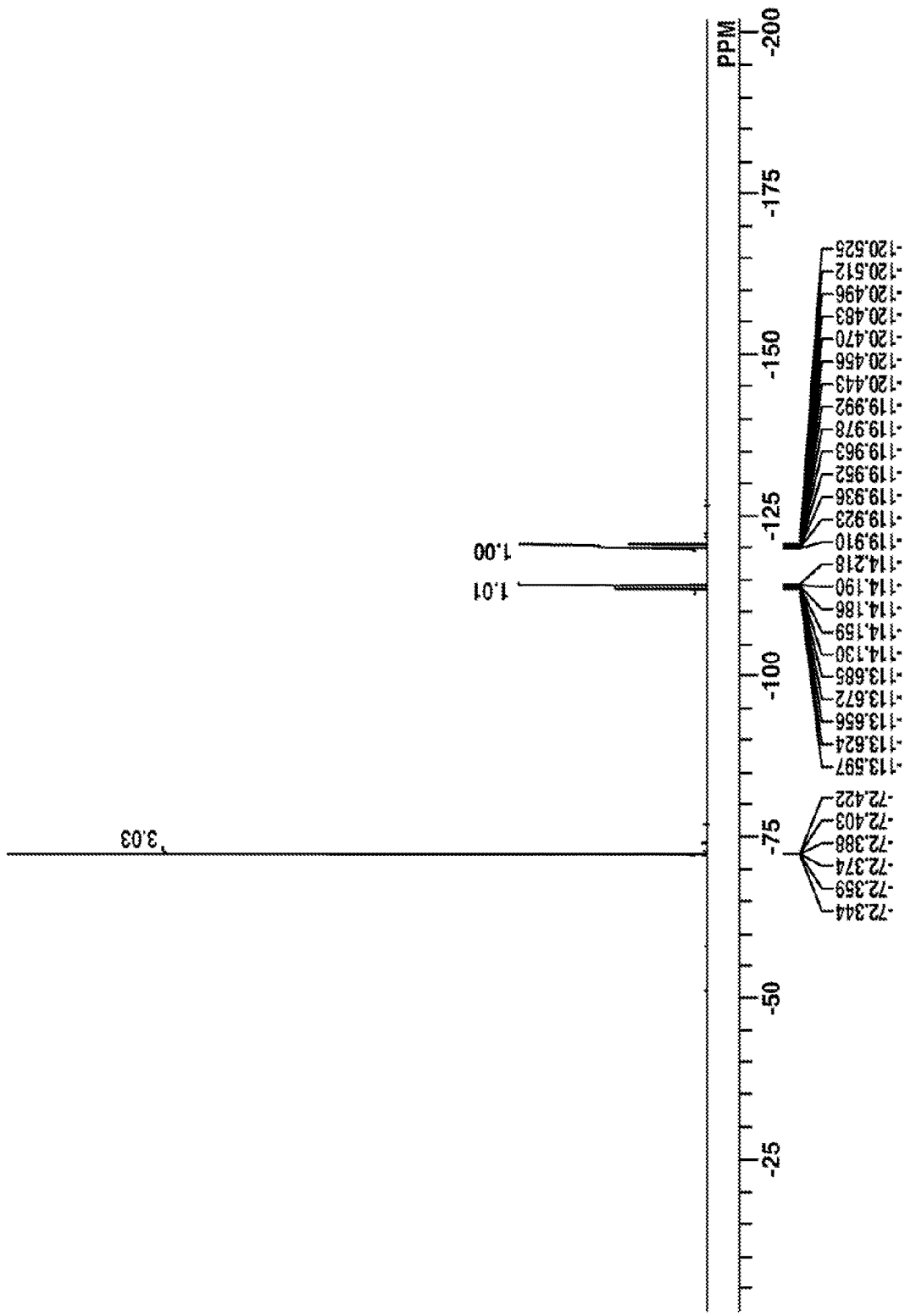

The sulfonium salt (PAG-2) was analyzed by NMR spectroscopy. The $^1$H- and $^{19}$F-NMR/DMSO-$d_6$ spectra are shown in FIGS. 3 and 4, respectively. It is noted that in the $^1$H-NMR spectroscopy, traces of residual solvents (tert-butyl methyl ether, methyl isobutyl ketone, water) were observed.

Example 1-3

Synthesis of Sulfonnun Salt (PAG-3)

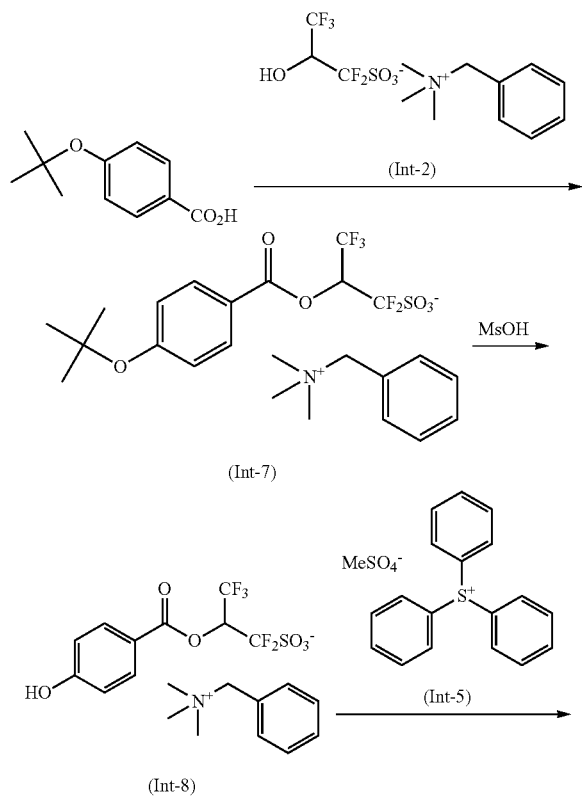

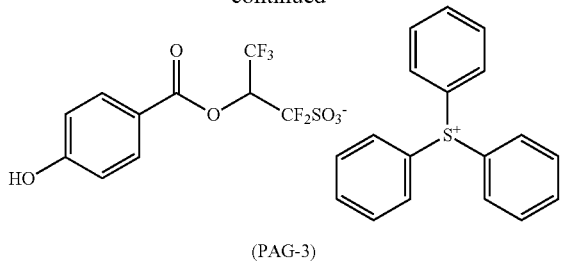

(PAG-3)

A mixture of 100 g of 4-tert-butoxybenzoic acid, 177.5 g of benzyltrimethylammnonium 2-hydroxy-1,1,3,3,3-pentafluoropropanesulfonate (Int-2), 5.7 g of N,N-dimethylaminopyridine, 107.7 g of 1-ethyl-3-(3-dimethylaminopropyl) carbodiimide hydrochloride, and 1,000 g of methylene chloride was stirred at room temperature overnight. To the mixture was added 400 g of 10 wt % sodium hydrogencarbonate aqueous solution. After stirring, the organic layer was taken out. It was washed with 200 g of 20 wt % benzyltrimethylammonium chloride aqueous solution and 200 g of deionized water, and concentrated under reduced pressure. Diisopropyl ether, 1,400 g, was added to the concentrate, which was held for crystallization. The solid precipitate was collected by filtration, washed with diisopropyl ether, and dried in vacuum. There was obtained 235.1 g (yield 90%) of an ammonium salt (Int-7) as white solid.

A mixture of 235.1 g of the ammonium salt (Int-7), 1,175 g of methanol, and 0.8 g of methanesulfonic acid was stirred under reflux for 25 hours. The solution was cooled to room temperature and concentrated under reduced pressure. The concentrate was diluted with methanol to a concentration of 30 wt %, and 1,266 g of deionized water was added to the dilution, which was held for crystallization. The solid precipitate was collected by filtration, washed consecutively with deionized water and methanol, and dried in vacuum. There was obtained 200 g (yield 94%) of an ammonium salt (Int-8) as white solid.

A mixture of 5 g of the ammonium salt (Int-8), 5.2 g of triphenylsulfonium methylsulfate (Int-5), 50 g of methylene chloride, and 30 g of deionized water was stirred at room temperature for 1 hour, after which the organic layer was taken out. It was washed with 20 g of deionized water and 20 g of 20 wt % methanol aqueous solution, and concentrated under reduced pressure. To the concentrate was added 70 g of diisopropyl ether. The liquid was stirred and held for precipitation. The solid precipitate was collected by filtration, washed with diisopropyl ether, and dried in vacuum. There was obtained 5.3 g (yield 86%) of the target sulfonium salt (PAG-3).

Figure 5:
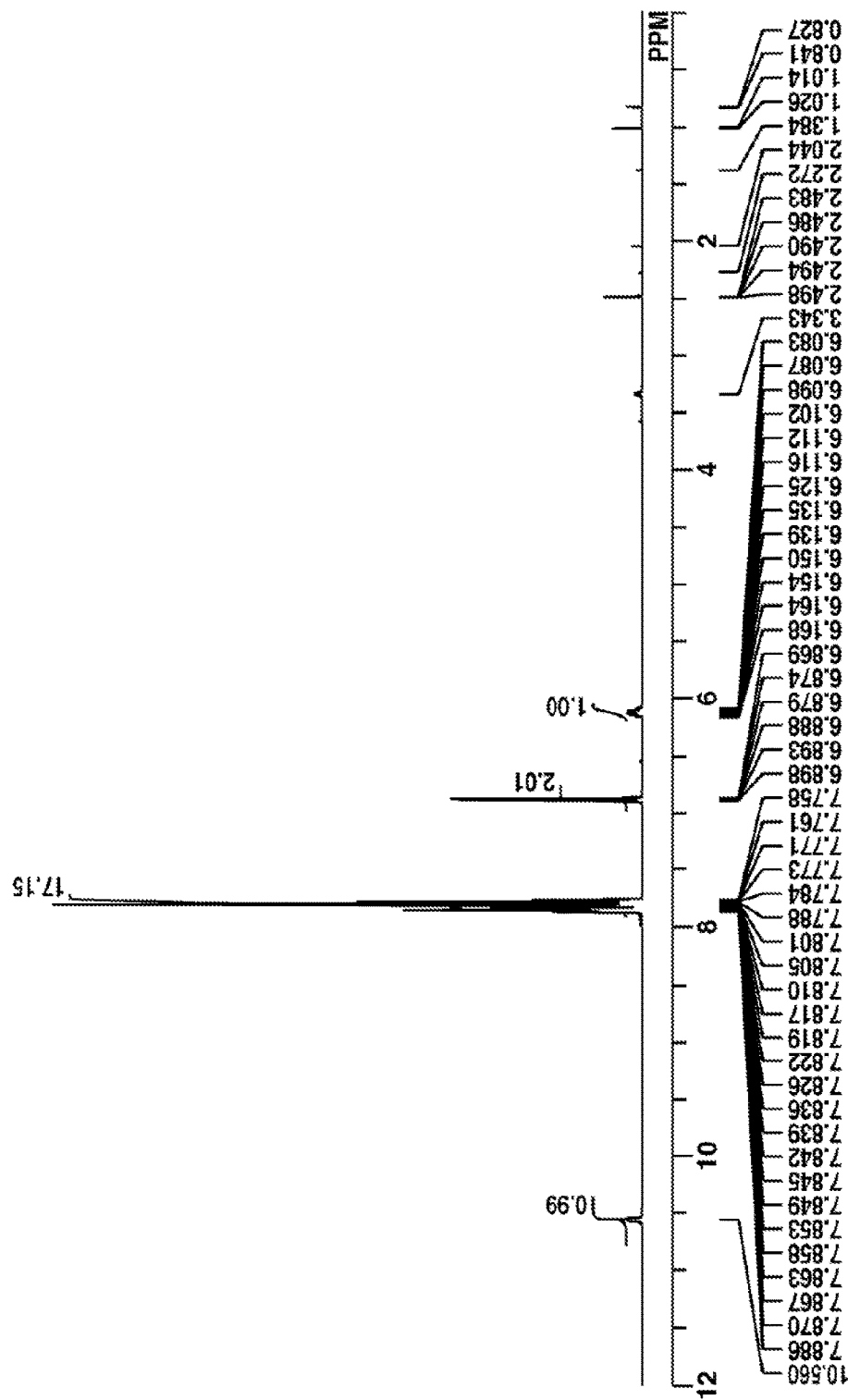
FIGS. 5 and 6 are diagrams showing the $^1$H-NMR and $^{19}$F-NMR spectra of sulfonium salt (PAG-3) in Example 1-3, respectively.
Figure 6:
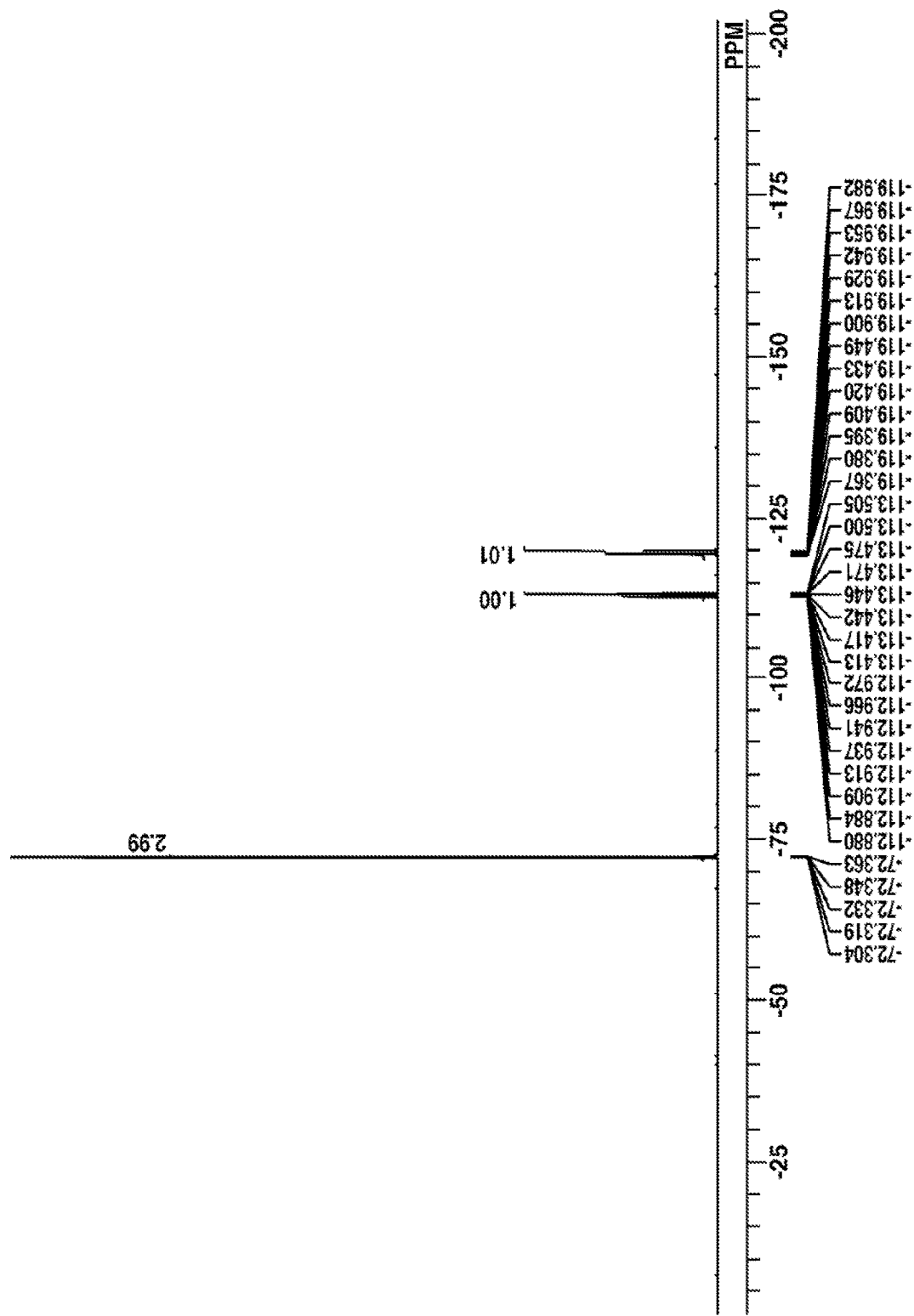

The sulfonium salt (PAG-3) was analyzed by NMR spectroscopy. The $^1$H- and $^{19}$F-NMR/DMSO-$d_6$ spectra are shown in FIGS. 5 and 6, respectively. It is noted that in the $^1$H-NMR spectroscopy, traces of residual solvents (diisopropyl ether, methyl isobutyl ketone, water) were observed.

Example 1-4

Synthesis of Sulfonium Salt (PAG-4)

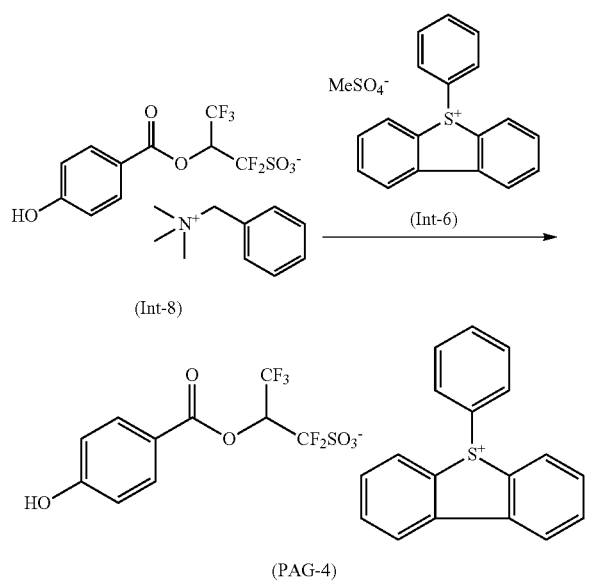

A mixture of 99.9 g of the ammonium salt (Int-8) and 350 g of methanol was stirred at 50° C. To the mixture, 558.7 g of 16 wt % aqueous solution of 5-phenyldibenzothiophenium methylsulfate (hit-6) was slowly added, followed by stirring at 50° C. for 10 minutes. Thereafter, 350 g of deionized water was added to the solution, which was stirred at 50° C. for 10 minutes and at room temperature for a further 6 hours. The solid precipitate was collected by filtration, washed with deionized water, and dried in to vacuum. The resulting solid was dissolved again by adding 730 g of methanol and stirring at 60° C. To the solution, 6 g of active carbon was added, followed by stirring at 60° C. for 5 hours. The active carbon was filtered off, and 1,500 g of deionized water was added to the filtrate for crystallization. The solid precipitate was collected by filtration, washed with deionized water, and dried in vacuum. There was obtained 110.6 g of the target sulfonium salt (PAG-4).

Figure 7:
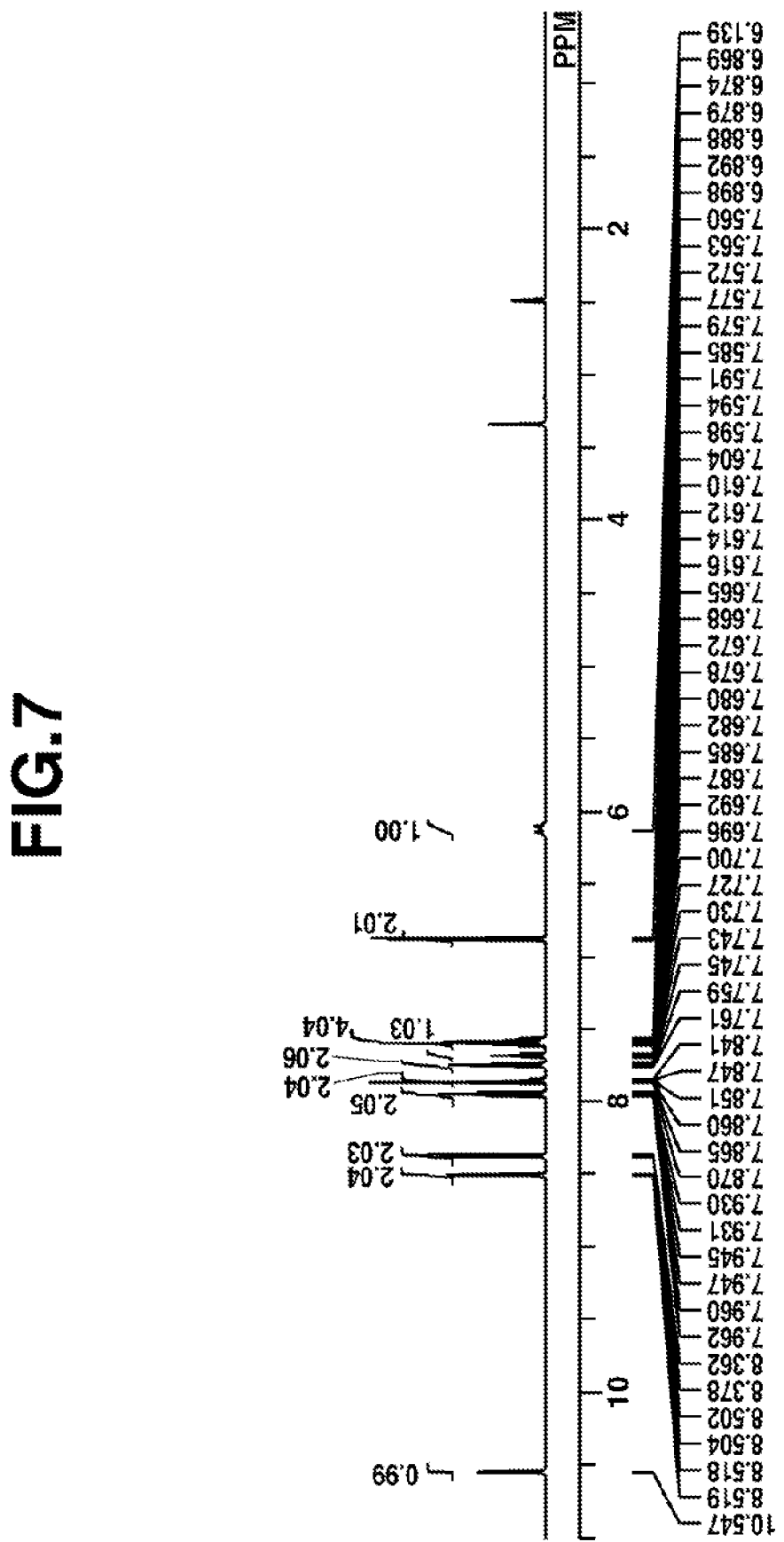
FIGS. 7 and 8 are diagrams showing the $^1$H-NMR and $^{19}$F-NMR spectra of sulfonium salt (PAG-4) in Example 1-4, respectively.
Figure 8:
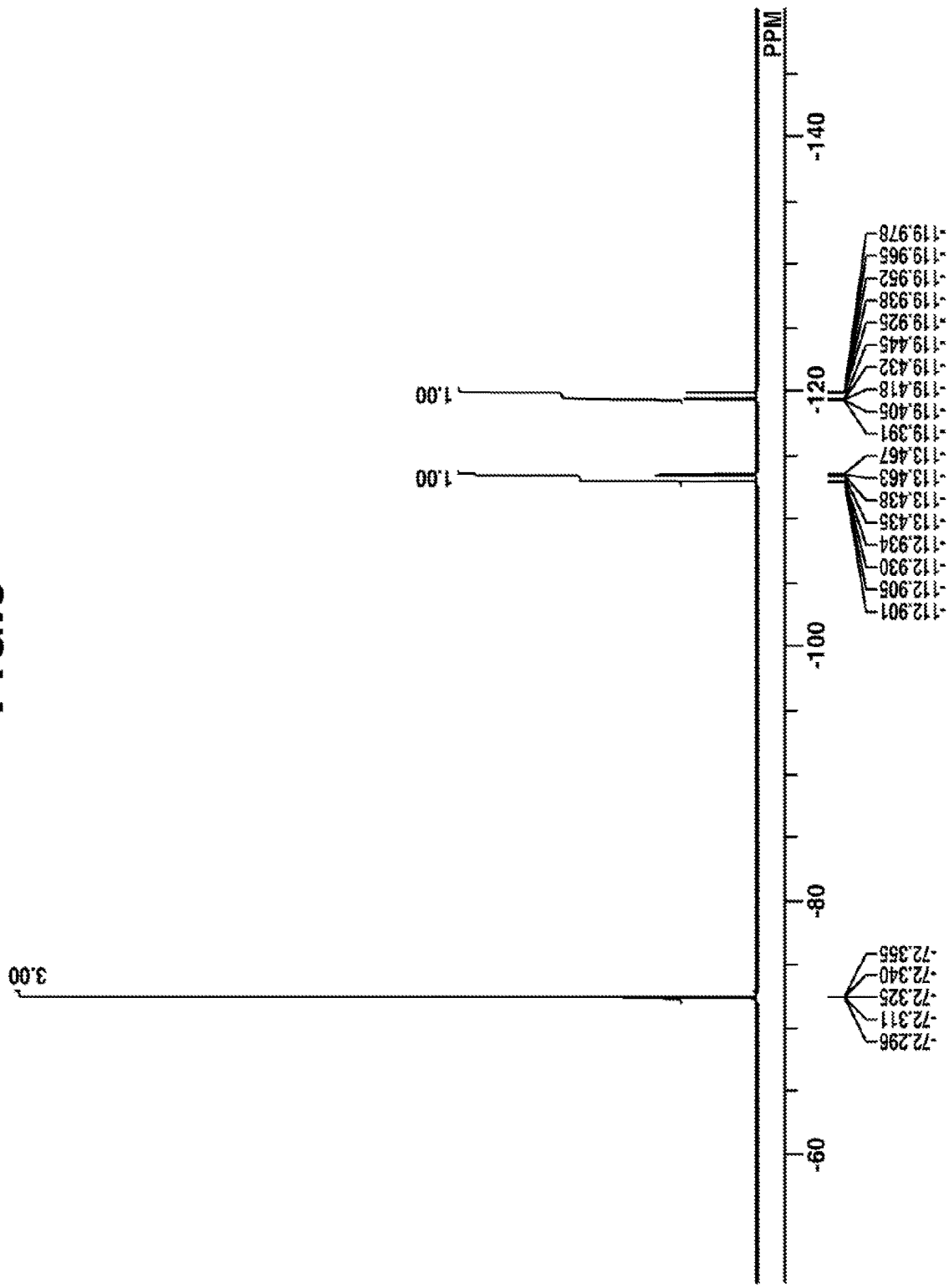

The sulfonium salt (PAG-4) was analyzed by IR absorption and NMR spectroscopy. The IR spectral data are shown below. The $^1$H- and $^{19}$F-NMR/DMSO-$d_6$ spectra are shown in FIGS. 7 and 8, respectively. It is noted that in the $^1$H-NMR spectroscopy, a trace of residual solvent (water) was observed.

IR Spectra (D-ATR):
3375, 3231, 3079, 2979, 1721, 1606, 1588, 1517, 1477, 1450, 1376, 1323, 1284, 1259, 1187, 1161, 1117, 1103, 1078, 1039, 991, 900, 858, 845, 781, 761, 750, 736, 706, 679, 644, 606, 575, 555 cm$^{-1}$

Example 1-5

Synthesis of Sulfonium Salt (PAG-5)

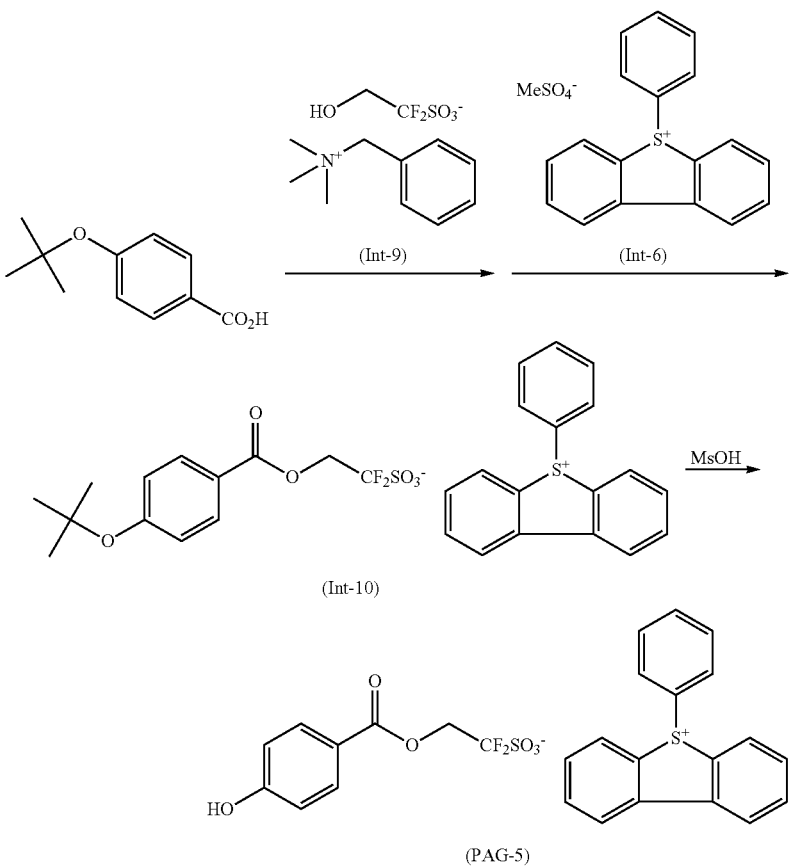

A mixture of 6.4 g of 4-tert-butoxybenzoic acid, 9.3 g of benzyltrimethylainmonium 2-hydroxy-1,1-difluoroethanesulfonate (Int-9), 0.4 g of N,N-dimethylaminopyridine, 6.9 g of 1-ethyl-3-(3-dimethylaminopropyl)carbodiimide hydrochloride, and 70 g of methylene chloride was stirred at room temperature overnight. To the mixture, 60 g of 10 wt % sodium hydrogencarbonate aqueous solution was added. After stirring, the organic layer was taken out and washed with 30 g of deionized water. Then 45 g of a 30 wt % aqueous solution of 5-phenyldibenzothiophenium methylsulfate (Int-6) was added to the organic layer, which was stirred for 30 minutes. The organic layer was taken out, washed with 30 g of deionized water and 20 wt % methanol aqueous solution in order, and concentrated under reduced pressure. Diisopropyl ether was added to the concentrate for crystallization. The solid precipitate was collected by filtration, washed with diisopropyl ether, and dried in vacuum. There was obtained 17.1 g (yield 94%) of a sulfonium salt (Int-10).

A mixture of 9.6 g of the sulfonium salt (Int-10), 48 g of 2-propanol, and 0.03 g of methanesulfonic acid was stirred at 70° C. for 22 hours. The mixture was cooled to room temperature for precipitation. The solid precipitate was collected by filtration, washed with deionized water and diisopropyl ether in order, and dried in vacuum. There was obtained 7 g (yield 80%) of the target sulfonium salt (PAG-5) as white solid.

Figure 9:
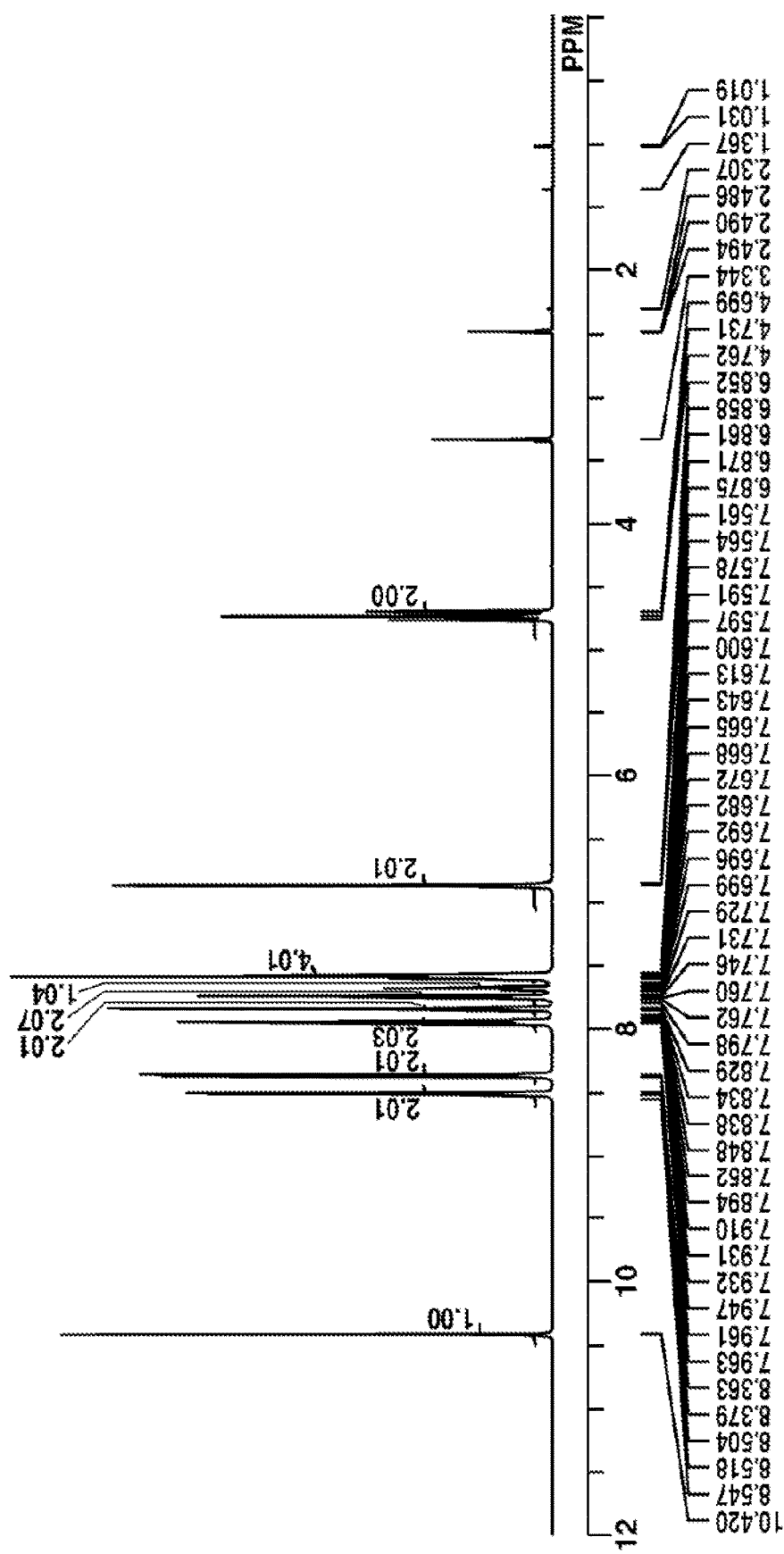
FIGS. 9 and 10 are diagrams showing the $^1$H-NMR and $^{19}$F-NMR spectra of sulfonium salt (PAG-5) in Example 1-5, respectively.
Figure 10:
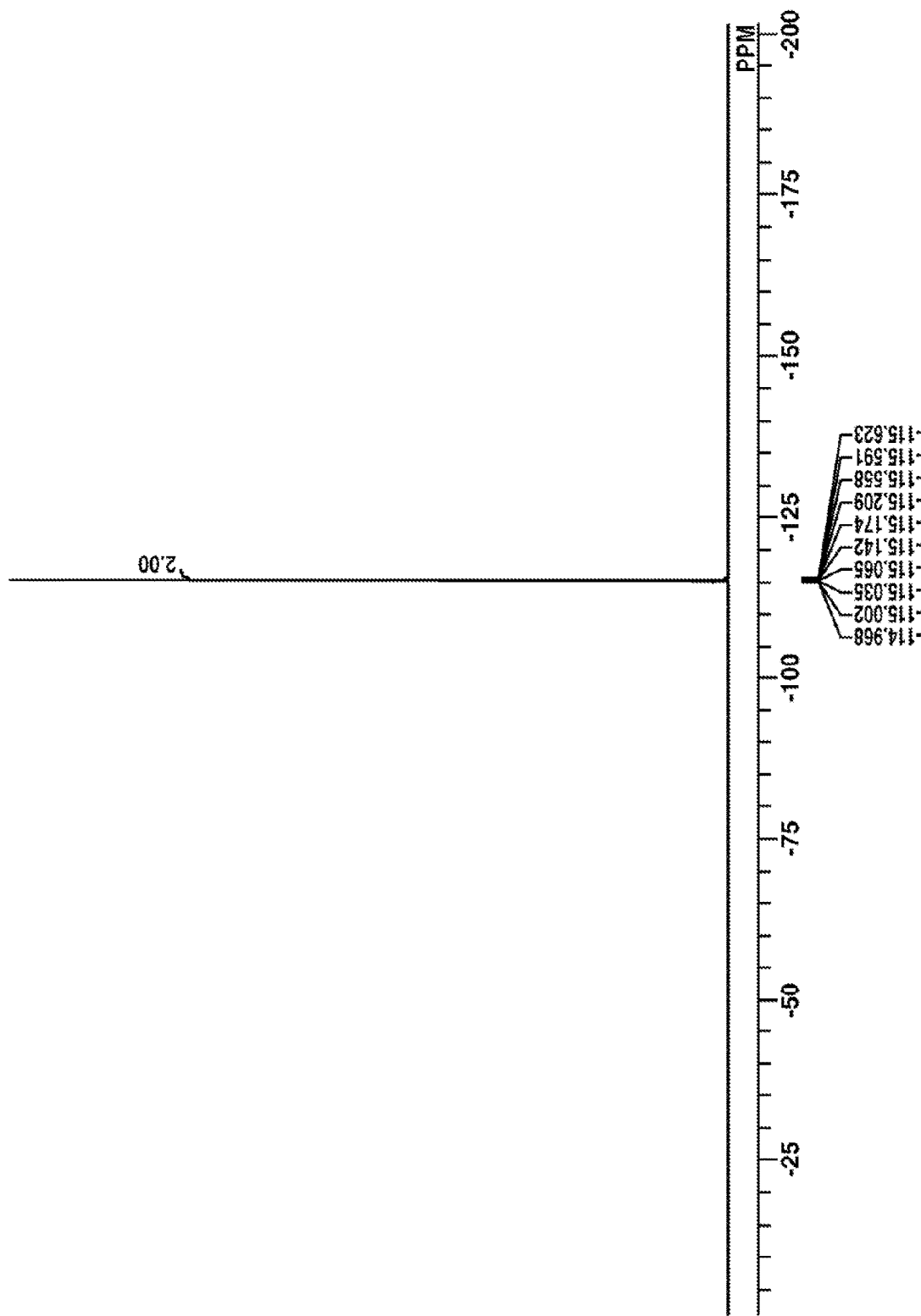

The sulfonium salt (PAG-5) was analyzed by NMR spectroscopy. The $^1$H- and $^{19}$F-NMR/DMSO-$d_6$ spectra are shown in FIGS. 9 and 10, respectively. It is noted that in the $^1$H-NMR spectroscopy, traces of residual solvents (diisopropyl ether, water) were observed.

Example 1-6

Synthesis of Sulfonium Salt (PAG-6)

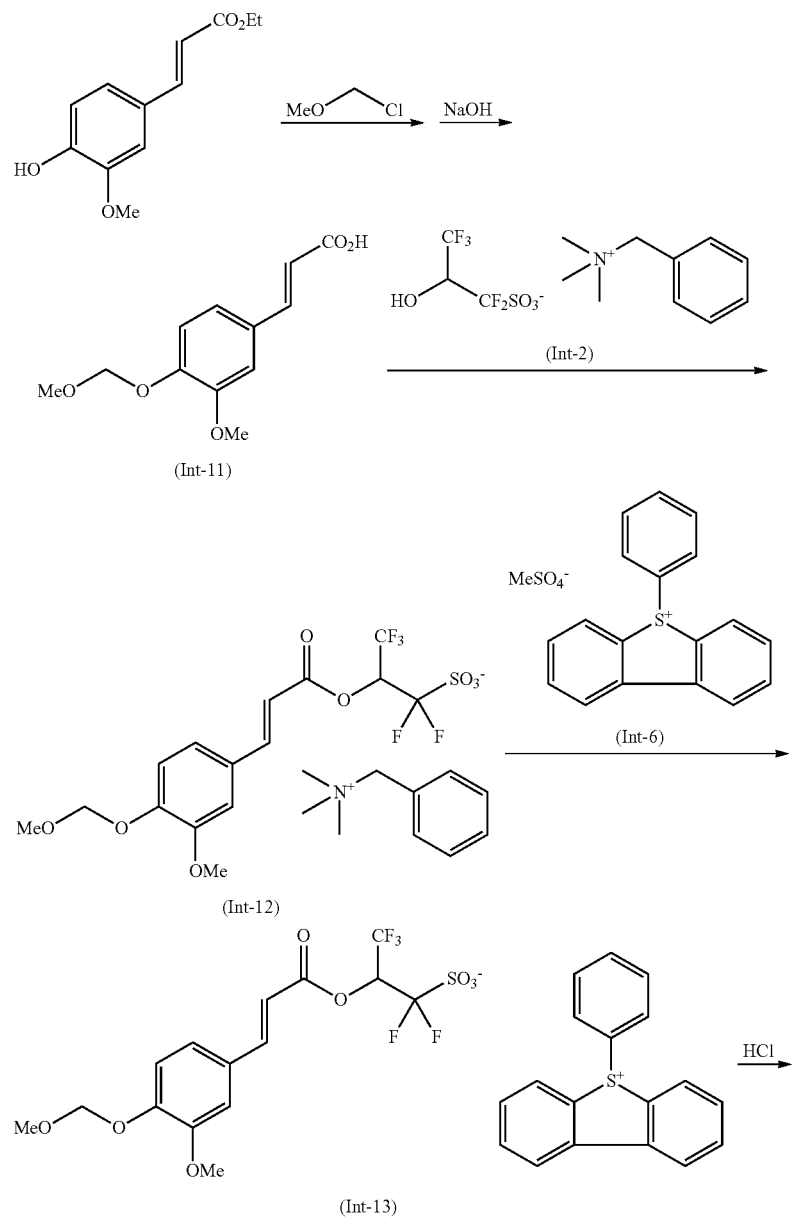

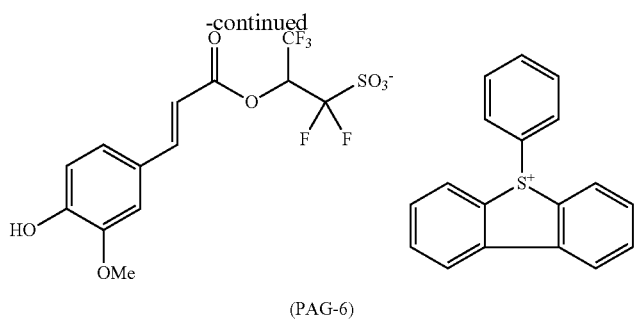

(PAG-6)

Under ice cooling, 483 g of chloromethyl methyl ether was added dropwise to a mixture of 111.1 g of ethyl ferulate, 90.5 g of diisopropylethylamine, and 600 g of methylene chloride. The reaction solution was stirred at 40° C. for 2 days, ice cooled, and combined with 500 g of deionized water. To the solution was added 150 g of methylene chloride. After stirring, the organic layer was taken out. Using a separatory funnel, the organic layer was washed with 150 g of deionized water, 500 g of dilute hydrochloric acid, 150 g of deionized water, 500 g of 5.0 wt % sodium hydrogencarbonate aqueous solution, and 150 g of deionized water in the described order. The organic layer was concentrated under reduced pressure, obtaining 122 g of a brown oily matter. To the oily matter, 500 g of THF and 500 g of deionized water were added. After stirring, 320 g of 25 wt % sodium hydroxide aqueous solution was added dropwise to the solution, which was stirred at 40° C. overnight. After the reaction solution was ice cooled, 360 g of 10 wt % hydrochloric acid was added dropwise to the solution to quench the reaction. 500 g of ethyl acetate was added to the solution. After stirring, the organic layer was taken out. It was washed with 500 g of 5 wt % saline and 500 g of deionized water in order, and concentrated under reduced pressure until the concentrate weighed 900 g. 1,500 g of hexane was added to the concentrate, which was stirred below 10° C. for 1 hour and held for re-crystallization. The wet crystals were collected by suction filtration and dried in vacuum. There was obtained 96 g of carboxylic acid (hit-11) (two-step yield 80%).

A mixture of 23.8 g of the carboxylic acid (Int-11), 27.5 g of benzyltrimethylammonium 2-hydroxy-1,1,3,3,3-pentafluoropropanesulfonate (Int-2), 0.12 g of N,N-dimethylaminopyridine, 23 g of 1-ethyl-3-(3-dimethylaminopropyl)carbodiimide hydrochloride, and 100 g of methylene chloride was stirred at room temperature overnight. Thereafter, 230 g of 20 wt % aqueous solution of benzyltrimethylammonium chloride was added to the mixture. After stirring, the organic layer was taken out. It was washed with 100 g of deionized water, 100 g of dilute hydrochloric acid, and 100 g of deionized water in order, and concentrated under reduced pressure. There was obtained 62 g of an ammonium salt (Int-12).

To 62 g of the ammonium salt (Int-12), 149 g of 30 wt % aqueous solution of 5-phenyldibenzothiophenium methylsulfate (Int-6) was added. After stirring for 30 minutes, the organic layer was taken out. It was washed with 100 g of deionized water twice, and concentrated under reduced pressure, obtaining 66.2 g of a sulfonium salt (Int-13).

A mixture of 66.2 g of the sulfonium salt (Int-13), 150 g of THF, and 60 g of 5 wt % hydrochloric acid was stirred at 40° C. overnight. To the solution, 70 g of 10 wt % sodium hydrogencarbonate aqueous solution was added to quench the reaction. To the solution was added 200 g of methylene chloride. After stirring, the organic layer was taken out. It was washed with 60 g of deionized water twice, and concentrated under reduced pressure. There was obtained 56.6 g of the target sulfonium salt (PAG-6) (three-step yield 85%).

Figure 11:
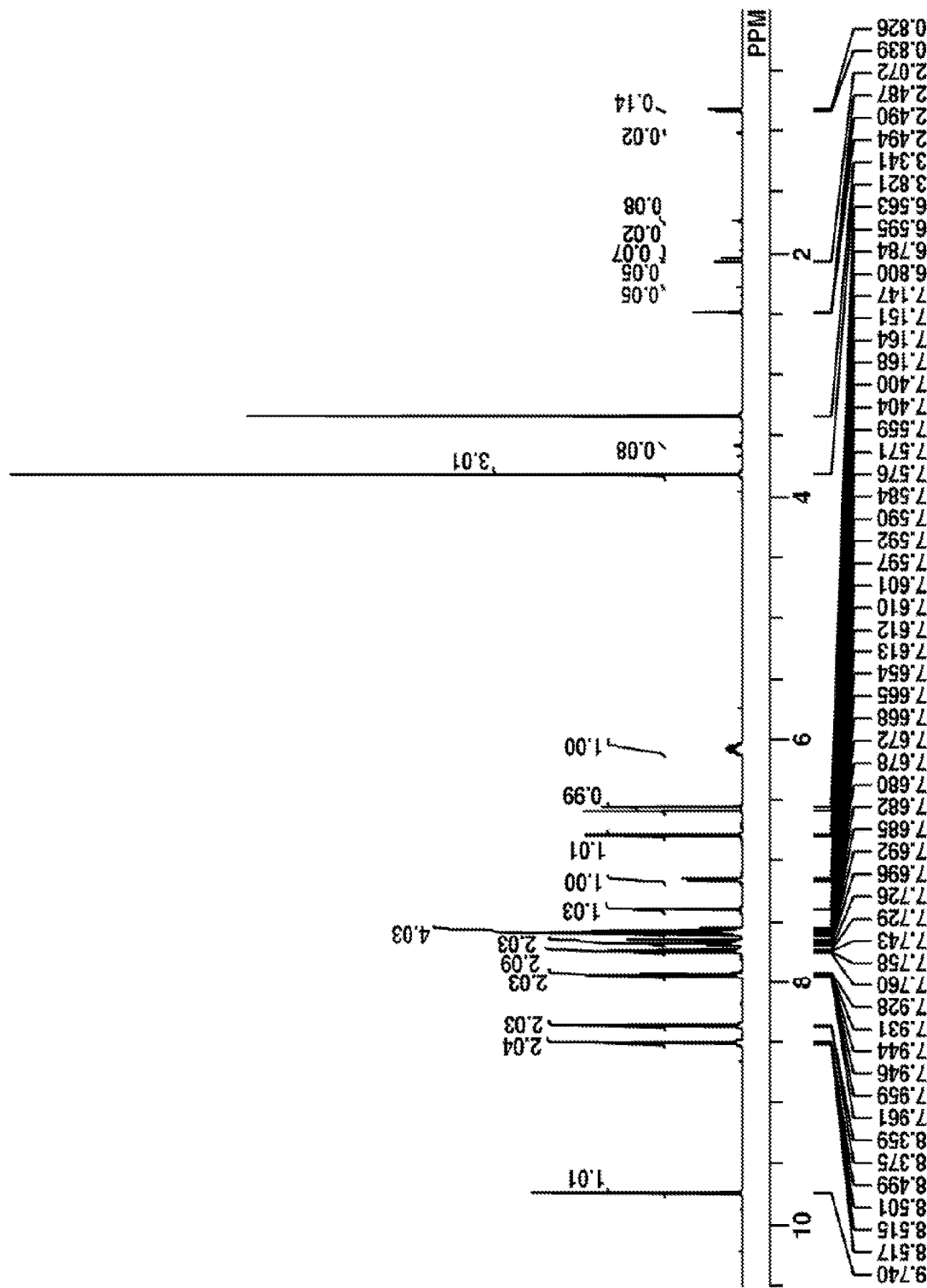
FIGS. 11 and 12 are diagrams showing the $^1$H-NMR and $^{19}$F-NMR spectra of sulfonium salt (PAG-6) in Example 1-6, respectively.
Figure 12:
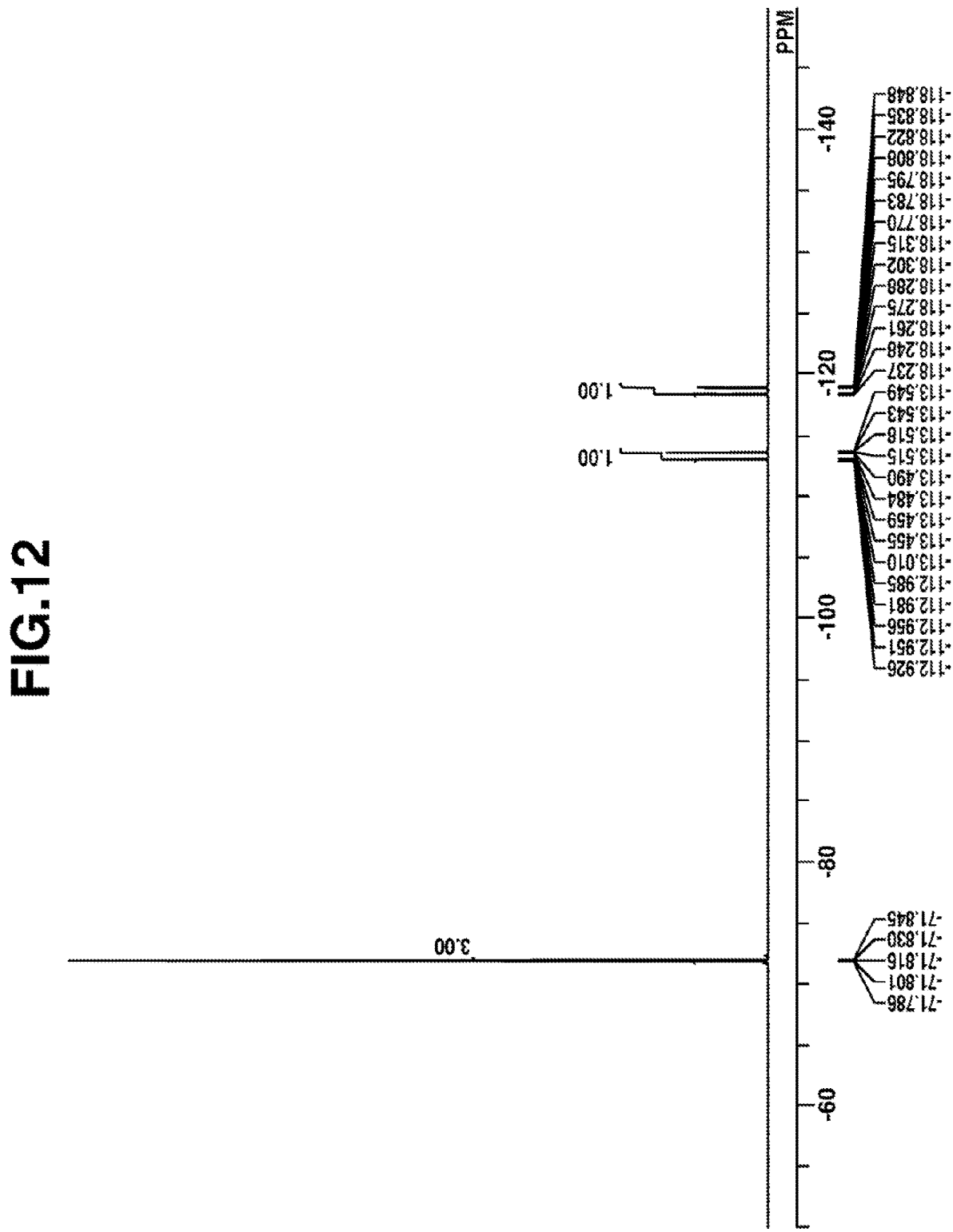

The sulfonium salt (PAG-6) was analyzed by NMR spectroscopy. The and $^{19}$F-NMR/DMSO-$d_6$ spectra are shown in FIGS. 11 and 12, respectively. It is noted that in the $^1$H-NMR spectroscopy, traces of residual solvents (diisopropyl ether, water) were to observed.

[3] Preparation of Resist Compositions

Examples 2-1 to 2-10 and Comparative Examples 1-1 to 1-2

Resist compositions in solution form were prepared by dissolving Polymer P-1 to P-4, onium salt PAG-1 to PAG-6, comparative photoacid generator PAG-X, PAG-Y, and quencher Q-1 in a solvent in accordance with the formulation shown in Table 2, and filtering through a Teflon® filter with a pore size of 0.2 μm.

The solvent, PAG-X, PAG-Y, and Q-1 in Table 2 are identified below.

PGMEA: propylene glycol monomethyl ether acetate

GBL: γ-butyrolactone

PAG-X, PAG-Y

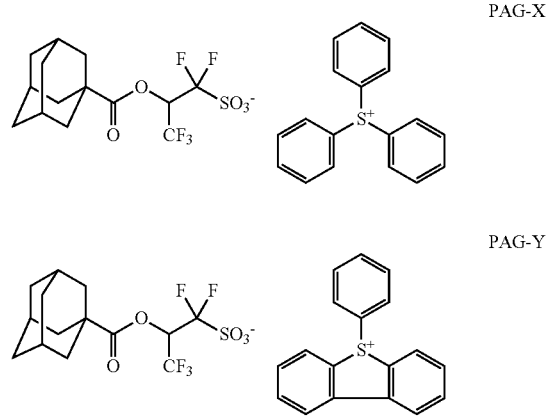

Q-1

-continued

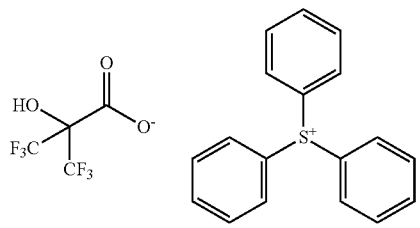

Q-1 and CDU were evaluated by the following methods. The optimum dose Eop was the dose ($\mu C/cm^2$) which provided a CH pattern with a hole size of 24 nm and a pitch of 48 nm, and reported as a sensitivity. A smaller dose value indicates a higher sensitivity. For the CH pattern formed by exposure at Eop, the hole size was measured at 10 areas subject to an identical dose of shot (9 contact holes per area), from which a 3-fold value ($3\sigma$) of standard deviation ($\sigma$) was determined and reported as CDU. A smaller value of $3\sigma$ indicates a CH pattern having improved CDU.

The results are shown in Table 3.

TABLE 2

| | Resist composition | Polymer (pbw) | Photoacid generator (pbw) | Quencher (pbw) | Solvent 1 (pbw) | Solvent 2 (pbw) |
|---|---|---|---|---|---|---|
| Example 2-1 | R-01 | P-1 (80) | PAG-3 (30.0) | Q-1 (7.0) | PGMEA (2,328) | GBL (449) |
| 2-2 | R-02 | P-1 (80) | PAG-5 (30.0) | Q-1 (7.0) | PGMEA (3,757) | GBL (1,600) |
| 2-3 | R-03 | P-2 (80) | PAG-4 (30.0) | Q-1 (7.0) | PGMEA (3,757) | GBL (1,600) |
| 2-4 | R-04 | P-2 (80) | PAG-1 (30.0) | Q-1 (7.0) | PGMEA (3,757) | GBL (1,600) |
| 2-5 | R-05 | P-2 (80) | PAG-2 (30.0) | Q-1 (7.0) | PGMEA (3,757) | GBL (1,600) |
| 2-6 | R-06 | P-3 (80) | PAG-4 (8.2) | Q-1 (6.9) | PGMEA (2,990) | GBL (843) |
| 2-7 | R-07 | P-3 (80) | PAG-2 (8.2) | Q-1 (6.9) | PGMEA (2,990) | GBL (843) |
| 2-8 | R-08 | P-4 (80) | PAG-4 (8.2) | Q-1 (6.9) | PGMEA (2,990) | GBL (843) |
| 2-9 | R-09 | P-4 (80) | PAG-2 (8.2) | Q-1 (6.9) | PGMEA (2,990) | GBL (843) |
| 2-10 | R-10 | P-3 (80) | PAG-6 (8.2) | Q-1 (6.9) | PGMEA (2,990) | GBL (843) |
| Comparative Example 1-1 | CR-01 | P-1 (80) | PAG-X (16.9) | Q-1 (7.0) | PGMEA (3,757) | GBL (1,600) |
| 1-2 | CR-02 | P-4 (80) | PAG-Y (9.8) | Q-1 (6.9) | PGMEA (2,990) | GBL (843) |

[4] EB lithography Test

Examples 3-1 to 3-10 and Comparative Examples 2-1 to 2-2

An antireflective coating solution (DUV-42, Nissan Chemical Corp.) was coated on a silicon substrate and baked at 200° C. for 60 seconds to form an ARC of 61 nm thick. Each of the resist compositions (R-01 to R-10, CR-01, CR-02) was spin coated onto the ARC and prebaked on a hotplate at 100° C. for 60 seconds to form a resist film of 45 nm thick. Using an EB lithography system ELS-F125 (Elionix Co., Ltd., accelerating voltage 125 kV), the resist film was exposed to EB through a mask bearing a contact hole (CH) pattern to with a hole size of 24 nm and a pitch of 48 nm (on-wafer size) while varying the dose from 50 $\mu C/cm^2$ at a step of 1 $\mu C/cm^2$. The resist film was baked (PEB) at the temperature shown in Table 3 for 60 seconds. The resist film was then puddle developed in a 2.38 wt % TMAH aqueous solution for 30 seconds, rinsed with deionized water, and spin dried, yielding a positive resist pattern.

The CH pattern was observed under CD-SEM S9380 (Hitachi High Technologies Corp.) whereupon sensitivity

TABLE 3

| | | Resist composition | PEB temp. (° C.) | Sensitivity ($\mu C/cm^2$) | CDU (nm) |
|---|---|---|---|---|---|
| Example | 3-1 | R-01 | 95 | 230 | 4.2 |
| | 3-2 | R-02 | 95 | 235 | 4.1 |
| | 3-3 | R-03 | 95 | 212 | 3.8 |
| | 3-4 | R-04 | 100 | 202 | 3.6 |
| | 3-5 | R-05 | 100 | 190 | 3.6 |
| | 3-6 | R-06 | 95 | 204 | 3.4 |
| | 3-7 | R-07 | 100 | 182 | 3.2 |
| | 3-8 | R-08 | 105 | 205 | 3.5 |
| | 3-9 | R-09 | 105 | 185 | 3.4 |
| | 3-10 | R-10 | 105 | 185 | 3.2 |
| Comparative Example | 2-1 | CR-01 | 95 | 251 | 4.8 |
| | 2-2 | CR-02 | 105 | 233 | 4.4 |

As is evident from Table 3, the resist compositions containing onium salts within the scope of the invention exhibit a good balance of sensitivity and CDU when patterns are formed by the EB lithography.

Japanese Patent Application No. 2019-097582 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:
1. An onium salt having the formula (1):

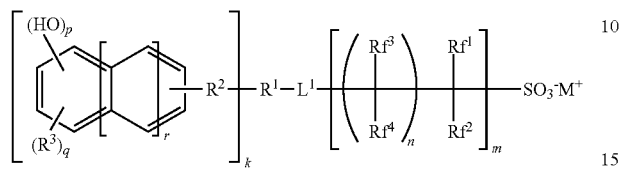

wherein $R^1$ is a $C_1$-$C_{20}$ di- to tetravalent hydrocarbon group,
$R^2$ is a single bond or a $C_1$-$C_{20}$ divalent hydrocarbon group,
$R^3$ is fluorine, a $C_1$-$C_{10}$ alkoxy group, nitro group, or $C_1$-$C_{10}$ monovalent hydrocarbon group,
$R^{f1}$ and $R^{f2}$ each are fluorine, $R^{f3}$ is trifluoromethyl, and $R^{f4}$ is hydrogen,
L1 is —CO—O—,
m is 1, n is 1, k is 1, 2 or 3, p is an integer of 1 to 3, q is an integer of 0 to 3, r is 0 or 1,
$M^+$ is a sulfonium cation having the formula (1A) or iodonium cation having the formula (1B):

wherein $R^{11}$ to $R^{15}$ are each independently a $C_1$-$C_{20}$ monovalent hydrocarbon group which may contain a heteroatom, any two of $R^{11}$, $R^{12}$ and $R^{13}$ may bond together to form a ring with the sulfur atom to which they are attached, and
wherein the sulfonate anion in the onium salt is selected from the group consisting of the following formulae:

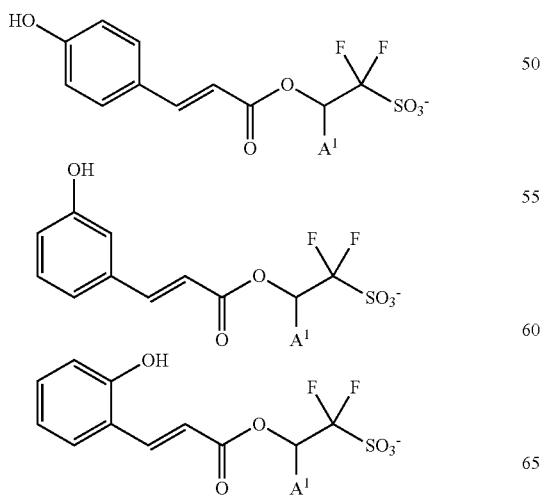

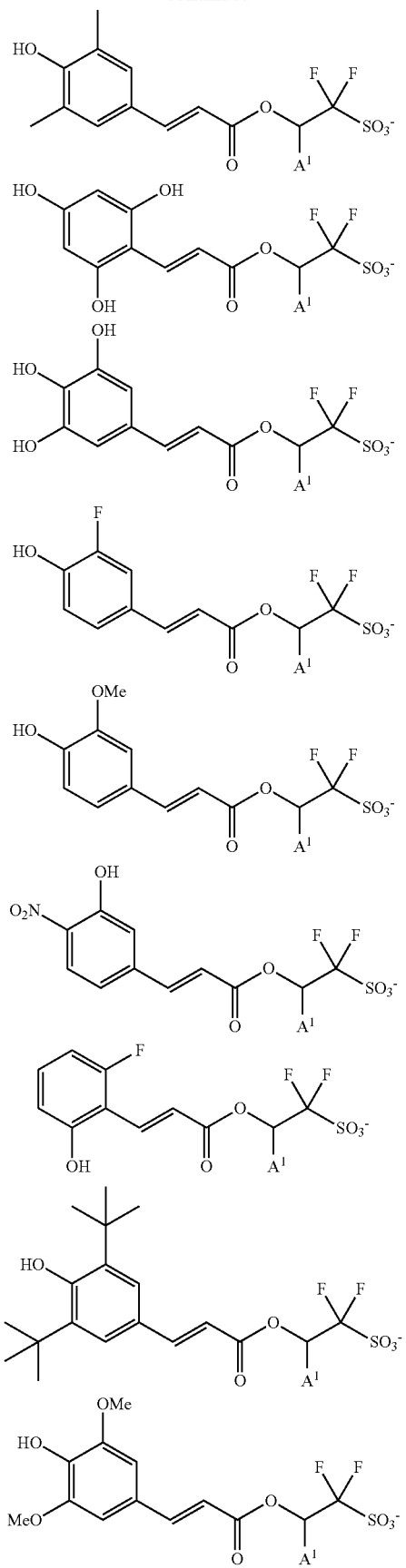

-continued

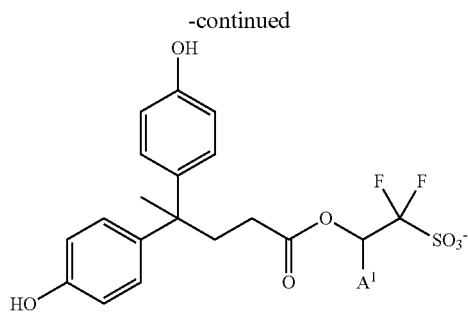

wherein $A^1$ is trifluoromethyl, and Me is methyl.

2. A photoacid generator comprising the onium salt of claim 1.

3. A chemically amplified resist composition comprising the photoacid generator of claim 2.

4. The resist composition of claim 3, further comprising a base polymer comprising recurring units adapted for polarity switch under the action of acid, of at least one type selected from recurring units having the formulae (A1) and (A2), and recurring units of at least one type selected from recurring units having the formulae (B) to (E):

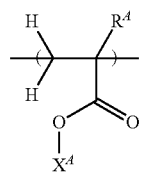 (A1)

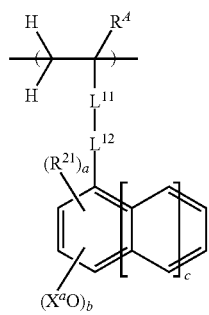 (B)

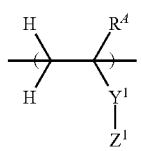 (C)

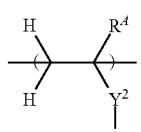 (D)

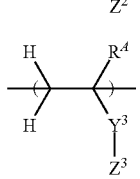 (E)

-continued

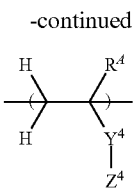 (E)

wherein $R^A$ is hydrogen, fluorine, methyl or trifluoromethyl,
$R^{21}$ is each independently hydrogen or a $C_1$-$C_6$ alkyl group which may contain an ether bond or carbonyl moiety,
$L^{11}$ is a single bond, carbonyloxy or amide group,
$L^{12}$ is a single bond or a $C_1$-$C_7$ alkanediyl group which may contain an ether bond or carbonyl moiety,
a is an integer satisfying a≤5+2c−b, b is an integer of 1 to 5, c is an integer of 0 to 2,
$X^A$ is an acid labile group,
$Y^1$ to $Y^4$ are each independently a single bond, methylene, ethylene, phenylene, fluorinated phenylene, naphthylene, —O—$Y^5$—, —C(=O)—O—$Y^5$— or —C(=O)—NH—$Y^5$—, $Y^5$ is a $C_1$-$C_6$ alkanediyl, $C_2$-$C_6$ alkenediyl, phenylene, or naphthylene group, which may contain a carbonyl moiety, ester bond, ether bond or hydroxyl moiety,
$Z^1$ is a $C_1$-$C_{20}$ fluoroalcohol-containing substituent group,
$Z^2$ is a $C_1$-$C_{20}$ phenolic hydroxyl-containing substituent group,
$Z^3$ is a $C_1$-$C_{20}$ carboxy-containing substituent group, and
$Z^4$ is a substituent group containing a lactone skeleton, sultone skeleton, carbonate skeleton, cyclic ether skeleton, acid anhydride skeleton, alcoholic hydroxyl moiety, alkoxycarbonyl moiety, sulfonamide moiety or carbamoyl moiety.

5. The resist composition of claim 4 wherein the base polymer further comprises recurring units of at least one type selected from recurring units having the formulae (F1) to (F4):

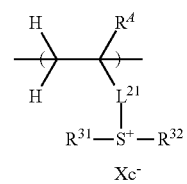 (F1)

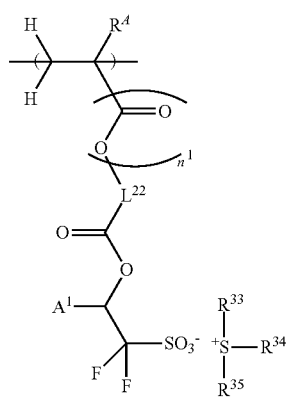 (F2)

-continued

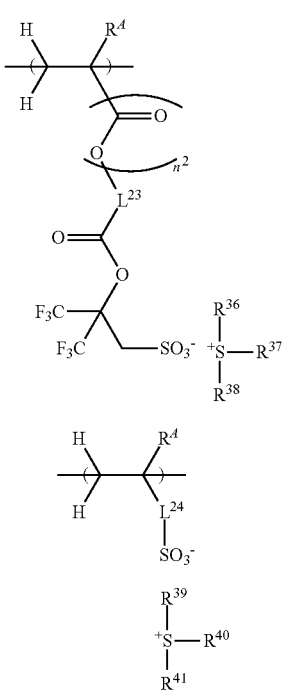

(F3)

(F4)

wherein $R^A$ is hydrogen, fluorine, methyl or trifluoromethyl, $L^{21}$ is a single bond, phenylene, —O—$L^{21A}$—, —C(=O)—O—$L^{21A}$—, or —C(=O)—NH—$L^{21A}$—, $L^{21A}$ is a $C_1$-$C_{20}$ alkanediyl, $C_2$-$C_{20}$ alkenediyl or phenylene group, which may contain a heteroatom, $L^{22}$ and $L^{23}$ are each independently a single bond or a $C_1$-$C_{20}$ divalent hydrocarbon group which may contain a heteroatom, $L^{24}$ is a single bond, methylene, ethylene, phenylene, fluorinated phenylene, —O—$L^{24A}$—, —C(=O)—O—$L^{24A}$— or —C(=O)—NH—$L^{24A}$—, $L^{24A}$ is an optionally substituted phenylene group, $R^{31}$ to $R^{41}$ are each independently a $C_1$-$C_{20}$ monovalent hydrocarbon group which may contain a heteroatom, any two of $L^{21}$, $R^{31}$ and $R^{32}$ may bond together to form a ring with the sulfur atom to which they are attached, any two of $R^{33}$, $R^{34}$ and $R^{35}$, any two of $R^{36}$, $R^{37}$ and $R^{38}$, or any two of $R^{39}$, $R^{40}$ and $R^{41}$ may bond together to form a ring with the sulfur atom to which they are attached, $X_C^-$ is a non-nucleophilic counter ion, $A^F$ is hydrogen or trifluoromethyl, $n^1$ is 0 or 1, $n^1$ is 0 when $L^{22}$ is a single bond, $n^2$ is 0 or 1, $n^2$ is 0 when $L^{23}$ is a single bond.

6. A process for forming a pattern comprising the steps of applying the resist composition of claim 5 onto a substrate to form a resist film thereon, exposing a selected region of the resist film to high-energy radiation, and developing the exposed resist film in a developer.

7. The pattern forming process of claim 6 wherein the developing step uses an alkaline aqueous solution as the developer, thereby forming a positive pattern in which an exposed region of the resist film is dissolved away and an unexposed region of the resist film is not dissolved.

8. The pattern forming process of claim 6 wherein the developing step uses an organic solvent as the developer, thereby forming a negative pattern in which an unexposed region of the resist film is dissolved away and an exposed region of the resist film is not dissolved.

* * * * *